US008372595B2

(12) United States Patent
Schaffer et al.

(10) Patent No.: US 8,372,595 B2
(45) Date of Patent: Feb. 12, 2013

(54) METHOD FOR OBTAINING A MICROBIAL STRAIN FOR PRODUCTION OF SPHINGOID BASES

(75) Inventors: Steffen Schaffer, Herten (DE); Marco Alexander Van Den Berg, Eh Poeldijk (NL); Daniel Boergel, Möerfelden-Walldorf (DE); Thomas Hueller, Marl (DE)

(73) Assignee: Evonik Industries AG, Essen (DE)

( * ) Notice: Subject to any disclaimer, the term of this patent is extended or adjusted under 35 U.S.C. 154(b) by 669 days.

(21) Appl. No.: 12/300,397

(22) PCT Filed: May 11, 2007

(86) PCT No.: PCT/EP2007/004192
§ 371 (c)(1),
(2), (4) Date: Dec. 1, 2008

(87) PCT Pub. No.: WO2007/131720
PCT Pub. Date: Nov. 22, 2007

(65) Prior Publication Data
US 2010/0190219 A1 Jul. 29, 2010

(30) Foreign Application Priority Data

May 11, 2006 (EP) .................................... 06009809

(51) Int. Cl.
*G01N 33/53* (2006.01)
*C12P 7/18* (2006.01)
*C12N 1/00* (2006.01)

(52) U.S. Cl. .................... 435/7.31; 435/158; 435/254.2; 435/254.23

(58) Field of Classification Search .................. None
See application file for complete search history.

(56) References Cited

U.S. PATENT DOCUMENTS

| 5,910,425 A | 6/1999 | De Boer et al. |
| 2006/0099681 A1 | 5/2006 | Obeid et al. |

FOREIGN PATENT DOCUMENTS

| WO | 95/12683 | | 5/1995 |
| WO | WO 95/12683 A1 | | 5/1995 |
| WO | WO 00/01839 | * | 1/2000 |
| WO | WO 01/55408 A1 | | 8/2001 |
| WO | WO 2006/048458 A2 | | 5/2006 |

OTHER PUBLICATIONS

Boergel, D., "Studies on the Sphingolipid Biosynthesis in Yeast *Pichia ciferrii*", Dissertation, Johann Wolfgang Goethe-University, Oct. 2007.*

Mao et al., J. Biol. Chem. 275:31369-31378, 2000.*
Borgel et al., Metabolic Engineer. (2012), http://dx.doi.org/10.1016/j.ymben.2012.03.003, 15 pages.*
Mao et al.,"Cloning and Characterization of a Mouse Endoplasmic Reticulum Alkaline Ceramidase. An Enzyme that Preferentially Regulates Metabolism of Very Long Chain Ceramides" The Journal of Biological Chemistry (2003) pp. 31184-31191, vol. 278(33).
Nierman, W.C. et al., "Ceramide Synthase Menbrance component (Lagl)" Database Uniprot (2006) XP002449868, Database Accession No. Q5A879.
Takakuwa, N. et al., "Isolation and Characterization of the Genes Encoding Δ8—Sphingolipid Desaturase from *Saccharomyces kluyveri* and *Kluyveromyces lactis*" Current Microbiology (2002) pp. 459-461, vol. 45(6).
Dujon, B. et al., Database Uniprot (2006) XP002449869, Database Accession No. Q6BVY2.
Riebeling, C. et al., "Two Mammalian Longevity Assurance Gene (LAG1) Family Members, trh1 and trh4, Regulate Dihydroceramide Synthesis Using Different Fatty Acyl-CoA Donors" The Journal of Biological Chemistry (2003) pp. 43452-43459, vol. 276(44).
Xu, Z. et al., "LASS5 is the Predominant Ceramide Synthase Isoform Involved in de novo Sphingolipid Synthesis in Lung Epithelia" Journal of Lipid Research (2005) pp. 1229-1238, vol. 46(6).
Mao, C. et al., "Cloning and Characterization of a Novel Human Alkaline Ceramidase" The Journal of Biological Chemistry (2001) pp. 26577-26588, vol. 276(28).
Kok, J. W. et al., "Dihydroceramide Biology Structure-Specific Metabolism and Intracellular Localization" The Journal of Biological Chemistry (1997) pp. 21128-21136, vol. 272(34).
Mizutani, Y. et al., "Mammalian Lass6 and its Related Family Members Regulate Synthesis of Specific Ceramides" Biochemical Journal (2005) pp. 263-271, vol. 390.

* cited by examiner

*Primary Examiner* — David J Steadman
(74) *Attorney, Agent, or Firm* — Scully, Scott, Murphy & Presser, P.C.

(57) ABSTRACT

The present invention provides genetically engineered microbial strains, in particular genetically engineered yeast strains, that produce at least 0.5 mg per g CDW of a sphingoid base according to Formula I or a salt or ester thereof. The present invention provides a method to obtain genetically engineered microbial strains producing at least 0.5 mg per g CDW of a sphingoid base according to Formula I or a salt or ester thereof. The method comprises the steps of: a) increasing the expression of a polynucleotide encoding an enzyme having ceramide synthase activity and/or an enzyme having ceramidase activity, the latter being capable of preferentially, or even specifically, hydrolyzing ceramides containing a sphingoid base according to Formula I, and/or b) decreasing the expression of a polynucleotide encoding an enzyme having sphingolipid Δ8-desaturase activity and/or an enzyme having ceramidase activity, the latter being capable of preferentially, or even specifically, hydrolyzing ceramides containing phytosphingosine or dihydrosphingosine as sphingoid base, and isolating strains with the required productivity.

10 Claims, 24 Drawing Sheets

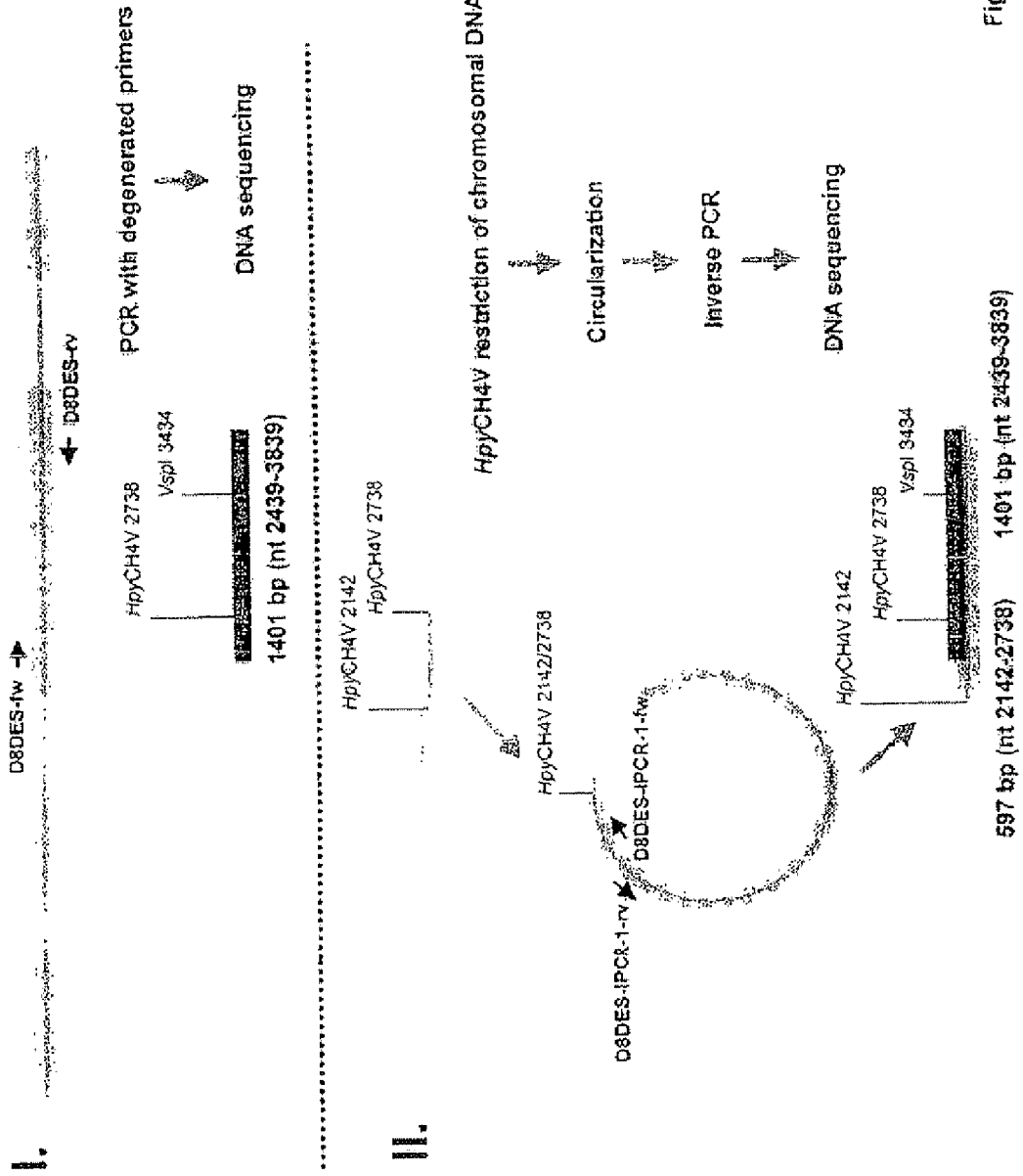

METHOD FOR OBTAINING A MICROBIAL STRAIN FOR PRODUCTION OF SPHINGOID BASES

Sphingolipids are a group of lipids whose members all have the common characteristic of being derived from sphingoid bases, such as phytosphingosine or sphingosine. Sphingolipids occur frequently in cellular membranes of animals, plants and fungi, even in some bacteria.

Ceramides are a specific group of sphingolipids which contain the sphingoid base in amide linkage with a fatty acid. In human skin ceramides, together with cholesterol, cholesterol sulphate and free fatty acids, form a permeability barrier essential for water retardation and protection of the skin from physical and chemical noxas. As component of the permeability barrier these ceramides are mostly found in the stratum corneum, the upper layer of the skin, and they contain sphingosine, phytosphingosine, dihydrosphingosine (sphinganine) or 6-hydroxysphingosine as sphingoid base. Topical application of compositions comprising sphingolipids, such as ceramides, improves the barrier function and moisture-retaining properties of the skin (Curratolo, 1987. Pharm. Res. 4:271-277; Kerscher et al., 1991. Eur. J. Dermatol. 1:39-43). Furthermore, sphingoid bases as such are known to mediate several physiological effects as inhibiting the activity of protein kinase C and are therefore included in cosmetic or dermatological compositions for their anti-inflammatory and antimicrobial activity.

As sphingosine is the major sphingoid base component of sphingolipids in human, it is of considerable commercial interest to produce sphingosine and sphingosine-containing sphingolipids for food, pharmaceutical and cosmetic applications.

Currently, several routes for the chemical synthesis of sphingosine have been developed. However, due to the presence of two stereocenters chemical synthesis results in a racemic mixture with only 25% representing the naturally occurring D-erythro-(2R,3S)-configuration. Moreover, extensive protection chemistry has to be applied due to the presence of three functional groups within the molecule. Consequently, sphingosine produced via chemical synthesis is extremely expensive not allowing for its incorporation into food and cosmetic formulations. This is also true for pure sphingosine isolated from natural sources, such as brain or chicken eggs. Heterogeneous sphingolipids preparations, which have been extracted from animal sources, are also available. Though cheaper than the pure compounds, they suffer from compositional heterogeneity and are potentially unsafe as they might contain pathogenic agents.

Microorganisms as the yeast *Pichia ciferrii* (Wickerham and Stodola, 1960, J. Bacteriol. 80:484-491) were shown to produce high levels of sphingoid bases and derivatives thereof, but mainly C18-phytosphingosine and acetylated derivatives thereof. These can be extracted and chemically converted into corresponding ceramides, thereby obtaining pure cosmetic ingredients (see e.g. WO 93/20038). However, these strains produce sphingoid bases other than phytosphingosine or its derivatives only in very low amounts.

Also in other yeasts the amounts of sphingoid base according to Formula I produced are very low and they can only be found in the glucosylceramide fraction of lipids, i.e. not in free form but bound to long chain N-acyl groups and sugars. Glucosylceramides make up 0 to 12 mg per g cell dry weight (CDW) in yeasts (Saito et al., 2005). Even if all sphingoid bases present in these glucosylceramides would be sphingoid bases according to Formula I, only 0.5 mg per g CDW would be found, taking the contribution of the sphingoid bases mass (40%; Kaufman et al., 1971) to the total mass into account. However, only 25% of the sphingoid bases present in the glucosylceramides of *Yarrowia lipolytica* (Rupcic et al., 1998. Appl Microbiol. Biotechnol. 50:583-588) are sphingoid base according to Formula I, corresponding to 0.13 mg per g CDW in that yeast species.

In recombinant *Saccharomyces cerevisiae* Δsyr2 cells overexpressing dihydroceramide desaturases from *Candida albicans* (Ternes et al., 2002. J. Biol. Chem. 277:25512-25518) and *Schizosaccharomyces pombe* (Garton et al., 2003. FEBS Lett. 538192-538196) less than 20% of the dihydrosphingosine pools were transformed into sphingosine. *Saccharomyces cerevisiae* Δsyr2 cells contain 346 μmol dihydrosphingosine per mg protein (Bae et al., 2004). This corresponds to 0.2 mg dihydrosphingosine per g cell dry weight (CDW), assuming that 60% of CDW is protein. Less than 0.04 mg sphingosine per g cell dry weight are thus found in the described recombinant *Saccharomyces cerevisiae* Δsyr2 cells. Though this was not analyzed, this minute amount of sphingosine is most probable also not found as free sphingoid base but rather bound to long chain N-acyl groups, i.e. ceramides, as the enzyme synthesizing sphingosine from dihydrosphingosine, dihydroceramide desaturase, does not act on the free sphingoid base but on its N-acylated form.

Biosynthesis of free sphingosine from dihydrosphingosine requires the consecutive action of three enzymes, ceramide synthase, dihydroceramide desaturase and ceramidase.

Ceramide synthase uses free sphingoid bases and fatty acyl-CoA thioesters as substrates and forms sphingoid base N-acyl esters. Ceramide synthase may consists of one (in mouse; Lahiri and Futerman, 2005. J. Biol. Chem. 280:33735-33738) or two subunits (in yeasts; Schorling et al., 2001. Mol. Biol. Cell 12:3417-3427). Schorling et al., 2001 (Mol. Biol. Cell 12:3417-3427) describe the overproduction of ceramide synthase in *Saccharomyces cerevisiae* in order to increase ceramide synthase activity and thereby cellular ceramide content. Even though both subunits were overproduced no increase in ceramide synthase activity nor cellular ceramide content could be observed. Also, the heterologous overexpression of mammalian ceramide synthases in *Saccharomyces cerevisiae* did not result in increased amounts of ceramides though alterations in sphingolipid composition could be observed (Guillas et al., 2003. J. Biol. Chem. 278:37083-37091).

Heterologous overproduction of the enzyme dihydroceramide desaturase from several organisms in *Saccharomyces cerevisiae* (Ternes et al., 2002. J. Biol. Chem. 277:25512-25518; Garton et al., 2003. FEBS Lett. 538192-538196) resulted in formation of trace amounts of sphingosine. However, most of the precursor molecule (>80%), the sphingoid base dihydrosphingosine, was not transformed.

Overexpression of the two ceramidases Ypc1 and Ydc1 of *Saccharomyces cerevisiae* (Mao et al., 2000. J. Biol. Chem. 275:6876-6884, and Mao et al., 2000. J. Biol. Chem. 275:31369-31378) did also not result in increased production of sphingosine. Increased expression and/or enzyme activity level of a mouse ceramidase specifically or preferentially hydrolyzing ceramides with a sphingoid base according to Formula I in a human cell line led to sphingosine levels increased by only 1.5 fold (Mao et al., 2003. J. Biol. Chem. 278:31184-31191). The substrate specificity of this ceramidase was further investigated by contacting microsomes of a yeast mutant expressing this mouse ceramidase with various exogenously added substrates. Thus, the data concerning increased sphingosine levels upon overproduction of the ceramidase are exclusively from human cell line experiments. In contrast to *Saccharomyces cerevisiae* most other yeast species such as *Kluyveromyces Hansenula polymorpha, Pichia pastoris, Pichia ciferrii, Yarrowia lipolytica, Candida albicans, Candida utilis, Debaryomyces hansenii* and *Ashbya gossypii* do contain only a single ceramidase. The characteristics and physiological role of this enzyme is not known.

The present invention now surprisingly shows that strains with improved productivity of the sphingoid base according to Formula I can be generated by modifying expression and/or enzyme activity level of ceramide synthase and/or ceramidase and/or sphingolipid Δ8 desaturase. It is preferred that these modifications are accompanied by modifying expression and/or enzyme activity level of dihydroceramide desaturase. The present invention enables the preparation of genetically engineered microbial strains that are capable of producing sphingoid bases other than phytosphingosine and dihydrosphingosine, in particular sphingosine.

The present invention also facilitates the preparation of genetically engineered microbial strains that are capable of producing complex sphingolipids containing those sphingoid bases, in particular ceramides, cerebrosides, gangliosides and inositol phosphorylceramides, more efficiently than those microbial strains known in the art. For instance, genetically engineered microbial strains that are modified to display an increased ceramide synthase, and, optionally, an increased dihydroceramide desaturase, may be used for production of such complex sphingolipids.

Thus, in a first aspect, the present invention provides a microbial strain, in particular a yeast strain, that produces at least 0.5 mg per g CDW of a sphingoid base according to Formula I:

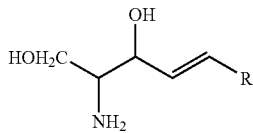

or a salt or ester thereof,
wherein R is X—$(CH_2)_m$—Y—$(CH_2)_n$—$CH_3$, with
  a) X is $CH_2$ or CHOH and
  b) m is between 0 and 4, most preferably m is 1, and
  c) Y is $CH_2$—$CH_2$, CH=CH or CH=$CCH_3$ and
  d) n is between 4 and 14, preferably n is 8 or 10.

Preferably, the microbial strain of the invention produces at least 5 mg per g CDW of a sphingoid base according to Formula I, more preferred produces at least 50 mg per g CDW, even more preferred at least 500 mg per g CDW.

The sphingoid base productivity and composition of the microbial strain of the invention is preferably measured when the sphingoid base-producing microbial strain is cultured under the following conditions, resulting in a stationary phase culture. Microbial cells are inoculated from an agar plate in 100 ml YEPD medium in a 500 ml baffled shake flask and incubated for 72 hours at 30° C. and 280 rpm. Subsequently, 1% of this culture is transferred to a new 500 ml baffled shake flask filled with 100 ml LCBNB production medium and incubated for 24-96 hours at 30° C. and 280 rpm. Alternatively, the main culture is done in 500 ml baffled shake flasks filled with 100 ml MM medium and incubated for 24-96 hours at 30° C. and 120 rpm.

For the determination of acetylated sphingoid bases (e.g. long chain bases like phytosphingosine, sphingosine and sphinganine) using HPLC, 1 ml of total culture broth was mixed with 4 ml of acetone in a falcon tube. The tube was mixed for 10 minutes at 250 rotations per minute to extract the lipids. The solution was centrifuged at 5.300 g for 10 minutes. 10 μl was injected onto a C18 reversed-phase HPLC column. The samples were analysed at a column temperature of 30° C. The mobile phase consisted of Water/Acetonitrile (10:90) with 0.05% TFA. The flow was 1 ml/min with UV detection at 200 nm.

In another embodiment, the sphingoid base according to Formula I is in the form of an acyl ester. The acyl group may be attached to the sphingoid base via a hydroxyl group, i.e. a "real" ester linkage. Preferably, the acyl group linked to the sphingoid base via an ester linkage is a straight short-chain acyl group of 1-4 carbon atoms, more preferably an acetyl group. Alternatively, the acyl group may be attached to the sphingoid base via an amino group, i.e. an amide linkage. Preferably, the acyl group linked to the sphingoid base via an amide linkage is a straight short-chain acyl group of 1-4 carbon atoms, more preferably an acetyl group.

In a preferred embodiment, the sphingoid base according to Formula I has the D-erythro-(2R,3S)-configuration according to Formula II:

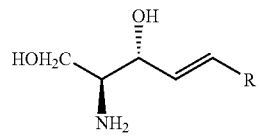

wherein R is as defined for Formula I.

Especially preferred are compounds according to Formula II, wherein R is $(CH_2)_{12}$—$CH_3$, CHOH—$(CH_2)_{11}$—$CH_3$, $(CH_2)_{14}$—$CH_3$ or CHOH—$(CH_2)_{13}$—$CH_3$.

The microbial strain preferably is a yeast, more preferably a yeast from the genera *Pichia* or *Ashbya*, most preferably from the species *Pichia ciferrii* or *Ashbya gossypii*.

In a second aspect, the present invention provides a method for the construction of a microbial strain according to the first aspect by genetic engineering.

Engineering the sphingolipid metabolic pathway by genetic engineering in a parent organism can be done in various ways. For instance by modifying, i.e. increasing or decreasing, the cellular levels of one or more enzymes from the metabolic pathway. Decreasing the cellular level may thereby be effectuated, for instance, by targeted inactivation of the gene encoding the enzyme of interest. Additionally or alternatively, by increasing the concentration of a sphingolipid biosynthetic enzyme naturally present in the host organism. Finally, by introducing sphingolipid biosynthetic enzymes differing in amino acid sequence and/or substrate specificity from those naturally found in the parent organism.

More precisely, the present invention envisages the modification of the activity of ceramide synthase, optionally in combination with the modification of dihydroceramide desaturase, optionally in combination with the modification of ceramidase, optionally in combination with the modification of sphingolipid Δ8 desaturase, in such a way that an increased flux from intracellular dihydrosphingosine towards free sphingosine, optionally towards acetylated sphingosine, is obtained.

Moreover, the present invention envisages the modification of the activity of ceramidase, optionally in combination with the modification of dihydroceramide desaturase, optionally in combination with the modification of ceramide synthase, optionally in combination with the modification of sphingolipid Δ8 desaturase, in such a way that an increased flux from intracellular dihydrosphingosine towards free sphingosine, optionally towards acetylated sphingosine, is obtained.

Also, the present invention envisages the modification of the activity of sphingolipid Δ8 desaturase, optionally in combination with the modification of dihydroceramide desaturase, optionally in combination with the modification of ceramide synthase, optionally in combination with the modification of ceramidase, in such a way that an increased flux from intracellular dihydrosphingosine towards free sphingosine, optionally towards acetylated sphingosine, is obtained.

In one embodiment, genetic engineering is used to generate microbial strains that display, as compared to a parent strain, an improved productivity of the sphingoid base according to Formula I, i.e. a productivity of at least 0.5 mg per g CDW, caused by an increase in expression and/or enzyme activity level of ceramide synthase and/or ceramidase and, optionally, dihydroceramide desaturase. In particular, these strains display an increase in expression of a polynucleotide encoding ceramide synthase and/or ceramidase. The microbial strains may further be modified to display an increase in expression of a polynucleotide encoding dihydroceramide desaturase.

The ceramide synthase to be used in such genetic engineering should be capable of synthesizing ceramides from its constituents, e.g. a sphingoid base constituent, in particular dihydrosphingosine, and a long chain acyl group constituent, in particular a fatty acid or a fatty acyl-coenzyme A thioester.

It is preferred that the ceramide synthase is selected from the group consisting of:
a. a polypeptide with an amino acid sequence of SEQ ID NO:2 and/or SEQ ID NO:4,
b. a polypeptide with an amino acid sequence having a sequence identity of at least 45% to the amino acid sequence of SEQ ID NO:2 and/or at least 45% to the amino acid sequence of SEQ ID NO:4,
c. a polypeptide with an amino acid sequence of SEQ ID NO:9,
d. a polypeptide with an amino acid sequence having a sequence identity of at least 45% to the amino acid sequence of SEQ ID NO:9,
e. a polypeptide with an amino acid sequence of SEQ ID NO:10, and
f. a polypeptide with an amino acid sequence having a sequence identity of at least 45% to the amino acid sequence of SEQ ID NO:10.

Preferably, the sequence identity to the amino acid sequence of SEQ ID NO:2, SEQ ID NO:4, SEQ ID NO:9 and/or SEQ ID NO:10 is 50%, more preferably 60%, 70%, 80%, 90%.

Examples of ceramide synthases having a sequence identity of at least 45% to the amino acid sequence of SEQ ID NO:2 or at least 45% to the amino acid sequence of SEQ ID NO:4 are the ceramide synthases having an amino acid sequence of SEQ ID NO: 12 or SEQ ID NO: 14.

Ceramide synthases are represented by polypeptides with a greatly divergent amino acid sequence, displaying a degree of identity of as less as 15%. Thus, a ceramide synthase suitable for use in the present invention may be obtainable from divergent sources like viruses, fungi, plants or animals, more preferably from algal viruses, yeasts or mammals, most preferably from Coccolithovirus, *Saccharomyces, Schizosaccharomyces, Debaryomyces, Kluyveromyces, Pichia, Yarrowia, Candida, Ashbya*, mouse, rat or human.

The ceramide synthase encoded by the Coccolithovirus infecting the microalga *Emiliana huxleyi* was surprisingly found to be especially suitable for fermentative production of sphingoid bases according to Formula 1.

In those embodiments wherein an increase in expression and/or enzyme activity level of ceramidase is provided, the ceramidase in question should be capable of preferentially, or even specifically, hydrolyzing ceramides containing a sphingoid base according to Formula I.

A preferred ceramidase that is capable of preferentially, or even specifically, hydrolyzing ceramides containing a sphingoid base according to Formula I is selected from the group consisting of:
1. a polypeptide with an amino acid sequence of SEQ ID NO: 15, and
2. a polypeptide with an amino acid sequence having a sequence identity of at least 70%, preferably at least 80%, more preferably at least 90%, to the amino acid sequence of SEQ ID NO: 15.

Such a ceramidase preferably is obtainable from an animal source, more preferably from a mammal, like a mouse, rat or human.

The dihydroceramide desaturase to be used in such genetic engineering should be capable of desaturating the bond between C-4 and C-5 of the sphingoid base, in particular dihydrosphingosine, as present in ceramide, in particular in dihydroceramide. Such a dihydroceramide desaturase is also known as sphingolipid desaturase.

A preferred dihydroceramide desaturase that is capable of desaturating the bond between C-4 and C-5 of the sphingoid base is selected from the group consisting of:
a. a polypeptide with an amino acid sequence of SEQ ID NO:17,
b. a polypeptide with an amino acid sequence having a sequence identity of at least 30%, preferably at least 40%, more preferably at least 50%, 60%, 70%, 80%, 90%, to the amino acid sequence of SEQ ID NO:17.

Examples of dihydroceramide desaturases having a sequence identity of at least 30% to the amino acid sequence of SEQ ID NO:17 are the dihydroceramide desaturases having an amino acid sequence of SEQ ID NO: 16, SEQ ID NO: 18 or SEQ ID NO: 19.

Such a dihydroceramide desaturase may be obtainable from viruses, fungi, plants or animals, preferably from algal viruses, yeasts or mammals, more preferably from Coccolithovirus, *Saccharomyces, Schizosaccharomyces, Debaryomyces, Kluyveromyces, Pichia, Yarrowia, Candida, Ashbya*, mouse, rat or human.

In another embodiment of the invention, genetic engineering is used to generate microbial strains that display, as compared to a parent strain, an improved productivity of the sphingoid base according to Formula I caused by a decrease in expression and/or enzyme activity level and/or a change in intracellular localisation of sphingolipid Δ8 desaturase and/or ceramidase, in particular by a decrease in expression of a polynucleotide encoding sphingolipid Δ8 desaturase and/or ceramidase.

The sphingolipid Δ8 desaturase to be used in such genetic engineering should be capable of desaturating the bond between C-8 and C-9 of the sphingoid base.

A preferred sphingolipid Δ8 desaturase is selected from the group consisting of:
a. a polypeptide with an amino acid sequence of SEQ ID NO:6, and
b. a polypeptide with an amino acid sequence having a sequence identity of at least 30%, preferably at least 40%, more preferably at least 50%, 60%, 70%, 80%, 90%, to the amino acid sequence of SEQ ID NO:6.

An example of a sphingolipid Δ8 desaturase having a sequence identity of at least 30% to the amino acid sequence of SEQ ID NO:6 is the sphingolipid Δ8 desaturase having an amino acid sequence of SEQ ID NO: 21.

Such a sphingolipid Δ8 desaturase may be obtainable from fungi, preferably from yeasts, more preferably from the yeasts *Saccharomyces cerevisiae, Kluyveromyces* lactic, *Hansenula polymorpha, Pichia pastoris, Pichia ciferrii, Yarrowia lipolytica, Candida albicans, Candida utilis* or *Ashbya gossypii*, most preferably from the yeasts *Pichia ciferrii, Ashbya gossypii* or *Yarrowia lipolytica*.

In those embodiments wherein a decrease in expression and/or enzyme activity level of ceramidase is provided, the ceramidase in question should be capable of preferentially, or even specifically, hydrolyzing ceramides containing phytosphingosine or dihydrosphingosine as sphingoid base.

A preferred ceramidase that is capable of preferentially, or even specifically, hydrolyzing ceramides containing phytosphingosine or dihydrosphingosine as sphingoid base is selected from the group consisting of:
a. a polypeptide with an amino acid sequence of SEQ ID NO: 8, and
b. a polypeptide with an amino acid sequence having a sequence identity of at least 25%, preferably at least 30%, more preferably at least 40%, 50%, 60%, 70%, 80%, 90%, to the amino acid sequence of SEQ ID NO: 8.

Such a ceramidase may be obtainable from fungi, preferably from yeasts, more preferably from the yeasts *Saccharomyces cerevisiae, Kluyveromyces lactis, Hansenula* polymorphs, *Pichia pastoris, Pichia ciferrii, Yarrowia lipolytica, Candida albicans, Candida utilis* or *Ashbya gossypii*, most preferably from the yeasts *Pichia ciferrii, Ashbya gossypii* or *Yarrowia lipolytica*.

In a preferred embodiment, microbial strains are constructed wherein an increase in expression level of relevant enzymes, as specified above, is combined with a decrease in expression level of other relevant enzymes, as specified above.

In the above embodiments, the percentage identity of a particular amino acid sequence to a reference amino acid sequence is determined by subjecting the reference sequence to the analysis as mentioned below.

In the context of the invention, an improved sphingoid base productivity of a genetically engineered strain thereby includes an increase in productivity of a sphingoid base as compared to the productivity of the parent strain from which the genetically engineered strain is derived and/or the production of a sphingoid base that is not substantially produced or not produced at all by the parent strain.

In the context of the invention, polypeptides with amino acid sequences fulfilling the required identity percentage, so called homologous polypeptides, may conveniently be identified by screening appropriate sequence databases with the reference amino acid sequence in question. Homologous polypeptides may also be derived from a reference polypeptide by subjecting this polypeptide to mutagenesis. Suitable mutagenesis techniques to be applied to the gene encoding the polypeptide in question include random mutagenesis (e.g. error-prone PCR), site-specific mutagenesis and/or gene shuffling. For instance, mutagenesis can be used to obtain ceramide synthase polypeptides, ceramidase polypeptides hydrolyzing ceramides containing a sphingoid base according to Formula I or dihydroceramide desaturase polypeptides with a higher affinity for their substrates than the wildtype polypeptides, and/or with higher specific enzyme activities and/or with altered substrate specificities, for instance with respect to the length of the alkyl chain of the sphingoid base or with respect to the sphingoid base itself. Also, mutagenesis can be used to obtain ceramidases polypeptides capable of preferentially, or even specifically, hydrolyzing ceramides containing phytosphingosine or dihydrosphingosine as sphingoid base or sphingolipid Δ8 desaturase polypeptides with a lower affinity for their substrates than the wildtype polypeptides, and/or with lower specific enzyme activities.

Genetic engineering of a microbial strain according to the invention to obtain an increase in expression of an enzyme of interest may be done by overexpressing endogenous genes encoding said enzyme, i.e. natively encoded already in the parent strain (homologous overexpression) or expressing genes that are not naturally present in the parent strain (heterologous (over)expression). Both homologous and heterologous (over)expression of a gene encoding an enzyme of interest can be obtained by integration of one copy or several copies of the gene(s) into the chromosome(s) of the parent strain or by providing one copy or several copies of the gene(s) on a DNA element capable of autonomous replication independent from replication of the chromosome(s) of the parent strain. Such an autonomously replicating DNA element could be a plasmid, an artificial chromosome or a virus.

A decrease in activity of an enzyme of interest in the context of the present invention includes a reduced expression of a gene naturally present in the parent strain and encoding the enzyme of interest. Reduced expression of such a gene could be brought about by targeted inactivation of the gene by genetic means, including deletion of portions of the nucleotide sequence and/or deletion of the entire nucleotide sequence and/or disruption of the nucleotide sequence of the gene encoding the enzyme(s) of interest. Alternatively or additionally, nucleotide sequences responsible for regulation of expression of genes encoding enzyme(s), nucleotide sequences responsible for processing, transport to specific cellular compartments and translation of messenger RNA may be disrupted, deleted or altered in order to decrease the activity of the enzyme of interest. In yet another embodiment, anti-sense RNAs can be expressed from nucleotide sequences which represent portions of gene(s) or the entire gene(s) encoding enzyme(s) of interest in order to induce degradation of hybrids of mRNA and anti-sense RNA derived from nucleotide sequences encoding these enzymes or to block translation of mRNA derived from nucleotide sequences encoding these enzymes.

In the context of the present invention, a parent strain may be a strain that does not produce the sphingoid base according to Formula I. A parent strain may also be a microbial strain producing the sphingoid base according to Formula I, but less than 0.5 mg per g CDW.

A parent strain may also be a strain that produces a substantial amount of a sphingoid base that is excluded from the sphingoid base according to Formula I, such as, preferably, *Pichia ciferrii* NRRL Y-1031 F-60-10 and/or any of the *Pichia ciferrii* strains disclosed in WO 95/12683, all producing predominantly C18-phytosphingosine.

A strain that is especially suitable to be used as a parent strain in the present invention is a strain that is defective in the gene encoding dihydrosphingosine C-4 hydroxylase, the enzyme that converts dihydrosphingosine into phytosphingosine, in particular a dihydrosphingosine C-4 hydroxylase-defective strain that is derived from a strain producing high amounts of the sphingoid base phytosphingosine. Dihydrosphingosine C-4 hydroxylase-defective strains may be obtained by exposing a strain of interest to the toxin syringomycinE and selecting syringomycinE-resistant strains (Grilley et al. (1998). J. Biol. Chem. 273, 11062-11068). Among these strains are strains defective in sphinganine hydroxylase (Δsyr2 strains). Alternatively, strains lacking dihydrosphingosine C-4 hydroxylase can be obtained by targeted inactivation of the SYR2 gene by deletion or disruption using genetic methods.

For instance, suitable for use as a parent strain are syr2 mutants of *Pichia ciferrii*, obtainable by subjecting *Pichia ciferrii* to syringomycinE selection (see non prepublished WO 2006/048458).

The polynucleotides encoding the polypeptides as described herein may be adapted to codon usage of the microbial strain in which they are to be expressed. Codon usage tables conveniently can be found in a database, for instance a database such as the Codon Usage Database provided online at the website provided by kazusa.

The vector into which the polynucleotides as described herein are inserted may be any vector that may conveniently be subjected to recombinant DNA procedures, and the choice of the vector will often depend on the host cell into which it is to be introduced. Thus, the vector may be an autonomously replicating vector, i.e. a vector which exists as an extra-chromosomal entity, the replication of which is independent of chromosomal replication, e.g. a plasmid, cosmid, virus or phage vector, usually provided with an origin of replication. Alternatively, the vector may be one which, when introduced into a host cell, is integrated into the host cell genome and replicated together with the chromosome(s) into which it has been integrated. The vector may be a circular, e.g. a plasmid, or a linear, e.g. an expression cassette.

An integrative vector may integrate at random or at a predetermined target locus in the chromosomes of the host cell. For targeted integration, the integrative vector comprises a DNA fragment that is homologous to a DNA sequence in a predetermined target locus in the genome of the host cell. In order to promote targeted integration, the vector is preferably linearized prior to transformation of the host cell. Linearization is preferably performed such that at least one but preferably either end of the cloning vector is flanked by sequences homologous to the target locus. The length of the homologous sequences flanking the target locus is preferably at least 0.1 kb, more preferably at least 0.2 kb, even more preferably at least 0.5 kb, even more preferably at least 1 kb, most preferably at least 2 kb. A homologous sequence does not need to be strictly identical to the target locus. The degree of required identity may thereby depend on the length of the homologous sequence. Typically, the identity percentage is at least about 80%.

Depending on the intended use of the polynucleotide to be used in the genetic engineering according to the invention, the polynucleotide may be inserted into an expression cassette, if expression of a gene is aimed at, or in a inactivation cassette, if inactivation of a gene is aimed at.

In an expression cassette, a coding sequence is operably linked to a regulatory sequence that is capable of providing for the expression of a polypeptide from the coding sequence by the host cell. The term "operably linked" refers to a juxtaposition wherein the components described are in a relationship permitting them to function in their intended manner. A regulatory sequence such as a promoter, an enhancer or another expression regulatory signal "operably linked" to a coding sequence is positioned in such a way that expression of a polypeptide from its coding sequence is achieved under conditions compatible with the regulatory sequences.

An inactivation cassette is constructed in such a way that it is capable of targeted integration into a gene to be inactivated. The inactivation cassette typically comprises a non-functional counterpart of the gene to be inactivated. Such a non-functional counterpart may be a polynucleotide wherein part or all of the coding sequence of the gene in question are deleted, such that targeted integration will result in replacement of the native coding sequence with a defective coding sequence. The polynucleotide sequence used for gene inactivation should at least be about 80% identical to the target sequence comprising the gene to be inactivated.

In a third aspect, novel polypeptides are provided that display ceramide synthase activity, sphingolipid Δ8 desaturase activity or ceramidase activity.

In one embodiment, a polypeptide is provided displaying ceramide synthase activity selected from the group consisting of a polypeptide with an amino acid sequence of SEQ ID NO: 2 and a polypeptide with an amino acid sequence having a sequence identity of at least 70%, preferably at least 80%, more preferably at least 90%, to the amino acid sequence of SEQ ID NO: 2; and/or selected from the group consisting of a polypeptide with an amino acid sequence of SEQ ID NO: 4 and a polypeptide with an amino acid sequence having a sequence identity of at least 55%, preferably at least 60%, more preferably at least 70%, more preferably at least 80%, most preferably at least 90%, to the amino acid sequence of SEQ ID NO: 4. The polypeptide is preferably obtainable from *Pichia*, more preferably form *Pichia ciferrii*.

In a further embodiment, a polypeptide is provided displaying sphingolipid Δ8 desaturase activity selected from the group consisting of a polypeptide with an amino acid sequence of SEQ ID NO: 6 and a polypeptide with an amino acid sequence having a sequence identity of at least 65%, preferably at least 70%, more preferably at least 80%, most preferably at least 90%, to the amino acid sequence of SEQ ID NO: 6. The polypeptide is preferably obtainable from *Pichia*, more preferably form *Pichia ciferrii*.

In a further embodiment, a polypeptide is provided displaying ceramidase activity, said ceramidase preferentially, or even specifically, hydrolyzing ceramides with phytosphingosine or dihydrosphingosine as sphingoid base, selected from the group consisting of a polypeptide with an amino acid sequence of SEQ ID NO: 8 and a polypeptide with an amino acid sequence having a sequence identity of at least 60%, preferably at least 70%, more preferably at least 80%, most preferably at least 90%, to the amino acid sequence of SEQ ID NO: 8. The polypeptide is preferably obtainable from *Pichia*, more preferably form *Pichia ciferrii*.

The terms "homology" or "percent identity" are used interchangeably herein. For the purpose of this invention, it is defined here that in order to determine the percent identity of two amino acid sequences, the sequences are aligned for optimal comparison purposes (e.g., gaps can be introduced in each sequence for optimal alignment). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical positions/total number of positions (i.e. overlapping positions including gaps)×100). Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-

453 (1970)) algorithm which has been incorporated into the GAP program in the Accelrys GCG software package, available, e.g., online at the website provided by accelrys using either a Blossom 62 matrix or a PAM250 matrix, and a gap weight of 16, 14, 12, 10, 8, 6, or 4 and a length weight of 0.5, 1, 2, 3, 4, 5, or 6. The skilled person will appreciate that all these different parameters will yield slightly different results but that the overall percentage identity of two sequences is not significantly altered when using different algorithms. Preferably, the matrix is a Blossom 62 matrix with a gap weight of 10.0 and a length weight of 0.5.

The protein sequences of the present invention can further be used as a "query sequence" to perform a search against public databases to, for example, identify other family members or related sequences. Such searches can be performed using the blastp, psi-blast, phi-blast and tblastn programs (version 2.0) of Altschul, et al. (1990) J. Mol. Biol. 215:403-10. When utilizing blastp, psi-blast, phi-blast and tblastn programs, the default parameters of the respective programs (e.g., blastp, psi-blast, phi-blast and tblastn programs) can be used. See the homepage of the National Center for Biotechnology Information (NCBI) provided by the National Library of Medicine (NLM) and the NIH.

The polypeptides with an amino acid sequence displaying a percentage identity to a reference amino acid sequence are called homologous polypeptides. Homologous polypeptides may be naturally occurring variants obtainable from other organisms, in particular yeasts or animals, or may be engineered variants.

In a fourth aspect, polynucleotides are provided that comprise nucleotide sequences encoding the polypeptides of the third aspect. The polynucleotide may comprise a nucleotide sequence encoding the amino acid sequence of SEQ ID NO: 2, SEQ ID NO: 4, SEQ ID NO: 6 and/or SEQ ID NO: 8. For example, the nucleotide sequences encoding the amino acid sequences of SEQ ID NO: 2, SEQ ID NO: 4, SEQ ID NO: 6 and SEQ ID NO: 8, respectively, are SEQ ID NO: 1, SEQ ID NO: 3, SEQ ID NO: 5 and SEQ ID NO: 7, respectively. It may be advantageous to optimize the nucleotide sequence with respect to the codon usage of the host organism. Examples of such optimized nucleotide sequences are provided by SEQ ID NO: 32, encoding an alkaline ceramidase having the amino acid sequence of SEQ ID NO: 15, SEQ ID NO: 33, encoding a ceramide synthase having the amino acid sequence of SEQ ID NO: 9, and SEQ ID NO: 34, encoding a ceramide synthase having the amino acid sequence of SEQ ID NO: 10.

In a further aspect the invention provides a process for preparing a sphingoid base of Formula I by cultivating a microbial cell according to the first aspect of the invention, obtainable by the method of the second aspect of the invention and/or a host cell transformed with a polynucleotide according to the fourth aspect of the invention (e.g. cloned in an expression and/or inactivation cassette as described above) under conditions to provide for expression of the sphingoid base and, if necessary, of the polypeptide to be used according to the invention, and optionally recovering the sphingoid base.

The cells according to the invention may be cultured using procedures known in the art. For each combination of a promoter and a host cell, culture conditions are available which are conducive to expression of the polypeptides of the invention. After reaching the desired cell density the culture is stopped and the polypeptides or the sphingoid base of the invention is recovered using known procedures.

The fermentation medium may comprise a known culture medium containing a carbon source (e.g. glucose, maltose, molasses), a nitrogen source (e.g. ammonia, ammonium sulphate, ammonium nitrate, ammonium chloride, organic nitrogen sources e.g. yeast extract, malt extract, peptone), and other inorganic nutrient sources (e.g. phosphate, magnesium, potassium, zinc, iron, etc.). Optionally, an inducer may be included.

The selection of the appropriate medium may be based on the choice of expression host and/or based on the regulatory requirements of the expression construct and/or based on requirements associated with optimal production of the sphingoid base according to the invention. Such media are known to those skilled in the art.

The fermentation can be performed over a period of 0.5-30 days. It may be a batch, continuous or fed-batch process, suitably at a temperature in the range of between 0 and 45° C. and, for example, at a pH between 2 and 10. Preferred fermentation conditions are a temperature in the range of between 20 and 37° C. and/or a pH between 3 and 9. The appropriate conditions are usually selected based on the choice of the expression host and the protein to be expressed.

After fermentation, if necessary, the cells can be removed from the fermentation broth by means of centrifugation or filtration. The sphingoid base of the invention may then be recovered from the cells and/or the fermentation broth and, if desired, purified and isolated by conventional means.

The present invention advantageously shows that the fully fermentative production of a sphingoid base according to Formula I or a salt or ester thereof can be significantly improved by increasing the intracellular concentration of active ceramide synthase polypeptide during the fermentation process. In particular, it is shown that fermentative production of sphingosine or a salt or ester thereof is significantly improved by either increasing the intracellular concentration of active ceramide synthase polypeptide or by producing enzymes with ceramide synthase activity novel (with respect to amino acid sequence) to the host during the fermentation process.

Conveniently, the sphingoid base of the invention may be combined with suitable excipients to produce a sphingoid base composition.

The sphingoid base of the invention may be used as starting material to prepare other sphingoid bases, or sphingolipids, like ceramides, gangliosides or cerebrosides.

Amplification of an internal part of PcLAG1 (I.) was followed by two rounds of inverse PCR (II. and III.) Oligonucleotides used in the individual steps are indicated and sequence representations in different shadings show the portions of the PcLAG1 locus whose DNA sequence were determined in the individual steps. Restriction sites relevant for the experimental procedures are also indicated.

FIG. 8 schematically describes the three-step procedure resulting in the isolation of the entire *Pichia ciferrii* LAF1 locus.

Amplification of an internal part of PcLAF1 (I.) was followed by two rounds of inverse PCR (II. and III.) Oligonucleotides used in the individual steps are indicated and sequence representations in different shadings show the portions of the PcLAF1 locus whose DNA sequence were determined in the individual steps. Restriction sites relevant for the experimental procedures are also indicated.

FIG. 9 schematically describes the six-step procedure resulting in the isolation of the entire *Pichia ciferrii* YXC1 locus. Amplification of an internal part of PcYXC1 (I.) was followed by five rounds of inverse PCR (II.-V.) Oligonucleotides used in the individual steps are indicated and sequence representations in different shadings show the portions of the PcYXC1 locus whose DNA sequence were determined in the individual steps. Restriction sites relevant for the experimental procedures are also indicated.

FIG. 10 schematically describes the four-step procedure resulting in the isolation of the entire *Pichia ciferrii* 8DES locus.

Amplification of an internal part of Pc8DES (I.) was followed by three rounds of inverse PCR (II.-IV.) Oligonucleotides used in the individual steps are indicated and sequence representations in different shadings show the portions of the Pc8DES locus whose DNA sequence were determined in the individual steps. Restriction sites relevant for the experimental procedures are also indicated.

Figure 11:
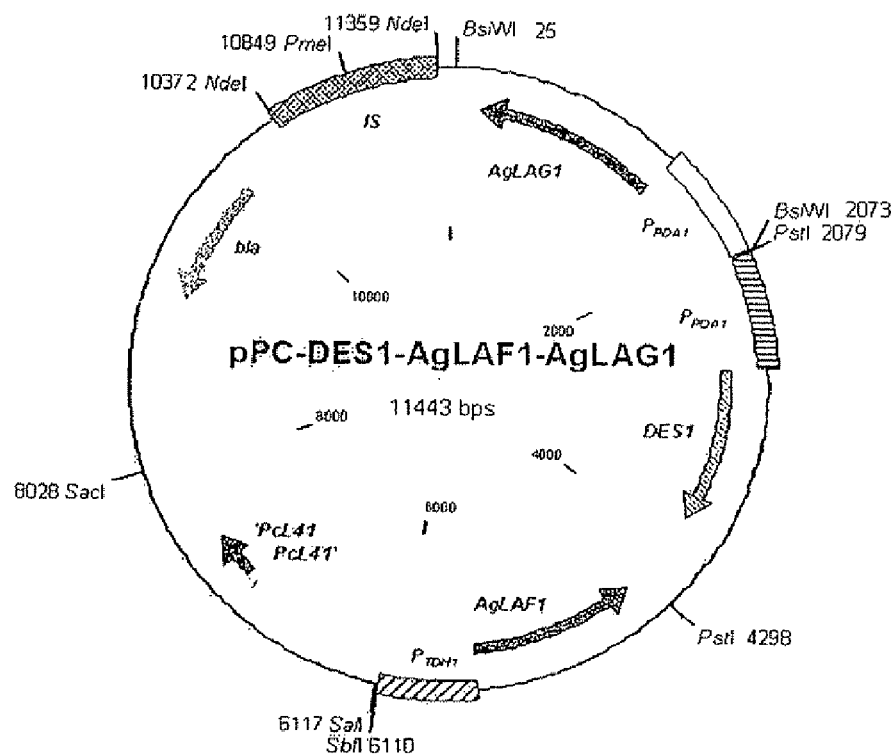

FIG. 11 shows a graphical representation of the plasmid pPC-DES1-AgLAF1-AgLAG1 for overexpression of PcDES1, AgLAF1 and AgLAG1 in *Pichia ciferrii*. The *Pichia ciferrii* TDH1 (diagonally hatched) and PDA1 promoters (either horizontally hatched or white), the *Ashbya gossypii* LAF1 and LAG1 gene (both dark grey), the *Pichia ciferrii* DES1 (diagonally hatched) and L41 gene (dark grey), the 5S-26S rDNA intergenic region which is used for homologous recombination (gridded) and the ampicillin resistance gene (bla; light grey) are shown. Restriction sites relevant for the cloning procedures are also indicated.

Figure 12:
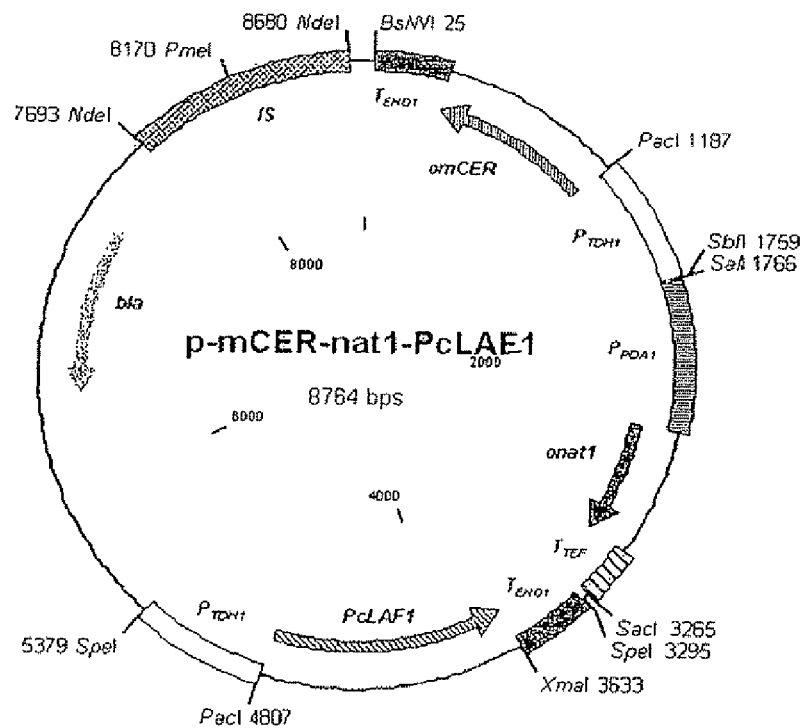

FIG. 12 shows a graphical representation of the plasmid p-mCER-nat1-PcLAF1 for overexpression of PcLAF1 and omCER in *Pichia ciferrii*. The *Pichia ciferrii* TDH1 promoters (white) and the PDA1 promoter (horizontally hatched), the *Pichia ciferrii* LAF1 (diagonally hatched), the codon-optimized omCER (vertically hatched) and the codon-optimized nail gene (dark grey), the 5S-26S rDNA intergenic region which is used for homologous recombination (gridded) and the ampicillin resistance gene (bla; light grey) are shown. Restriction sites relevant for the cloning procedures are also indicated.

Figure 13:
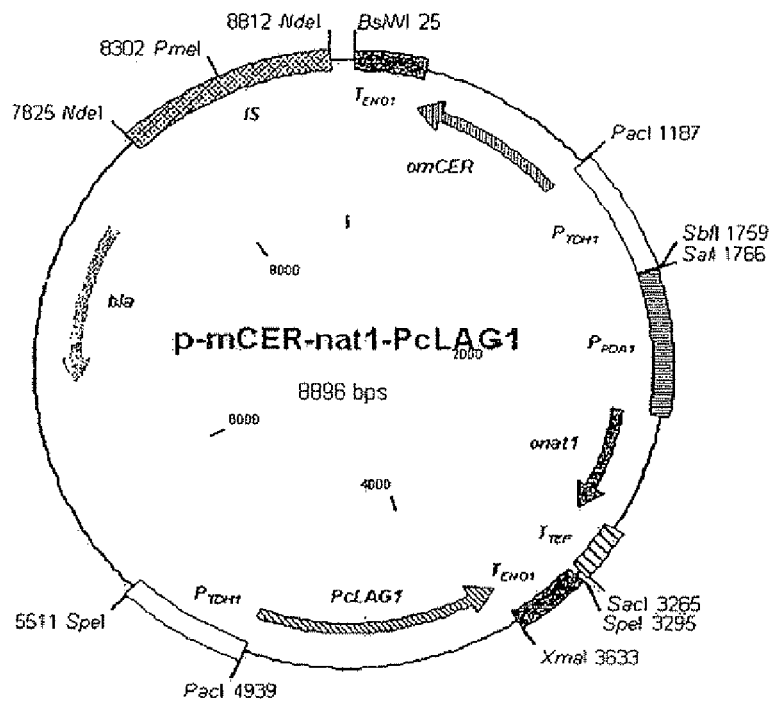

FIG. 13 shows a graphical representation of the plasmid p-mCER-nail-PcLAG1 for overexpression of PcLAG1 and omCER in *Pichia ciferrii*. The *Pichia ciferrii* TDH1 promoters (white) and the PDA1 promoter (horizontally hatched), the *Pichia ciferrii* ENO1 terminators (dark grey), the TEF terminator (diagonally hatched), the *Pichia ciferrii* LAG1 (diagonally hatched), the codon-optimized omCER (vertically hatched) and the codon-optimized nail gene (dark grey), the 5S-26S rDNA intergenic region which is used for homologous recombination (gridded) and the ampicillin resistance gene (bla; light grey) are shown. Restriction sites relevant for the cloning procedures are also indicated.

Figure 14:
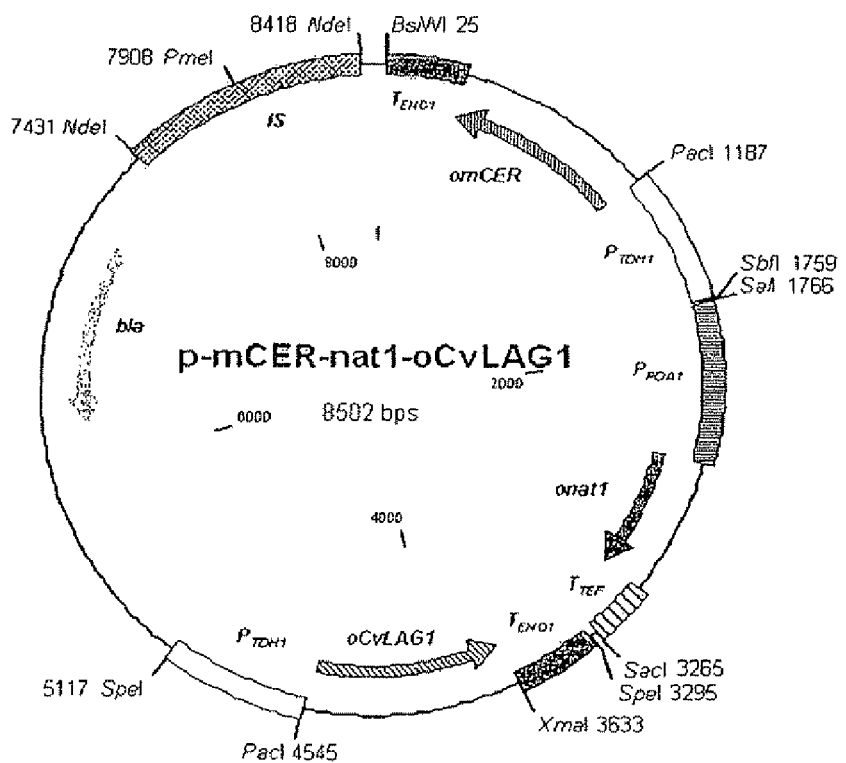

FIG. 14 shows a graphical representation of the plasmid p-mCER-nat1-oCvLAG1 for overexpression of oCvLAG1 and omCER in *Pichia ciferrii*. The *Pichia ciferrii* TDH1 promoters (white) and the PDA1 promoter (horizontally hatched), the *Pichia ciferrii* ENO1 terminators (dark grey), the TEF terminator (diagonally hatched), the codon optimized oCvLAG1 (diagonally hatched), the codon-optimized omCER (vertically hatched) and the codon-optimized nat1 gene (dark grey), the 5S-26S rDNA intergenic region which is used for homologous recombination (gridded) and the ampicillin resistance gene (bla; light grey) are shown. Restriction sites relevant for the cloning procedures are also indicated.

Figure 15:
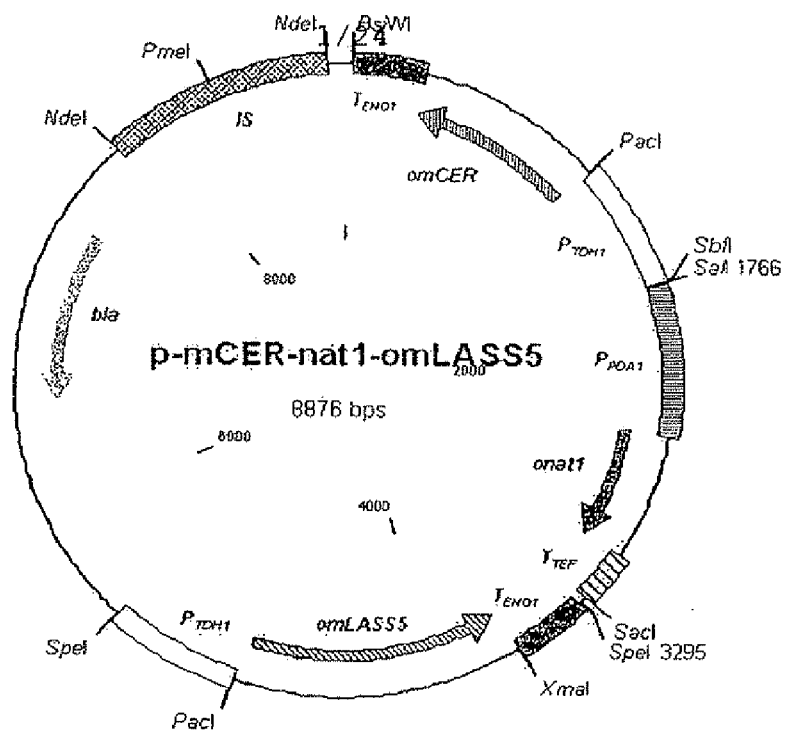

FIG. 15 shows a graphical representation of the plasmid p-mCER-nat1-omLASS5 for overexpression of omLASS5 and omCER in *Pichia ciferrii*. The *Pichia ciferrii* TDH1 promoters (white) and the PDA1 promoter (horizontally hatched), the *Pichia ciferrii* ENO1 terminators (dark grey), the TEF terminator (diagonally hatched), the codon optimized omLASS5 (diagonally hatched), the codon-optimized omCER (vertically hatched) and the codon-optimized nat1 gene (dark grey), the 5S-26S rDNA intergenic region which is used for homologous recombination (gridded) and the ampicillin resistance gene (bla; light grey) are shown. Restriction sites relevant for the cloning procedures are also indicated.

Figure 16:
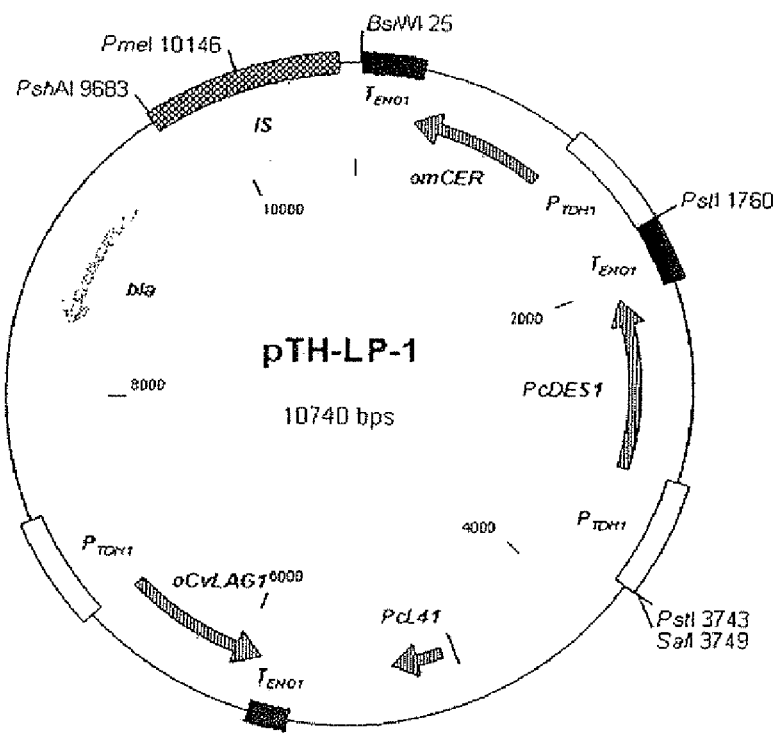

FIG. 16 shows a graphical representation of the plasmid pTH-LP-1 for targeted integration into the *Pichia ciferrii* 5S-26S rDNA intergenic region and overexpression of *Pichia ciferrii* DES1, overexpression of codon-optimized omCER and overexpression of codon-optimized oCvLAG1, each of the genes under control of the *Pichia ciferrii* TDH1 promoter. The *Pichia ciferrii* TDH1 promoter (white), the *Pichia ciferrii* ENO1 terminator (black), the *Pichia ciferrii* DES1 (vertically hatched), the codon-optimized omCER (vertically hatched), the codon-optimized oCvLAG1 (vertically hatched), the *Pichia ciferrii* PcL41 cycloheximide resistance gene (black), the 5S-26S rDNA intergenic region integration site (IS; dotted) and the ampicillin resistance gene (bla; light grey) are shown. Restriction sites relevant for the cloning procedures and transformation are also indicated.

Figure 17:
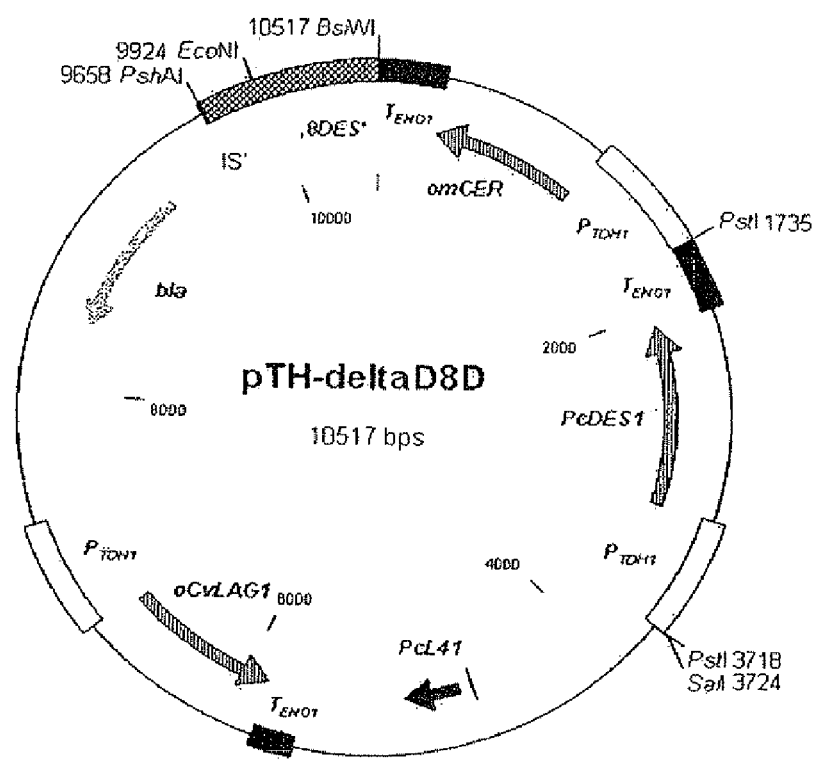

FIG. 17 shows a graphical representation of the plasmid pTH-deltaD8D for targeted disruption of the *Pichia ciferrii* sphingolipid Δ8-desaturase-encoding gene 8DES and overexpression of *Pichia ciferrii* DES1, overexpression of codon-optimized omCER and overexpression of codon-optimized oCvLAG1, each of the genes under control of the *Pichia ciferrii* TDH1 promoter. The *Pichia ciferrii* TDH1 promoter (white), the *Pichia* ciferrii ENO1 terminator (black), the *Pichia ciferrii* DES1 (vertically hatched), the codon-optimized omCER (vertically hatched), the codon-optimized oCvLAG1 (vertically hatched), the *Pichia ciferrii* PcL41 cycloheximide resistance gene (black), the chromosomal integration site 8DES (dotted) and the ampicillin resistance gene (bla; light grey) are shown. Restriction sites relevant for the cloning procedures and transformation are also indicated.

Figure 18:
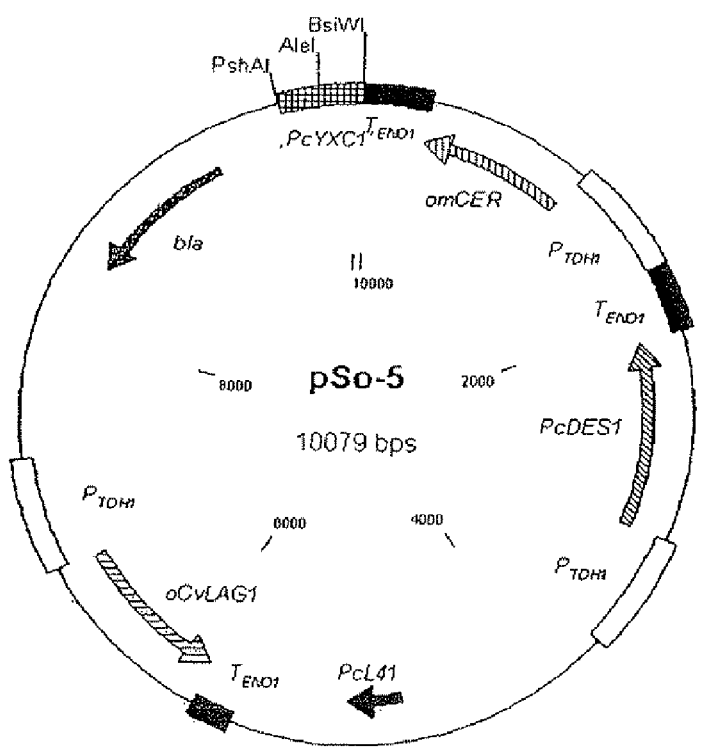

FIG. 18 shows a graphical representation of plasmid pSo-5 used for targeted inactivation of *Pichia ciferrii* alkaline ceramidase gene (PcYXC1) and simultaneous overexpression of oCvLAG1, PcDES1, and omCER in *Pichia ciferrii*. The *Pichia ciferrii* TDH1 promoters ($P_{TDH1}$, white), the *Pichia ciferrii* ENO1 terminators ($T_{ENO1}$, black), the *Pichia ciferrii* DES1 (diagonally hatched), the codon-optimized omCER (vertically hatched) and the codon-optimized oCvLAG1 gene (horizontally hatched), the internal *Pichia ciferrii* YXC1 alkaline ceramidase fragment which is used for targeted integration (gridded), and the ampicillin resistance gene (b/a; light grey) are shown. Restriction sites relevant for the cloning procedures are also indicated.

Figure 19:
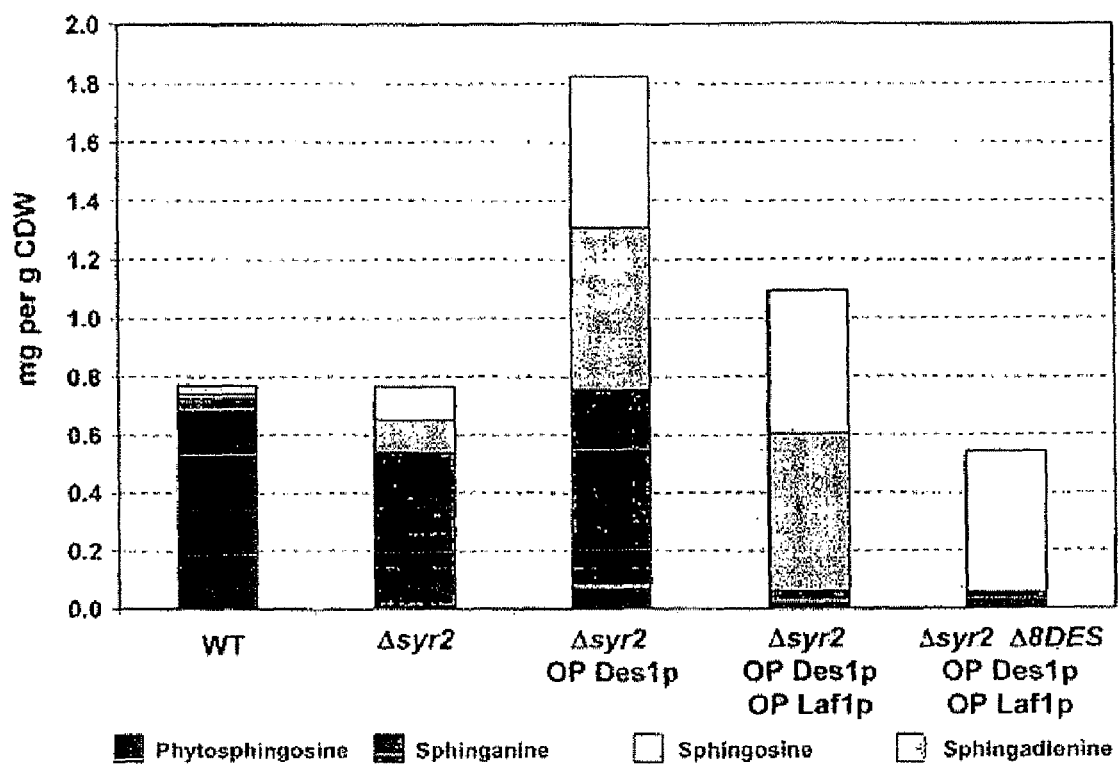

FIG. 19 shows the results of RP-HPLC analysis of sphingoid base composition in *Ashbya gossypii* strains. The strains analyzed were the wildtype ATCC19895 (WT) and derivatives of it with the following genotypes: Δsyr2 (Δsyr2), Δsyr2 $P_{TDH3}$-DES1 (Δsyr2 OP Des1p), Δsyr2 $P_{TDH3}$-DES1 $P_{ENO1}$-LAF1 (Δsyr20P Des1p OP Laf1p) and Δsyr2 $P_{ENO1}$-DES1 $P_{ENO1}$-LAF1 8DES::pAG32-D8D (Δsyr2 Δ8DES OP Des1p OP Laf1p).

EXAMPLES

Example 1

Construction of *Ashbya gossypii* syr2 Mutants Simultaneously Overproducing the *Ashbya Gossypii* Enzymes Laf1p and Des1p or Lag1p and Des1p, Respectively The plasmid pUG6-AgSUR2::kanMX was designed to replace the *Ashbya gossypii* SYR2 gene by the kanMX resistance gene, thereby inactivating it, and the plasmid pAG-LAG1-1 or pAG-LAF1-1 in order to simultaneously overexpress the *Ashbya gossypii* DES1 and LAG1 or LAF1, respectively. The *Ashbya gossypii* SYR2 sequence was obtained by performing a BLASTP search using the functionally characterized sphinganine C4-hydroxylase of *Saccharomyces cerevisiae* named SUR2/SYR2 (Grilley et al., 1998; NCBI accession number NC_001136.7) as template against the Ashbya Genome Database, available online at the Duke University website resulting in a significant match to the *Ashbya gossypii* gene AAL066W (GenBank accession # AAS50300; located on chromosome I at position 232310-233326, with a score of 409 bits (62% and 78% positional identity and similarity, respectively). The following oligonucleotides were synthesized by MWG Biotech (Ebersberg, Germany) to amplify the downstream region of the *Ashbya gossypii* SYR2 coding sequence by colony PCR using *Ashbya gossypii* ATCC19895 cells as template, afterwards to be cloned into pUG6 (EUROSCARF, Oberursel, GERMANY):

```
AgSUR2T-fw:
TAT ATA GTT AAC AGG CAA AGC TGA CGC TGC TCT CC (nt
1719-1741 in SEQ ID NO: 23; including a HpaI
recognition site)

AgSUR2T-rv:
TAT ATA ACT AGT ATG GAC GCT GCA GTG CAG AAC C (nt
2500-2521 in SEQ ID NO: 23; including a SpeI
recognition site)
```

The oligonucleotides were used to set up a PCR reaction according to Innis et al., (PCR protocols. A guide to methods and applications, 1990, Academic Press) with Phusion™ High Fidelity PCR Master Mix (Finnzymes, cat.# F-531 L) according to the manufacturers' instructions. A 815 bp fragment could be obtained by applying this method. The fragment was purified using the MinElute Gel Extraction Kit (QIAGEN, cat.#28606) according to the instructions of the manufacturer. It was then digested for 2 hours with HpaI (New England Biolabs, cat.# R0138L) and SpeI (New England Biolabs, cat.# R0151S) and ligated with EcoRV (New England Biolabs, cat.# R0195L) and SpeI cut pUG6 using T4 DNA Ligase (New England Biolabs, cat# M0202L) according to the manufacturers' instructions. 2.5 µl of the ligation product was used to transform chemically competent *E. coli* (Invitrogen One Shot® TOP10, cat.# C4040-03) as described in the manufacturers' protocol. The plasmid pUG6-AgSUR2-T (4806 bp) was obtained herewith. The following oligonucleotides were synthesized to amplify the upstream region to be cloned likewise into pUG6:

```
AgSUR2P-fw2:
TAT ATA CAG CTG CGT CTG TAC CAG AAC CTG TGC (nt
1-21 in SEQ ID NO: 23; including a PvuII
recognition site)

AgSUR2P-rv2:
TAT ATA GTC GAC CTA CGT CAT CCA TGA ACG ACA CT (nt
800-821 in SEQ ID NO: 23; including a SalI
recognition site)
```

Figure 1:
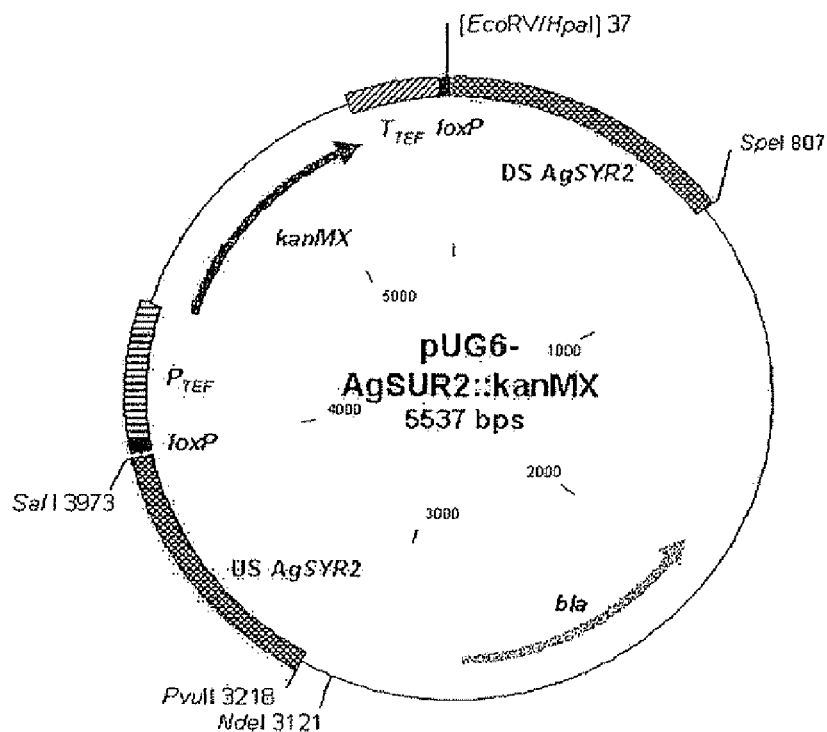
FIG. 1 shows a graphical representation of the plasmid pUG6-AgSUR2::kanMX for targeted inactivation of SYR2 in *Ashbya gossypii*. The *Ashbya gossypii* TEF promoter (horizontally hatched), the *Ashbya gossypii* TEF terminator (diagonally hatched), the loxP sites (black), the kanamycin resistance gene (dark grey), the regions upstream (US) and downstream (DS) of *Ashbya gossypii* SYR2 which were used for homologous recombination (gridded) and the ampicillin resistance gene (bla; light grey) are shown. Restriction sites relevant for the cloning procedures are also indicated.

The oligonucleotides were used to set up a colony PCR reaction with Phusion™ High Fidelity PCR Master Mix and *Ashbya gossypii* ATCC19895 cells as template. A 840 bp fragment could be obtained by applying this method. The fragment was purified using the MinElute Gel Extraction Kit. It was then digested for 2 hours with SalI (New England Biolabs, cat.# R0138L) and PvuII (New England Biolabs, cat.# R0151S) and ligated with SalI and PvuII cut pUG6-AgSUR2-T as described above, creating plasmid pUG6-AgSUR2::kanMX (5537 bp) shown in FIG. 1. This plasmid is suitable to *Ashbya gossypii* SYR2 by kanMX after being transformed into *Ashbya gossypii*, thereby inactivating SYR2.

The *Ashbya gossypii* DES1 sequence was obtained by performing a BLASTP search using the functionally characterized dihydroceramide Δ4-desaturase of *Candida albicans* (Ternes et al., 2002; NCBI accession number NW_139432.1) as template against the *Ashbya* Genome Database, available online at the Duke University website resulting in a significant match to the *Ashbya gossypii* gene AGR025W (GenBank accession # AAS54514; located on chromosome VII at position 761515-762654 bp) with a score of 378 bits (52% and 65% positional amino acid identity and similarity, respectively). The following oligonucleotides were synthesized to amplify the DNA region upstream of the *Ashbya gossypii* DES1 coding sequence:

```
AgDES1-US-fw:
TAT ATA GTT AAC TCC ATC AGC GCG ACA ACA GG (nt
1-20 in SEQ ID NO: 22; including a HpaI
recognition site)

AgDES1-US-rv:
TAT ATA GAG CTC TCC GAA TCG AGG CGT GTG TAG (nt
830-850 in SEQ ID NO: 22; including a SacI
recognition site)
```

The oligonucleotides were used to set up a colony PCR reaction with Phusion™ High Fidelity PCR Master Mix and *Ashbya gossypii* ATCC19895 cells as template. A 874 bp fragment could be obtained by applying this method. The fragment was purified using the MinElute Gel Extraction Kit. It was then digested for 2 hours with HpaI (New England Biolabs, cat.# R0105S) and SacI (New England Biolabs, cat.# R01563) and ligated with respectively cut vector pAG32 (EUROSCARF, Oberursel, GERMANY), resulting in plasmid pAG32-AgDES1-US (4916 bp), an intermediate plasmid for further cloning procedures. The following oligonucleotides were subsequently synthesized to amplify the 5'-end of the *Ashbya gossypii* DES1 coding sequence:

```
AgDES1-DS-fw:
ATG AAC CAA CGG GGT ATA GCG AC (nt 905-927 in SEQ
ID NO: 22)

AgDES1-DS-rv:
TAT ATA AAG CTT CTC TTC AAT GCT GAA GAG GTA GTG
(nt 1652-1675 in SEQ ID NO: 22; including a
HindIII recognition site)
```

The oligonucleotides were used to set up a colony PCR reaction with Phusion™ High Fidelity PCR Master Mix and Ashbya gossypii ATCC19895 cells as template. A 783 bp fragment could be obtained by applying this method. The fragment was purified using the MinElute Gel Extraction Kit. The *Ashbya gossypii* promoter of the glyceraldehyde-3-phosphate dehydrogenase (SEQ ID NO: 24) was fused to the start codon of the previously amplified 5'-end of the *Ashbya gossypii* DES1 coding sequence by performing a crossover PCR with Phusion™ High Fidelity PCR Master Mix. The promoter sequence was obtained by performing a BLASTP search using the functionally characterized glyceraldehyde-3-phosphate dehydrogenase of *Saccharomyces cerevisiae* (Holland et al., 1979; NCBI accession number NC_001142.6) as template against the Ashbya Genome Database, available online at the Duke University website resulting in a significant match to the *Ashbya gossypii* gene AER031C (GenBank accession # AAS52715; located on chromosome V at position 695233-696228 bp) with a score of 530 bits (78% and 89% positional amino acid identity and similarity, respectively). The following oligonucleotides were synthesized to amplify the promoter region upstream of the start codon of *Ashbya gossypii* glyceraldehyde-3-phosphate dehydrogenase coding sequence:

```
PGAP-fw:
TAT ATA GTC GAC GGC TCT CCT CGC TCT GCT CAA G (nt
1-23 in SEQ ID NO: 24; including a SalI
recognition site)

PGAP-rv:
GTC GCT ATA CCC CGT TGG TTC ATT GTG CGG TGT GTA
TGT GTG GAC (nt 497-518 in SEQ ID NO: 24 and nt
1-23 in SEQ ID NO: 22)
```

Figure 2:
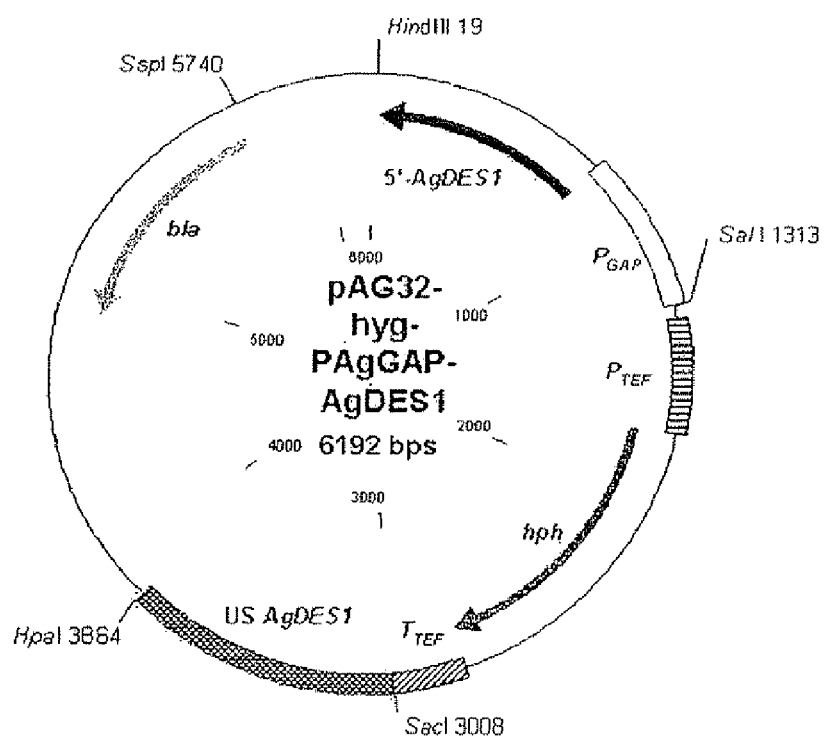
FIG. 2 shows a graphical representation of the plasmid pAG32-hyg-PAgGAP-AgDES1 for targeted replacement of the native promoter in front of DES1 by the GAP promoter in *Ashbya gossypii*. The *Ashbya gossypii* TEF promoter (horizontally hatched), the *Ashbya gossypii* TEF terminator (diagonally hatched), the hygromycin resistance gene (dark grey), the region upstream (US) of *Ashbya gossypii* DES1 (gridded) and the 5'-region of *Ashbya gossypii* DES1 (black) which were used for homologous recombination and the ampicillin resistance gene (bla; light grey) are shown. Restriction sites relevant for the cloning procedures and transformation are also indicated.

The oligonucleotides were used to set up a colony PCR reaction with Phusion™ High Fidelity PCR Master Mix and *Ashbya gossypii* ATCC19895 cells as template. A 550 bp fragment could be obtained by applying this method. The fragment was purified using the MinElute Gel Extraction Kit. The crossover PCR was carried out using the oligonucleotides PGAP-fw and AgDES1-DS-rv as well as 1 μl of the previously amplified and purified promoter of the *Ashbya gossypii* glyceraldehyde-3-phosphate dehydrogenase encoding gene and the 5'-end of the *Ashbya gossypii* DES1 coding sequence. The 1310 bp fragment obtained by applying this method was purified using the MinElute Gel Extraction Kit. It was then digested with SalI (New England Biolabs, cat.# R0138S) and HindIII (New England Biolabs, cat.# R0104S) and ligated with respectively cut vector pAG32-AgDES1-US as described above, creating plasmid pAG32-hyg-PAgGAP-AgDES1 (6192 bp) shown in FIG. 2. This plasmid is suitable to replace the native *Ashbya gossypii* DES1 promoter by the promoter of the *Ashbya gossypii* glyceraldehyde-3-phosphate dehydrogenase encoding gene in order to obtain an increased Des1p activity. The authenticity of the cloned DNA region upstream of the *Ashbya gossypii* DES1 gene, the cloned 5'-end of the *Ashbya gossypii* DES1 gene and the cloned promoter of the *Ashbya gossypii* glyceraldehyde-3-phosphate dehydrogenase encoding gene was confirmed by DNA sequencing done by Sequiserve (Vaterstetten, GERMANY), using the dideoxy chain termination method developed by Sanger et al. (Proceedings of the National Academy of Sciences, U.S.A., 74:5463-5467). Nucleotide 382, 489 and 405 of the published DES1 coding sequence (GenBank accession # AAS50300; AGR025W in the Ashbya Genome Database, available online at the Duke University website, were absent in the corresponding cloned DNA sequence of plasmid pAG32-hyg-PAgGAP-AgDES1 resulting in a change of the published protein sequence at amino acid positions 29 to 34 to ANLPI, which is identical to the corresponding region in all other yeast Des1p. Consequently, the published *Ashbya gossypii* DES1 DNA sequence probably does contain sequencing errors.

The *Ashbya gossypii* LAG1 sequence was obtained by performing a BLASTP search using the functionally characterized ceramide synthase component of *Saccharomyces cer-* evisiae named LAC1 (Schorling et al., 2001; NCBI accession number NC_001143.7) as template against the Ashbya Genome Database, available online at the Duke University website, resulting in a significant match to the *Ashbya gossypii* gene ABR009W (NP_982955; located on chromosome II at position 408463-409704 bp) with a score of 531 bits (64% and 79% positional amino acid identity and similarity, respectively). The *Ashbya gossypii* LAG1 sequence was obtained by performing a BLASTP search using the functionally characterized ceramide synthase component of *Saccharomyces cerevisiae* named LAF1 (Schorling et al., 2001; NCBI accession number NC_001140.5) as template against the Ashbya Genome Database, available online at the Duke University website, resulting in a significant match to the *Ashbya gossypii* gene ADL206W (GenBank accession # AAS51714; located on chromosome IV at position 340556-341674 bp) with a score of 117 bits (32% and 48% positional amino acid identity and similarity, respectively). The following oligonucleotides were synthesized to amplify the LAG1 coding sequence:

AgLAC1-fw:
ATG GCT GAA AAT TCG TTA TTG AAG C (nt 1-25 in SEQ ID NO: 11)

AgLAC1-PacI-rv:
TAT ATA <u>TTA ATT AAG</u> ACC TGT ATA TAT TCT AGT AGT G (nt 1388-1410 in SEQ ID NO: 11; including a PacI recognition site)

The oligonucleotides were used to set up a colony PCR reaction with Phusion™ High Fidelity PCR Master Mix and Ashbya gossypii ATCC19895 cells as template. A 1241 bp fragment could be obtained by applying this method. The fragment was purified using the MinElute Gel Extraction Kit. A crossover PCR was applied to fuse promoter in front of the *Ashbya gossypii* enolase-encoding gene to the LAG1 coding sequence as described above. The promoter sequence of the *Ashbya gossypii* enolase-encoding gene was obtained by performing a BLASTP search using the functionally characterized enolase isoenzymes designated ENO1 and ENO2 of *Saccharomyces cerevisiae* (McAlister et al., 1982; NCBI accession number NC_001139.7 and NC_001140.5) as template against the Ashbya Genome Database, available online at the Duke University website, resulting in a significant match to the *Ashbya gossypii* gene AER294C (GenBank accession # AAS52975; located on chromosome V at position 1176724-1178037 bp) with a score of 734 bits (83% and 91% positional amino acid identity and similarity, respectively) for *Saccharomyces cerevisiae* ENO1 and a score of 709 bits (80% and 87% positional amino acid identity and similarity, respectively) for *Saccharomyces cerevisiae* ENO2. A region of approximately 455 b upstream the start codon of ENO1 was chosen and amplified using the following oligonucleotides:

P-ENO-PacI-fw:
TAT ATA <u>TTA ATT AAC</u> TGT TCA CAG CCT TCT GAG AC (nt 1-21 in SEQ ID NO: 25; including a PacI recognition site)

P-ENO-CO-LAG1-rv:
CCT GAC TTG GCC CGA CAT TTT GAA TTA TTT GAG TTT CGG AGG TGT TAA TC (nt 436-467 in SEQ ID NO: 25 and nt 1-18 in SEQ ID NO: 13)

Figure 3:
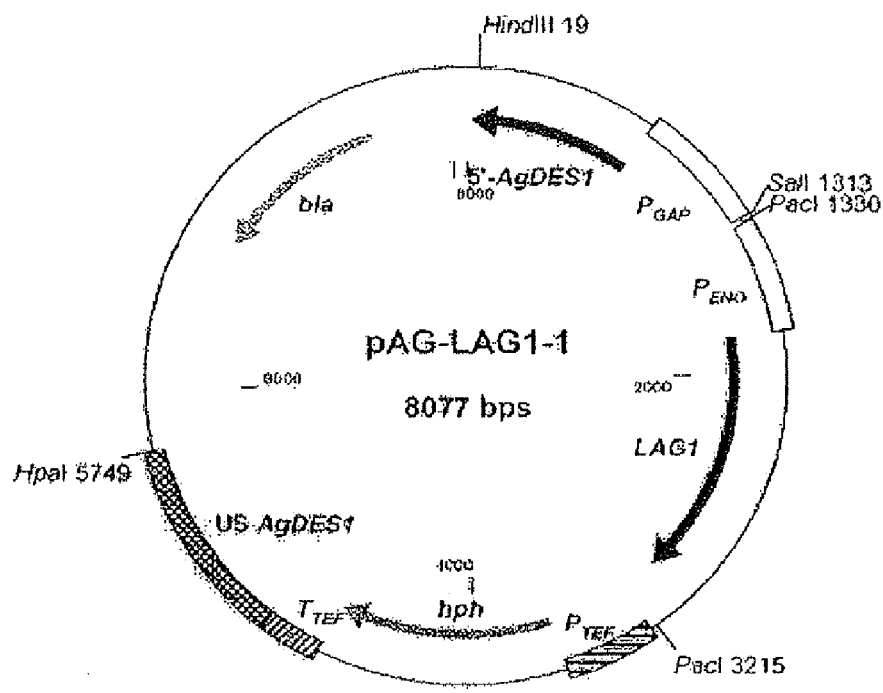
FIG. 3 shows a graphical representation of the plasmid pAG-LAG1-1 for targeted replacement of the native promoter in front of DES1 by the GAP promoter in *Ashbya gossypii* and overexpression of *Ashbya gossypii* LAG1 under control of the *Ashbya gossypii* ENO promotor. The *Ashbya gossypii* TEF promoter (horizontally hatched), the *Ashbya gossypii* TEF terminator (diagonally hatched), the hygromycin resistance gene (dark grey), the region upstream (US) of *Ashbya gossypii* DES1 (gridded) and the 5'-region of *Ashbya gossypii* DES1 (black) which were used for homologous recombination, the *Ashbya gossypii* LAG1 (black) and the ampicillin resistance gene (bla; light grey) are shown. Restriction sites relevant for the cloning procedures and transformation are also indicated.

The oligonucleotides were used to set up a colony PCR reaction with Phusion™ High Fidelity PCR Master Mix and Ashbya gossypii ATCC19895 cells as template. A 475 bp fragment was obtained by applying this method. The fragment was purified using the MinElute Gel Extraction Kit. The oligonucleotides P-ENO-PacI-fw and AgLAC1-PacI-ry as well as 1 µl of the previously amplified and purified PCR products representing the promoter of the *Ashbya gossypii* enolase-encoding gene and the *Ashbya gossypii* LAG1 coding sequence were used to set up a crossover PCR with Phusion™ High Fidelity PCR Master Mix. A 1716 bp fragment could be obtained by applying this method. The fragment was purified using the MinElute Gel Extraction Kit. It was then digested for 2 hours with PacI (New England Biolabs, cat.# R0547S), and ligated with PacI cut and dephosphorylated (New England Biolabs, alkaline phosphatase, calf intestinal, cat.# M0290S) vector pAG32-hyg-PAgGAP-AgDES1 as described in the manufacturers' protocol, resulting in plasmid pAG-LAG1-1 (8077 bp) shown in FIG. 3. This plasmid is suitable to simultaneously overexpress *Ashbya gossypii* DES1 and LAG1 after being transformed into *Ashbya gossypii*. The authenticity of the cloned promoter of the *Ashbya gossypii* enolase-encoding gene and the *Ashbya gossypii* LAG1 coding sequence was confirmed by DNA sequencing done by Sequiserve (Vaterstetten, GERMANY Subsequently, the following oligonucleotides were synthesized to amplify the LAF1 coding sequence:

AgLAG1-fw:
ATG TCG GGC CAA GTC AGG C (nt 1-20 in SEQ ID NO: 13)

AgLAG1-PacI-rv:
TAT ATA <u>TTA ATT AAC</u> TGC ATG CGC TGT CTG GCG (nt 1291-1309 in SEQ ID NO: 13; including a PacI recognition site)

Figure 4:
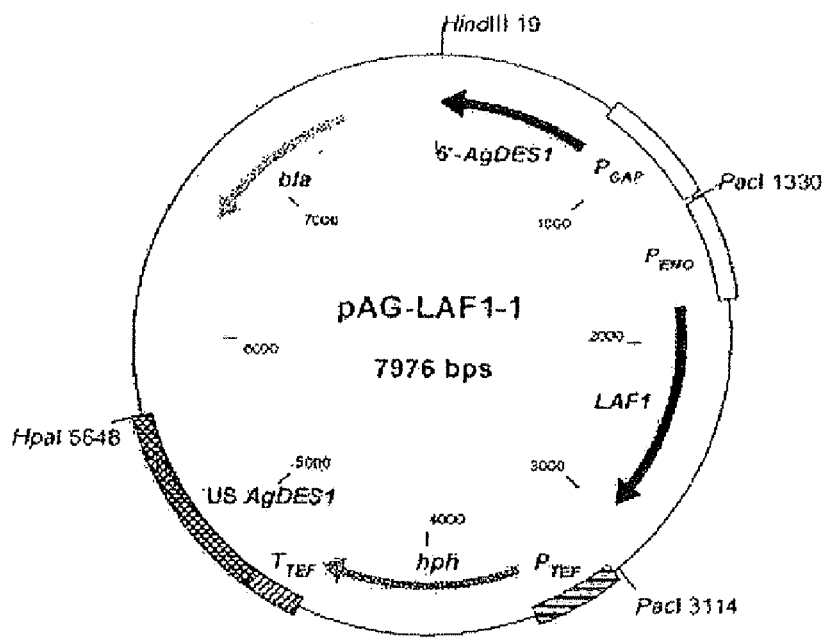
FIG. 4 shows a graphical representation of the plasmid pAG-LAF1-1 for targeted replacement of the native promoter in front of DES1 by the GAP promoter in *Ashbya gossypii* and overexpression of *Ashbya gossypii* LAF1 under control of the *Ashbya gossypii* ENO promotor. The *Ashbya gossypii* TEF promoter (horizontally hatched), the *Ashbya gossypii* TEF terminator (diagonally hatched), the hygromycin resistance gene (dark grey), the region upstream (US) of *Ashbya gossypii* DES1 (gridded) and the 5'-region of *Ashbya gossypii* DES1 (black) which were used for homologous recombination, the *Ashbya gossypii* LAF1 (black) and the ampicillin resistance gene (bla; light grey) are shown. Restriction sites relevant for the cloning procedures and transformation are also indicated.

The oligonucleotides were used to set up a colony PCR reaction with Phusion™ High Fidelity PCR Master Mix and Ashbya gossypii ATCC19895 cells as template. A 1118 bp fragment could be obtained by applying this method. The fragment was purified using the MinElute Gel Extraction Kit. A crossover PCR was applied to fuse the promoter of the *Ashbya gossypii* enolase-encoding gene to the LAF1 coding sequence as described above. The oligonucleotides P-ENO-PacI-fw and AgLAG1-PacI-rv as well as 1 µl of the previously amplified and purified PCR products representing the promoter of the *Ashbya gossypii* enolase-encoding gene and the *Ashbya gossypii* LAF1 coding sequence were used to set up a crossover PCR with Phusion™ High Fidelity PCR Master Mix. A 1593 bp fragment could be obtained by applying this method. The fragment was purified using the MinElute Gel Extraction Kit. It was then digested for 2 hours with PacI, and ligated with PacI cut and dephosphorylated vector pAG32-hyg-PAgGAP-AgDES1 as described above, resulting in plasmid pAG-LAF1-1 (7976 bp) shown in FIG. 4. This plasmid is suitable to simultaneously overexpress *Ashbya gossypii* DES1 and LAF1 after being transformed into *Ashbya gossypii*. The authenticity of the cloned promoter of the *Ashbya gossypii* enolase-encoding gene and the *Ashbya gossypii* LAF1 coding sequence was confirmed by DNA sequencing done by Sequiserve (Vaterstetten, GERMANY).

Transformation of *Ashbya gossypii* ATCC19895 was done by an electroporation method. To prevent clotting of the fungal mycelium during cultivation in liquid medium, it was homogenized as follows: One full loop of mycelium grown for 24 h at 30° C. on an agar plate (1 g/l yeast extract, 10 g/l peptone, 10 g/l glucose, 0.3 g/l myo-inositol and 20 g/l agar-agar) was taken and resuspended in 2 ml of sterile water in a 15 ml reaction tube. Sterile glass beads with a diameter of 3 mm were added up to the meniscus. The solution was treated on a minishaker (IKA, Staufen, GERMANY) for 2 min at full speed. The homogenized mycelium suspension was removed with a syringe and transferred into a 250 ml shaking flask with baffles containing 70 ml of liquid complex medium (1 g/l yeast extract, 10 g/l peptone, 10 g/l glucose and 0.3 g/l myo-inositol). It was grown overnight at 30° C. and 250 rounds per minute and harvested by vacuum filtration (Schleicher & Schuell Vacuflo PV 050/2 vacuum filtration units), washed with 50 mM phosphate buffer containing 25 mM dithiothreitol (DTT), incubated in the same solution for 30 min at 28° C., and collected by vacuum filtration again. The cells were subsequently washed with 10 mM Tris-HCl (pH 7.5) containing 270 mM sucrose and 1 mM $MgCl_2$, resuspended in 1 ml of the same solution and splitted into 200 µl aliquots. The transforming plasmid DNA, pUG6-AgSUR2::kanMX, pAG-LAG1-1 or pAG-LAF1-1, was linearized with HpaI (New England Biolabs, cat.# R0105S) according to the manufacturers' instructions. The DNA was purified using a standard phenol:chloroform extraction and ethanol precipitation protocol. Up to 20 µg of the purified DNA was added to a 200 µl aliquot of the mycelium suspension, not exceeding 10% of the volume, dispensed into a chilled 2 mm electroporation cuvette and pulsed with a Gene Pulser (Bio-Rad, Munich, Germany) set at 1.5 kV/cm, 100Ω, and 25 µF. After electroporation, the mycelium was removed from the electroporation cuvette with a pipette and transferred into 10 ml of liquid complex medium as described above and incubated in a 100 ml shaking flask without baffles for 4-6 h at 30° C. and 200 rounds per minute to allow regeneration of the cells. To apply selection pressure, 10 ml of top agar (1 g/l yeast extract, 10 g/l peptone, 10 g/l glucose and 0.3 g/l myo-inositol with 1% agarose (w/v) plus 750 µg/ml Geneticin G418 and/or 750 µg/ml Hygromycin B) was subsequently added to the regenerated cells, mixed and poured onto non-selective complex medium agar plates (1 g/l yeast extract, 10 g/l peptone, 10 g/l glucose, 0.3 g/l myo-inosit and 20 g/l agar-agar). Transformants were obtained after 2-3 days incubation at 30° C. Clonal purification of Ashbya gossypii transformants was carried out by the selection of Geneticin- and/or Hygromycin-resistant spores. To that end, transformants were streaked out on sporulation plates (10 g/l yeast extract, 10 g/l glucose and 20 g/l agar-agar) and incubated for 5 days at 30° C. Subsequently, a full loop of fungal mycelium was resuspended in 1 ml of 0.9% (w/v) NaCl containing 10 mg/ml Lysing Enzymes from Trichoderma harzianum (Sigma-Aldrich, Taufkirchen, Germany) and incubated for 1 h at room temperature. Released pores and cell debris sedimented by centrifugation (30 s, 13,200 rpm) and washed twice with 1 ml of 0.9% NaCl solution and finally extracted with an equal volume of paraffin to enrich the spores by thorough mixing of the two phases in a mixer mill (Retsch, Hahn, Germany) by shaking for 30 s at 30 Hz. Phases were separated by centrifugation (30 s, 800 rpm). A dilution series of the paraffin phase in 0.9 (w/v) NaCl was plated onto selective medium 800 30 (1 g/l yeast extract, 10 g/l peptone, 10 g/l glucose, 0.3 g/l myo-inosit and 20 g/l agar-agar containing 750 µg/ml Geneticin and/or 750 µg/ml Hygromycin) and incubated for 2-3 days at 30° C. Arising colonies were selected and cultivated for quantification and characterization of sphingoid bases by reversed phase HPLC as described in Example 3.

Example 2

Construction of a Ashbya gossypii SYR28DES Double Mutant Simultaneously Overproducing the Ashbya gossypii Enzymes Laf1p and Des1p The plasmid pSSTH-LAF1-2 was designed to replace the Ashbya gossypii SYR2 gene by the kanMX resistance gene, thereby inactivating the Ashbya gossypii SYR2 gene and to simultaneously overexpress the Ashbya gossypii DES1 and LAF1 genes. The Ashbya gossypii SYR2, DES1 and LAF1 coding sequences as well as the sequence of the promoter of the Ashbya gossypii enolase-encoding gene were obtained as described in Example 1. The following oligonucleotides were synthesized by MWG Biotech (Ebersberg, Germany) to amplify the coding sequence of DES1 from Ashbya gossypii ATCC19895:

```
AgDES1-DS-fw:
ATG AAC CAA CGG GGT ATA GCG AC (nt 905-927 in SEQ
ID NO: 22)

AgDES1-rv-SalI:
TAT ATA GTC GAC GAG TTT TGA CTC CTT CTG TCT C (nt
2246-2267 in SEQ ID NO: 22; including a SalI
recognition site)
```

The oligonucleotides were used to set up a colony PCR reaction using Ashbya gossypii ATCC19895 cells as template and according to Innis et al., (PCR protocols. A guide to methods and applications, 1990, Academic Press) with Phusion™ High Fidelity PCR Master Mix (Finnzymes, cat.# F-531 L) according to the instructions of the manufacturer. A 1372 bp fragment could be obtained by applying this method. The fragment was purified using the MinElute Gel Extraction Kit (QIAGEN, cat.#28606) according to the instructions of the manufacturer. The following oligonucleotides were synthesized to amplify the promoter of the Ashbya gossypii enolase-encoding gene:

```
AgPENO-fw-XbaI:
TAT ATA TCT AGA CTG TTC ACA GCC TTC TGA GAC (nt
1-21 in SEQ ID NO: 25; including a XbaI
recognition site)

AgPENO-OEPCR-rv:
GTC GCT ATA CCC CGT TGG TTC ATT TTG AAT TAT TTG
AGT TTC GGA GGT GTT AAT C (nt 436-467 in SEQ ID
NO: 25 and nt 905-927 in SEQ ID NO: 22)
```

The oligonucleotides were used to set up a colony PCR reaction with Phusion™ High Fidelity PCR Master Mix and using Ashbya gossypii ATCC19895 cells as template. A 496 bp fragment could be obtained by applying this method. The fragment was purified using the MinElute Gel Extraction Kit. The oligonucleotides AgPENO-fw-XbaI and AgDES1-rv-SalI as well as 1 µl of the previously amplified and purified PCR products representing the promoter of the Ashbya gossypii enolase-encoding gene and the Ashbya gossypii DES1 coding sequence were used to set up a crossover PCR with Phusion™ High Fidelity PCR Master Mix. A 1846 bp fragment could be obtained by applying this method. The fragment was purified using the MinElute Gel Extraction Kit. It was then digested for 2 hours with SaiI (New England Biolabs, cat.# R0138S) and XbaI (New England Biolabs, cat.# R0145S), and ligated with SalI and XbaI cut vector pUG6-AgSUR2::kanMX (see Example 1) as described in the manufacturers' protocol. 2.5 µl of the ligation product was used to transform chemically competent E. coli (Invitrogen One Shot® TOP10, cat.# C4040-03) according to the manufacturers' instructions. The plasmid pSSTH (7323 bp) was obtained herewith. The authenticity of the DNA sequence the cloned fragments representing the Ashbya gossypii enolase-encoding gene and the Ashbya gossypii DES1 coding sequence sequence was confirmed by DNA sequencing done by Sequiserve (Vaterstetten, GERMANY). The following oligonucleotides were subsequently synthesized to amplify the *Ashbya gossypii* LAF1 coding sequence:

```
AgLAG1-fw:
ATG TCG GGC CAA GTC AGG C (nt 1-19 in SEQ ID NO:
13)

AgLAG1-PacI-rv:
TAT ATA TTA ATT AAC TGC ATG CGC TGT CTG GCG (nt
291-1309 in SEQ ID NO: 13; including a PacI
recognition site)
```

The oligonucleotides were used to set up a colony PCR reaction with Phusion™ High Fidelity PCR Master Mix and using *Ashbya gossypii* ATCC19895 cells as template. A 1118 bp fragment could be obtained by applying this method. The fragment was purified using the MinElute Gel Extraction Kit. The following oligonucleotides were synthesized to amplify the promoter of the *Ashbya gossypii* enolase-encoding gene:

```
P-ENO-PacI-fw:
TAT ATA TTA ATT AAC TGT TCA CAG CCT TCT GAG AC (nt
1-21 in SEQ ID NO: 25; including a PacI
recognition site)

P-ENO-CO-LAG1-rv:
CCT GAC TTG GCC CGA CAT TTT GAA TTA TTT GAG TTT
CGG AGG TGT TAA TC (nt 436-467 in SEQ ID NO: 25
and nt 1-18 in SEQ ID NO: 13)
```

Figure 5:
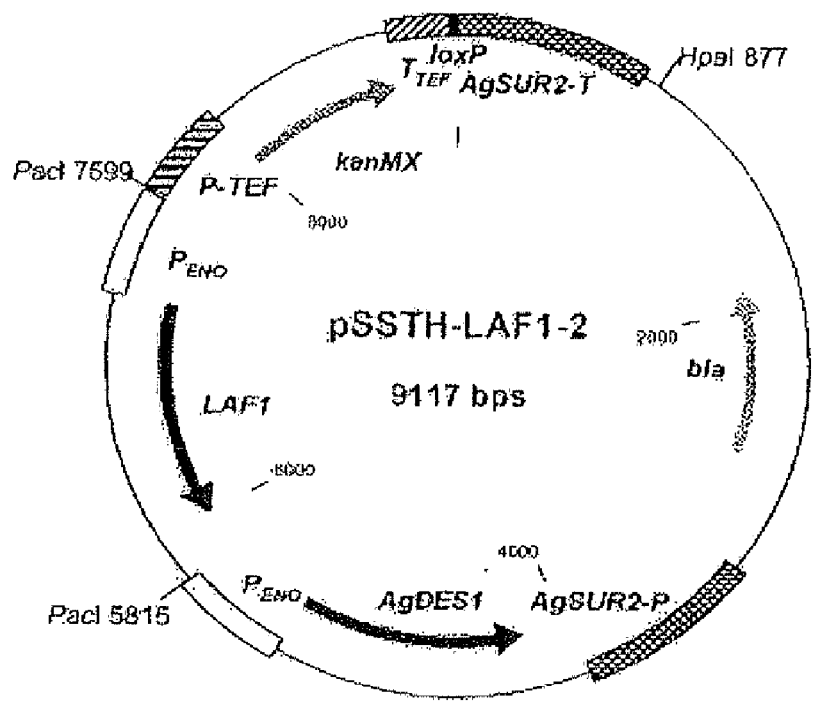
FIG. 5 shows a graphical representation of the plasmid pSSTH-LAF1-2 for targeted replacement of *Ashbya gossypii* SYR2 and overexpression of *Ashbya gossypii* DES1 and LAF1 under control of the *Ashbya gossypii* ENO promotor, respectively. The *Ashbya gossypii* TEF promoter (horizontally hatched), the *Ashbya gossypii* TEF terminator (diagonally hatched), the kanMX resistance gene (dark grey), the promotor region (AgSUR2-P) and terminator region (AgSUR2-T) of *Ashbya gossypii* SYR2 (gridded), the *Ashbya gossypii* DES1 (black), the *Ashbya gossypii* LAF1 (black) and the ampicillin resistance gene (bla; light grey) are shown. Restriction sites relevant for the cloning procedures and transformation are also indicated.

The oligonucleotides were used to set up a colony PCR reaction with Phusion™ High Fidelity PCR Master Mix and using *Ashbya gossypii* ATCC19895 cells as template. A 475 bp fragment could be obtained by applying this method. The fragment was purified using the MinElute Gel Extraction Kit. The oligonucleotides P-ENO-PacI-fw and AgLAG1-PacI-rv as well as 1 µl of the previously amplified and purified PCR products representing the promoter of the *Ashbya gossypii* enolase-encoding gene and the *Ashbya gossypii* LAF1 coding sequence were used to set up a crossover PCR with Phusion™ High Fidelity PCR Master Mix. A 1593 bp fragment could be obtained by applying this method. The fragment was purified using the MinElute Gel Extraction Kit. It was then digested for 2 hours with PacI (New England Biolabs, cat.# R0547S), and ligated with PacI cut and dephosphorylated (New England Biolabs, alkaline phosphatase, calf intestinal, cat.# M0290S) vector pSSTH as described above, resulting in plasmid pSSTH-LAF1-2 (9117 bp) shown in FIG. 5. This plasmid is suitable to replace *Ashbya gossypii* SYR2 by kanMX, thereby inactivating *Ashbya gossypii* SYR2, and simultaneously overexpressing *Ashbya gossypii* DES1 and LAF1 after being transformed into *Ashbya gossypii*. The authenticity of the DNA sequence the cloned fragments representing the *Ashbya gossypii* enolase-encoding gene and the *Ashbya gossypii* LAF1 coding sequence was confirmed by DNA sequencing done by Sequiserve (Vaterstetten, GERMANY).

The plasmid pAG32-D8D was designed to disrupt the *Ashbya gossypii* 8DES gene. The 8DES coding sequence was obtained by performing a BLASTP search using the functionally characterized delta(8)-sphingolipid desaturase of *Kluyveromyces lactis* (Takakuwa et al., 2002; EMBL accession number AB085690) as template against the Ashbya Genome Database, available online at the Duke University website, resulting in a significant match to the *Ashbya gossypii* gene AFL079W (Genbank accession # AAS53293; located on chromosome VI at position 290134-291750 bp) with a score of 616 bits (56% and 69% positional amino acid identity and similarity, respectively). The following oligonucleotides were synthesized to amplify an internal region of the 8DES coding sequence:

```
AgD8D-HindIII-fw:
TAT ATA AAG CTT GCG CTG GAA GAT TGG GCA TGT G (nt
204-225 in SEQ ID NO: 20; including a HindIII
recognition site)

AgD8D-BamHI-rv:
TAT ATA GGA TCC GAG TCC AGC TTA ACA CGT AGA G (nt
1000-1021 in SEQ ID NO: 20; including a BamHI
recognition site)
```

Figure 6:
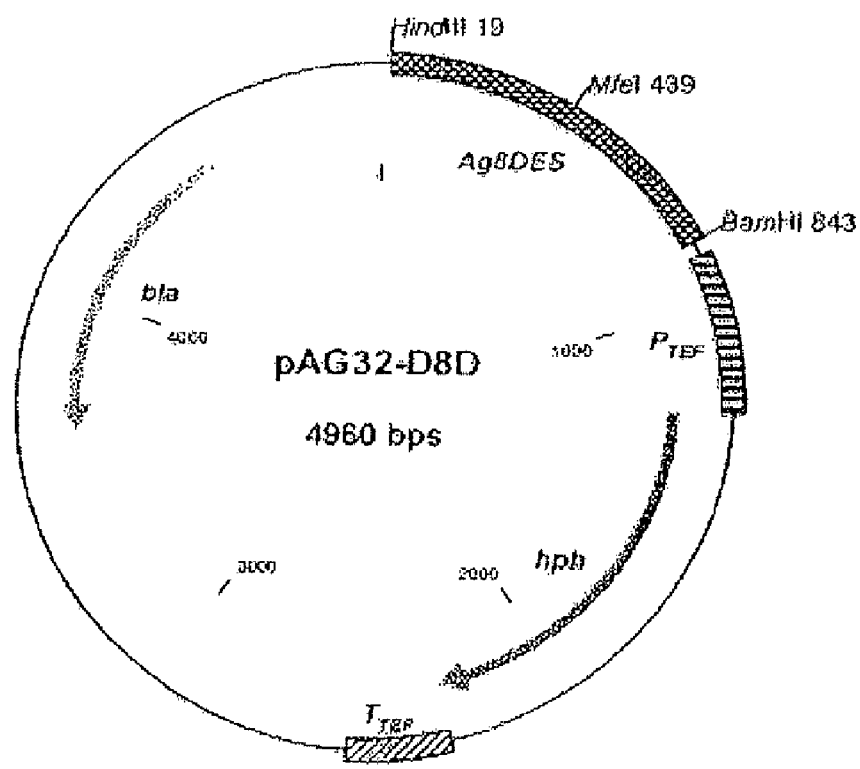
FIG. 6 shows a graphical representation of the plasmid pAG32-D8D for targeted disruption of *Ashbya gossypii* 6DES. The *Ashbya gossypii* TEF promoter (horizontally hatched), the *Ashbya gossypii* TEF terminator (diagonally hatched), the hygromycin resistance gene (dark grey) and the ampicillin resistance gene (bla; light grey) are shown. Restriction sites relevant for the cloning procedures and transformation are also indicated.

The oligonucleotides were used to set up a colony PCR reaction with Phusion™ High Fidelity PCR Master Mix and using *Ashbya gossypii* ATCC19895 cells as template. A 824 bp fragment could be obtained by applying this method. The fragment was purified using the MinElute Gel Extraction Kit. It was then digested for 2 hours with BamHI (New England Biolabs, cat.# R0136S) and HindIII (New England Biolabs, cat.# R0104S), and BamHI and HindIII cut vector pAG32 (EUROSCARF, Oberursel, GERMANY) as described above, resulting in plasmid pAG32-08D (4960 bp) shown in FIG. 6. This plasmid is suitable for disruption of the *Ashbya gossypii* 8DES gene after being transformed into *Ashbya gossypii*. The authenticity of the DNA sequence of the cloned internal *Ashbya gossypii* 8DES sequence was confirmed by DNA sequencing done by Sequiserve (Vaterstetten, GERMANY).

Transformation of *Ashbya gossypii* was performed as described in Example 1. The plasmid pSSTH-LAF1-2 was linearized with HpaI (New England Biolabs, cat.# R0105S), the plasmid pAG32-D8D was linearized with MfeI (New England Biolabs, cat.# R0589S) and purified analogously to Example 1.

Example 3

Quantification and Characterization of Sphingoid Bases by Reversed Phase HPLC in *Ashbya gossypii* Strains For HPLC analysis, mycelium of *Ashbya gossypii* mutant strains grown on YEPD plates containing appropriate antibiotics was homogenized as described in Example 1, inoculated in 20 ml YEPD medium (peptone 2% (w/v), yeast extract 1% (w/v) and glucose 2% (w/v) in 100 ml Erlenmeyer flasks with baffles and grown at 30° C. and 250 rpm for 3 days. At that time cells were in stationary phase. 1 ml of mycelium suspension was transferred into a 1.5 ml reaction tube, centrifuged for 1 min at 13200 rpm and the liquid medium removed with a pipette. The sample was filled up to 1.5 ml with 1 M HCl and incubated for 16 h at 80° C. The sample was mixed briefly and 500 µl of the suspension transferred to a new 1.5 ml reaction tube. 1 ml chloroform:methanol (2:1) (v/v) was added and the lipids extracted with a mixer mill (Retsch, Hahn, Germany) by shaking for 30 min at 30 Hz. The sample was centrifuged for 5 min at 13200 rpm and 500 µl of the lower chloroform phase transferred to a new 1.5 ml reaction tube. The solvent was evaporated by vacuum centrifugation (Christ Vakuumzentrifuge, Christ AG, Osterode) for 20 min at 60° C., the pellet resuspended in an appropriate volume of 2-propanol:H$_2$O (1:1) (v/v) and dissolved for 10 min in an ultra sonic water bath at 40° C.

For determination of mycelial dry weight, samples were taken from the liquid cultures and filtered through paper filters as described in Example 1. The collected mycelium was dried overnight at 110° C. and weighed.

Sphingoid base concentrations were determined using reverse phase high pressure liquid chromatography (RP-HPLC). Quantification was performed by calibration with commercially available reference substances in case of C18 phytosphingosine, C18 sphinganine and C18 sphingosine. In case of C18 sphingadiene a reference substances is not commercially available. Therefore, the concentration of C18 sphingadiene was determined using C18 sphingosine as calibrant.

| RP-HPLC details: | |
|---|---|
| Instrument | Jasco; pump PU-2080, autosampler AS-2055, fluorescence detector FP-2020 |
| Column | Kromasil C18, 250 mm × 4.6 mm |

| RP-HPLC conditions: | |
|---|---|
| Flow | 2.00 ml per min |
| Sample volume | 10 µl |
| Pre-column derivatization | 2 min with an equal volume of o-phtaldialdehyde (OPA) |
| Injection volume | 10 µl |
| Column temperature | 40° C. |
| Tray temperature | ambient temperature |
| Mobile phase | methanol:water (92:8) (w/v) |
| Run time | 8 min |
| Detection method | fluorescence |
| Excitation wavelength | 340 nm |
| Emission wavelength | 455 nm |

| Retention times: | |
|---|---|
| C18 phytosphingosine | 4.00 min |
| C18 sphingadiene | 4.40 min |
| C18 sphingosine | 5.50 min |
| C18 sphinganine | 7.00 min |

The results of these analyses are shown in FIG. 19. While the *Ashbya gossypii* wildtype strain produced only negligible amounts of sphingosine, all strains overexpressing DES1 and lacking a functional SYR2 gene produced 0.5 mg sphingosine per g cellular dry weight. Additional overexpression of LAF1 alone or in combination with insertional inactivation of 8DES resulted in a drastic decrease in formation of the unwanted side products sphinganine and sphingadienine.

Example 4

Isolation of Genomic DNA from *Pichia ciferrii* F-60-10A NRRL 1031

*Pichia ciferrii* F-60-10A NRRL 1031 was grown in 50 ml YEPD medium (peptone 2% (w/v), yeast extract 1% (w/v) and glucose 2% (w/v) in 250 ml Erlenmeyer flasks at 200 rpm and 30° C. and harvested after 18 h at an $OD_{600}$ of 1.5. Chromosomal DNA was isolated using the PUREGENE® DNA Purification Kit for Yeast and Gram-positive bacteria (Gentra Systems Inc., cat.# D-6000A) according to the instructions of the manufacturer. A quality check of the isolated DNA by agarose gel electrophoresis demonstrated its high molecular weight (>16 kbp).

Example 6

Cloning and Determination of the Nucleotide Sequence of the *Pichia ciferrii* LAG1 Gene Amplification of an Internal Part of the *Pichia ciferrii* LAG1 Gene First, the amino acid sequences of putative ceramide synthases from *Saccharomycotina* species were extracted from NCBI's database of completed and unfinished eukaryotic genomes, available online at the website for the National Center for Biotechnology Information (NCBI) by performing a TBLASTN search with the *Ashbya gossypii* Lag1p (GenBank acc.# NP_982955) as template. This protein is very similar to the characterized S. cerevisiae Lac1p and Lag1p proteins (65% and 69% positional amino acid identity, respectively) (Schorling et al., 2001; Guillas et al., 2003) and therefore is very likely to have ceramide synthase activity. The extracted sequences (all entries with E-values <2× $10^{-123}$) were aligned using the ClustalW program, see the UK website for the European Bioinformatics Institute (EBI). Suitable oligonucleotides for amplification of an internal part of the *Pichia ciferrii* LAG1 gene were derived by back-translating highly conserved stretches of amino acids within the Lag1p sequence taking into account the highly biased *Pichia ciferrii* codon usage. The following oligonucleotides were then synthesized by MWG Biotech (Ebersberg, Germany):

```
LAC1-deg-fw:
TTY GTY GGT TTY TAY GCW ATH TTY TTY ACW TTY TTR
MGW GAA TT (nt 1636-1679 in SEQ ID NO: 1)

LAC1-deg-rv:
GGT TGW SWD ATC CAA CAT TTR TAT TGT TGW GT (nt
2297-2266 in SEQ ID NO: 1)
```

These oligonucleotides were used to set up a PCR reaction according to Innis et al., (PCR protocols. A guide to methods and applications, 1990, Academic Press) with Phusion™ High Fidelity PCR Master Mix (Finnzymes, cat# F-531L) according to the instructions of the manufacturer. A 662 bp fragment could be obtained by applying this method. The fragment was purified using the QIAquick Gel Extraction Kit (Qiagen, cat.#28706) according to the instructions of the manufacturer.

Figure 7A:
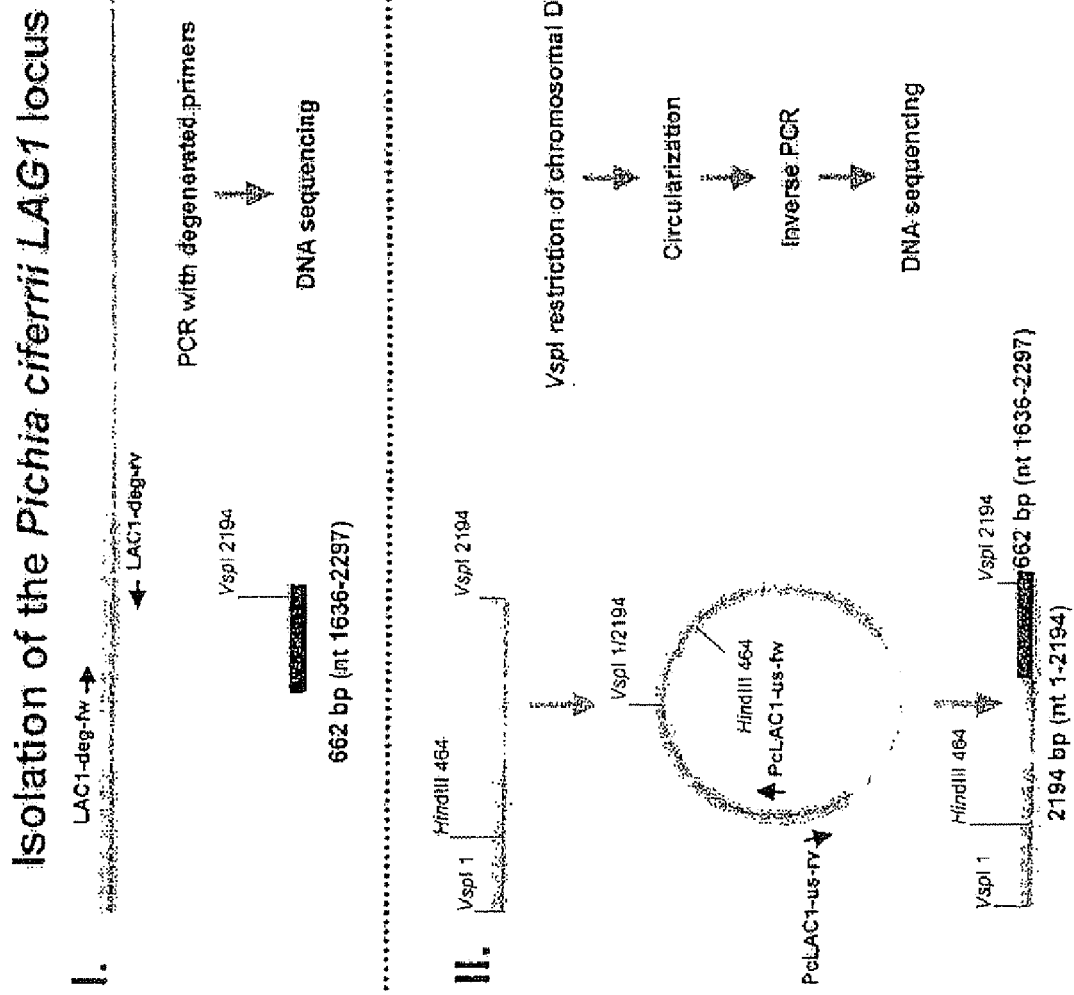
FIG. 7 schematically describes the three-step procedure resulting in the isolation of the entire *Pichia ciferrii* LAG1 locus.

Determination of the DNA Sequence of an Internal Part of the *Pichia ciferrii* LAG1 Gene The DNA sequence of the purified PCR product was determined using the dideoxy chain termination method developed by Sanger et al. (Proceedings of the National Academy of Sciences, U.S.A., 74:5463-5467). As sequencing primers those used for PCR amplification were used. DNA sequencing was performed by Sequiserve (Vaterstetten, Germany). The generated sequence information (662 bp, corresponding to nt 1636-2297 in SEQ ID NO: 1; FIG. 7A) was translated into protein using the Clone Manager 7 software (Scientific & Educational Software) and the resulting amino acid sequence used as template for a BLASTP search with NCBI's non-redundant protein database, available online at the NCBI database (BLAST), The search resulted in the identification of a *Kluyveromyces lactis* protein (NCBI acc.# XP_452132) highly similar to *Saccharomyces cerevisiae* Lac1p, a ceramide desaturase subunit, as being the protein in the database most similar to the new sequence, confirming that in fact portions of the *Pichia ciferrii* LAG1 ortholog had been amplified.

Amplification of the Entire *Pichia ciferrii* LAG1 Gene and Determination of its DNA Sequence In order to determine the DNA sequence of the entire *Pichia ciferrii* LAG1 gene (coding sequence, promoter region and 3'-untranslated region) an inverse PCR approach was followed. Chromosomal DNA (300 ng) from *Pichia ciferrii* F-60-10A NRRL 1031 (isolated as described in Example 4) was digested overnight with VspI (MBI Fermentas, cat.# ER0911) according to the instructions of the manufacturer in a total volume of 50 μl. The digested DNA was purified using the QIAquick PCR Purification Kit (Qiagen, cat.#28106) according to the instructions of the manufacturer. The eluted DNA (50 μl) was subjected to overnight ligation using the T4 DNA Ligase (New England Biolabs, cat.# M0202L) according to the instructions of the manufacturer in a total is volume of 200 μl with 800 U of T4 DNA Ligase. The ligated DNA was purified using the QIAquick PCR Purification Kit according to the instructions of the manufacturer. 2.5 μl of the eluate was used as template for a inverse PCR reaction according to Innis et al., (PCR protocols. A guide to methods and applications, 1990, Academic Press). For this two oligonucleotides targeted on the already known portion of the *Pichia ciferrii* LAG1 gene were applied:

```
PcLAC1-us-fw:
CCT TCT AAA ATC AAG AGA TTT ATG GAA CAA TC (nt
1732-1763 in SEQ ID NO: 1)

PcLAC1-us-rv:
CCA ACA ATT GGT GCA AGG GGA C (nt 1721-1700 in SEQ
ID NO: 1)
```

Amplification was performed with Phusion™ High Fidelity PCR Master Mix according to the instructions of the manufacturer. Using this procedure a 2.2 kbp PCR product could be obtained. The fragment was purified using the Min Elute PCR Purification Kit (Qiagen, cat.#28006) according to the instructions of the manufacturer. The DNA sequence of this fragment was determined as described previously, using oligonucleotides PcLAC1-us-fw, PcLAC1-us-rv,

```
DBöPcLAC1-us-rv2:
                (nt 1032-1013 in SEQ ID NO: 1)
TTA GAC AGA AGC TCA ACA GG,

DBö-PcLAC1intfw:
                (nt 1240-1259 in SEQ ID NO: 1)
TTC AGC TGG TTA TTT GTC TC
and DBö-PcLAC1intrv:
                 (nt 94-77 in SEQ ID NO: 1)
TAA CCC AGA ATC AAG GTC
``` as sequencing primers. The newly obtained sequence information covered nt 1-1635 in SEQ ID NO: 1. No new sequence information downstream of the DNA sequence could be obtained as the 3' VspI site is located immediately downstream of this portion (FIG. 7A). In order to obtain the DNA sequence of the 3'-end of the coding region of the *Pichia ciferrii* LAG1 gene and its 3'-untranslated region another round of inverse PCR had to be performed. Therefore, the above described experimental protocol was repeated, except that HindIII (New England Biolabs, cat.# R0104S) was used for digesting *Pichia ciferrii* chromosomal DNA and the following oligonucleotides, synthesized by MWG Biotech (Ebersberg, Germany), were employed during inverse PCR:

```
PcLAC1-ds-fw:
                (nt 2241-2272 in SEQ ID NO: 1)
GGG AGA TTT TAA ATT AAA TTT TGC AAC TCA AC

PcLAC1-ds-rv:
                (nt 2239-2213 in SEQ ID NO: 1)
CTG TTC TAA ATT CTG TTA AAA CTG ACC
```

Figure 7B:
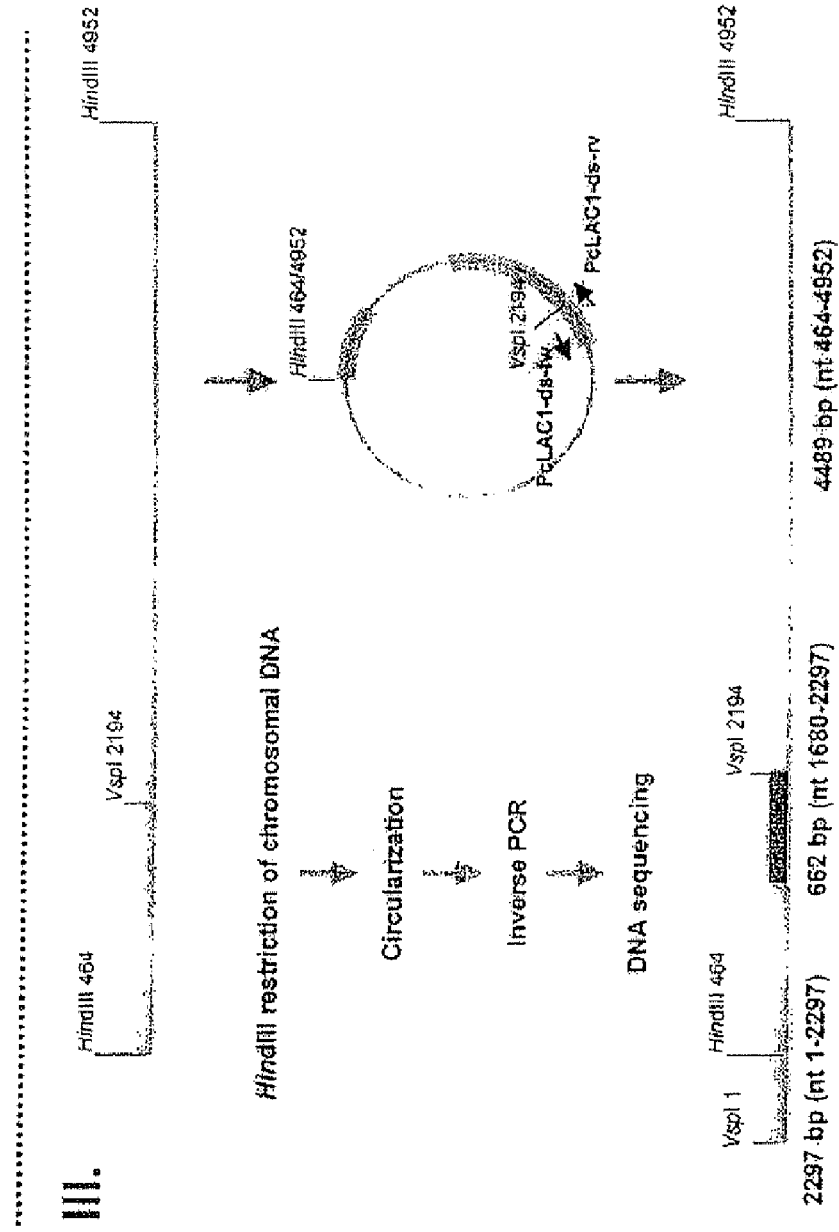

Using this procedure a 4.5 kbp PCR product could be obtained. The fragment was purified using the Min Elute PCR Purification Kit according to the instructions of the manufacturer. The DNA sequence of this fragment was determined as described previously with the oligonucleotides PcLAC1-ds-fw; PcLAC1-ds-rv;

```
DBö-PcLAC1dsfw2:
            (nt 3152-3171 in SEQ ID NO: 1)
AAA TCA GGT TTA ACA ATG GC DBö-PcLAC1dsfw3:
            (nt 4060-4079 in SEQ ID NO: 1)
AGT TGA TAA ATG ACG AAT GG
and DBö-PcLAC1dsrv2:
            (nt 1343-1323 in SEQ ID NO: 1)
GAA CGT ACT CTT GTA TCA CCC
``` as sequencing primers. 2655 bp of new sequence information (nt 2298-4952 in SEQ ID NO: 1) could be obtained which stretches to the next HindIII restriction site downstream of the 3' VspI site (FIG. 7B). Using the described three-step procedure, a total of 4952 bp of the *Pichia ciferrii* LAG1 locus could be isolated and its DNA sequence be determined (see SEQ ID NO: 1 and FIG. 7).

Figure 7C:
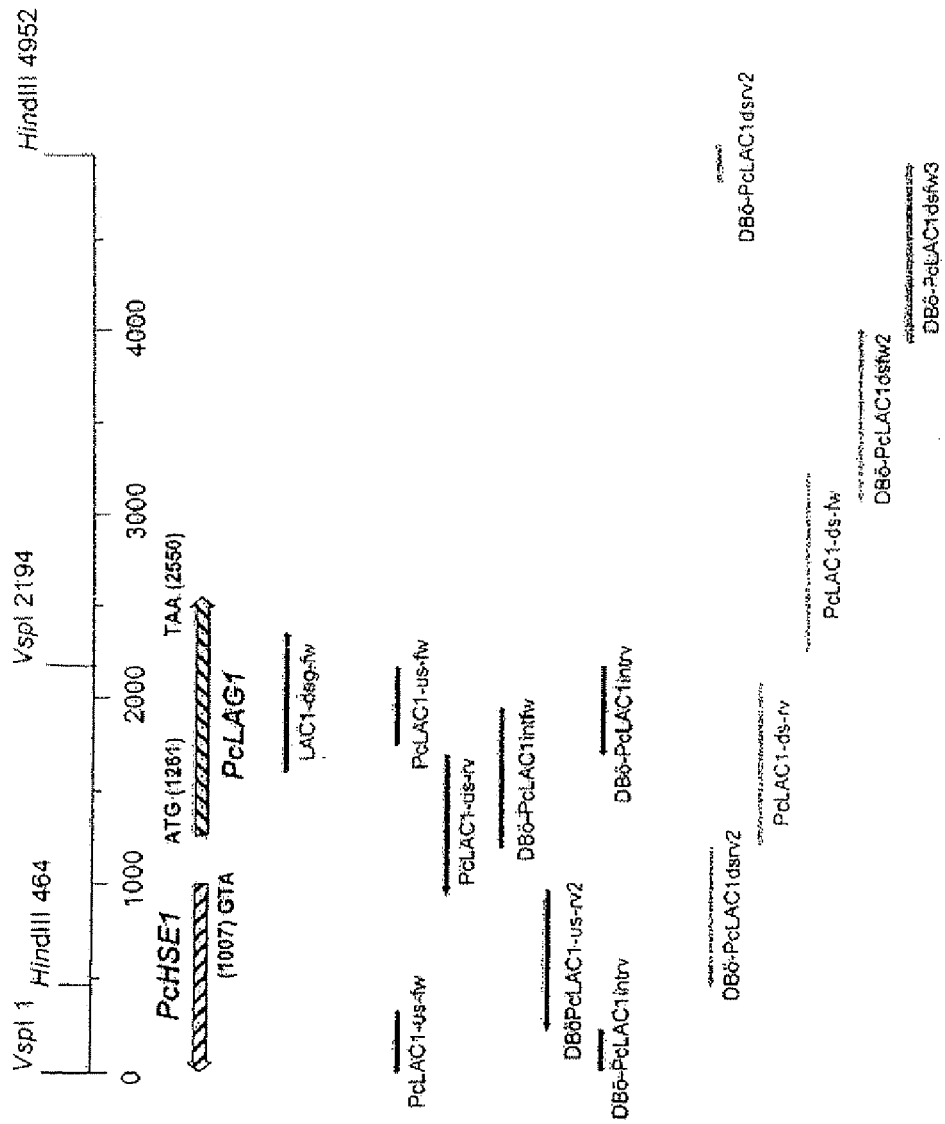

The *Pichia ciferrii* LAG1 locus as depicted in FIG. 7C encodes the *Pichia ciferrii* Lag1p protein of 429 amino acids in length (SEQ ID NO: 2). *Pichia ciferrii* Lag1p has 64% (80%) and 62% (75%) positional amino acid identity (similarity) to predicted ceramide synthases from *Kluyveromyces lactis* (GenBank acc.# XP_452132) and *Saccharomyces cerevisiae* (GenBank acc.# NC_001143), respectively. The Lac1p protein from *Saccharomyces cerevisiae* has been characterized biochemically and been shown to display ceramide synthase activity in vivo (Schorling et al., Molecular Biology of the Cell, 12: 3417-3427).

Example 6

Cloning and Determination of the Nucleotide Sequence of the *Pichia ciferrii* LAF1 Gene Amplification of an internal part of the *Pichia ciferrii* SSN8 gene As amplification of an internal portion of the *Pichia ciferrii* LAF1 gene (The gene name was chosen in analogy to the gene names LAC1 and LAG1 encoding two ceramidase synthase subunits in *Saccharomyces cerevisiae*. They are the result of a duplication of the LAG1 gene also present in all other yeasts, including *Pichia ciferrii*. The second ceramidase synthase subunit in other yeasts, including *Pichia ciferrii* is an paralogue rather than an orthologue of LAC1 and LAG1 apparently absent in *Saccharomyces cerevisiae*. Therefore, the designation LAF1 was chosen.) with degenerate oligonucleotides derived from a multiple sequence alignment of Laf1p proteins from various *Saccharomycotina* failed, we made use of the fact, that in most *Saccharomycotina* species the SSN8 gene encoding cyclin C is located upstream of the LAF1 gene. First, the amino acid sequences of cyclin C from *Saccharomycotina* species were extracted from NCBI's database of completed and unfinished eukaryotic genomes, available online at the NCBI database by performing a TBLASTN search with the *Ashbya gossypii* Ssn8p (GenBank acc.# AAS51713) as template. The extracted sequences (all entries with E-values <2×10$^{-52}$) were aligned using the ClustalW program, see the UK website for the European Bioinformatics Institute (EBI) Suitable oligonucleotides for amplification of an internal part of the *Pichia ciferrii* SSN8 gene were derived by back-translating highly conserved stretches of amino acids within the Ssn8p sequence taking into account the highly biased *Pichia ciferrii* codon usage. The following oligonucleotides were then synthesized by MWG Biotech (Ebersberg, Germany):

```
PcSSN8-deg-fw3:
                    (nt 1-24 in SEQ ID NO: 3)
GAA GAA TGT CCW CAA CAT ATH MGW PcSSN8-deg-rv2:
                  (nt 628-608 in SEQ ID NO: 3)
YAA YAA CTG YAA ATC WGT DAT
```

These oligonucleotides were used to set up a PCR reaction according to Innis et al., (PCR protocols. A guide to methods and applications, 1990, Academic Press) with Phusion™ High Fidelity PCR Master Mix (Finnzymes, cat.# F-531 L) according to the instructions of the manufacturer. A 393 bp fragment could be obtained by applying this method. The fragment was purified using the MinElute Gel Extraktion Kit (Qiagen, cat.#28606) according to the instructions of the manufacturer.

Figure 8A:
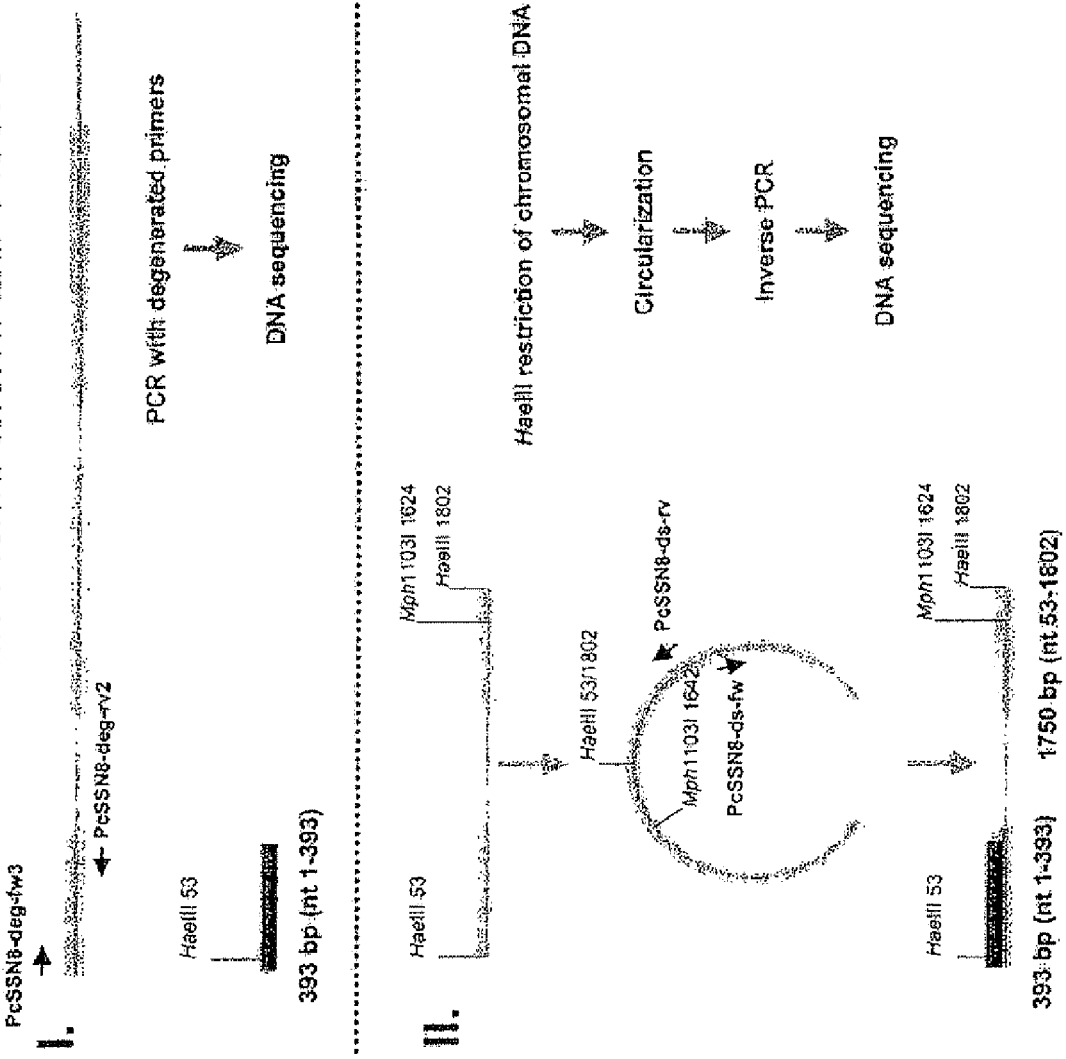

Determination of the DNA Sequence of an Internal Part of the *Pichia ciferrii* SSN8 Gene The DNA sequence of the purified PCR product was determined using the dideoxy chain termination method developed by Sanger et al. (Proceedings of the National Academy of Sciences, U.S.A., 74:5463-5467). As sequencing primers those used for PCR amplification were used. DNA sequencing was performed by Sequiserve (Vaterstetten, Germany). The generated sequence information (339 bp, corresponding to nt 1-339 in SEQ ID NO: 3; FIG. 8A) was translated into protein using the Clone Manager 7 software (Scientific & Educational Software) and the resulting amino acid sequence used as template for a BLASTP search with NCBI's non-redundant protein database, available online at the NCBI database (BLAST), The search resulted in the identification of *Candida albicans* Ssn8p (NCBI acc.# EAK97601), as being the protein in the database most similar to the new sequence, confirming that in fact portions of the *Pichia ciferrii* SSN8 ortholog had been amplified.

Amplification of the *Pichia ciferrii* LAF1 Gene and Determination of its DNA Sequence In order to determine the DNA sequence of the *Pichia ciferrii* LAF1 gene (coding sequence, promoter region and 3'-untranslated region), which should in case of conserved organization be located downstream of the SSN8 gene, an inverse PCR approach was followed. Chromosomal DNA (300 ng) from *Pichia ciferrii* F-60-10A NRRL 1031 (isolated as described in Example 4) was digested overnight with HaeII (New England Biolabs, cat.#R0108S) according to the instructions of the manufacturer in a total volume of 50 The digested DNA was purified using the QIAquick PCR Purification Kit (Qiagen, cat.#28106) according to the instructions of the manufacturer. The eluted DNA (50 µl) was subjected to overnight ligation using the T4 DNA Ligase (New England Biolabs, cat.# M0202L) according to the instructions of the manufacturer in a total volume of 200 µl with 800 U of T4 DNA Ligase. The ligated DNA was purified using the QIAquick PCR Purification Kit according to the instructions of the manufacturer. 2.5 µl of the eluate was used as template for a inverse PCR reaction according to Innis et al., (PCR protocols. A guide to methods and applications, 1990, Academic Press). For this two oligonucleotides targeted on the already known portion of the *Pichia ciferrii* SSN8 gene were applied:

```
PcSSN8-ds-fw:
                (nt 293-319 in SEQ ID NO: 3)
GCT GGT CAA TTA TAA ATG ATA GTT ATG

PcSSN8-ds-rv:
                (nt 240-211 in SEQ ID NO: 3)
GTT ATT GCT ATT ATT ATT ATG ATT ATG ACC
```

Amplification was performed with Phusion™ High Fidelity PCR Master Mix according to the instructions of the manufacturer. Using this procedure a 1.8 kbp PCR product could be obtained. The fragment was purified using the MinElute Gel Extraktion Kit (Qiagen, cat#28606) according to the instructions of the manufacturer. The DNA sequence of this fragment was determined as described previously, using oligonucleotides PcSSN8-ds-fw and PcSSN8-ds-rv as sequencing primers. The newly obtained sequence information covered nt 340-1800 in SEQ ID NO: 3. The LAF1 gene could not be amplified completely as the 3' HaeIII site is located within the LAF1 gene (FIG. 8A). In order to obtain the DNA sequence of the 3'-end of the coding region of the *Pichia ciferrii* LAF1 gene and its 3'-untranslated region another round of inverse PCR had to be performed. Therefore, the above described experimental protocol was repeated, except that Mph11031 (MBI Fermentas, cat.# ER0731) was used for digesting *Pichia ciferrii* chromosomal DNA and the following oligonucleotides, synthesized by MWG Biotech (Ebersberg, Germany), were employed during inverse PCR:

```
PcLAG1-ds-fw:
                (nt 1738-1766 in SEQ ID NO: 3)
GTT GGA TCT TGG TTA TAT TAT CAT TCA TC

PcLAG1-ds-rv:
                (nt 1700-1670 in SEQ ID NO: 3)
TGT TCC ATA AAT CTT TGT TTA TCC TTT TGT G
```

Using this procedure a 2.5 kbp PCR product could be obtained. The fragment was purified using the Min Elute PCR Purification Kit according to the instructions of the manufacturer. The DNA sequence of this fragment was determined as described in Example 5 with the oligonucleotides PcLAg1-ds-fW, PcLAg1-ds-rv and

Figure 8B:
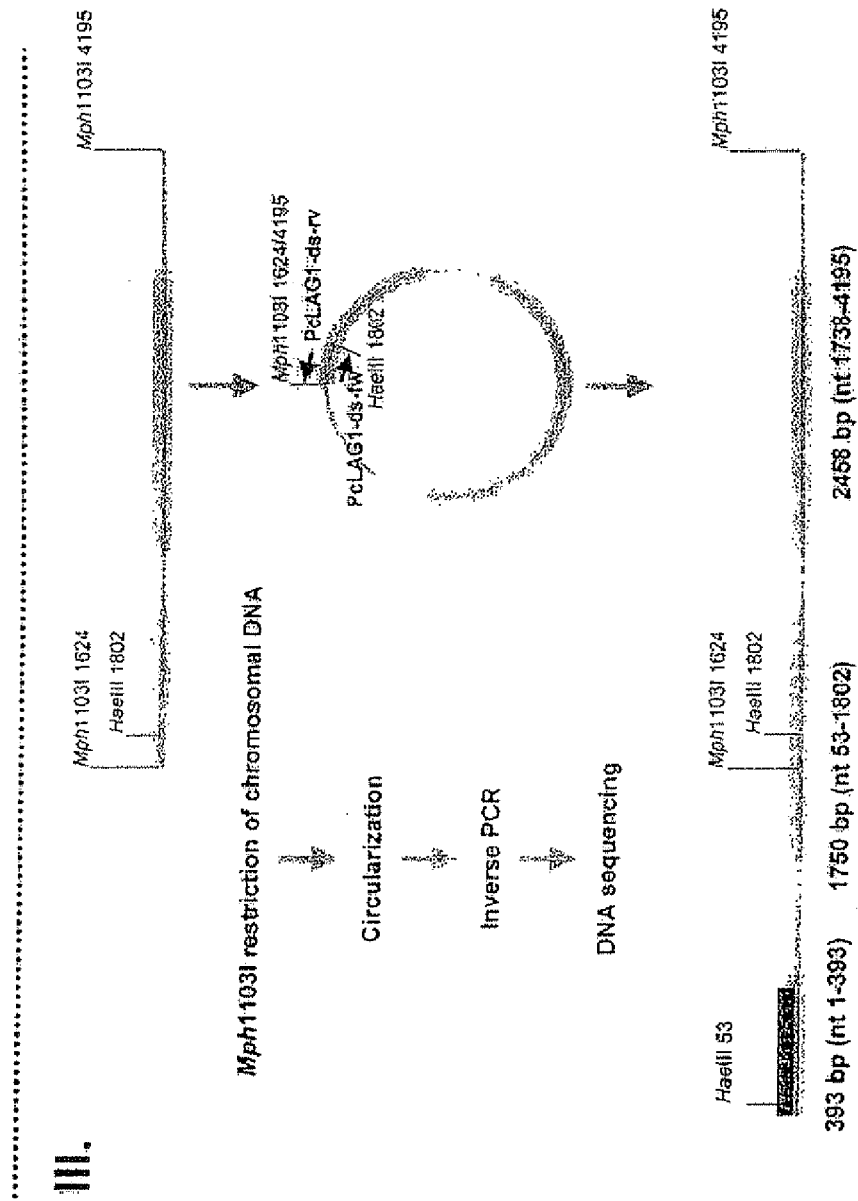

```
DBö-PcLAG1dsfw2:
                (nt 2620-2639 in SEQ ID NO: 3)
TTA AAC CCA AAT AAA CCT GG
``` as sequencing primers. 2396 bp of new sequence information (nt 1801-4195 in SEQ ID NO: 3) could be obtained which stretches to the next Mph11031 restriction site downstream of the 3' HaeIII site (FIG. 8B). Using the described three-step procedure, a total of 4195 bp of the *Pichia ciferrii* LAF1 locus could be isolated and its DNA sequence be determined (see SEQ ID NO: 3 and FIG. 8).

Figure 8C:
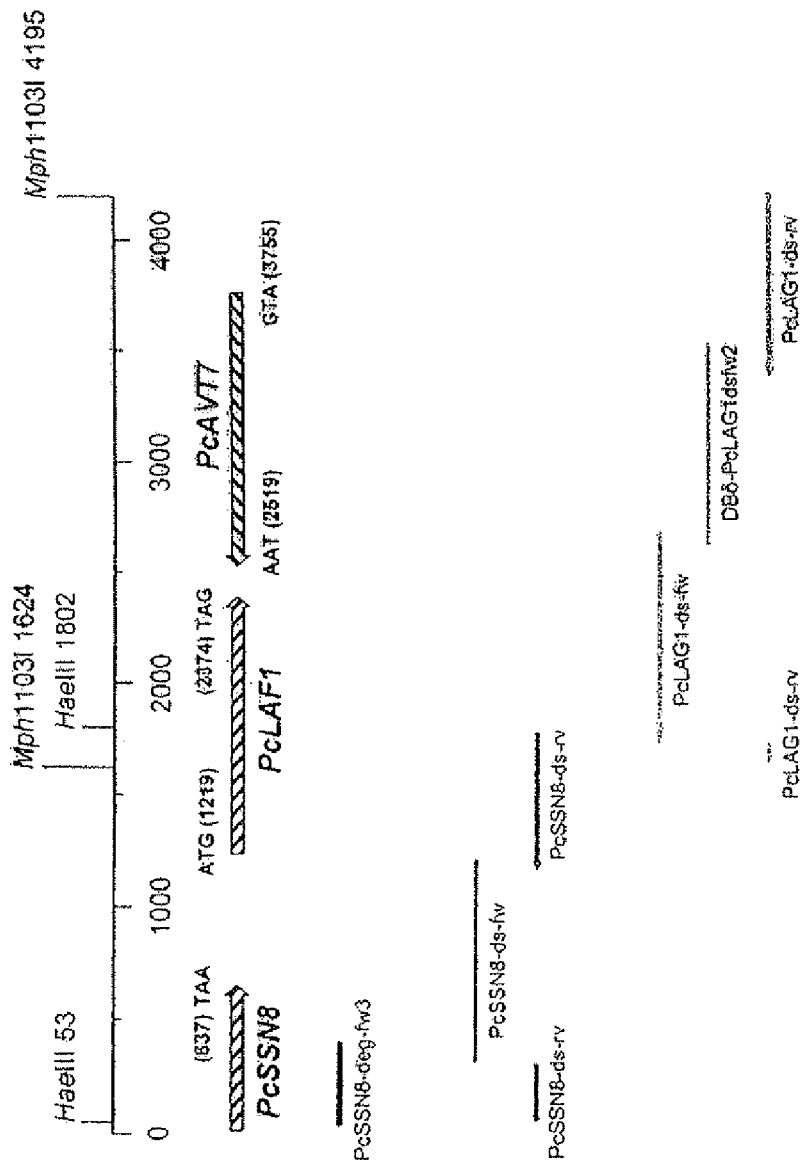

The *Pichia ciferrii* LAF1 locus as depicted in FIG. 8C encodes the *Pichia ciferrii* Laf1p protein of 385 amino acids in length (SEQ ID NO: 4). *Pichia ciferrii* Laf1p has 64%

(80%) and 65% (79%) positional amino acid identity (similarity) to predicted ceramide synthases from *Kluyveromyces lactis* (Gen Bank acc.# XP_452132) and *Ashbya gossypii* (Gen Bank acc.# AAS51714), respectively.

Example 7

Cloning and Determination of the Nucleotide Sequence of the *Pichia ciferrii* YXC1 Gene Amplification of an Internal Part of the *Pichia ciferrii* YXC1 Gene First, the amino acid sequences of putative ceramidases from *Saccharomycotina* species were extracted from NCBI's database of completed and unfinished eukaryotic genomes available online at the NCBI database by performing a TBLASTN search with the *Ashbya gossypii* YXC1 gene (GenBank acc.# NP_986865) as template. This protein is very similar to the characterized ceramidases Ypc1p and Ydc1p from *Saccharomyces cerevisiae* (43% and 44% positional amino acid identity, respectively) (Mao et al., 2000 a, b) and therefore is very likely to have ceramidase activity. The extracted sequences (all entries with E-values <1×10$^{-43}$) were aligned using the ClustalW program, see the UK website for the European Bioinformatics Institute (EBI) Suitable oligonucleotides for amplification of an internal part of the *Pichia ciferrii* YXC1 (The gene name was chosen in analogy to the gene names YPC1 and YDC1 encoding two ceramidases in *Saccharomyces cerevisiae*, where the second letter indicates the preferred substrates of the corresponding enzymes, Phytoceramide and Dihydroceramide. The substrate preference of the single ceramidase present in other yeast species, such as *Pichia ciferrii*, is not known, therefore YXC1) gene were derived by back-translating highly conserved stretches of amino acids within the Yxc1p sequence taking into account the highly biased *Pichia ciferrii* codon usage. The following oligonucleotides were then synthesized by MWG Biotech (Ebersberg, Germany):

```
ACER-deg-fw:
           (nt 995-1020 in SEQ ID NO: 7)
ATY GAT TGG TGT GAA GAA AAY TAY GT ACER-deg-rv-L2:
           (nt 1633-1607 in SEQ ID NO: 7)
ACC DGT YAA NAH ATG CCA CCA ACC ATG
```

These oligonucleotides were used to set up a PCR reaction according to Innis et al., (PCR protocols. A guide to methods and applications, 1990, Academic Press) with Phusion™ High Fidelity PCR Master Mix (Finnzymes, cat.# F-531L) according to the instructions of the manufacturer. A 639 bp fragment could be obtained by applying this method. The fragment was purified using the QIAquick Gel Extraktion Kit (Qiagen, cat.#28706) according to the instructions of the manufacturer.

Figure 9A:
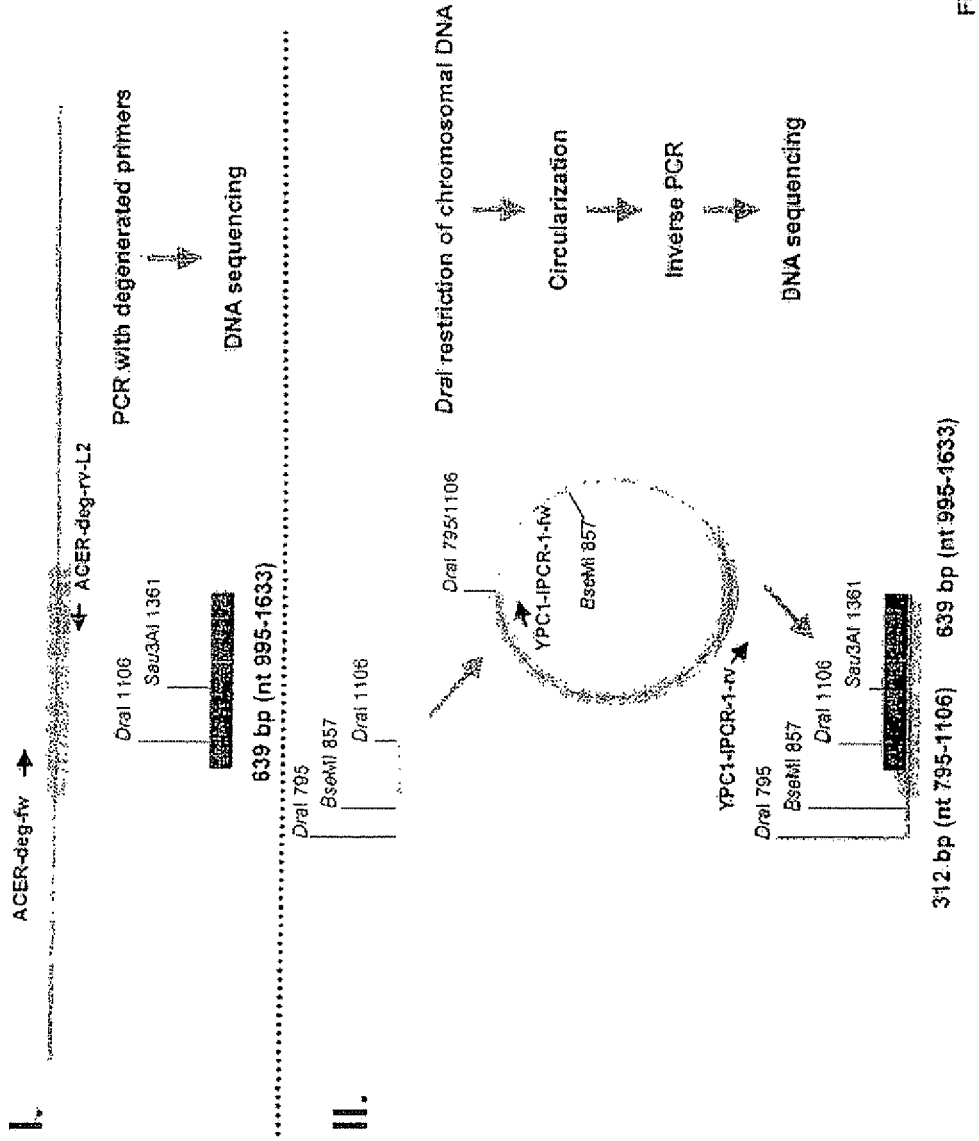

Determination of the DNA Sequence of an Internal Part of the *Pichia ciferrii* YXC1 Gene The DNA sequence of the purified PCR product was determined using the dideoxy chain termination method developed by Sanger et al. (Proceedings of the National Academy of Sciences, U.S.A., 74:5463-5467). As sequencing primers those used for PCR amplification were used. DNA sequencing was performed by Sequiserve (Vaterstetten, Germany). The generated sequence information (639 bp, corresponding to nt 995-1633 in SEQ ID NO: 7; FIG. 9A) was translated into protein using the Clone Manager 7 software (Scientific & Educational Software) and the resulting amino acid sequence used as template for a BLASTP search with NCBI's non-redundant protein database, available online at the NCBI database (BLAST), The search resulted in the identification of *Debaryomyces hansenii* Yxc1p (NCBI acc.# XP_457637), as being the protein in the database most similar to the new sequence, confirming that in fact portions of the *Pichia ciferrii* YXC1 ortholog had been amplified.

Amplification of the Entire *Pichia ciferrii* YXC1 Gene and Determination of its DNA Sequence In order to determine the DNA sequence of the entire *Pichia ciferrii* YXC1 gene (coding sequence, promoter region and 3'-untranslated region) an inverse PCR approach was followed. Chromosomal DNA (300 ng) from *Pichia ciferrii* F-60-10A NRRL 1031 (isolated as described in Example 4) was digested overnight with DraI (MBI Fermentas, cat.# ER0221) according to the instructions of the manufacturer in a total volume of 50 µl. The digested DNA was purified using the QIAquick PCR Purification Kit (Qiagen, cat.#28106) according to the instructions of the manufacturer. The eluted DNA (50 µl) was subjected to overnight ligation using the T4 DNA Ligase (New England Biolabs, cat.# M0202L) according to the instructions of the manufacturer in a total volume of 200 µl with 800 U of T4 DNA Ligase. The ligated DNA was purified using the QIAquick PCR Purification Kit according to the instructions of the manufacturer. 2.5 µl of the eluate was used as template for a inverse PCR reaction according to Innis et al., (PCR protocols. A guide to methods and applications, 1990, Academic Press). For this two oligonucleotides targeted on the already known portion of the *Pichia ciferrii* YXC1 gene were applied:

```
YPC1-IPCR-1-fw:
           (nt 1082-1104 in SEQ ID NO: 7)
GCT GGA TTT GCC ATG TTT TCT GC

YPC1-IPCR-1-rv:
           (nt 1044-1020 in SEQ ID NO: 7)
GCT TCT GCA ATA TAT GGA GTC ACA AC
```

Amplification was performed with Phusion™ High Fidelity PCR Master Mix according to the instructions of the manufacturer. Using this procedure a 0.3 kbp PCR product could be obtained. The fragment was purified using the Min Elute PCR Purification Kit (Qiagen, cat.#28006) according to the instructions of the manufacturer. The DNA sequence of this fragment was determined as described previously, using oligonucleotides YPC1-IPCR-1-fw and YPC1-IPCR-1-rv as sequencing primers. The newly obtained sequence information covered nt 795-994 in SEQ ID NO: 7. No new sequence information downstream of the DNA sequence could be obtained as the 3' Oral site is located immediately downstream of this portion (FIG. 9A). In order to obtain the DNA sequence of the 3'-end of the coding region of the *Pichia ciferrii* YXC1 gene and its 3'-untranslated region another round of inverse PCR had to be performed. Therefore, the above described experimental protocol was repeated, except that Sau3AI (New England Biolabs, cat.# R0169S) was used for digesting *Pichia ciferrii* chromosomal DNA and the following oligonucleotides, synthesized by MWG Biotech (Ebersberg, Germany), were employed during inverse PCR:

```
PcYPC1-IP-3-fw:
           (nt 1607-1632 in SEQ ID NO: 7)
CAT GGT TGG TGG CAT DTN TTY ACH GG

PcYPC1-IP-3-rv:
           (nt 1512-1479 in SEQ ID NO: 7)
CCA GAA AGG AAA ATA CCA ATT CCT TTA ATC ATT G
```

Figure 9B:
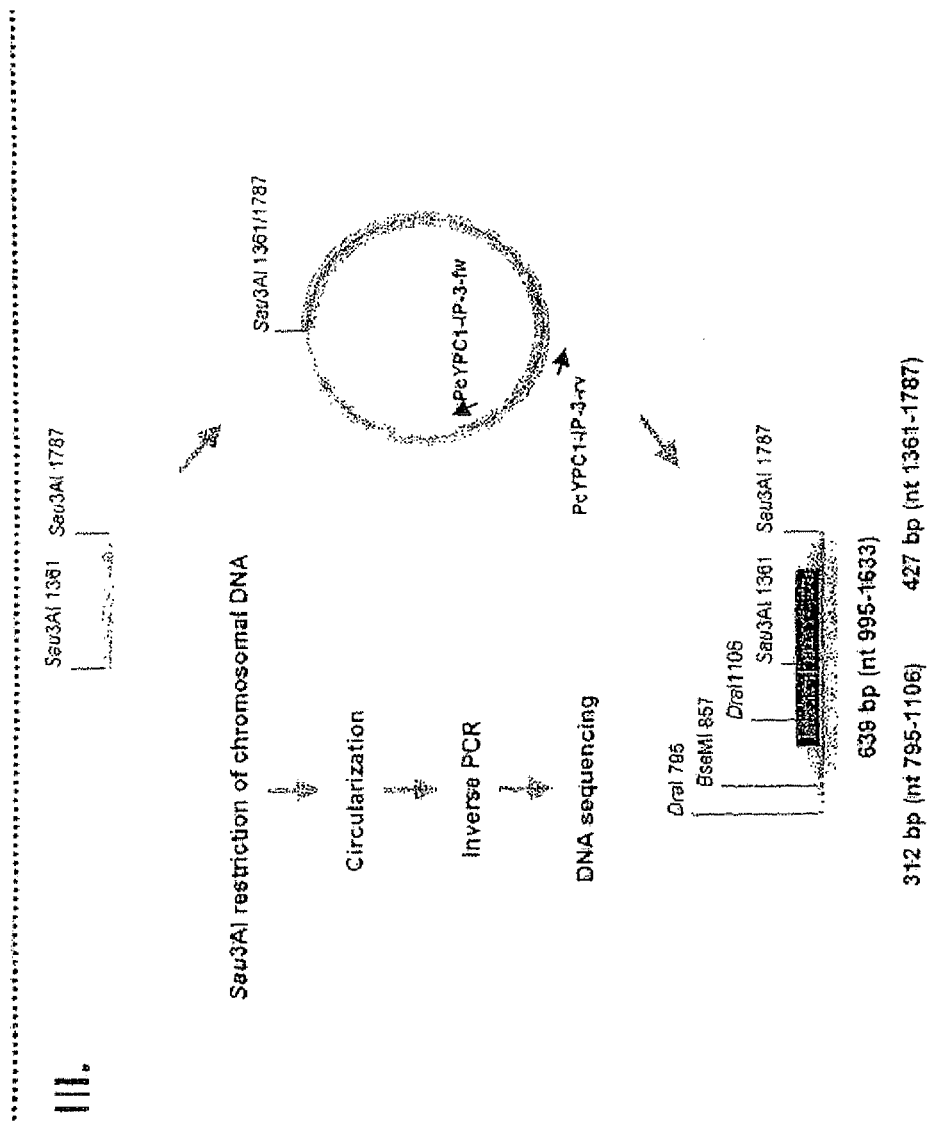

Using this procedure a 0.4 kbp PCR product could be obtained. The fragment was purified using the Min Elute PCR Purification Kit according to the instructions of the manufacturer. The DNA sequence of this fragment was determined as described previously with the oligonucleotides PcYPC1-IP-3-fw and PcYPC1-IP-3-rv as sequencing primers. 153 bp of new sequence information (nt 1634-1787 in SEQ ID NO: 7) could be obtained which stretches to the next Sau3AI restriction site downstream of the 3' Oral site (FIG. 9B). In order to obtain further information about the upstream region of the *Pichia ciferrii* YXC1 another round of inverse PCR had to be performed. Therefore, the above described experimental protocol was repeated, except that BseMI (MBI Fermentas, cat.# ER1261) was used for digesting *Pichia ciferrii* chromosomal DNA and the following oligonucleotides, synthesized by MWG Biotech (Ebersberg, Germany), were employed during inverse PCR:

```
PcYXC1-ds-fw:
                (nt 1687-1711 in SEQ ID NO: 7)
GGG GAA ACA AGA TGA TTA TGA ATT G

PcYXC1-ds-rv:
                (nt 1637-1615 in SEQ ID NO: 7)
CTA AAC CAG TTA AAA CAT GCC AC
```

Figure 9C:
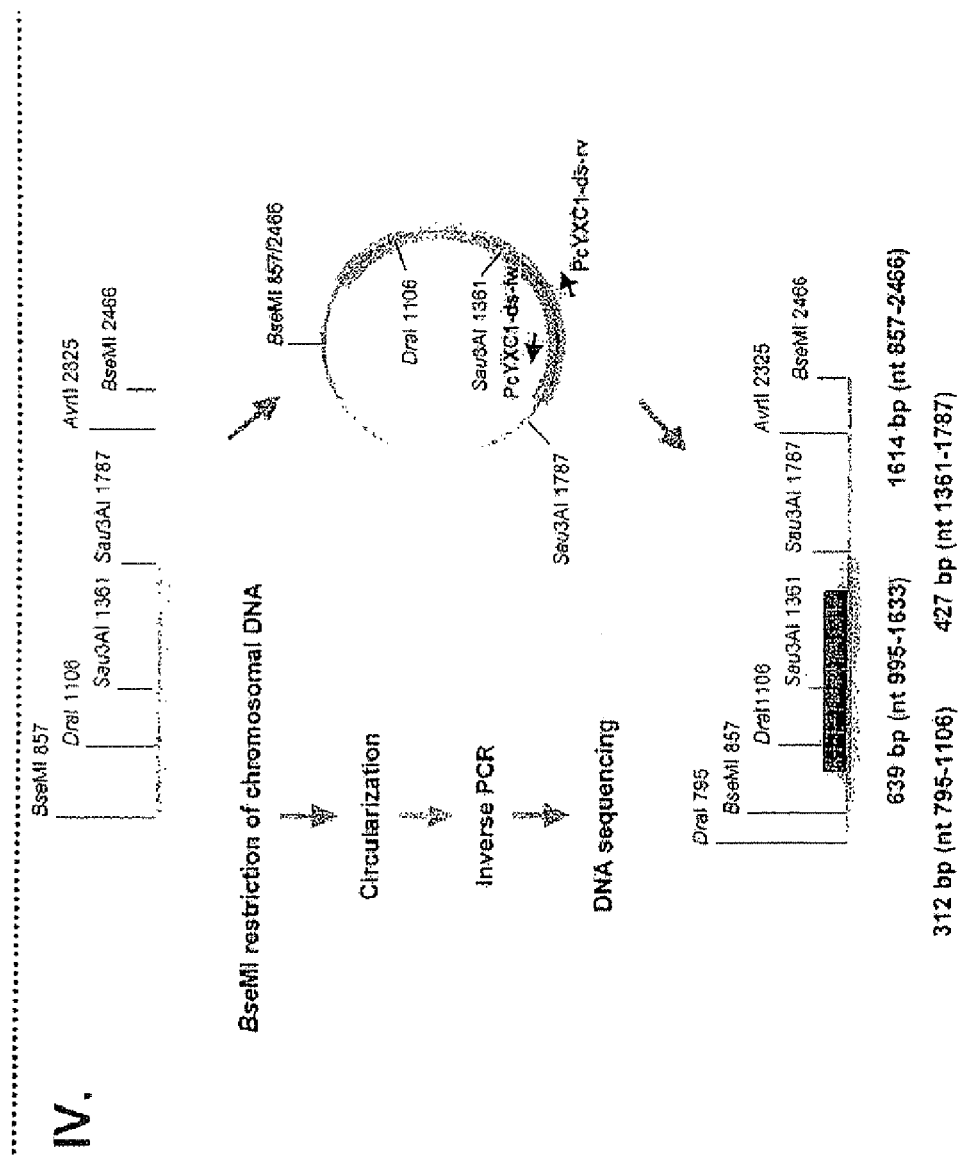

Using this procedure a 1.6 kbp PCR product could be obtained. The fragment was purified using the Min Elute PCR Purification Kit according to the instructions of the manufacturer. The DNA sequence of this fragment was determined as described previously with the oligonucleotides PcYXC1-ds-fw and PcYXC1-ds-rv as sequencing primers. 684 bp of new sequence information (nt 1788-2466 in SEQ ID NO: 7) could be obtained which stretches to the next BseMI restriction site downstream of the 3' Sau3AI site (FIG. 9C). In order to obtain further information about the upstream region of the *Pichia ciferrii* YXC1 another round of inverse PCR had to be performed. Therefore, the above described experimental protocol was repeated, except that AvrII (New England Biolabs, cat.# R0174S) was used for digesting *Pichia ciferrii* chromosomal DNA and the following oligonucleotides, synthesized by MWG Biotech (Ebersberg, Germany), were employed during inverse PCR:

```
PcYXC1-ds-fw2:
                (nt 2417-2439 in SEQ ID NO: 7)
GGA GAG TTC ACG TAG TTT AGG AG

PcYXC1-ds-rv2:
                (nt 2358-2331 in SEQ ID NO: 7)
GGA GTA TGA ATA CAT TGA TCC GAT AAT G
```

Figure 9D:
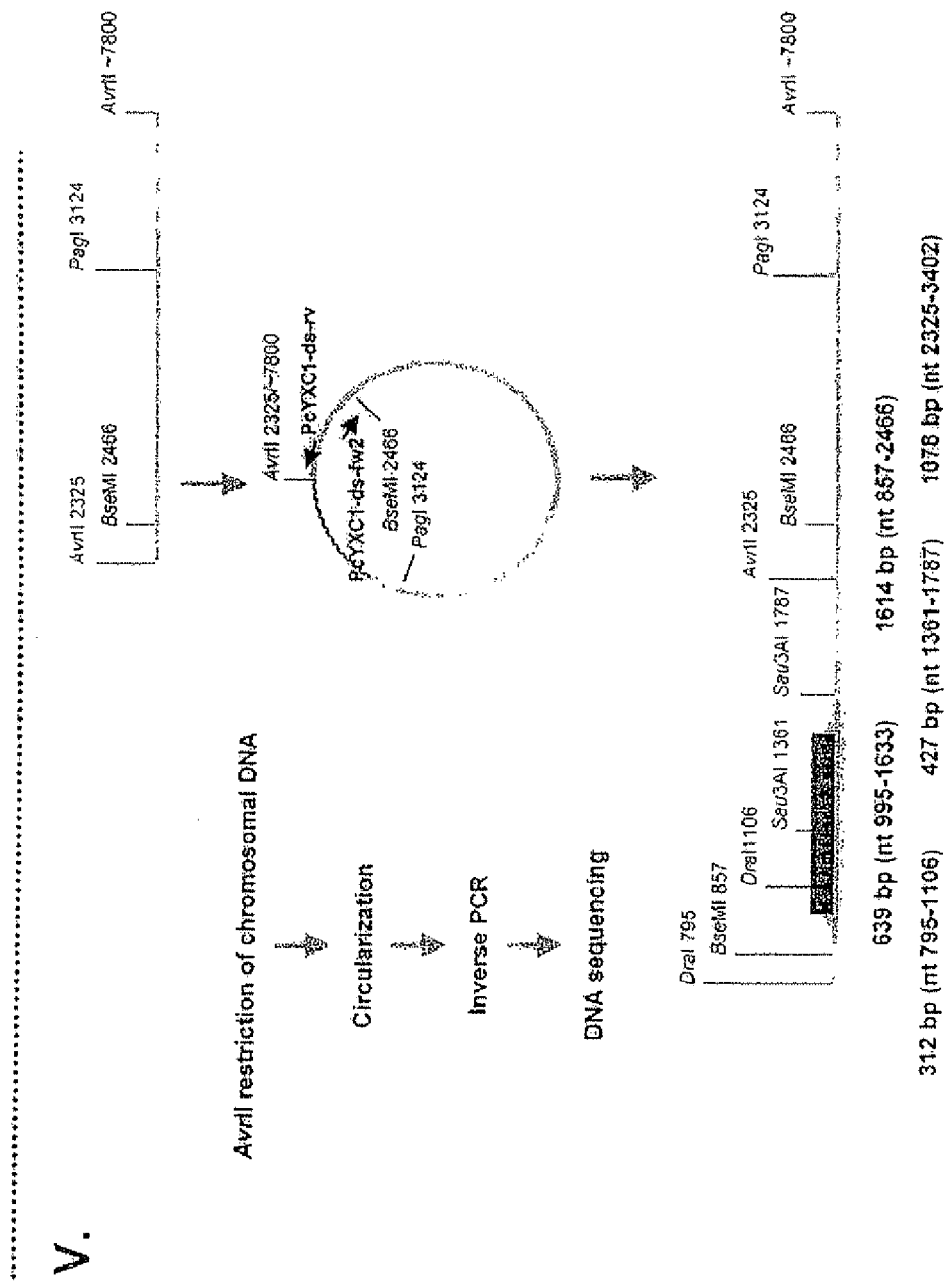

Using this procedure a approximately 5.5 kbp PCR product could be obtained. The fragment was purified using the PCR Purification Kit according to the instructions of the manufacturer. The DNA sequence of this fragment was determined in parts as described previously with the oligonucleotide PcYXC1-ds-fw2 as sequencing primer. 937 bp of new sequence information (nt 2467-3402 in SEQ ID NO: 7) could be obtained (FIG. 9D). In order to obtain further information about the downstream region of the *Pichia* ciferrii YXC1 another round of inverse PCR had to be performed. Therefore, the above described experimental protocol was repeated, except that PagI (MBI Fermentas, cat.# #ER1281) was used for digesting *Pichia ciferrii* chromosomal DNA and the following oligonucleotides, synthesized by MWG Biotech (Ebersberg, Germany), were employed during inverse PCR:

```
PcYXC1-us-fw:
                (nt 831-854 in SEQ ID NO: 7)
GGA TAA TCA GTT TAC CAT CAA AAG

PcYXC1-us-rv:
                (nt 830-803 in SEQ ID NO: 7)
TAT TGA TAA ACA ATT GAT ATT AGA TTA G
```

Figure 9E:
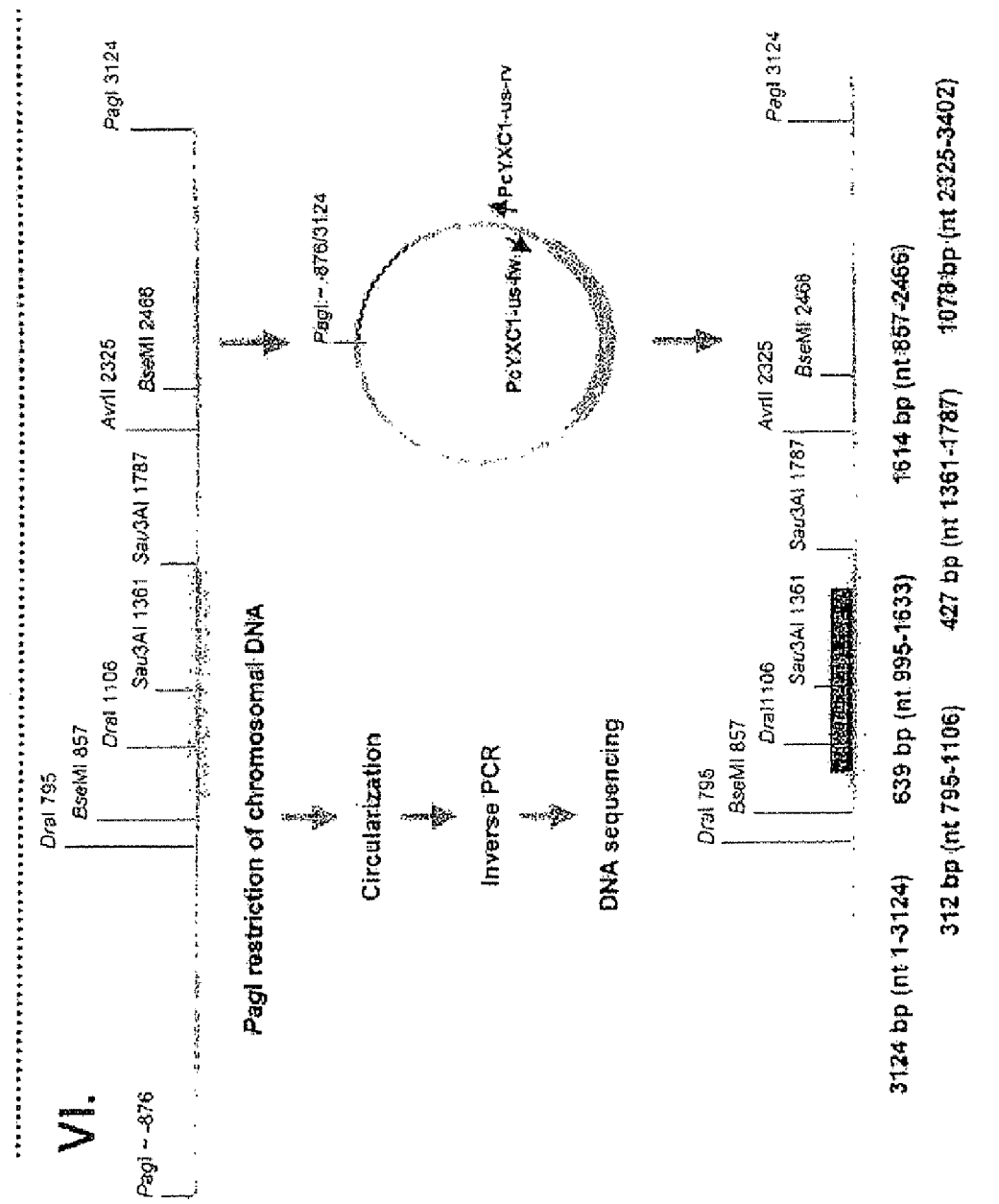

Using this procedure an approximately 4.0 kbp PCR product could be obtained. The fragment was purified using the Min Elute PCR Purification Kit according to the instructions of the manufacturer. The DNA sequence of this fragment was determined in parts as described previously with the oligonucleotide PcYXC1-us-rv as sequencing primer. 794 bp of new sequence information (nt 1-794 in SEQ ID NO: 7) could be obtained (FIG. 9E).

Using the described six-step procedure, a total of 3402 bp of the *Pichia ciferrii* YXC1 locus could be isolated and its DNA sequence be determined (see SEQ ID NO: 7 and FIG. 9).

Figure 9F:
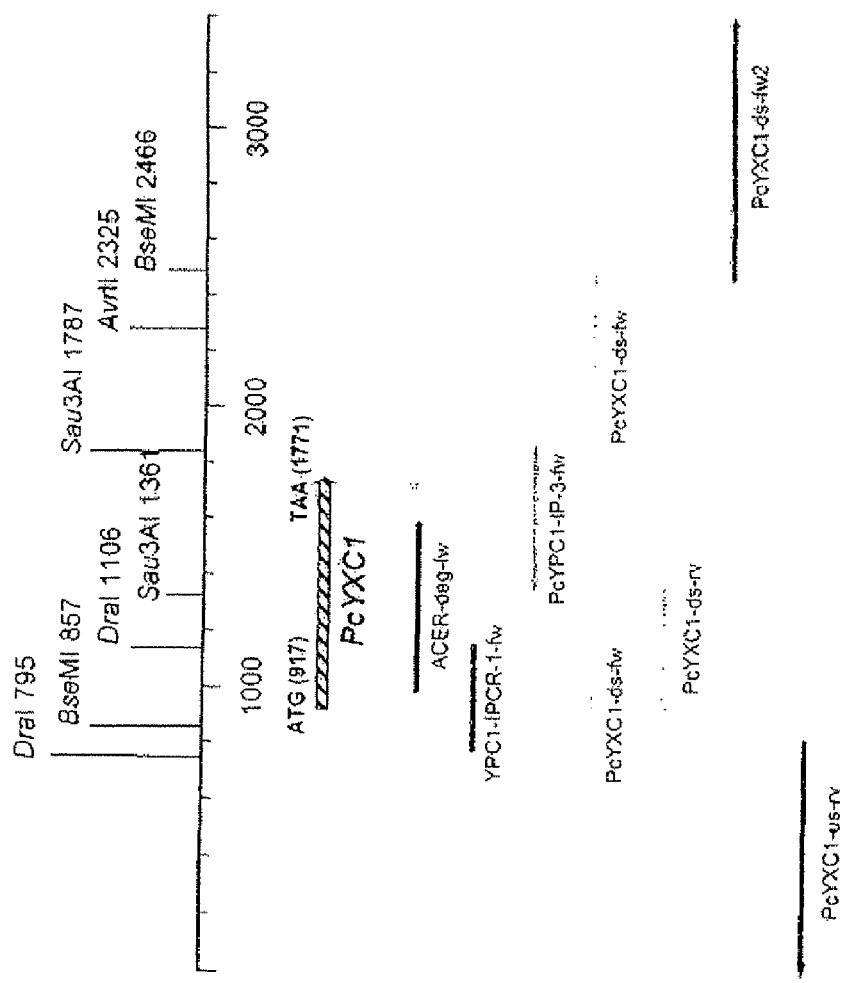

The *Pichia ciferrii* YXC1 locus as depicted in FIG. 9F encodes the *Pichia ciferrii* Yxc1p protein of 284 amino acids in length (SEQ ID NO: 8). *Pichia ciferrii* Yxc1p has 61% (75%) and 46% (66%) positional amino acid identity (similarity) to predicted ceramidases from *Debaryomyces hansenii* (GenBank acc.# XP_457637) and *Saccharomyces cerevisiae* (GenBank acc.# NP_015238), respectively. The Ydc1p protein from *Saccharomyces cerevisiae* has been characterized biochemically and been shown to display ceramidase activity in vivo (Mao et al., The Journal of Biological Chemistry, 275: 31369-31378).

Example 8

Cloning and Determination of the Nucleotide Sequence of the *Pichia ciferrii* Sphinqolipid Δ8-Desaturase Gene Amplification of an Internal Part of the *Pichia ciferrii* Sphingolipid Δ8-Desaturase Gene First, the amino acid sequences of putative sphingolipid Δ8-desaturases from *Saccharomycotina* species were extracted from NCBI's database of completed and unfinished eukaryotic genomes, available online at the NCBI database by performing a TBLASTN search with the *Ashbya gossypii* sphingolipid Δ8-desaturase (GenBank acc.# AAS53293) as template. This protein is very similar to the characterized sphingolipid Δ8-desaturase from *Klyuveromyces lactis* (65% and 59% positional amino acid identity, respectively) (Takakuwa et al., 2002) and therefore is very likely to have sphingolipid Δ8-desaturase activity. The extracted sequences (all entries with E-values $<7 \times 10^{-121}$) were aligned using the ClustalW program, see the UK website for the European Bioinformatics Institute (EBI) Suitable oligonucleotides for amplification of an internal part of the *Pichia ciferrii* sphingolipid Δ8-desaturase gene were derived by back-translating highly conserved stretches of amino acids within the sphingolipid Δ8-desaturase sequence taking into account the highly biased *Pichia ciferrii* codon usage. The following oligonucleotides were then synthesized by MWG Biotech (Ebersberg, Germany):

```
D8DES-fw:
                (nt 2439-2466 in SEQ ID NO: 5)
5'-GAT GCW ACH GAT GAA ATG MAY GCW TAY C-3'

D8DES-rv:
                (nt 3839-3805 in SEQ ID NO: 5)
5'-TTG RAA TTG YAA ACC ACC RTG NAA RAA ATC
YAA CC-3'
```

These oligonucleotides were used to set up a PCR reaction according to Innis et al., (PCR protocols. A guide to methods and applications, 1990, Academic Press) with Phusion™ High Fidelity PCR Master Mix (Finnzymes, cat.# F-531L) according to the instructions of the manufacturer. A 1401 bp fragment could be obtained by applying this method. The fragment was purified using the QIAquick Gel Extraktion Kit (Qiagen, cat.#28706) according to the instructions of the manufacturer.

Determination of the DNA sequence of an Internal Part of the *Pichia ciferrii* 8DES Gene The DNA sequence of the purified PCR product was determined using the dideoxy chain termination method developed by Sanger et al. (Proceedings of the National Academy of Sciences, U.S.A., 74:5463-5467). As sequencing primers those used for PCR amplification were used. DNA sequencing was performed by Sequiserve (Vaterstetten, Germany). The generated sequence information (1401 bp, corresponding to nt 2439-3839 in SEQ ID NO: 5; FIG. 10A) was translated into protein using the Clone Manager 7 software (Scientific & Educational Software) and the resulting amino acid sequence used as template for a BLASTP search with NCBI's non-redundant protein database, available online at the NCBI database (BLAST), The search resulted in the identification of *Kluyveromyces lactis* sphingolipid Δ8-desaturase (NCBI acc.# XP_454832), as being the protein in the database most similar to the new sequence, confirming that in fact portions of the *Pichia ciferrii* ortholog encoding sphingolipid Δ8-desaturase had been amplified.

Amplification of the Entire *Pichia ciferrii* Sphingolipid Δ8-Desaturase Gene and Determination of its DNA Sequence In order to determine the DNA sequence of the entire *Pichia ciferrii* sphingolipid β8-desaturase gene (coding sequence, promoter region and 3'-untranslated region) an inverse PCR approach was followed. Chromosomal DNA (300 ng) from *Pichia ciferrii* F-60-10A NRRL 1031 (isolated as described in Example 4) was digested overnight with HpyCH4V (New England Biolabs, cat.# R0620S) according to the instructions of the manufacturer in a total volume of 50 μl. The digested DNA was purified using the QIAquick PCR Purification Kit (Qiagen, cat.#28106) according to the instructions of the manufacturer. The eluted DNA (50 μl) was subjected to overnight ligation using the T4 DNA Ligase (New England Biolabs, cat.# M02020 according to the instructions of the manufacturer in a total volume of 200 μl with 800 U of T4 DNA Ligase. The ligated DNA was purified using the QIAquick PCR Purification Kit according to the instructions of the manufacturer. 2.5 μl of the eluate was used as template for a inverse PCR reaction according to Innis et al., (PCR protocols. A guide to methods and applications, 1990, Academic Press). For this two oligonucleotides targeted on the already known portion of the *Pichia ciferrii* sphingolipid Δ8-desaturase gene were applied:

```
D8DES-IPCR-1-fw:
            (nt 2553-2577 in SEQ ID NO: 5)
GGT GGG AAG TTC AGA ACT TTA GAA G

D8DES-IPCR-1-rv:
            (nt 2552-2527 in SEQ ID NO: 5)
TTG AAT AGG CGG CAC AAA ATT GAT CC
```

Amplification was performed with Phusion™ High Fidelity PCR Master Mix according to the instructions of the manufacturer. Using this procedure a 0.6 kbp PCR product could be obtained. The fragment was purified using the Min Elute PCR Purification Kit (Qiagen, cat.#28006) according to the instructions of the manufacturer. The DNA sequence of this fragment was determined as described previously, using oligonucleotides D8DES-IPCR-1-fw, D8DES-IPCR-1-rv as sequencing primers. The newly obtained sequence information covered nt 2142-2438 in SEQ ID NO: 5. In order to obtain further information about the upstream region of the gene encoding *Pichia ciferrii* sphingolipid Δ8-desaturase another round of inverse PCR had to be performed. Therefore, the above described experimental protocol was repeated, except that VspI (MeI Fermentas, cat.# ER0911) was used for digesting *Pichia ciferrii* chromosomal DNA and the following oligonucleotides, synthesized by MWG Biotech (Ebersberg, Germany), were employed during inverse PCR:

```
PcD8DIPCR-US-fw:
            (nt 2229-2251 in SEQ ID NO: 5)
GGG TCC TGT TGA AAA AAG CTA GG

PcD8DIPCR-US-rv:
            (nt 2211-2188 in SEQ ID NO: 5)
CCA ACT GCT GGT TCA CCA AAA TAG
```

Figure 10B:
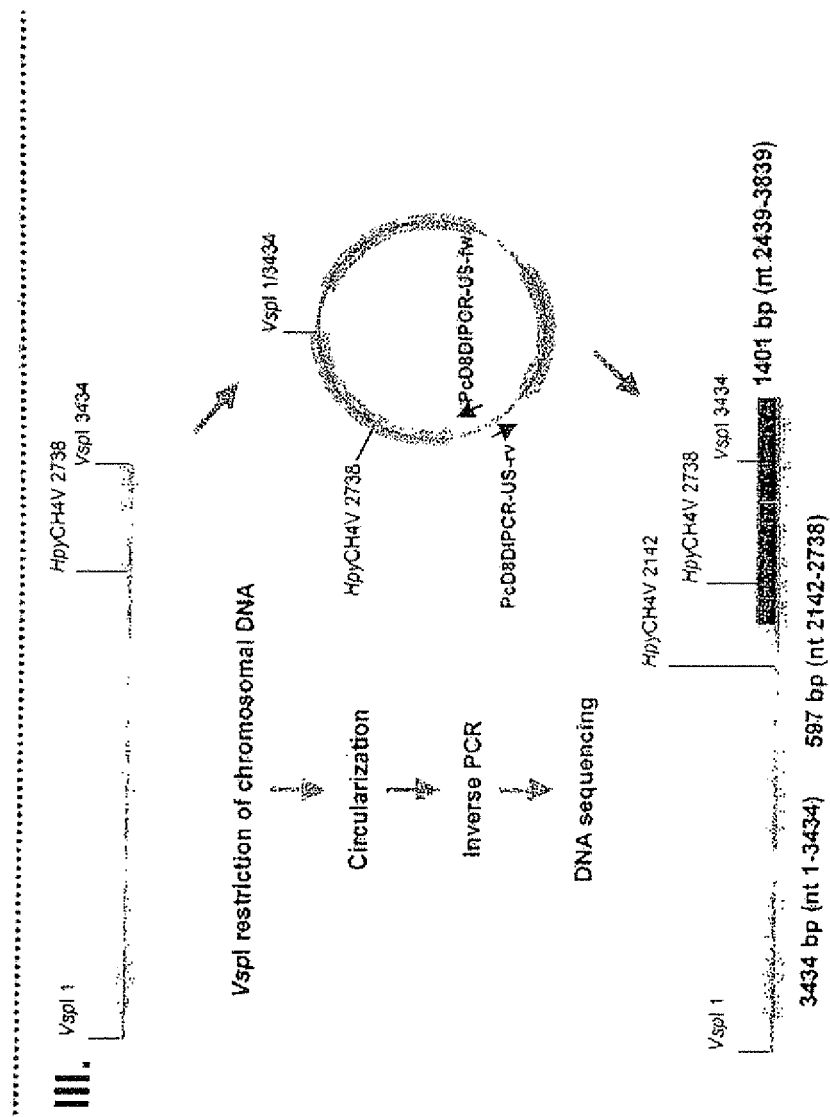

Using this procedure a 3.4 kbp PCR product could be obtained. The fragment was purified using the Min Elute PCR Purification Kit according to the instructions of the manufacturer. The DNA sequence of this fragment was determined as described previously with the oligonucleotides PcD8DIPCR-US-fw; PcD8DIPCR-US-rv;

```
DBö-PcD8D-us-fw2:
            (nt 3109-3130 in SEQ ID NO: 5)
TTA AAT GGT ATT TCC TTA GTG C and DBö-PcD8D-us-rv2:
            (nt 1343-1321 in SEQ ID NO: 5)
GAT TCA TCT TCC ATT ATC ATC TC
``` as sequencing primers. 2141 bp of new sequence information (nt 1-2141 in SEQ ID NO: 5) could be obtained which stretches to the next VspI restriction site upstream of the 3' VspI site (FIG. 10B). No new sequence information downstream of the DNA sequence could be obtained as the 3' VspI site is located immediately downstream of this portion (FIG. 10B). In order to obtain the DNA sequence of the 3'-end of the coding region of the gene encoding *Pichia ciferrii* sphingolipid Δ8-desaturase and its 3'-untranslated region another round of inverse PCR had to be performed. Therefore, the above described experimental protocol was repeated, except that PagI (MBI Fermentas, cat.# ER1281) was used for digesting *Pichia ciferrii* chromosomal DNA and the following oligonucleotides, synthesized by MWG Biotech (Ebersberg, Germany), were employed during inverse PCR:

```
PcD8D-ds-fw:
            (nt 3769-3793 in SEQ ID NO: 5)
AAA TAA GAA CAA CAA TGG AAT GTT G

PcD8D-ds-rv:
            (nt 3754-3733 in SEQ ID NO: 5)
CTT TCT GAA GTT CCT AAA TCT G
```

Figure 10C:
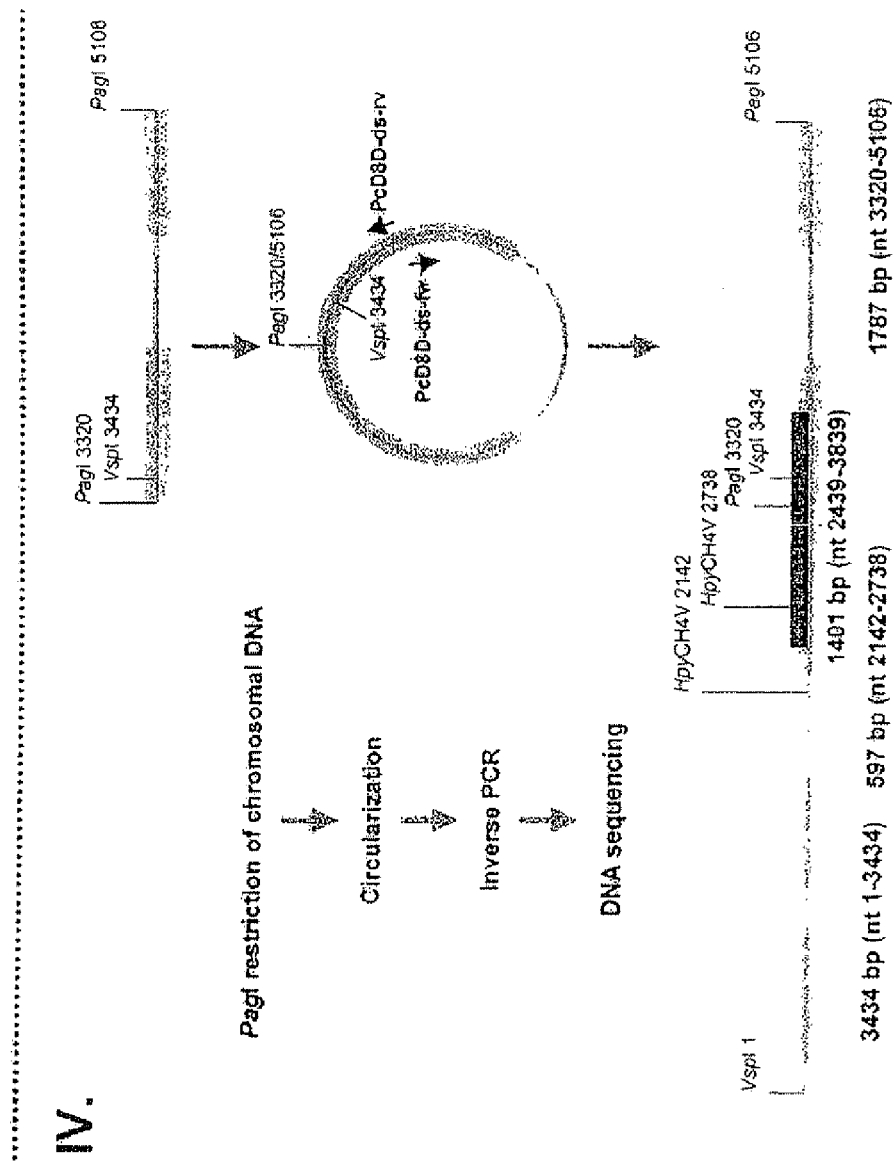

Using this procedure a 1.8 kbp PCR product could be obtained. The fragment was purified using the Min Elute PCR Purification Kit according to the instructions of the manufacturer. The DNA sequence of this fragment was determined as described previously with the oligonucleotides PcD8D-ds-fw and PcD8D-ds-rv as sequencing primers. 1312 bp of new sequence information (nt 3840-5106 in SEQ ID NO: 5) could be obtained which stretches to the next PagI restriction site downstream of the 3' VspI site (FIG. 10C). Using the described four-step procedure, a total of 5106 bp of the *Pichia ciferrii* sphingolipid Δ8-desaturase encoding locus could be isolated and its DNA sequence be determined (see SEQ ID NO: 5 and FIG. 10).

Figure 10D:
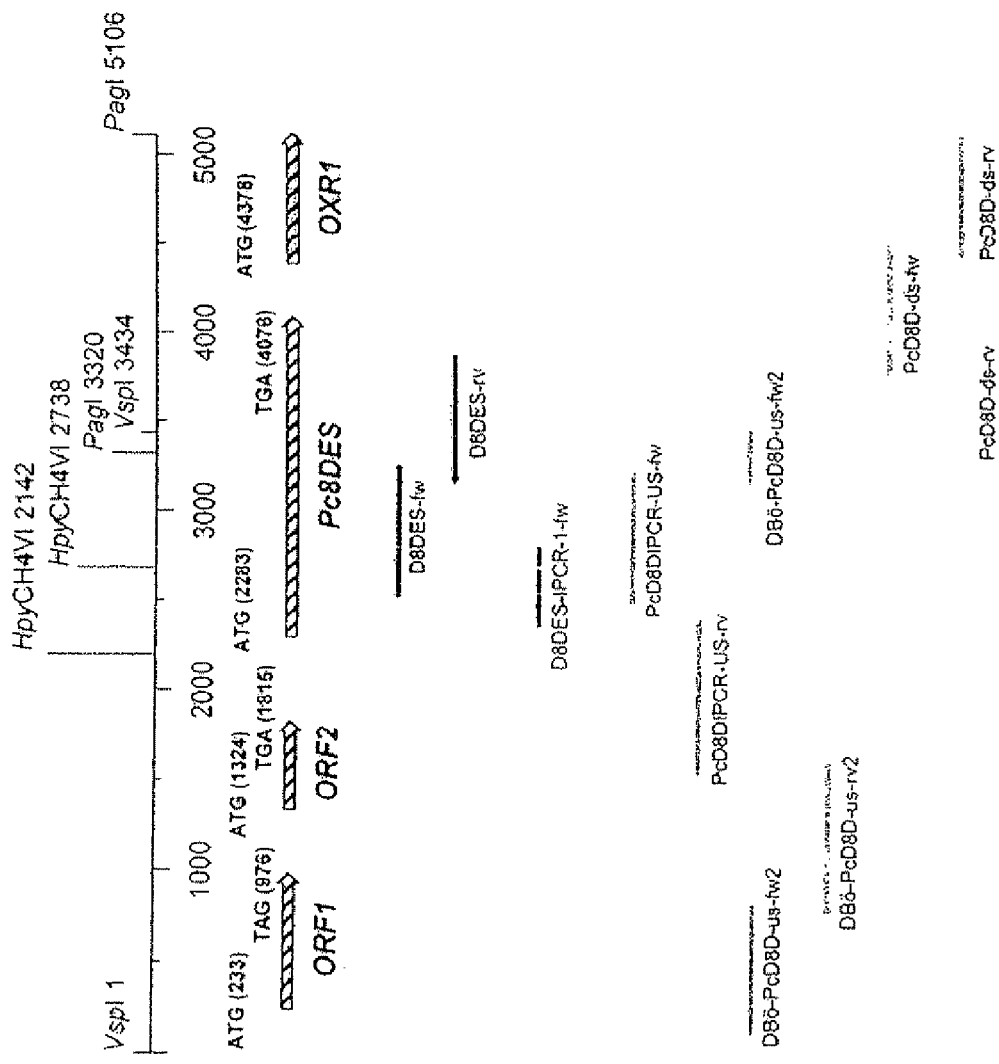

The *Pichia ciferrii* locus as depicted in FIG. 10D encodes the *Pichia ciferrii* sphingolipid Δ8-desaturase Pc8Desp protein of 597 amino acids in length (SEQ ID NO: 6). Pc8Desp *Pichia ciferrii* sphingolipid Δ8-desaturase has 62% (74%) and 57% (70%) positional amino acid identity (similarity) to sphingolipid Δ8-desaturases from *Kluyveromyces lactis* (GenBank acc.# XP_454832) and *Debaryomyces hansenii* (GenBank acc.# XP_461611), respectively. The sphingolipid Δ8-desaturase8Desp protein from *Kluyveromyces lactis* has been characterized biochemically and been shown to display sphingolipid Δ8-Delta(8)-sphingolipid desaturase activity in vivo (Takakuwa et al., Current Microbiology, 45: 459-461).

Example 9

Construction of a *Pichia ciferrii* Mutant Simultaneously Overproducing the *Pichia ciferrii* Enzymes Lag1p, Laf1p and Des1p In order to construct a syringomycinE-resistant mutant overexpressing the *Pichia ciferrii* enzymes Lag1p, Laf1p and Des1p we first constructed an integrative DES1 expression vector.

To that end 200 ng of chromosomal DNA of *Pichia ciferrii* F-60-10A NRRL 1031 (isolated as described in Example 4) was used as template for a PCR according to Innis et al., (PCR protocols. A guide to methods and applications, 1990, Academic Press) to amplify the promoter region of glyceraldehyde-3-phospate dehydrogenase *P. ciferrii* (TDH1). For this the following oligonucleotides were applied:

pGAP-BglII-for:
5'-TAT ATA AGA TCT GTG GTA CCT ACA TAC AAT TGA
CCC-3' (including a BglII-recognition sequence
at the 5' end)

pGAP-NcoI-rev:
5'-TAT ATACCA TGG TTA ATT AAT TAT TTG TTT GTT
TG-3' (including a
NcoI-recognition sequence at the 5' end)

The fragment was purified using the QIAquick PCR Purification Kit according to the instructions of the manufacturer. Then digestion of the PCR product with BglII and NcoI (according to the instructions of the manufacturer of the restriction endonuclease: New England Biolabs, Schwalbach, Germany) yielded a 575 bp fragment, which was ligated into respectively cut pAG25 (Goldstein et al., Three new dominant gene disruption cassettes for gene disruption in *Saccharomyces cerevisiae*, 1999, Yeast) creating vector pTH-GAP-nat1 (3892 bp) with the promoter region of glyceraldehyde-3-phospate dehydrogenase gene (TDH3) of *P. ciferrii* fused to nat1. The orientation and authenticity of the insert was determined by DNA sequencing. Ligation, preparation and transformation of chemically competent *Escherichia coli* cells was performed by methods known to the skilled person.

For insertion of intergenic spacer as an integration site into the vector, the 5S-26S rDNA intergenic spacer (IS) of a *Pichia ciferrii* ribosomal RNA operon was amplified by PCR using 200 ng of chromosomal DNA of *Pichia ciferrii* F-60-10A NRRL 1031 as template and following oligonucleotides:

pIS-NdeI-for:
5'-TAT ATA CAT ATG CTA ATC ACA ACA GAA CAT TCT
CTA ACG-3' (including a NdeI-recognition
sequence at the 5' end)

pIS-NdeI-rev:
5'-TAT ATA CAT ATG GCT AGA TTG ACA GAA GTC GAT
CAG-3' (including a
NdeI-recognition sequence at the 5' end)

The fragment was purified using the QIAquick PCR Purification Kit according to the instructions of the manufacturer. Vector pTH-GAP-nat1 and the PCR product were digested with NdeI (according to the instructions of the manufacturer of the restriction endonuclease: New England Biolabs, Schwalbach, Germany) followed by ligation, creating vector pTH-GAP-nat1-IS2 (4864 bp). The orientation and authenticity of the insert was determined by DNA sequencing. Ligation, preparation and transformation of chemically competent *Escherichia coli* cells was performed by methods known to the skilled person.

To insert a single PmeI-recognition sequence for linearization of vector pTH-GAP-nat1-IS2, two fragments of the 5S-26S rDNA intergenic spacer (IS) of a *Pichia* ciferrii ribosomal RNA operon integrated into pTH-GAP-nat1-IS2 were amplified by PCR using vector pTH-GAP-nat1-IS2 as template. Fragment 1 was amplified using oligonucleotides:

pIS-NdeI-rev:
5'-TAT ATA CAT ATG GCT AGA TTG ACA GAA GTC GAT
CAG-3' (including a
NdeI-recognition sequence at the 5' end)

PmeI-rv:
5'-CCC ATC CAC TAA GTT TAA ACA CCC ATA CAA AAT
CGA GCT TCA AAT C-3' (including a 21 bp
complementary sequence at the 5' end to the
PmeI-fw-oligonucleotide and a PmeI-recognition
sequence)

Fragment 2 was amplified using oligonucleotides:

p-IS-NdeI-for:
5'-TAT ATA CAT ATG CTA ATC ACA ACA GAA CAT TCT
CTA ACG-3' (including a NdeI-recognition sequence
at the 5' end)

PmeI-fw:
5'-TGTTTA AAC TTA GTG GAT GGG AAA CCC TGT AGA
ACT GGG ACA AAC-3'

The fragments were purified using the QIAquick PCR Purification Kit according to the instructions of the manufacturer. Finally, a fusion of fragments 1 and 2 was obtained by setting up a PCR with 10 ng of each of the two primary PCR products as templates with oligonucleotides:

p-IS-NdeI-for:
5'-TAT ATA CAT ATG CTA ATC ACA ACA GAA CAT TCT
CTA ACG-3' (including a NdeI-recognition sequence
at the 5' end)

pIS-NdeI-rev:
5'-TAT ATA CAT ATG GCT AGA TTG ACA GAA GTC GAT
CAG-3' (including a NdeI-recognition
sequence at the 5' end)

generating a 978 bp fragment with NdeI-recognition sequences at both ends and a PmeI-recognition sequence in the middle of the fragment.

The fragment was purified using the QIAquick PCR Purification Kit according to the instructions of the manufacturer. PCR product and vector pTH-GAP-nat1-IS2 were cut with NdeI (according to the instructions of the manufacturer of the restriction endonuclease: New England Biolabs, Schwalbach, Germany). Ligation was performed to generate vector pTH-GAP-nat1-IS2-PmeI (4879 bp). The orientation and authenticity of the insert was determined by DNA sequencing. Ligation, preparation and transformation of chemically competent *Escherichia coli* cells was performed by methods known to the skilled person. To introduce the DES1-gene of *Pichia ciferrii* under control of the promoter region of the pyruvate dehydrogenase subunit A gene (PDA1) of *Pichia ciferrii* the DES1 gene was amplified using 200 ng of chromosomal DNA of *Pichia* ciferrii F-60-10A NRRL 1031 as template for a PCR with the following oligonucleotides:

```
DES1-fw:
5'-TAG AAG TTC CAG AAA CTA CTT TCC AAA CTT CAA AAT CAA CTT TAT
TAT CAA TGG CTA CAA TTA CAC ATA GAA AAA ACC CTT CAC AAC-3'
(including a 50 base complementary sequence at the 5' end to the PDA1-rv
oligonucleotide)

DES1-rv:
5'-TAT ACT GCA GGC ATA TTG TCA ATT CTA TTG TAC TTG AGT ATT AAT
GAT TA-3' (including a PstI-recognition sequence at the 5' end)
```

Accordingly the promoter region of the pyruvate dehydrogenase subunit A gene of *Pichia ciferrii* (PDA1) was amplified with the following oligonucleotides:

```
PDA1-fw:
5'-TAT ACT GCA GTG TGC TCT AAA TTT GCC CGG TTC
GCG ACG-3' (including a PstI-recognition
sequence at the 5' end)

PDA1-rv:
5'-TGA TAA TAA AGT TGA TTT TGA AGT TTG GAA AGT
AGT TTC TGG AAC TTC TA-3'
```

The fragments were purified using the QIAquick PCR Purification Kit according to the instructions of the manufacturer. Finally, a fusion of the DES1 gene and the PDA1 promoter region was obtained by setting up a PCR with 10 ng of each of the two PCR products comprising the *Pichia ciferrii* DES1 gene and the PDA1 promoter region with oligonucleotides:

```
PDA1-fw:
5'-TAT ACT GCA GTG TGC TCT AAA TTT GCC CGG TTC
GCG ACG-3' (including a PstI-recognition
sequence at the 5' end)

DES1-rv:
5'-TAT ACT GCA GGC ATA TTG TCA ATT CTA TTG TAC TTG
AGT ATT AAT GAT TA-3' (including a PstI-
recognition sequence at the 5' end)
```

Using this procedure a 2.2 kbp PCR product could be obtained. The fragment was purified using the QIAquick PCR Purification Kit according to the instructions of the manufacturer. Then the PCR product was subjected to digestion with the restriction endonuclease PstI (according to the instructions of the manufacturer of the restriction endonuclease: New England Biolabs, Schwalbach, Germany) and ligated into PstI cut vector pTH-GAP-nat1-IS2-PmeI to generate vector pTH/DB-002a.1. The orientation and authenticity of the insert was determined by DNA sequencing. Ligation, preparation and transformation of chemically competent *Escherichia coli* cells was performed by methods known to the skilled person.

To replace the nourseothricin resistance cassette by cycloheximide conferring resistance cassette the vector pTH/DB-002a.1 was subjected to digest by SacI and SalI (according to the instructions of the manufacturer of the restriction endonuclease: New England Biolabs, Schwalbach, Germany). The 5667 bp vector backbone without nourseothricin-resistance cassette was gel purified using the QIAquick Gel Extraction Kit according to the instructions of the manufacturer.

To generate the cycloheximide conferring resistance cassette, two fragments were amplified by PCR using genomic DNA of *Pichia ciferrii* F-60-10A NRRL 1031 as a template: fragment 1 was amplified using oligonucleotides:

```
PcL41-SalI-fw:
5'-TAT AGT CGA CGA ATT CTC TTA AAT GAT GTT GG-3' (including a SalI-
recognition sequence at the 5' end)

PcL41-internal-rv:
5'-GTT TTA GCT TTT TTA TGG AAA ACT tGT TTG GTT TGA CCA CCG TAA
CCG G-3' (including a 49 base complementary sequence at the 5' end to the
PcL41-internal-fw-oligonucleotide inserting a point mutation mutation (C to A)
replacing aa 56 of L41p from proline to glutamine to confer cycloheximide
resistance)
```

Fragment 2 was amplified using oligonucleotides:

```
PcL41-internal-fw:
5'-CCG GTT ACG GTG GTC AAA CCA AAC aAG TTT TCC ATA
AAA AAG CTA AAA CTA CCA AAA AAG TTG TTT TAC G-3'

PcL41-SacI-rv:
5'-TAT AGA GCT CAA TTC CAA TGT TTT GAT CTG TC-3'
(including a SacI-recognition sequence at the
5' end)
```

The fragments were purified using the QIAquick PCR Purification Kit according to the instructions of the manufacturer. Finally, a fusion of the two fragments was obtained by setting up a PCR with 10 ng of each of the two PCR products with oligonucleotides:

PcL41-SalI-fw:
5'-TAT AGT CGA CGA ATT CTC TTA AAT GAT GTT GG-3'
(including a SalI-recognition sequence at the
5' end)

PcL41-SacI-rv:
5'-TAT AGA GCT CAA TTC CAA TGT TTT GAT CTG
TC-3' (including a SacI-
recognition sequence at the 5' end)

Resulting 1.9 kbp fragment was purified using the QIAquick PCR Purification Kit according to the instructions of the manufacturer. Then the PCR product was subjected to digest with the restriction endonuclease SalI and SacI (according to the instructions of the manufacturer of the restriction endonuclease: New England Biolabs, Schwalbach, Germany) and ligated into 5667 bp vector backbone of vector pTH/DB-002a.1 (see above) to generate vector pDB007. The orientation and authenticity of the insert was determined by DNA sequencing. Ligation, preparation and transformation of chemically competent *Escherichia coli* cells was performed by methods known to the skilled person.

To introduce the LAF1-gene of *Pichia ciferrii* under control of the promoter region of the glyceraldehyde-3-phosphate dehydrogenase isozyme 1 (TDH1) of *Pichia ciferrii* the LAF1 gene was amplified using 200 ng of chromosomal DNA of *Pichia ciferrii* F-60-10A NRRL 1031 as template for a PCR with the following oligonucleotides:

PcLAG1-fw:
5'-CAA ACA AAC AAA CAA ATA ATT AAT TAA CAA TGA TTT CAA CTT CAA
CAA ATT CAT CAT C-3' (including a 29 base complementary sequence at the 5'
end to the PGAP-rv-oligonucleotide)

PcLAG1-rv:
5'-CAG ACA AGT TTA ATA TAG ATA CTT AAA C-3'

Accordingly the promoter region of the glyceraldehyde-3-phosphate dehydrogenase isozyme 1 gene of *Pichia ciferrii* (TDH1) was amplified with the following oligonucleotides:

PGAP-SbfI:
5'-TAT ATA CCT GCA GGT TAC CCA GTG GTA CCT ACA
TAC-3' (including a SbfI-recognition sequence at
the 5' end)

PGAP-rv:
5'-CAT TGT TAA TTA ATT ATT TGT TTG TTT GTT TG-3'

The fragments were purified using the QIAquick PCR Purification Kit according to the instructions of the manufacturer. Finally, a fusion of the LAF1 gene and the TDH1 promoter region was obtained by setting up a PCR with 10 ng of each of the two PCR products comprising the *Pichia ciferrii* LAF1 gene and the TDH1 promoter region with oligonucleotides:

PGAP-SbfI:
5'-TAT ATA CCT GCA GGT TAC CCA GTG GTA CCT ACA
TAC-3' (including a SbfI-recognition sequence at
the 5' end)

PcLAG1-rv:
5'-CAG ACA AGT TTA ATA TAG ATA CTT AAA C-3'

Using this procedure a 1.9 kbp PCR product could be obtained. The fragment was purified using the QIAquick PCR Purification Kit according to the instructions of the manufacturer. Then the PCR product was subjected to digest with the restriction endonuclease SbfI (according to the instructions of the manufacturer of the restriction endonuclease: New England Biolabs, Schwalbach, Germany) and ligated into vector pDB007 digested with SalI (according to the instructions of the manufacturer of the restriction endonuclease: New England Biolabs, Schwalbach, Germany), followed by Klenow fill-in with DNA Polymerase I (according to the instructions of the manufacturer: New England Biolabs, Schwalbach, Germany) and digestion with SbfI (according to the instructions of the manufacturer of the restriction endonuclease: New England Biolabs, Schwalbach, Germany), creating vector pPC-DES1-PcLAF1. The orientation and authenticity of the insert was determined by DNA sequencing. Ligation, preparation and transformation of chemically competent *Escherichia coli* cells was performed by methods known to the skilled person.

To introduce the LAG1-gene of *Pichia ciferrii* under control of the promoter region of the pyruvate dehydrogenase subunit A gene (PDA1) of *Pichia ciferrii* the LAG1 gene was amplified using 200 ng of chromosomal DNA of *Pichia ciferrii* F-60-10A NRRL 1031 as template for a PCR with the following oligonucleotides:

PcLAC1-fw:
5'-GAA ACT ACT TTC CAA ACT TCA AAA TCA ACT TTA TTA
TCA ATG TCC ACT TCC AGA CCA CAG-3' (including a 39
base complementary sequence at the 5' end to the
PPDA-rv-oligonucleotide)

PcLAC1-BsiWI-rv:
5'-TAT ACG TAC GTG GTA CAT ACG ATA TAA TCC ATG
TAG-3' (including a BsiWI-recognition sequence at
the 5' end)

Accordingly the promoter region of the pyruvate dehydrogenase subunit A gene of *Pichia ciferrii* (PDA1) was amplified with the following oligonucleotides:

PPDA-BsiWI-fw-new:
5'-TAT ACG TAC GGA CGC ACC GGC CAT TTT CAA AC-3'
(including a BsiWI-recognition sequence at the
5' end)

PPDA-rv:
5'-CAT TGA TAA TAA AGT TGA TTT TGA AGT TTG GAA AGT
AGT TTC-3'

The fragments were purified using the QIAquick PCR Purification Kit according to the instructions of the manufacturer. Finally, a fusion of the LAG1 gene and the PDA1 promoter region was obtained by setting up a PCR with 10 ng of each of the two PCR products comprising the *Pichia ciferrii* LAG1 gene and the PDA1 promoter region with oligonucleotides:

PPDA-BsiWI-fw-new:
5'-TAT ACG TAC GGA CGC ACC GGC CAT TTT CAA AC-3'
(including a BsiWI-recognition sequence at the
5' end)

-continued

PcLAC1-BsiWI-rv:
5'-TAT ACG TAC GTG GTA CAT ACG ATA TAA TCC ATG
TAG-3' (including a BsiWI-recognition sequence at
the 5' end)

Using this procedure a 2.2 kbp PCR product could be obtained. The fragment was purified using the QIAquick PCR Purification Kit according to the instructions of the manufacturer. Then the PCR product was subjected to digest with the restriction endonuclease BsiWI (according to the instructions of the manufacturer of the restriction endonuclease: New England Biolabs, Schwalbach, Germany) and ligated into BsiWI cut vector pPC-DES1-PcLAF1 to generate vector pPC-DES1-PcLAF1-PcLAG1, which is shown in FIG. 12. The orientation and authenticity of the insert was determined by DNA sequencing. Ligation, preparation and transformation of chemically competent Escherichia coli cells was performed by methods known to the skilled person.

The vector pPC-DES1-PcLAF1-PcLAG1 was linearized with PmeI (according to the instructions of the manufacturer of the restriction endonuclease: New England Biolabs, Schwalbach, Germany) and then purified using the QIAquick PCR Purification Kit according to the instructions of the manufacturer.

Example 10

Construction of Plasmids for Simultaneous Overproduction of the Enzymes Des1p and Laf1p of Pichia ciferrii, Laf1p and Laq1p of Ashbya gossypii, as Well as an Alkaline Ceramidase of Mouse in syrinqomycinE-Resistant Pichia ciferrii Mutants In order to construct a syringomycinE-resistant mutant overexpressing the enzymes Des1p and Laf1p of Pichia ciferrii, Laf1p and Lag1p of Ashbya gossypii, as well as a codon-optimized form of an alkaline ceramidase of mouse, first an integrative DES1 expression vector was designed.

To that end, 200 ng of chromosomal DNA of Pichia ciferrii F-60-10A NRRL 1031 was used as template for a PCR according to Innis et al. (PCR protocols. A guide to methods and applications, 1990, Academic Press) to amplify the promoter region of glyceraldehyde-3-phospate dehydrogenase P. ciferrii (TDH1) (GenBank accession # AF053300). For this the following oligonucleotides were applied:

pGAP-BglII-for:
5'-TAT ATA AGA TCT GTG GTA CCT ACA TAC AAT TGA
CCC-3' (including a BglII-recognition sequence at
the 5' end)

pGAP-NcoI-rev:
5'-TAT ATA CCA TGG TTA ATT AAT TAT TTG TTT GTT TG-
3' (including a NcoI-recognition sequence at the
5' end).

The fragment was purified using the QIAquick PCR Purification Kit according to the instructions of the manufacturer. Then digestion of the PCR product with BglII and NcoI (according to the instructions of the manufacturer of the restriction endonuclease: New England Biolabs, Schwalbach, Germany) yielded a 575 bp fragment, which was ligated into respectively cut pAG25 (Goldstein et al., Three new dominant gene disruption cassettes for gene disruption in Saccharomyces cerevisiae, 1999, Yeast) creating vector pTH-GAP-nat1 (3892 bp) with the promoter region of glyceraldehyde-3-phospate dehydrogenase gene (TDH3) of P. ciferrii fused to nat1. The orientation and authenticity of the insert was determined by DNA sequencing. Ligation, preparation and transformation of chemically competent Escherichia coli cells were performed by methods known to the skilled person.

For insertion of a ribosomal rDNA intergenic spacer as an integration site into the vector, the 5S-26S rDNA intergenic spacer (IS) of a Pichia ciferrii ribosomal RNA operon (GenBank accession # AF053301) was amplified by PCR using 200 ng of chromosomal DNA of Pichia ciferrii F-60-10A NRRL 1031 as template and following oligonucleotides:

pIS-NdeI-for:
5'-TAT ATA CAT ATG CTA ATC ACA ACA GAA CAT TCT CTA
ACG-3' (including a NdeI-recognition sequence at
the 5' end)

pIS-NdeI-rev:
5'-TAT ATA CAT ATG GCT AGA TTG ACA GAA GTC GAT
CAG-3' (including a NdeI-recognition sequence at
the 5' end).

The fragment was purified using the QIAquick PCR Purification Kit according to the instructions of the manufacturer. Vector pTH-GAP-nat1 and the PCR product were digested with NdeI (according to the instructions of the manufacturer of the restriction endonuclease: New England Biolabs, Schwalbach, Germany) followed by ligation, creating vector pTH-GAP-nat1-IS2 (4864 bp). The orientation and authenticity of the insert was determined by DNA sequencing. Ligation, preparation and transformation of chemically competent Escherichia coli cells were performed by methods known to the skilled person.

To insert a single PmeI-recognition sequence for linearization of vector pTH-GAP-nat1-IS2, two fragments of the 5S-26S rDNA intergenic spacer (IS) of a Pichia ciferrii ribosomal RNA operon (GenBank accession # AF053301) integrated into pTH-GAP-nat1-IS2 were amplified by PCR using vector pTH-GAP-nat1-IS2 as template. Fragment 1 was amplified using oligonucleotides:

pIS-NdeI-rev:
5'-TAT ATA CAT ATG GCT AGA TTG ACA GAA GTC GAT
CAG-3' (including a NdeI-recognition sequence at
the 5' end)

PmeI-rv:
5'-CCC ATC CAC TAA GTT TAA ACA CCC ATA CAA AAT CGA
GCT TCA AAT C-3' (including a 21 bp complementary
sequence at the 5' end to the PmeI-fw-oligonucleotide and a PmeI-recognition sequence).

Fragment 2 was amplified using oligonucleotides:

p-IS-NdeI-for:
5'-TAT ATA CAT ATG CTA ATC ACA ACA GAA CAT TCT CTA
ACG-3' (including a NdeI-recognition sequence at
the 5' end)

PmeI-fw:
5'-TGT TTA AAC TTA GTG GAT GGG AAA CCC TGT AGA ACT
GGG ACA AAC-3'.

The fragments were purified using the QIAquick PCR Purification Kit according to the instructions of the manufacturer. Finally, a fusion of fragments 1 and 2 was obtained by setting up a PCR reaction with 10 ng of each of the two primary PCR products as templates with oligonucleotides:

p-IS-NdeI-for:
5'-TAT ATA CAT ATG CTA ATC ACA ACA GAA CAT TCT CTA
ACG-3' (including a NdeI-recognition sequence at
the 5' end)

pIS-NdeI-rev:
5'-TAT ATA CAT ATG GCT AGA TTG ACA GAA GTC GAT
CAG-3' (including a NdeI-recognition sequence at
the 5' end)

generating a 978 bp fragment with NdeI-recognition sequences at both ends and a PmeI-recognition sequence in the middle of the fragment.

The fragment was purified using the QIAquick PCR Purification Kit according to the instructions of the manufacturer. PCR product and vector pTH-GAP-nat1-IS2 were cut with NdeI (according to the instructions of the manufacturer of the restriction endonuclease: New England Biolabs, Schwalbach, Germany). Ligation was performed to generate vector pTH-GAP-nat1-IS2-PmeI (4879 bp). The orientation and authenticity of the insert was determined by DNA sequencing. Ligation, preparation and transformation of chemically competent *Escherichia coli* cells were performed by methods known to the skilled person.

To introduce the DES1 gene of *Pichia ciferrii* (SEQ ID NO:26) under control of the promoter region of the pyruvate dehydrogenase subunit A gene (PDA1) of *Pichia ciferrii* (SEQ ID NO:27) the DES1 gene (SEQ ID NO:26) was amplified using 200 ng of chromosomal DNA of *Pichia ciferrii* F-60-10A NRRL 1031 as template for a PCR reaction with the following oligonucleotides:

DES1-fw:
5'-TAG AAG TTC CAG AAA CTA CTT TCC AAA CTT CAA AAT
CAA CTT TAT TAT CAA TGG CTA CAA TTA CAC ATA GAA
AAA ACC CTT CAC AAC-3' (including a 50 base
complementary sequence at the 5' end to the PDA1-
rv oligonucleotide)

DES1-rv:
5'-TAT ACT GCA GGC ATA TTG TCA ATT CTA TTG TAC TTG
AGT ATT AAT GAT TA-3' (including a PstI-
recognition sequence at the 5' end).

Accordingly the promoter region of the pyruvate dehydrogenase subunit A gene of *Pichia ciferrii* (PDA1) (SEQ ID NO:27) was amplified with the following oligonucleotides:

PDA1-fw:
5'-TAT ACT GCA GTG TGC TCT AAA TTT GCC CGG TTC GCG
ACG-3' (including a PstI-recognition sequence at
the 5' end)

PDA1-rv:
5'-TGA TAA TAA AGT TGA TTT TGA AGT TTG GAA AGT AGT
TTC TGG AAC TTC TA-3'.

The fragments were purified using the QIAquick PCR Purification Kit according to the instructions of the manufacturer. Finally, a fusion of the DES1 gene and the PDA1 promoter region was obtained by setting up a PCR reaction with 10 ng of each of the two PCR products comprising the *Pichia ciferrii* DES1 gene and the PDA 1 promoter region with oligonucleotides:

PDA1-fw:
5'-TAT ACT GCA GTG TGC TCT AAA TTT GCC CGG TTC GCG
ACG-3' (including a PstI-recognition sequence at
the 5' end)

DES1-rv:
5'-TAT ACT GCA GGC ATA TTG TCA ATT CTA TTG TAC TTG
AGT ATT AAT GAT TA-3' (including a PstI-
recognition sequence at the 5' end).

Using this procedure, a 2.2 kbp PCR product could be obtained. The fragment was purified using the QIAquick PCR Purification Kit according to the instructions of the manufacturer. Then the PCR product was subjected to digestion with the restriction endonuclease PstI (according to the instructions of the manufacturer of the restriction endonuclease: New England Biolabs, Schwalbach, Germany) and ligated into PstI cut vector pTH-GAP-nat1-IS2-PmeI to generate vector pTH/DB-002a.1. The orientation and authenticity of the insert was determined by DNA sequencing. Ligation, preparation and transformation of chemically competent *Escherichia coli* cells were performed by methods known to the skilled person.

To replace the nourseothricin resistance cassette by a cycloheximide resistance cassette the vector pTH/DB-002a1 was subjected to digestion with SacI and SaII (according to the instructions of the manufacturer of the restriction endonuclease: New England Biolabs, Schwalbach, Germany). The 5667 bp vector backbone without the nourseothricin-resistance cassette was gel-purified using the QIAquick Gel Extraction Kit according to the instructions of the manufacturer.

To generate the cycloheximide resistance cassette, two fragments of the *Pichia* ciferrii L41 gene (GenBank accession # AF053457) were amplified by PCR using genomic DNA of *Pichia ciferrii* F-60-10A NRRL 1031 as a template: fragment 1 was amplified using oligonucleotides:

PcL41-SalI-fw:
5'-TAT AGT CGA CGA ATT CTC TTA AAT GAT GTT GG-3'
(including a SalI-recognition sequence at the
5' end)

PcL41-internal-rv:
5'-GTT TTA GCT TTT TTA TGG AAA ACT tGT TTG GTT TGA
CCA CCG TAA CCG G-3' (including a 49 base
complementary sequence at the 5' end to the PcL41-
internal-fw-oligonucleotide inserting a point
mutation mutation (C to A) replacing aa 56 of L41p
from proline to glutamine to confer cycloheximide
resistance).

Fragment 2 was amplified using oligonucleotides:

PcL41-internal-fw:
5'-CCG GTT ACG GTG GTC AAA CCA AAC AAG TTT TCC ATA
AAA AAG CTA AAA CTA CCA AAA AAG TTG TTT TAC G-3'

PcL41-SacI-rv:
5'-TAT AGA GCT CAA TTC CAA TGT TTT GAT CTG TC-3'
(including a SacI-recognition sequence at the
5' end).

The fragments were purified using the QIAquick PCR Purification Kit according to the instructions of the manufacturer. Finally, a fusion of the two fragments was obtained by setting up a PCR reaction with 10 ng of each of the two PCR products with oligonucleotides:

PcL41-SalI-fw:
5'-TAT AGT CGA CGA ATT CTC TTA AAT GAT GTT GG-3'
including a SalI-recognition sequence at the
5' end)

-continued

```
PcL41-SacI-rv:
5'-TAT AGA GCT CAA TTC CAA TGT TTT GAT CTG TC-3'
(including a SacI-recognition sequence at the
5' end).
```

The resulting 1.9 kbp fragment was purified using the QIAquick PCR Purification Kit according to the instructions of the manufacturer. Then the PCR product was subjected to digestion with the restriction endonucleases SalI and SacI (according to the instructions of the manufacturer of the restriction endonuclease: New England Biolabs, Schwalbach, Germany) and ligated into the 5667 bp vector backbone of vector pTH/DB-002a.1 (see above) to generate vector pDB007. The orientation and authenticity of the insert was determined by DNA sequencing. Ligation, preparation and transformation of chemically competent *Escherichia coli* cells were performed by methods known to the skilled person.

To introduce the LAF1 gene of *Ashbya gossypii* (SEQ ID NO:13) under control of the promoter region of the glyceraldehyde-3-phosphate dehydrogenase isozyme 1 (TDH1) of *Pichia ciferrii* (GenBank accession # AF053300) the LAF1 gene (SEQ ID NO:13) was amplified using 200 ng of chromosomal DNA of *Ashbya gossypii* ATCC 19895 as template for a PCR reaction with the following oligonucleotides:

```
AgLAG1-fw:
5'-CAA ACA AAC AAA CAA ATA ATT AAT TAA CAA TGT CGG
GCC AAG TCA GGC AG-3' (including a 32 base
sequence at the 5' end complementary to the
oligonucleotide PGAP-rv)

AgLAG1-rv:
5'-CAT TAC CGA TCA CCA GGT AGG-3'.
```

Accordingly the promoter region of the glyceraldehyde-3-phosphate dehydrogenase isozyme 1 gene of *Pichia ciferrii* (TDH1) (GenBank accession # AF053300) was amplified with the following oligonucleotides:

```
PGAP-SbfI:
5'-TAT ATA CCT GCA GGT TAC CCA GTG GTA CCT ACA
TAC-3' (including a SbfI-recognition sequence
at the 5' end)

PGAP-rv:
5'-CAT TGT TAA TTA ATT ATT TGT TTG TTT GTT TG-3'.
```

The fragments were purified using the QIAquick PCR Purification Kit according to the instructions of the manufacturer. Finally, a fusion of the LAF1 gene and the TDH1 promoter region was obtained by setting up a PCR reaction with 10 ng of each of the two PCR products comprising the *Ashbya gossypii* LAF1 gene and the TDH1 promoter region of *Pichia ciferrii* with oligonucleotides:

```
PGAP-SbfI:
5'-TAT ATA CCT GCA GGT TAC CCA GTG GTA CCT ACA
TAC-3' (including a SbfI-recognition sequence
at the 5' end)

AgLAG1-rv:
5'-CAT TAC CGA TCA CCA GGT AGG-3'.
```

Using this procedure, a 1.8 kbp PCR product could be obtained. The fragment was purified using the QIAquick PCR Purification Kit according to the instructions of the manufacturer. Then the PCR product was subjected to digestion with the restriction endonuclease SbfI (according to the instructions of the manufacturer of the restriction endonuclease: New England Biolabs, Schwalbach, Germany) and ligated into vector pDB007 digested with SalI (according to the instructions of the manufacturer of the restriction endonuclease: New England Biolabs, Schwalbach, Germany), followed by Klenow fill-in with Klenow fragment of DNA Polymerase 1 (according to the instructions of the manufacturer: New England Biolabs, Schwalbach, Germany) and digestion with SbfI (according to the instructions of the manufacturer of the restriction endonuclease: New England Biolabs, Schwalbach, Germany), creating vector pPC-DES1-AgLAF1. The orientation and authenticity of the insert was determined by DNA sequencing. Ligation, preparation and transformation of chemically competent *Escherichia coli* cells were performed by methods known to the skilled person.

To introduce the LAG1 gene of *Ashbya gossypii* (SEQ ID NO:11) under control of the promoter region of the pyruvate dehydrogenase subunit A gene (PDA1) of *Pichia ciferrii* (SEQ ID NO:27) the LAG1 (SEQ ID NO:11) gene was amplified using 200 ng of chromosomal DNA of *Ashbya gossypii* ATCC 19895 as template for a PCR reaction with the following oligonucleotides:

```
AgLAC1-fw:
5'-GAA ACT ACT TTC CAA ACT TCA AAA TCA ACT TTA TTA
TCA ATG GCT GAA AAT TCG TTA TTG AAG CCA C-3'
(including a 42 base sequence at the 5' end
complementary to the oligonucleotide PPDA-rv)

AgLAC1-BsiWI-rv:
5'-TAT ACG TAC GGT GTA ATG GCG GTG AAA
CAC-3' (including a BsiWI-recognition sequence
at the 5' end).
```

Accordingly, the promoter region of the pyruvate dehydrogenase subunit A gene of *Pichia ciferrii* (PDA1) (SEQ ID NO:27) was amplified with the following oligonucleotides:

```
PPDA-BsiWI-fw-new:
5'-TAT ACG TAC GGA CGC ACC GGC CAT TTT CAA
AC-3' (including a BsiWI-recognition sequence
at the 5' end)

PPDA-rv:
5'-CAT TGA TAA TAA AGT TGA TTT TGA AGT TTG GAA AGT
AGT TTC-3'.
```

The fragments were purified using the QIAquick PCR Purification Kit according to the instructions of the manufacturer. Finally, a fusion of the LAG1 gene and the PDA1 promoter region was obtained by setting up a PCR reaction with 10 ng of each of the two PCR products comprising the *Ashbya gossypii* LAG1 gene and the PDA1 promoter region of *Pichia ciferrii* with oligonucleotides:

```
PPDA-BsiWI-fw-new:
5'-TAT ACG TAC GGA CGC ACC GGC CAT TTT
CAA AC-3' (including a BsiWI-recognition sequence
at the 5' end)

AgLAC1-BsiWI-rv:
5'-TAT ACG TAC GGT GTA ATG GCG GTG AAA
CAC-3' (including a BsiWI-recognition sequence
at the 5' end).
```

Using this procedure a 2.1 kbp PCR product could be obtained. The fragment was purified using the QIAquick PCR Purification Kit according to the instructions of the manufacturer. Then the PCR product was subjected to digestion with the restriction endonuclease BsiWI (according to the instructions of the manufacturer of the restriction endonuclease: New England Biolabs, Schwalbach, Germany) and ligated into BsiWI cut vector pPC-DES1-AgLAF1 to generate vector pPC-DES1-AgLAF1-AgLAG1, which is shown in FIG. 11. The orientation and authenticity of the insert was determined by DNA sequencing. Ligation, preparation and transformation of chemically competent *Escherichia coli* cells were performed by methods known to the skilled person.

The vector pPC-DES1-AgLAF1-AgLAG1 was linearized with PmeI (according to the instructions of the manufacturer of the restriction endonuclease: New England Biolabs, Schwalbach, Germany) and then purified using the QIAquick PCR Purification Kit according to the instructions of the manufacturer prior to transformation.

Moreover, a second vector harbouring the LAF1 gene of *Pichia ciferrii* and a codon-optimized form of an alkaline ceramidase of mouse optimized for expression in *Pichia ciferrii* was constructed.

To that end, 100 ng of FirstChoice PCR-Ready mouse kidney cDNA (Ambion, Inc., Austin, Tex., U.S.A.) was used as template for a PCR reaction to amplify the open reading frame of alkaline mouse ceramidase (mCER) (GenBank accession #AF347023). Therefore, the following oligonucleotides were used:

```
mCER-fw:
5'-CAA ACA AAC AAA CAA ATA ATT AAT TAA CAA TGC ATG
TAC CGG GCA CCA G-3' (including a 32 base sequence
at the 5' end complementary to the oligonucleotide
PGAP-rv)

mCER-rv:
5'-CGT TAT ATA GGA AAG CAC CGA AGC TAA ATT CAG CAG
TTC TTG TCA TTC TC-3' (including a 29 base
sequence at the 5' end complementary to the
oligonucleotide TENO-fw).
```

Accordingly the promoter region of the glyceraldehyde-3-phosphate dehydrogenase isozyme 1 gene of *Pichia ciferrii* (TDH1) (GenBank accession # AF053300) was amplified with the following oligonucleotides:

```
PGAP-SbfI:
5'-TAT ATA CCT GCA GGT TAC CCA GTG GTA CCT ACA
TAC-3' (including a SbfI-recognition sequence
at the 5' end)

PGAP-rv:
5'-CAT TGT TAA TTA ATT ATT TGT TTG TTT GTT TG-3'.
```

The fragments were purified using the QIAquick PCR Purification Kit according to the instructions of the manufacturer. Finally, a fusion of the mCER gene and the TDH1 promoter region was obtained by setting up a PCR reaction with 10 ng of each of the two PCR products comprising the *Mus musculus* CER gene and the TDH1 promoter region of *Pichia ciferrii* with oligonucleotides:

```
PGAP-SbfI:
5'-TAT ATA CCT GCA GGT TAC CCA GTG GTA CCT ACA
TAC-3' (including a SbfI-recognition sequence
at the 5' end)

mCER-rv:
5'-CGT TAT ATA GGA AAG CAC CGA AGC TAA ATT CAG CAG
TTC TTG TCA TTC TC-3' (including a 29 base
sequence at the 5' end complementary to the
oligonucleotide TENO-fw).
```

Using this procedure, a 1A kbp PCR product could be obtained. The fragment was purified using the QIAquick PCR Purification Kit according to the instructions of the manufacturer.

To fuse the terminator region of the enolase gene of *Pichia ciferrii* (ENO1) (SEQ ID NO:28) with the previously amplified construct, the terminator region of ENO1 was amplified first using the following oligonucleotides:

```
TENO-fw:
5'-ATT TAG CTT CGG TGC TTT CCT ATA TAA CG-3'
TENO-fw-SbfI:

5'-TAT ATA CCT GCA GGT TAT AAC GGT TGG GCA
ATG TTG AG-3' (including a SbfI-recognition
sequence at the 5' end).
```

The fragment was purified using the QIAquick PCR Purification Kit according to the instructions of the manufacturer. Finally, a fusion of the mCER gene under control of TDH1 promoter and the ENO1 terminator region was obtained by setting up a PCR reaction with 10 ng of each of the two PCR products with oligonucleotides:

```
PGAP-SbfI:
5'-TAT ATA CCT GCA GGT TAC CCA GTG GTA CCT ACA
TAC-3' (including a SbfI-recognition sequence
at the 5' end)

TENO-fw-SbfI:
5'-TAT ATA CCT GCA GGT TAT AAC GGT TGG GCA
ATG TTG AG-3' (including a SbfI-recognition
sequence at the 5' end).
```

Using this procedure a 1.8 kbp PCR product could be obtained. The fragment was purified using the QIAquick PCR Purification Kit according to the instructions of the manufacturer. Then the PCR product was subjected to digestion with the restriction endonuclease SbfI (according to the instructions of the manufacturer of the restriction endonuclease: New England Biolabs, Schwalbach, Germany) and ligated into SbfI cut vector pDB007 to generate vector pPC-DES1-mCER. The orientation and authenticity of the insert was determined by DNA sequencing. Ligation, preparation and transformation of chemically competent *Escherichia coli* cells were performed by methods known to the skilled person.

To replace the cycloheximide resistance cassette by a nourseothricin resistance cassette the vector pPC-DES1-mCER was subjected to digest by SacI and SalI (according to the instructions of the manufacturer of the restriction endonuclease: New England Biolabs, Schwalbach, Germany). The 7403 bp vector backbone without the cycloheximide-resistance cassette was gel-purified using the QIAquick Gel Extraction Kit according to the instructions of the manufacturer.

To generate the nourseothricin conferring resistance cassette, three fragments were amplified by PCR. First, a codon-optimized form of the nat1 gene conferring resistance to nourseothricin and optimized for expression in *Pichia ciferrii* (SEQ ID NO:29) was amplified with vector pPCR-Script-nat1 as template which was supplied by Geneart GmbH (Regensburg, Germany) using oligonucleotides:

```
opt-nat1-fw:
5'-CAA AAT CAA CTT TAT TAT CAA TGG GTA CTA CTT TAG
ATG ATA C-3' (including a 23 base sequence at the
5' end complementary to the oligonucleotide
PPDA-rv)
``` opt-nat1-rv:
5'-TCT TTT TAT TGT CAG TAC TGA TTA TTA TGG ACA TGG
CAT TGA C-3' (including a 21 base sequence at the
5' end complementary to the oligonucleotide
T-TEF-fw).

Accordingly the promoter region of the pyruvate dehydrogenase subunit A gene of *Pichia ciferrii* (PDA1) (SEQ ID NO:27) was amplified with the following oligonucleotides:

PPDA-SalI-fw:
5'-TAT GTC GAC TGT GCT CTA AAT TTG CCC
GGT TC-3' (including a SalI-recognition sequence
at the 5' end)

PPDA-rv:
5'-CAT TGA TAA TAA AGT TGA TTT TGA AGT TTG GAA AGT
AGT TTC-3'.

The fragments were purified using the QIAquick PCR Purification Kit according to the instructions of the manufacturer. Finally, a fusion of the codon-optimized gene and the PDA1 promoter region, was obtained by setting up a PCR reaction with 10 ng of each of the two PCR products comprising the nat9 gene and the PDA1 promoter region of *Pichia ciferrii* with oligonucleotides:

PPDA-SalI-fw:
5'-TAT GTC GAC TGT GCT CTA AAT TTG CCC
GGT TC-3' (including a SalI-recognition sequence
at the 5' end)

opt-nat1-rv:
5'-TCT TTT TAT TGT CAG TAC TGA TTA TTA TGG ACA TGG
CAT TGA C-3' (including a 21 base sequence at the
5' end complementary to the oligonucleotide
T-TEF-fw).

Using this procedure a 1.3 kbp PCR product could be obtained. The fragment was purified using the QIAquick PCR Purification Kit according to the instructions of the manufacturer.

To fuse the *Ashbya gossypii* TEF terminator region with the previously amplified construct, the *Ashbya gossypii* TEF terminator region (GenBank accession #A29820) was amplified using 200 ng of chromosomal DNA of *Ashbya gossypii* ATCC 19895 as template using the following oligonucleotides:

T-TEF-fw:
5'-TCA GTA CTG ACA ATA AAA AGA TTC TTG-3'

T-TEF-SacI-rv:
5'-TGA GCT CTC GAC ACT GGA TGG CGG CGT TAG-3'
(including a SacI-recognition sequence at the
5' end).

The fragment was purified using the QIAquick PCR Purification Kit according to the instructions of the manufacturer. Finally, a fusion of the nat1 gene under control of the *Pichia ciferrii* PDA1 promoter and the *Ashbya gossypii* TEF terminator region was obtained by setting up a PCR reaction with 10 ng of each of the two PCR products with oligonucleotides:

PPDA-SalI-fw:
5'-TAT GTC GAC TGT GCT CTA AAT TTG CCC GGT TC-3'
(including a SalI-recognition sequence at the
5' end)

T-TEF-SacI-rv:
5'-TGA GCT CTC GAC ACT GGA TGG CGG CGT TAG-3'
(including a SacI-recognition sequence at the
5' end).

The resulting 1.5 kbp fragment was purified using the QIAquick PCR Purification Kit according to the instructions of the manufacturer. Then the PCR product was subjected to digestion with the restriction endonucleases SalI and SacI (according to the instructions of the manufacturer of the restriction endonuclease: New England Biolabs, Schwalbach, Germany) and ligated into the 7403 bp vector backbone of vector pPC-DES1-mCER (see above) to generate vector p-PC-DES1-mCER-nat1. The orientation and authenticity of the insert was determined by DNA sequencing. Ligation, preparation and transformation of chemically competent *Escherichia coli* cells were performed by methods known to the skilled person.

To replace the mCER gene by a codon-optimized form of the gene (omCER), optimized for expression in *Pichia ciferrii*, the vector pPC-DES1-mCER-nail was subjected to digestion with PacI and BsiWI (according to the instructions of the manufacturer of the restriction endonuclease: New England Biolabs, Schwalbach, Germany). The 5514 bp vector backbone without the mCER and DES1 genes was gel-purified using the QIAquick Gel Extraction Kit according to the instructions of the manufacturer.

To introduce the omCER gene of *Mus musculus* with the terminator region of the ENO1 gene of *Pichia ciferrii* the omCER gene (SEC) ID NO:30) was amplified using vector pUC-kana-mCER, supplied by Geneart GmbH (Regensburg, Germany) as template for a PCR reaction with the following oligonucleotides:

opt-mCER-PacI-fw:
5'-GGT ACC TTA ATT AAC AAT GCA TG-3' (including
a PacI-recognition sequence at the 5' end)

opt-mCER-rv:
5'-AGG AAA GCA CCG AAG CTA AAT TTA ACA ATT TTT
ATC ATT TTC-3' (including a 21 base sequence
at the 5' end complementary to the oligonucleotide
TENO-fw-).

Accordingly the terminator region of the *Pichia ciferrii* ENO1 (SEQ ID NO:28) gene was amplified with the following oligonucleotides:

TENO-fw:
5'-ATT TAG CTT CGG TGC TTT CCT ATA TAA CG-3'

T-ENO-BsiWI-rv:
5'-TAC GTA CGT TAT AAC GGT TGG GCA ATG
TTG-3' (including a BsiWI-
recognition sequence at the 5' end).

The fragments were purified using the QIAquick PCR Purification Kit according to the instructions of the manufacturer. Finally, a fusion of the omCER gene and the ENO1 terminator region was obtained by setting up a PCR reaction with 10 ng of each of the two PCR products comprising the codon-optimized form of the *Mus musculus* CER gene and the ENO1 terminator region of *Pichia ciferrii* with oligonucleotides:

```
opt-mCER-PacI-fw:
5'-GGT ACC TTA ATT AAC AAT GCA TG-3' (including
a PacI-recognition sequence at the 5' end)

T-ENO-BsiWI-rv:
5'-TAC GTA CGT TAT AAC GGT TGG GCA ATG TTG-3'
(including a BsiWI-recognition sequence at
the 5' end).
```

Using this procedure a 1.2 kbp PCR product could be obtained. The fragment was purified using the QIAquick PCR Purification Kit according to the instructions of the manufacturer. Then the PCR product was subjected to digestion with the restriction endonucleases PacI and BsiWI (according to the instructions of the manufacturer of the restriction endonuclease: New England Biolabs, Schwalbach, Germany) and ligated into the 5514 bp backbone of vector pPC-DES1-mCER-nat1 (see above) to generate vector p-mCER-nat1. The orientation and authenticity of the insert was determined by DNA sequencing. Ligation, preparation and transformation of chemically competent *Escherichia coli* cells were performed by methods known to the skilled person.

For the construction of a vector overexpressing omCER and a second gene under control of the TDH1 promoter (GenBank accession # AF053300) and ENO1 (SEQ ID NO:28) terminator region of *Pichia ciferrii*, the TDH1 promoter was amplified first with chromosomal DNA of *Pichia ciferrii* F-60-10A NRRL 1031 as template using oligonucleotides:

```
GAPDH-SpeI-fw:
5'-TAT ATA ACT AGT TTA CCC AGT GGT ACC TAC
ATA C-3' (including a SpeI-recognition sequence
at the 5' end)

GAPDH-CO-rv:
5'-CCC GGG ATT TAA ATG GCG CGC CGT TAA TTA
ATT ATT TGT TTG TTT GTT TG-3' (including a 22 base
sequence at the 5' end complementary to the
oligonucleotide ENO-CO-fw-).
```

Accordingly, the terminator region of the ENO1 gene of *Pichia ciferrii* was amplified with the following oligonucleotides:

```
ENO-CO-fw:
5'-GGC GCG CCA TTT AAA TCC CGG GAT TTA GCT TCG
GTG CTT TCC TA-3'

ENO-SpeI-rv:
5'-TAT ATA CCG CGG TTA TAA CGG TTG GGC AAT GTT
G-3' (including a SpeI-recognition sequence at
the 5' end).
```

The fragments were purified using the QIAquick PCR Purification Kit according to the instructions of the manufacturer. Finally, a fusion of the two fragments was obtained by setting up a PCR reaction with 10 ng of each of the two PCR products with oligonucleotides:

```
GAPDH-SpeI-fw:
5'-TAT ATA ACT AGT TTA CCC AGT GGT ACC TAC ATA
C-3' (including a SpeI-recognition sequence at
the 5' end)

ENO-SpeI-rv:
5'-TAT ATA CCG CGG TTA TAA CGG TTG GGC AAT GTT
G-3' (including a SpeI-recognition sequence at
the 5' end).
```

A 0.9 kbp PCR product could be obtained herewith. The fragment was purified using the QIAquick PCR Purification Kit according to the instructions of the manufacturer. Then the PCR product was subjected to digestion with the restriction endonuclease SpeI (according to the instructions of the manufacturer of the restriction endonuclease: New England Biolabs, Schwalbach, Germany) and ligated into SpeI cut vector p-mCER-nat1 to generate vector p-mCER-nat1-X-B, where the *Pichia ciferrii* TDH1 promoter is divergently oriented to the nat1 expression cassette. The orientation and authenticity of the insert was determined by DNA sequencing. Ligation, preparation and transformation of chemically competent *Escherichia coli* cells were performed by methods known to the skilled person.

To finally insert the LAF1 gene of *Pichia ciferri* (SEQ ID NO:3) into the omCER carrying vector p-mCER-nat1-X-B the LAF1 gene (SEQ ID NO:3) was amplified with chromosomal DNA of *Pichia ciferrii* F-60-10A NRRL 1031 as template using oligonucleotides:

```
PcLAF1-HpaI-fw:
5'-TAT ATA GTT AAC ATG ATT TCA ACT TCA ACA AAT
TC-3' (including a HpaI-recognition sequence at
the 5' end)

PcLAF1-XmaI-rv:
5'-TAT ATA CCC GGG CTA ATC ATC ATC TTC ATC
ATC-3' (including a XmaI-recognition sequence
at the 5' end).
```

The fragment was purified using the QIAquick PCR Purification Kit according to the instructions of the manufacturer. Then the PCR product was subjected to digestion with the restriction endonucleases HpaI and XmaI (according to the instructions of the manufacturer of the restriction endonuclease: New England Biolabs, Schwalbach, Germany) and ligated into vector p-mCER-nat1-X-B cut with AscI (according to the instructions of the manufacturer of the restriction endonuclease: New England Biolabs, Schwalbach, Germany), followed by Klenow fill-in with Klenow fragment of DNA Polymerase I (according to the instructions of the manufacturer: New England Biolabs, Schwalbach, Germany) and digestion with XmaI (according to the instructions of the manufacturer of the restriction endonuclease: New England Biolabs, Schwalbach, Germany), creating vector p-mCER-nat1-PcLAF1, which is shown in FIG. 12. The orientation and authenticity of the insert was determined by DNA sequencing. Ligation, preparation and transformation of chemically competent *Escherichia coli* cells were performed by methods known to the skilled person.

The vector p-mCER-nat1-PcLAF1 was linearized with PmeI (according to the instructions of the manufacturer of the restriction endonuclease: New England Biolabs, Schwalbach, Germany) and then purified using the QIAquick PCR Purification Kit according to the instructions of the manufacturer prior to transformation in syringomycinE-resistant *Pichia ciferrii* mutants.

Example 11

Construction of Plasmids for Simultaneous Overproduction of the Enzymes Des1p and Lag1p of *Pichia ciferrii*, Laf1p and Lag1p of *Ashbya gossypii*, as well as an Alkaline Ceramidase of Mouse in syringomycinE-Resistant *Pichia ciferrii* Mutants For overexpression of Des1p of *Pichia ciferrii* and Laf1p and Lag1p of *Ashbya gossypii* vector pPC-DES1-AgLAF1-

AgLAG1 was used (see example 11). Additionally, a vector for overexpression of the omCER gene and Lag1p of *Pichia ciferrii* was constructed.

To that end, the LAG1 gene of *Pichia ciferrii* (SEQ ID NO:1) was inserted into the omCER carrying vector p-mCER-nat1-X-B (see example 11). First, the LAG1 (SEQ ID NO:1) gene was amplified with chromosomal DNA of *Pichia ciferrii* F-60-10A NRRL 1031 as template using oligonucleotides:

```
PcLAG1-EcoRV-fw:
5'-TAT ATA GAT ATC ATG TCC ACT TCC AGA CCA
CAG-3' (including a EcoRV-recognition sequence
at the 5' end)

PcLAG1-XmaI-rv:
5'-TAT ATA CCC GGG TTA TTC ACT CTT TTT TTC
TTG-3' (including a XmaI-recognition sequence
at the 5' end).
```

The fragment was purified using the QIAquick PCR Purification Kit according to the instructions of the manufacturer. Then the PCR product was subjected to digestion with the restriction endonucleases EcoRV and XmaI (according to the instructions of the manufacturer of the restriction endonuclease: New England Biolabs, Schwalbach, Germany) and ligated into vector p-mCER-nat1-X-B cut with AscI (according to the instructions of the manufacturer of the restriction endonuclease: New England Biolabs, Schwalbach, Germany), followed by Klenow fill-in with Klenow fragment of DNA Polymerase I (according to the instructions of the manufacturer: New England Biolabs, Schwalbach, Germany) and digestion with XmaI (according to the instructions of the manufacturer of the restriction endonuclease: New England Biolabs, Schwalbach, Germany), creating vector p-mCER-nat1-PcLAG1, which is shown in FIG. 13. The orientation and authenticity of the insert was determined by DNA sequencing. Ligation, preparation and transformation of chemically competent *Escherichia coli* cells were performed by methods known to the skilled person.

The vector p-mCER-nat1-PcLAG1 was linearized with PmeI (according to the instructions of the manufacturer of the restriction endonuclease: New England Biolabs, Schwalbach, Germany) and then purified using the QIAquick PCR Purification Kit according to the instructions of the manufacturer prior to transformation in syringomycinE-resistant *Pichia ciferrii* mutants.

Example 12

Construction of Plasmids for Simultaneous Overproduction of the Enzymes Des1p of *Pichia ciferrii*, Laf1p and Lag1p of *Ashbya gossypii*, a Codon-Optimized Form of an Alkaline Ceramidase of Mouse, as Well as a Codon-Optimized Form of a Ceramide Synthase of Coccolithovirus in syrineomycinE-Resistant *Pichia ciferrii* Mutants For overexpression of Des1p of *Pichia ciferrii* and Laf1p and Lag1p of *Ashbya gossypii* vector pPC-DES1-AgLAF1-AgLAG1 was used (see example 10). Additionally, a vector for overexpression of the omCER gene and the codon-optimized gene encoding a ceramide synthase of Coccolithovirus (oCvLAG1) and optimized for expression in *Pichia ciferrii* was constructed.

To that end, the oCvLAG1 gene of Coccolithovirus (SEQ ID NO:31) was inserted into the omCER carrying vector p-mCER-nat1-X-B (see example 11). First, the oCvLAG1 gene (SEQ ID NO:31) was cut out of the vector pGΔ4-CV-LAG1, supplied by Geneart GmbH (Regensburg, Germany) with restriction endonucleases HpaI and XmaI (according to the instructions of the manufacturer of the restriction endonuclease: New England Biolabs, Schwalbach, Germany) and ligated into vector p-mCER-nat1-X-B cut with SwaI and XmaI (according to the instructions of the manufacturer of the restriction endonuclease: New England Biolabs, Schwalbach, Germany), creating vector p-mCER-nat1-oCvLAG1, which is shown in FIG. 14. The orientation and authenticity of the insert was determined by DNA sequencing. Ligation, preparation and transformation of chemically competent *Escherichia coli* cells were performed by methods known to the skilled person.

The vector p-mCER-nat1-oCvLAG1 was linearized with PmeI (according to the instructions of the manufacturer of the restriction endonuclease: New England Biolabs, is Schwalbach, Germany) and then purified using the QIAquick PCR Purification Kit according to the instructions of the manufacturer prior to transformation in syringomycinE-resistant *Pichia ciferrii* mutants.

Example 13

Construction of Plasmids for Simultaneous Overproduction of the Enzymes Des1p of *Pichia ciferrii*, Laf1p and Lag1p of *Ashbya gossypii*, a Codon-Optimized Form of an Alkaline Ceramidase of Mouse, as Well as a Codon-Optimized Form of a Ceramide Synthase of Mouse in syringomycinE-Resistant *Pichia ciferrii* Mutants For overexpression of Des1p of *Pichia ciferrii* and Laf1p and Lag1p of *Ashbya gossypii* vector pPC-DES1-AgLAF1-AgLAG1 was used (see example 10). Additionally a vector for overexpression of omCER gene and codon-optimized ceramide synthase of mouse (omLASS5) was constructed.

To that end, the omLASS5 gene of mouse (SEQ ID NO:32) was inserted into the omCER carrying vector p-mCER-nat1-X-B (see example 11). First, the omLASS5 gene (SEQ ID NO:32) was cut out of the vector pUK-kana-omLASS5, supplied by Geneart GmbH (Regensburg, Germany) with restriction endonucleases HpaI and XmaI (according to the instructions of the manufacturer of the restriction endonuclease: New England Biolabs, Schwalbach, Germany) and ligated into vector p-mCER-nat1-X-B cut with AscI (according to the instructions of the manufacturer of the restriction endonuclease: New England Biolabs, Schwalbach, Germany), followed by Klenow fill-in with Klenow fragment of DNA Polymerase I (according to the instructions of the manufacturer: New England Biolabs, Schwalbach, Germany) and digestion with XmaI (according to the instructions of the manufacturer of the restriction endonuclease: New England Biolabs, Schwalbach, Germany), creating vector p-mCER-nat1-omLASS5, which is shown in FIG. 15. The orientation and authenticity of the insert was determined by DNA sequencing. Ligation, preparation and transformation of chemically competent *Escherichia coli* cells were performed by methods known to the skilled person.

The vector p-mCER-nat1-omLASS5 was linearized with PmeI (according to the instructions of the manufacturer of the restriction endonuclease: New England Biolabs, Schwalbach, Germany) and then purified using the QIAquick PCR Purification Kit according to the instructions of the manufacturer prior to transformation in syringomycinE-resistant *Pichia ciferrii* mutants.

Example 14

Transformation of syringomycinE-Resistant *Pichia ciferrii* Mutants

Transformation of syringomycinE-resistant *Pichia ciferrii* mutants was performed as described recently (Bae et at., Integrative transformation system for the metabolic engineering of the sphingoid base-producing yeast *Pichia ciferrii*. 2003. Appl Environ Microbiol.; U.S. Pat. No. 6,638,735).

A syringomycinE-resistant *Pichia ciferrii* strain (SYR21-2C from WO2006/048458, FIG. 4) was grown in YPD medium to an optical density at 600 nm of 1 to 1.5. The cells were harvested by centrifugation and resuspended in 0.1 culture volume of 50 mM phosphate buffer (pH 7.5) to which 25 mM dithiothreitol had been added prior to use. After incubation at 37° C. for 15 min, the cells were washed twice with one culture volume of ice-cold stabilization solution [270 mM sucrose, 10 mM Tris-HCl (pH 7.5), 1 mM $MgCl_2$] and resuspended in 0.01 culture volume of stabilization solution. 5 µl of linearized vectors pPC-DES1-AgLAF1-AgLAG1, p-mCER-nat1-PcLAF1, p-mCER-nat1-PcLAG1, p-mCER-nail-oCvLAG1 or p-mCER-nat1-omLASS5 (containing 1.6 µg DNA) were mixed with 50 µl of cells and incubated on ice for 10 min. Then the transformation mixture was transferred to a 2 mm electroporation cuvette. Electroporation was performed with a GenePulser Xcell (Bio-Rad Laboratories, München, Germany) at 500 V, 50 µF and 700Ω according to the instructions of the manufacturer. After electroporation the cells were resuspended in 500 µl of stabilization solution and transferred to a culture tube containing 2 ml YPD medium. After regeneration of cells overnight at 30° C. and 250 rotations per minute, aliquots of the regeneration culture were plated on YPD plates with 0.5 µg cycloheximide per ml (pPC-DES1-AgLAF1-AgLAG1) or 0.5 µg cycloheximide per ml and 50 µg/ml nourseothricin (strains already containing pPC-DES1-AgLAF1-AgLAG1 and transformed with p-mCER-nat1-PcLAF1, p-mCER-nat1-PcLAG1, p-mCER-nail-oCvLAG1 or p-mCER-nat1-omLASS5). After seven days of incubation at 30° C. several dozen colonies appeared.

Example 15

Shake Flask Production of Acetylated Sphingosine by syringomycinE Resistant *Pichia ciferrii* Mutants Overexpressing Sphingoid Base Biosynthesic Genes In order to test for increased production of acetylated sphingosine by syringomycinE-resistant mutants overexpressing the above mentioned genes (PcDES1, AgLAF1, AgLAG1 alone or in combination with omCER, moreover, in combination with PcLAF1, PcLAG1, oCvLAG1 or omLASS5) the corresponding strains were cultivated for shake flask production of acetylated sphingosine (see Table 3 for corresponding plasmids).

To that end, the strains was inoculated as a pre-culture in 5 ml YPD medium (in a test tube) at 30° C. and 250 rotations per minute for 3 days. Subsequently, 1% of the preculture was used to inoculate 20 ml TAPS-Medium (in a 100 ml Erlenmeyer flask with baffles) and grown at 30° C. and 250 rotations per minute for 4 days.

TABLE 1

Composition of TAPS medium

| Component | Formula | per liter |
|---|---|---|
| Yeast extract | — | 1.0 g |
| Dextrose | $C_6H_{12}O_6$•1aq | 33 g |
| Magnesium sulfate•7aq | $MgSO_4$•$7H_2O$ | 0.88 g |

TABLE 1-continued

Composition of TAPS medium

| Component | Formula | per liter |
|---|---|---|
| Calcium chloride•2aq | $CaCl_2$•$2H_2O$ | 0.20 g |
| Ammonium chloride | $NH_4Cl$ | 4.83 g |
| Sodium chloride | NaCl | 0.06 g |
| Potassium dihydrogen phosphate | $KH_2PO_4$ | 1.0 g |
| Potassium dihydrogen phthalate | $KH_2C_8H_4O_4$ | 20 g |
| myo-Inositol | $C_6H_{12}O_6$ | 0.059 g |
| Trace elements | Sol. A | 0.30 ml |
| Vitamin solution | Sol. B | 1.00 ml |

TABLE 2

Composition of trace element and vitamins stock solutions

| Trace elements | Solution A (g/L) |
|---|---|
| $(NH_4)_2Fe(SO_4)_2$ | 0.027 g |
| $ZnSO_4$•$7H_2O$ | 0.005 g |
| $CuSO_4$•$5H_2O$ | 0.0075 g |
| $MnSO_4$•$1H_2O$ | 0.0006 g |
| $H_3BO_3$ | 0.0006 g |
| $NaMoO_4$•$2H_2O$ | 0.0006 g |
| KI | 0.0015 g |

| Vitamine solution | Solution B |
|---|---|
| Nicotinic acid | 0.003 g |
| Calcium-D pantothenaat | 0.003 g |
| Thiamin (vitamin B1) | 0.003 g |
| p-aminobenzoic acid | 0.002 g |
| Pyridoxin (vitamin B6) | 0.0003 g |
| d-Biotin | 0.00001 g |

Example 16

Quantification of Aceylated Sphingoid Bases in the Cultivation Broth

In order to extract the lipids, 4 ml of acetone was added to 1 ml of unfractionated broth in a 15 ml falcon tube, and shaken horizontally for 10 minutes at room temperature and 250 rotations per minutes. The mixture was then centrifuged at 5.300 g for 10 minutes, and the supernatant analysed on a Jasco HPLC system (LC-2000 series). The following conditions were applied:

| | |
|---|---|
| Mobile phase: | acetonitrile/water 90:10 (v/v) with 0.05% (v/v) trifluoric acid (TFA) |
| Flow rate: | 1.0 ml/min |
| Run time: | 11 min |
| Injection volume: | 100 µl |
| Column: | Kromasil 100 C18 (250 × 4.6 mm, particle size 5 µm) |
| Column temperature: | 30° C. |
| Tray temperature: | ambient |
| UV detection wave length: | 200 nm |

Identification of acetylated bases was done by comparison of retention time and UV spectrum with defined reference substances (DSM, Delft), quantification accordingly by comparison of the peak area of the sample and the reference substance.

The shake flask production of acetylated sphingoid bases by syringomycinE resistant *Pichia ciferrii* mutants overexpressing the above mentioned genes is summarized in Table 3. Concentrations are given in mg per g biomass dry weight.

TABLE 3

Triacetylated sphingoid base amounts of genetically engineered *Pichia ciferrii* strains.

| Plasmids | Overexpressed genes | TriASo | TriASa | total |
|---|---|---|---|---|
| pPC-DES1-AgLAF1-AgLAG1 | PcDES1, AgLAF1, AgLAG1 | 0.5 | 53.7 | 54.2 |
| pPC-DES1-AgLAF1-AgLAG1 p-mCER-nat1 | PcDES1, AgLAF1, AgLAG1, omCER | 1.4 | 43.3 | 44.7 |
| pPC-DES1-AgLAF1-AgLAG1 p-mCER-nat1-PcLAF1 | PcDES1, AgLAF1, AgLAG1, omCER, PcLAF1 | 3.1 | 29.0 | 32.1 |
| pPC-DES1-AgLAF1-AgLAG1 p-mCER-nat1-PcLAG1 | PcDES1, AgLAF1, AgLAG1, omCER, PcLAG1 | 2.2 | 63.0 | 65.2 |
| pPC-DES1-AgLAF1-AgLAG1 p-mCER-nat1-oCvLAG1 | PcDES1, AgLAF1, AgLAG1, omCER, oCvLAF1 | 5.3 | 25.7 | 31.0 |
| pPC-DES1-AgLAF1-AgLAG1 p-mCER-nat1-omLASS5 | PcDES1, AgLAF1, AgLAG1, omCER, omLASS5 | 3.0 | 42.2 | 45.2 |

Concentrations are given in mg per g biomass dry weight.

Example 17

Inactivation of the Sphingolipid Δ8-Desaturase-Encoding Gene in syringomycinE-Resistant *Pichia ciferrii* Strains and Simultaneous Overproduction of the Enzymes Des1p of *Pichia ciferrii*, a Codon-Optimized Form of an Alkaline Ceramidase of Mouse, as Well as a Codon-Optimized Form of a Ceramide Synthase of Coccolithovirus

*Pichia ciferrii* harbours a gene encoding an enzyme with high similarity to a sphingolipid Δ8-desaturase from *Kluyveromyces lactis* (see Example 8) known to introduce a double bond between C-8 and C-9 of sphingoid bases (Takakuwa et al., Current Microbiology, 45:459-61). Therefore, the activity of this enzyme might be counterproductive for sphingosine production, as introduction of such a double bond into dihydrosphingosine, be it as free sphingoid base or as a component of dihydroceramide, would result in competition with (a) common precursor(s) for sphingosine formation. To combine overexpression of the above-mentioned sphingolipid biosynthesis genes with inactivation of the *Pichia ciferrii* sphingolipid Δ8-desaturase-encoding gene 8DES, first, the nat1 gene in vector p-mCER-nat1-oCvLAG1 (see example 12) was replaced by the *Pichia ciferrii* PcL41 gene obtained from vector pDB006 containing a point mutation at aa position 56, that allows *Pichia ciferrii* to grow in presence of the antibiotic cycloheximide. To that end, vector pTH-GAP-nat1-IS2-Pme1 (see example 10) was digested with the restriction endonucleases SacI and SalI, and the 3448 bp fragment gel-purified using the QIAGEN QIAquick Gel Extraction Kit. In order to obtain the PcL41 gene (GenBank accession # AF053457) and introduce the desired point mutation, two fragments were amplified with PCR using chromosomal DNA of *Pichia ciferrii* F-60-10A NRRL 1031 as template. Fragment 1 was amplified using the following oligonucleotides:

```
PcL41-SalI-fw:
5'-TATAGTCGACGAATTCTCTTAAATGATGTTGG-3' (including
a SalI recognition sequence at the 5'-end)

PcL41-internal-rv:
5'-GTTTTAGCTTTTTTATGGAAAACTtGTTTGGTTTGACCACCGTAA
CCGG-3'
``` generating a 1222 bp fragment including a 49 bp sequence complementary to the oligonucleotides PcL41-internal-fw, inserting a point mutation from C to A replacing aa 56 from proline by glutamine. Fragment 2 was amplified using the following oligonucleotides:

```
PcL41-internal-fw:
5'-
CCGGTTACGGTGGTCAAACCAAACaAGTTTTCCATAAAAAAGCTAAAACT
ACCA AAAAAGTTGTTTTACG-3'

PcL41-SacI-rv:
5'-TATAGAGCTCAATTCCAATGTTTTGATCTGTC-3' (including
a SacI recognition sequence at the 5'-end)
``` generating a 753 bp fragment including a 49 bp sequence complementary to the oligonucleotides PcL41-internal-rv, inserting a point mutation (C to A) replacing aa 56 from proline to glutamine. The two fragments were gel-purified using the QIAGEN MinElute Gel Extraction Kit. A crossover PCR was performed with 2 μl of each fragment as template, as well as the oligonucleotides PcL41-SalI-fw and PcL41-SacI-rv (see above). A 1906 bp fragment with a SalI- and SacI-restriction site at its ends was created herewith. The fragment was then digested with Sail and SacI, purified using the QIAGEN MinElute PCR Purification Kit, and ligated into the 3448 bp backbone of pTH-GAP-nat1-IS2-PmeI. Ligation, preparation and transformation of chemically competent *Escherichia coli* cells as well as verifying the presence of the desired plasmid was performed by methods known to the skilled person. The obtained plasmid was named pDB006.

The plasmid p-mCER-nat1-oCvLAG1 was digested with the restriction endonucleases PstI and SacI (according to the instructions of the manufacturer: New England Biolabs, Schwalbach, Germany), and the 6997 bp fragment gel-purified using the QIAGEN QIAquick Gel Extraction Kit. The insert PcL41 was obtained by digestion of pDB006 with PstI and SacI, the 1918 bp fragment gel-purified analogously, and then ligated into the vector. Ligation, preparation and transformation of chemically competent *Escherichia coli* cells as well as verifying the presence of the desired plasmid was performed by methods known to the skilled person. In the course of this verification it became obvious, that the SacI restriction site used for the cloning procedure was no longer present in the resulting plasmid named p-mCER-LP-PcvL41-oCvLAG1. Therefore, the whole insert and the neighbouring regions were sequenced to verify the authenticity. It could be confirmed, that possibly due to star activity of Sad the vector p-mCER-nat1-oCvLAG1 was not cut at the recognition sequence GAGCTC, but at the sequence GAGCTT instead, within the enolase terminator region that belongs to the gene oCvLAG1. Consequently, the Sad recognition site was no longer present after ligation, and the termiator was shortened to 211 bp instead of 332 bp. The fact was considered as not relevant, and the vector used for the next step, the introduction of the *Pichia ciferrii* DES1 gene (SEQ ID NO:26). It was amplified via PCR using the following oligonucleotides:

```
PcDES1-PstI-fw:
5'-TATATACTGCAGTTACCCAGTGGTACCTACATAC-3'
(including a PstI recognition sequence at
the 5'-end)

PcDES1-PstI-rv (5'-TATATACTGCAGTTATAACGGTTGGGC
AATG-3' (including a PstI recognition sequence
at the 5'-end)
``` and chromosomal DNA of *Pichia ciferrii* F-60-10A NRRL 1031 as template. The resulting 1983 bp fragment was gel-purified as described above, digested with the restriction endonuclease PstI, and PCR purified using the QIAGEN QIAquick PCR Purification Kit. The vector p-mCER-LP-PcvL41-oCvLAG1 was cut and purified likewise. Ligation, preparation and transformation of chemically competent *Escherichia coli* cells as well as verifying the presence of the desired plasmid was performed by methods known to the skilled person. The plasmid obtained by applying this method was named pTH-LP-1. The orientation and authenticity of the insert was determined by DNA sequencing.

An internal region of the *Pichia ciferrii* sphingolipid Δ8-desaturase-encoding gene (SEQ ID NO:5) was amplified with PCR using chromosomal DNA of *Pichia ciferrii* F-60-10A NRRL 1031 as template and the following oligonucleotides:

```
PcD8D-PshAI-fw:
5'-TATATAGACAAAAGTCCAGTTCCAAAGTGCTC-3'
(including a PshAI recognition sequence at
the 5'-end)

PcD8D-BsiWI-rv:
5'-TATATACGTACGAAAATTGCACTAAGGAAATAC-3'
(including a BsiWI recognition site at the 5'-end)
```

The 855 bp fragment was gel-purified using the QIAGEN MinElute Gel Extraction Kit, and then digested with the restriction endonucleases PshAI and BsiWI according to the instructions given by the manufacturer (New England Siolabs, Schwalbach, Germany). It was then purified using the QIAGEN MinElute PCR Purification Kit. The vector pTH-LP-1 was digested likewise, and the 9662 bp fragment gel-purified using the QIAGEN QIAquick Gel Extraction Kit. Ligation, preparation and transformation of chemically competent *Escherichia coli* cells as well as verifying the presence of the desired plasmid was performed by methods known to the skilled person. The plasmid obtained by applying this method was named pTH-deltaD8D, which is shown in FIG. 17. The orientation and authenticity of the insert was determined by DNA sequencing.

Example 18

Inactivation of the Alkaline Ceramidase-Encoding Gene in syringomycinE-Resistant *Pichia ciferrii* Strains and Simultaneous Overproduction of the Enzymes Des1p of *Pichia ciferrii*, a Codon-Optimized Form of an Alkaline Ceramidase of Mouse, as Well as a Codon-Optimized Form of a Ceramide Synthase of Coccolithovirus

*Pichia ciferrii* harbours a gene encoding an enzyme with high similarity to an alkaline ceramidase from *S. cerevisiae* (see Example 7) known to preferentially hydrolyzing ceramides containing phytosphingosine or dihydrosphingosine, but not sphingosine, as sphingoid base (Mao et al., The Journal of Biological Chemistry, 275:31369-31378). Therefore, the activity of this enzyme might be counterproductive for sphingosine production, as ceramide containing dihydrosphingosine as sphingoid base is a precursor for sphingosine formation. To combine overexpression of the above-mentioned sphingolipid biosynthesis genes with inactivation of the *Pichia ciferrii* endogenous alkaline ceramidase gene YXC1, the intergenic spacer (IS)-region on plasmid pTH-deltaD8D (see example 17 and FIG. 17) was replaced by an internal region of the *Pichia ciferrii* ceramidase-encoding gene (SEQ ID NO: 8).

First, two internal, partially overlapping fragments of the *Pichia ciferrii* ceramidase-encoding gene (SEQ ID NO: 8) were amplified by PCR using chromosomal DNA of *Pichia ciferrii* F-60-10A NRRL 1031 as template and oligonucleotide pairs OTKD284/OTKD285 and OTKD286/OTKD287, respectively:

```
OTKD284:
5'-TAT ATA GAC AGA AGT CCA TAT CAT TTA CCA
TTT GCT AAA CC-3'
(underlined: PshAI recognition sequence)

OTKD285:
5'-TAA ATC TCA ATT CAC ACT GGT GCT AAA TTA TTT TTA
AAT GCA GA-3' (underlined: AleI recognition
sequence)

OTKD286:
5'-TAAAAATAATTTAGCACCAGTGTGAATTGAGATTTATATT
GATAAGTT-3' (underlined: AleI recognition
sequence)

OTKD287:
5'-TAT ATA CGT ACG CAA TAT TAT AGA AAT ACC AAT
TGT-3' (underlined: BsiWI recognition sequence)
```

The two partially overlapping fragments (239 and 236 bp, respectively) were gel-purified using the QIAGEN QIAquick Gel Extraction Kit. A crossover PCR was performed with 2 µl of each fragment as template, as well as the oligonucleotides OTKD284 and OTKD287 (see above). A 439 bp DNA fragment with single PshAI and BsiWI sites at its ends and a central AleI site was obtained. The fragment was digested with PshAI and BsiWI according to the instructions given by the manufacturer (New England Biolabs, Schwalbach, Germany). It was then purified using the QIAGEN PCR Purification Kit. The vector pTH-LP-1 was digested likewise, and the 9662 bp fragment gel-purified using the QIAGEN QIAquick Gel Extraction Kit. Ligation of the two fragments, preparation and transformation of chemically competent *Escherichia coli* cells as well as verifying the presence of the desired plasmid was performed by methods known to the skilled person. The plasmid obtained by applying this method was named pSo-5, which is shown in FIG. 18. The orientation and authenticity of the insert was determined by DNA sequencing.

Example 19

Shake Flask Production of Acetylated Sphingoid Bases by syrinqomycinE Resistant *Pichia ciferrii* Mutants Overexpressing Sphingoid Base Biosynthesic Genes and Quantification of Acetylated Sphingoid Bases in the Cultivation Broth Transformation of a syringomycinE-resistant *Pichia ciferrii* strains with the plasmids of Examples 17 and 18, after digestion of pSo-5 with AleI, was done as described in example 14. Shake flask production of acetylated sphingoid bases by syringomycinE resistant *Pichia ciferrii* mutants was done as described in example 15, detection and quantification of acetylated sphingoid bases with RP-HPLC was done accordingly example 16.

The results are shown in Table 4. Strikingly, the amount of triacetylated sphingosine (TriASo) was markedly increased when a fragment of the *Pichia ciferrii* sphingolipid Δ8-desaturase-encoding gene was used as targeting sequence (pTH-deltaD8D) instead of the rDNA intergenic spacer (pTH-LP-1), which resulted in inactivation of *Pichia ciferrii* 8DES upon homologous integration of the plasmid pTH-deltaD8D into the chromosome. In addition, both the total amount of triacetylated sphingosine (TriASo) as well as the TriASo/TriASa ratio were markedly increased when a fragment of the *Pichia ciferrii* YXC1 alkaline ceramidase-encoding gene was used as targeting sequence (pSo-5) instead of the rDNA intergenic spacer (pTH-LP-1), which resulted in inactivation of *Pichia ciferrii* YXC1 upon homologous integration of the plasmid pSo-5 into the chromosome.

TABLE 4

Influence of plasmid-integration site on triacetylated sphingoid base-levels in genetically engineered *Pichia ciferrii* strains. Concentrations are given in mg per g biomass dry weight.

| Plasmid | Integration site | TriASo | TriASa | Total | Ratio TriASo/TriASa |
|---|---|---|---|---|---|
| pTH-LP-1 | Intergenic spacer (IS) | 21.66 | 59.47 | 81.13 | 0.36 |
| pTH-deltaD8D | Pc8DES | 33.45 | 69.90 | 103.35 | 0.48 |
| pSo-5 | PcYXC1 | 28.47 | 52.76 | 81.23 | 0.53 |

The invention claimed is:

1. A method to obtain a *Pichia ciferrii* strain that produces at least 0.5 mg per g cell dry weight of sphingosine and triacetylated sphingosine comprising
obtaining a syringomycinE-resistant *Pichia ciferrii* strain defective in dihydrosphingosine C-4 hydroxylase;
inactivating or deleting a genomic sphingolipid Δ8-desaturase (8DES) gene encoding a polypeptide comprising the amino acid sequence of SEQ ID NO:6 and/or inactivating a genomic alkaline ceramidase (YXC1) gene encoding a polypeptide comprising the amino acid sequence of SEQ ID NO:8 in the syringomycinE-resistant *Pichia ciferrii* strain defective in dihydrosphingosine C-4 hydroxylase;
increasing expression of
i) a polynucleotide encoding an enzyme having dihydroceramide-Δ4-desaturase activity and comprising the amino acid sequence of SEQ ID NO:17 or an amino acid sequence that has at least 90% identity to the amino acid sequence of SEQ ID NO:17,
ii) a polynucleotide encoding an enzyme having ceramidase activity, said ceramidase hydrolyzing sphingosine and triacetylated sphingosine, and comprising the amino acid sequence of SEQ ID NO:15 or an amino acid sequence that has at least 90% identity to the amino acid sequence of SEQ ID NO:15, and
iii) a polynucleotide encoding an enzyme having ceramide synthase activity and comprising the amino acid sequence of SEQ ID NO:2, 4, 9, 10, 12, or 14 or an amino acid sequence that has at least 90% identity to the amino acid sequence of SEQ ID NO:2, 4, 9, or 10,
wherein increasing expression is by transformation of the *Pichia ciferrii* strain with the polynucleotides and optionally integrating one or several copies of the polynucleotides into the chromosome of the *Pichia ciferrii* strain; and
isolating a *Pichia ciferrii* strain that produces at least 0.5 mg per g cell dry weight of sphingosine and triacetylated sphingosine.

2. The method according to claim 1 wherein inactivation or deletion of the genomic 8DES gene and inactivation or deletion of the genomic YXC1 gene comprises deletion of portions of the nucleotide sequence or deletion of the entire nucleotide sequence.

3. The method according to claim 1, wherein the enzyme having ceramide synthase activity is selected from the group consisting of:
a. a polypeptide with the amino acid sequence of SEQ ID NO:2 or SEQ ID NO:4,
b. a polypeptide with an amino acid sequence having at least 90% amino acid sequence identity to the amino acid sequence of SEQ ID NO:2 or at least 90% amino acid sequence identity to the amino acid sequence of SEQ ID NO:4,
c. a polypeptide with the amino acid sequence of SEQ ID NO:9,
d. a polypeptide with an amino acid sequence having at least 90% amino acid sequence identity to the amino acid of SEQ ID NO:9,
e. a polypeptide with the amino acid sequence of SEQ ID NO: 10, and
f. a polypeptide with an amino acid sequence having at least 90% amino acid sequence identity to the amino acid sequence of SEQ ID NO: 10.

4. The method according to claim 1, wherein the genomic 8DES gene comprises the nucleotide sequence of SEQ ID NO: 5.

5. The method according to claim 1, wherein the genomic alkaline ceramidase (YXC1) gene comprises the nucleotide sequence of SEQ ID NO:7.

6. The method according to claim 1, wherein the enzyme having dihydroceramide-Δ4-desaturase activity comprises the amino acid sequence of SEQ ID NO: 17.

7. The method according to claim 1, wherein increasing the expression is by transformation of the *Pichia ciferrii* strain with the polynucleotides.

8. A method to obtain an *Ashbya gossypii* strain that produces at least 0.5 mg per g cell dry weight of sphingosine and triacetylated sphingosine comprising inactivating or deleting a genomic sphinganine hydroxylase (SYR2) gene encoding a polypeptide having sphinganine hydroxylase activity, wherein the polypeptide having sphinganine hydroxylase activity is encoded by the polynucleotide of SEQ ID NO:23 and inactivating or deleting a genomic sphingolipid Δ8 desaturase (8DES) gene encoding a polypeptide comprising the amino acid sequence of SEQ ID NO:21 in a *Ashbya gossypii* strain;
increasing expression of
i) a polynucleotide encoding an enzyme having dihydroceramide-Δ4-desaturase activity and comprising the amino acid sequence of SEQ ID NO:16,
ii) a polynucleotide encoding an enzyme having ceramide synthase activity and comprising the amino acid sequence of SEQ ID NO:12 or 14,
wherein increasing expression is by transformation of the *Ashbya gossypii* strain with the polynucleotides and optionally integrating one or several copies of the polynucleotides into the chromosome of the *Ashbya gossypii* strain; and
isolating said *Ashbya gossypii* strain that produces at least 0.5 mg per g cell dry weight of sphingosine and triacetylated sphingosine.

9. The method according to claim 8, wherein inactivation or deletion of the genomic 8DES gene and inactivation or deletion of the genomic SYR2 gene comprises deletion of portions of the nucleotide sequence or deletion of the entire nucleotide sequence.

10. The method according to claim 8, wherein increasing expression is by transformation of the *Ashbya gossypii* strain with the polynucleotides.

* * * * *

SEQUENCE LISTING

<160> NUMBER OF SEQ ID NOS: 32

<210> SEQ ID NO 1
<211> LENGTH: 4952
<212> TYPE: DNA
<213> ORGANISM: Pichia ciferrii
<220> FEATURE:
<221> NAME/KEY: CDS
<222> LOCATION: (1261)..(2550)
<223> OTHER INFORMATION: Product: Pichia ciferrii ceramide synthase Lag1p

<400> SEQUENCE: 1

```
ccacctaatt caggtttaat tataatagtt tcttgatata attttttgaaa ttcatttgat      60 gataacaagt catcttgacc ttgattctgg gttaataaag ttaataattt ttcaacctttt     120 cttgattgat ttaatattaa agtttctttt tcaacttcta attttaattc ttcaggagtt     180
ggatcatata atggagttac ataattaaaa ggaaatataaac caatttctcc acgtaatgaa     240
cctttccccc aatctttata aacacgatct aatactgtaa ttatatcacc tttacggaaa     300
tgtaaatctg caggatcttg actaaatgaa tcatatagag cacggaccct agagaatgaa     360
ggttgtgctt ttgagattgg tggaggttgt tgaactggag cttgttgttg ttgttgctgt     420
tgttgctgtt gttgttgttg aatatcttgt tgagttggaa ttgaagcttg attattttca     480
cttagggata atgcaatagc agctttcaaa tcttcttctt ctttaatacg atcattatct     540
aaatttctct tttgaggttt atcaggaggg aaatattgtg aataaaactt ttccacctcg     600
ttattagcat cttggatagg tctcagtgaa ggatcatttg caaatgaatc agataattgt     660
ttgataactt ggacaatctt gattttaatt tccttatgta ctgtgggttc tcttaactta     720
ttcaacaata ttgaagtgaa tcctctagtg gcaatttcct gtttaactct tgaaccacaa     780
ttctcagcaa tcgaagtgag taaacttagt gatctcaatt gaacattagc atctctttga     840
cccaaccttg tggaaaccaa ttgaataact tgttttgaac cttcttccgg ttcttcacca     900
accaagtcac aaacatcaag aataaactgc caattgtccg ccaacaacgt cgcatccgtt     960
gccttctcca ctgcgttctt caactgttca ctataatctc tgaccatgat atcctgttga    1020
gcttctgtct aatctctgtc tagcttccct ttggcttccc tttggctccc ttcaactccc    1080
tttaaattta aatcaacgcc tcttttaaa acacgtaaaa gaattcgcga attttaacgg    1140
tttcggtttt ttttcaaata ggggaaattt aaaatttaaa tgaaaacatc aacaaaatga    1200
ttttaagtac tttgactatt cattggtttt aattgattgt tcagctggtt atttgtctca    1260
```

```
atg tcc act tcc aga cca cag ttc aac cgt cgc aga act tct tct gtc    1308
Met Ser Thr Ser Arg Pro Gln Phe Asn Arg Arg Arg Thr Ser Ser Val
1               5                   10                  15 ggc aaa atc gac ttg ggt gat aca aga gta cgt tca ttc tca act tca    1356
Gly Lys Ile Asp Leu Gly Asp Thr Arg Val Arg Ser Phe Ser Thr Ser
            20                  25                  30 cgt act tca cat caa aga aat gct tca gat tca aga gtt aat gaa tta    1404
Arg Thr Ser His Gln Arg Asn Ala Ser Asp Ser Arg Val Asn Glu Leu
        35                  40                  45 tca aat tat tcc aag act gat tta gaa att ata aca aaa att aaa act    1452
Ser Asn Tyr Ser Lys Thr Asp Leu Glu Ile Ile Thr Lys Ile Lys Thr
    50                  55                  60 ggt cta gtt gaa tta agt tat cgt cac aca tgg gct tta cct gct ttg    1500
Gly Leu Val Glu Leu Ser Tyr Arg His Thr Trp Ala Leu Pro Ala Leu
65              70                  75                  80 atc ttg tta att gtt tat act gct tat ttc act tca ggt aat tat aca    1548
Ile Leu Leu Ile Val Tyr Thr Ala Tyr Phe Thr Ser Gly Asn Tyr Thr
            85                  90                  95 gaa tca aat ttt tta cac atg ttt gta tca ata tca tat caa atc cct    1596
Glu Ser Asn Phe Leu His Met Phe Val Ser Ile Ser Tyr Gln Ile Pro
        100                 105                 110 ggt aca aat caa tat gat aaa ggt att aaa gat tta gca ttt gtg cta    1644
Gly Thr Asn Gln Tyr Asp Lys Gly Ile Lys Asp Leu Ala Phe Val Leu
    115                 120                 125 ttt tat atg att ttt ttc aca ttt ttc aga gaa ttt tgt atg gaa gtt    1692
Phe Tyr Met Ile Phe Phe Thr Phe Phe Arg Glu Phe Cys Met Glu Val
130                 135                 140 ata tta cgt ccc ctt gca cca att gtt ggt gtt aaa aaa cct tct aaa    1740
Ile Leu Arg Pro Leu Ala Pro Ile Val Gly Val Lys Lys Pro Ser Lys
145                 150                 155                 160 atc aag aga ttt atg gaa caa tct tat tct gtt att tat tct ggt tta    1788
Ile Lys Arg Phe Met Glu Gln Ser Tyr Ser Val Ile Tyr Ser Gly Leu
                165                 170                 175 tca ggt cct ttt ggt ctt tat gtt atg tat gga act gat tta tgg tta    1836
Ser Gly Pro Phe Gly Leu Tyr Val Met Tyr Gly Thr Asp Leu Trp Leu
            180                 185                 190 ttt aga act gat act atg tat gca aca tat cca gat tta aca aat gat    1884
Phe Arg Thr Asp Thr Met Tyr Ala Thr Tyr Pro Asp Leu Thr Asn Asp
        195                 200                 205 tac ttg tac aaa tta ttt tat tta ggt caa gct gca ttt tgg tgt caa    1932
Tyr Leu Tyr Lys Leu Phe Tyr Leu Gly Gln Ala Ala Phe Trp Cys Gln
    210                 215                 220 caa tct gtt atc ttg ata tta caa gtt gaa aaa cca aga aaa gat ttc    1980
Gln Ser Val Ile Leu Ile Leu Gln Val Glu Lys Pro Arg Lys Asp Phe
225                 230                 235                 240 aaa gaa tta gtc ttg cat cat att gtt aca att tta atg att tgg tta    2028
Lys Glu Leu Val Leu His His Ile Val Thr Ile Leu Met Ile Trp Leu
                245                 250                 255 tca tat gtt ttc cat ttc acc aaa atg gga tta gca att tat att aca    2076
Ser Tyr Val Phe His Phe Thr Lys Met Gly Leu Ala Ile Tyr Ile Thr
            260                 265                 270 atg gat gtt tca gat ttt ttc ctt gca gtt tcc aag aat tta aat tat    2124
Met Asp Val Ser Asp Phe Phe Leu Ala Val Ser Lys Asn Leu Asn Tyr
        275                 280                 285 tta gat tct ccg tta aca atg cct tgg ttt atc ctt ttt gtt ata tca    2172
Leu Asp Ser Pro Leu Thr Met Pro Trp Phe Ile Leu Phe Val Ile Ser
    290                 295                 300 tgg att tat tta cgt cat tat att aat tta aaa att tta tgg tca gtt    2220
Trp Ile Tyr Leu Arg His Tyr Ile Asn Leu Lys Ile Leu Trp Ser Val
305                 310                 315                 320
```

| | | |
|---|---|---|
| tta aca gaa ttt aga aca gtg gga gat ttt aaa tta aat ttt gca act<br>Leu Thr Glu Phe Arg Thr Val Gly Asp Phe Lys Leu Asn Phe Ala Thr<br>325                             330                     335 | | 2268 |
| caa caa tat aaa tgt tgg att tca tta cca att gta ttt gta tta att<br>Gln Gln Tyr Lys Cys Trp Ile Ser Leu Pro Ile Val Phe Val Leu Ile<br>340                             345                     350 | | 2316 |
| ggt gct tta caa tta tta aat atg tat tgg tta ttc tta att tta aga<br>Gly Ala Leu Gln Leu Leu Asn Met Tyr Trp Leu Phe Leu Ile Leu Arg<br>355                            360                     365 | | 2364 |
| att ctt tat aga ttt atc ttt ggt act ggt gtt gtg gaa gat gat cgt<br>Ile Leu Tyr Arg Phe Ile Phe Gly Thr Gly Val Val Glu Asp Asp Arg<br>370                            375                     380 | | 2412 |
| agt gat gat gaa agt gaa gat agt gaa gat gtt caa tta gaa aat gat<br>Ser Asp Asp Glu Ser Glu Asp Ser Glu Asp Val Gln Leu Glu Asn Asp<br>385                             390                     395                     400 | | 2460 |
| ggt gaa gaa tta tct aaa aat caa tca att caa tca cca cca gaa att<br>Gly Glu Glu Leu Ser Lys Asn Gln Ser Ile Gln Ser Pro Pro Glu Ile<br>405                            410                     415 | | 2508 |
| aca att gaa ttt aaa tct gat caa gaa aaa aag agt gaa taa<br>Thr Ile Glu Phe Lys Ser Asp Gln Glu Lys Lys Ser Glu<br>420                            425 | | 2550 |
| gtcatcaact cataaaatca atttattgca tacaacatat tctcataatc atatatccca | | 2610 |
| catataaaaa aaaacaaaca taaatcacat aaacacacat aaaaacatat atatatcagc | | 2670 |
| taatttttac ccatttttttt gttcaacttg tcttatagaa gtatatatct aattcaaact | | 2730 |
| taatcttaat aataatttat aatataattg tcgttgtagt tcttctacat ggattatatc | | 2790 |
| gtatgtacca tttattttc tatttacaaa acttatatga atgtataaag atatctaatt | | 2850 |
| tgattcaatt tcttttggtg atttacccctt ttgtttatct tttaatcttt tttcaaaatc | | 2910 |
| ttgttgattt ttttttataat tttcaatctt attaatacgt ttcttttgcac ccatttctgc | | 2970 |
| agcttttgat aaaataccaa caattaaact tattgaacga actgaatcat cattacctgg | | 3030 |
| aattggataa gtaacaagac ttgcctctga atcagtatca attaatccaa ttgttggaat | | 3090 |
| tcttgattgt atacattcat taaccaagac tctattttca gttggattta aaataacaac | | 3150 |
| taaatcaggt ttaacaatgg cttttttcttc atctgcattt aatgaacgat tgttggaga | | 3210 |
| atttaataaa tcaacttcat gacgtgacca agttgaaatt tctgtacaat tgttatagt | | 3270 |
| accaggaacc catcttgttg ccacgtaata accatttgat cttttttgcag ctaattctaa | | 3330 |
| aggtcttctt aaattttctc ttgtaccaac atacaagata ataccaccac gttctgaaac | | 3390 |
| tccttcaata atcttggaag cacgacgtaa atatgttaaa gtttgttcta aatcaataat | | 3450 |
| atggattcct ttatatgaac caaggataaa tggttgattt gatgatctat ataatgaagt | | 3510 |
| tgattgacct aaatgaacac ctgcagctaa taattttgaa attgaaacat ctttaatagt | | 3570 |
| tgccggataa aaaacatcat gatgtggtaa ataaacattt tttaaattag aacctaattg | | 3630 |
| atcaacattt gatttagaat gttgacgacg taaatataat tcttgatttg tataagattc | | 3690 |
| ttccttggtg gaaggtatta aatatgggaa atctttattt ggacctttt gaacttgaac | | 3750 |
| agattttct ggtaaaaatt tatcattaac taaatcatca ataattttt gtaattcatt | | 3810 |
| ttttaatttt ttattttgtg ctaatttaga atttaattca tttgatgatc cattattaaa | | 3870 |
| taaaaatca ataatttgtt gatcaatttt ttcagcttct tcttttggaa ctttaacaaa | | 3930 |
| acttgaatct tcaacaattt cttgatttgg ggtgcctgcg gctaaagttt gttcattaac | | 3990 |
| tggtgaatct tgaacaagtt gtggatttat tgttgatct tttgttatag tatttaatct | | 4050 |
| ttttatacta gttgataaat gacgaatggg cgctgggaat ttgttagaat taaatcaata | | 4110 |

```
aagagtggaa ataagaatat actcacttag tcttcgactg aacatgctca tcttgtaaaa    4170
ataatctatt agttcttcac aagtcttcct ttttctattt gaaacttctt caatatttca    4230
ttttgtttat ttcataatt ttccaatttt ttcaatgggt attaattttc gcgaatttcg    4290
atgattttga ttttttttac ccggtgttga acttttcaaa taattaacta ctataaaaga    4350
attgaaacat cacttgaaaa agtggttatt ctgagtggtc tctgagtgat ctaagtggtc    4410
ttagtggttg gttatgcagt tgtttactgg ttcttttgac caatttgtgg acaaaatagt    4470
tggattacga gaatctgcaa cattaattat atgtaatatt gatcaagatt tatcaatact    4530
tccaattttt catagatcaa gtattgaata tctttataat tcgaaatttg ttgaagttat    4590
ttatattgat actagtcaga aattattagt ttatttggct aatcaagaat tagaacaatt    4650
gaatggtgaa attaatggta atttatttat ttgggattta ccatgtcttg atttaatttg    4710
ttcaaaatta tgtaaattga ataatatttg tttaattggt tcatcaggta ataatcctga    4770
attcttatca atgattgaaa aatggatacg atgaattgaa atcaattttt tgaaccccca    4830
gaaaaagaat ttattttat tttaaaatgc tattatacaa atatgatcta tactcaagtg    4890
aatttatttt tcttccatat taagatcaac aattttaatt tcagatgttt cattatcata    4950
at                                                                   4952

<210> SEQ ID NO 2
<211> LENGTH: 429
<212> TYPE: PRT
<213> ORGANISM: Pichia ciferrii

<400> SEQUENCE: 2

Met Ser Thr Ser Arg Pro Gln Phe Asn Arg Arg Thr Ser Ser Val
1               5                   10                  15

Gly Lys Ile Asp Leu Gly Asp Thr Arg Val Arg Ser Phe Ser Thr Ser
            20                  25                  30

Arg Thr Ser His Gln Arg Asn Ala Ser Asp Ser Arg Val Asn Glu Leu
        35                  40                  45

Ser Asn Tyr Ser Lys Thr Asp Leu Glu Ile Ile Thr Lys Ile Lys Thr
    50                  55                  60

Gly Leu Val Glu Leu Ser Tyr Arg His Thr Trp Ala Leu Pro Ala Leu
65                  70                  75                  80

Ile Leu Leu Ile Val Tyr Thr Ala Tyr Phe Thr Ser Gly Asn Tyr Thr
                85                  90                  95

Glu Ser Asn Phe Leu His Met Phe Val Ser Ile Ser Tyr Gln Ile Pro
            100                 105                 110

Gly Thr Asn Gln Tyr Asp Lys Gly Ile Lys Asp Leu Ala Phe Val Leu
        115                 120                 125

Phe Tyr Met Ile Phe Phe Thr Phe Phe Arg Glu Phe Cys Met Glu Val
    130                 135                 140

Ile Leu Arg Pro Leu Ala Pro Ile Val Gly Val Lys Lys Pro Ser Lys
145                 150                 155                 160

Ile Lys Arg Phe Met Glu Gln Ser Tyr Ser Val Ile Tyr Ser Gly Leu
                165                 170                 175

Ser Gly Pro Phe Gly Leu Tyr Val Met Tyr Gly Thr Asp Leu Trp Leu
            180                 185                 190

Phe Arg Thr Asp Thr Met Tyr Ala Thr Tyr Pro Asp Leu Thr Asn Asp
        195                 200                 205

Tyr Leu Tyr Lys Leu Phe Tyr Leu Gly Gln Ala Ala Phe Trp Cys Gln
    210                 215                 220
```

```
Gln Ser Val Ile Leu Ile Leu Gln Val Glu Lys Pro Arg Lys Asp Phe
225                 230                 235                 240

Lys Glu Leu Val Leu His His Ile Val Thr Ile Leu Met Ile Trp Leu
            245                 250                 255

Ser Tyr Val Phe His Phe Thr Lys Met Gly Leu Ala Ile Tyr Ile Thr
        260                 265                 270

Met Asp Val Ser Asp Phe Phe Leu Ala Val Ser Lys Asn Leu Asn Tyr
    275                 280                 285

Leu Asp Ser Pro Leu Thr Met Pro Trp Phe Ile Leu Phe Val Ile Ser
    290                 295                 300

Trp Ile Tyr Leu Arg His Tyr Ile Asn Leu Lys Ile Leu Trp Ser Val
305                 310                 315                 320

Leu Thr Glu Phe Arg Thr Val Gly Asp Phe Lys Leu Asn Phe Ala Thr
                325                 330                 335

Gln Gln Tyr Lys Cys Trp Ile Ser Leu Pro Ile Val Phe Val Leu Ile
            340                 345                 350

Gly Ala Leu Gln Leu Leu Asn Met Tyr Trp Leu Phe Leu Ile Leu Arg
        355                 360                 365

Ile Leu Tyr Arg Phe Ile Phe Gly Thr Gly Val Val Glu Asp Asp Arg
    370                 375                 380

Ser Asp Asp Glu Ser Glu Asp Ser Glu Asp Val Gln Leu Glu Asn Asp
385                 390                 395                 400

Gly Glu Glu Leu Ser Lys Asn Gln Ser Ile Gln Ser Pro Pro Glu Ile
                405                 410                 415

Thr Ile Glu Phe Lys Ser Asp Gln Glu Lys Lys Ser Glu
                420                 425

<210> SEQ ID NO 3
<211> LENGTH: 4195
<212> TYPE: DNA
<213> ORGANISM: Pichia ciferrii
<220> FEATURE:
<221> NAME/KEY: CDS
<222> LOCATION: (1219)..(2376)
<223> OTHER INFORMATION: Product: Pichia ciferrii ceramide synthase
      Laf1p

<400> SEQUENCE: 3
gaagaatgtc cwcaacatat aagaactatt gtttcagaag caagaaatct ttggccagaa      60
tatataccac atgatgcaac aaaagttgca gaatttgaat tttatttaat tgaagaaatg     120
gatacttatt taattgttca tcatccttat agatctttat tacttataaa tgaagtttta     180
tcaaattata atcaatcaca taaatcagag ggtcataatc ataataataa tagcaataac     240
aataatgaca cttcacaacc atttgcatta tcaccagaag aattacaatc atgctggtca     300
attataaatg atagttatgt tacagattta cctttaattc atgcaccaca tattatagca     360
tcagcttcaa ttttttttaac tatagtacta aaatataatc atttaaaaca tatttccaaa     420
gattcattaa agaattcaaa accaaataca atgataactg aagaatatct taaaagtgga     480 ttttaaaga atttttattaa atttttaggt tattcaaata tagatctcgg aggtgttata     540
gaagctgttc aagaattaat aacactttat gaaatatggg aaacttatga tgaatcaagt     600
tgtaaaaaac cattagaatc agttcttta atagataaa tacccataca aacaataca     660 attaaaacca atcaggtaa ttaaatattg aaatttgata gttacccta tgaaatcatc     720 cgcgaatttt agatttcgg tgcttttat tttttttat tttttttg ttggtttgat     780 ttttttcttg aaaaaagaag gatacgctgt cagaatttta aagacgttg agaaataaat     840
```

```
tttaagatct tgataagaa ttttgttttg tgctgttatt atttgttcag gggatcatca    900
tatgctggta gttcaggttt aggctcatag gtttaggtat ctcatcactg gtttttgtta    960
ttcttcgttc gttcattcat tgttcccacg cgttgcattt agatctcagg taccattatt   1020
tcaagatcta gaagtcctcc aaaaacgtca atacaattca aatcattaag aatatattca   1080
ttcattagac cactataaca ggtgtctatt ctatttattt aatctcattt tcattatcat   1140
tttcattcat tattaaaaca atttagtcac gtgattagat ctataattat aaatatcatc   1200
```

```
aaatatcatt attatatt atg att tca act tca aca aat tca tca tct aaa    1251
                    Met Ile Ser Thr Ser Thr Asn Ser Ser Ser Lys
                     1               5                      10 aag aat gaa act act ata tct caa gtt aga tta tca gat tct tca agt    1299
Lys Asn Glu Thr Thr Ile Ser Gln Val Arg Leu Ser Asp Ser Ser Ser
             15                  20                  25 gat tca tca tca tat gaa gat gaa aaa tta gat ata aaa tca gaa gaa    1347
Asp Ser Ser Ser Tyr Glu Asp Glu Lys Leu Asp Ile Lys Ser Glu Glu
         30                  35                  40 ggt tta ata tca gaa cat caa gaa caa ata aaa caa cat aat caa act    1395
Gly Leu Ile Ser Glu His Gln Glu Gln Ile Lys Gln His Asn Gln Thr
 45                  50                  55 aaa act tac aaa aca aat aaa att gat aaa tat caa att gaa att tct    1443
Lys Thr Tyr Lys Thr Asn Lys Ile Asp Lys Tyr Gln Ile Glu Ile Ser
 60                  65                  70                  75 tta att gcc tta ata ata tta aat tta tta aat aaa ttt gaa aat ttc    1491
Leu Ile Ala Leu Ile Ile Leu Asn Leu Leu Asn Lys Phe Glu Asn Phe
             80                  85                  90 caa cct tat aca cat aaa ttt tta caa tta caa tat aaa tat cct gaa    1539
Gln Pro Tyr Thr His Lys Phe Leu Gln Leu Gln Tyr Lys Tyr Pro Glu
         95                 100                 105 aca aat tat tat gat att ggt aaa gat gat att tat gtt gtt atc aca    1587
Thr Asn Tyr Tyr Asp Ile Gly Lys Asp Asp Ile Tyr Val Val Ile Thr
        110                 115                 120 ggg atg ttt gct gca act ttt ata aga gct ttt tca atg cat tat ata    1635
Gly Met Phe Ala Ala Thr Phe Ile Arg Ala Phe Ser Met His Tyr Ile
125                 130                 135 tta aaa cct tta gca aaa ttt aat aaa att tat tca caa aag gat aaa    1683
Leu Lys Pro Leu Ala Lys Phe Asn Lys Ile Tyr Ser Gln Lys Asp Lys
140                 145                 150                 155 caa aga ttt atg gaa caa ggt tgg tgt gta atg tta tat gct tca tct    1731
Gln Arg Phe Met Glu Gln Gly Trp Cys Val Met Leu Tyr Ala Ser Ser
            160                 165                 170 ttt agt gtt gga tct tgg tta tat tat cat tca tca tat ttc aac aat    1779
Phe Ser Val Gly Ser Trp Leu Tyr Tyr His Ser Ser Tyr Phe Asn Asn
        175                 180                 185 ttt gat aat ttt tat ata aat tgg cct cat gat gaa atg tct gga tta    1827
Phe Asp Asn Phe Tyr Ile Asn Trp Pro His Asp Glu Met Ser Gly Leu
        190                 195                 200 ttt aaa tta tat tat tta atg tca ata gca tca tgg tct caa caa att    1875
Phe Lys Leu Tyr Tyr Leu Met Ser Ile Ala Ser Trp Ser Gln Gln Ile
205                 210                 215 ttt aca tta aat att gaa gct aaa aga aaa gat cat tat caa atg ttt    1923
Phe Thr Leu Asn Ile Glu Ala Lys Arg Lys Asp His Tyr Gln Met Phe
220                 225                 230                 235 agt cat cat ata att acc gtg gca tta gtt att gga tca tat tat tat    1971
Ser His His Ile Ile Thr Val Ala Leu Val Ile Gly Ser Tyr Tyr Tyr
            240                 245                 250 tat ttt act aga att ggg aat gtt ata tta gtt ata atg gat ttt gtt    2019
Tyr Phe Thr Arg Ile Gly Asn Val Ile Leu Val Ile Met Asp Phe Val
        255                 260                 265
```

```
gat att tta tta tca act gca aaa tta tta aaa tat tgt ggt tat caa    2067
Asp Ile Leu Leu Ser Thr Ala Lys Leu Leu Lys Tyr Cys Gly Tyr Gln
        270                 275                 280 aat tta tgt gat ttt atg ttt ggt gtt ttc gta tta ggt tgg att gca    2115
Asn Leu Cys Asp Phe Met Phe Gly Val Phe Val Leu Gly Trp Ile Ala
        285                 290                 295 tta aga cat ggt gtt tat aat tat att ttt tat cat gct gct aca aaa    2163
Leu Arg His Gly Val Tyr Asn Tyr Ile Phe Tyr His Ala Ala Thr Lys
300                 305                 310                 315 gca aga gat ctt atg gtt tca ggt aga tgt att gat gga tta att caa    2211
Ala Arg Asp Leu Met Val Ser Gly Arg Cys Ile Asp Gly Leu Ile Gln
                320                 325                 330 aaa aga tgt tat act gat cga att gtt gat gtt ttt tta tct tta ttg    2259
Lys Arg Cys Tyr Thr Asp Arg Ile Val Asp Val Phe Leu Ser Leu Leu
        335                 340                 345 gga ggt tta caa atc att aca ttg att tgg atg tat tta att gct aaa    2307
Gly Gly Leu Gln Ile Ile Thr Leu Ile Trp Met Tyr Leu Ile Ala Lys
        350                 355                 360 gtt att ata aaa gtt tta aca ggt aat ggt gct gat gat gtt aga agt    2355
Val Ile Ile Lys Val Leu Thr Gly Asn Gly Ala Asp Asp Val Arg Ser
365                 370                 375 gat gat gaa gat gat gat tag attatgaacc catttaattc attacataga       2406
Asp Asp Glu Asp Asp Asp
380                 385 taaacatttt tttttcaatt cgtacctgtt tttattcatt gcatttattt tattatatat   2466
catgttttaa taaaaagttt aagtatctat attaaacttg tctgtatttt ttaatagtat   2526
aaagttgcaa aaactgatgc aatcataact ataaatccaa atatagttaa acttaaactt   2586
aatgatttat taatatcatt atctggaaat aatttaaacc caaataaacc tggtaatata   2646
aaacaaatta atgttgaacc agtggcacca actaatgata atactaattc aaatgattta   2706
attgataatg ctaatccata tgtacccaaa gttaataaag tagtaactaa tacaaatcta   2766
tttgttgaaa atggaacttc atcatttgat tcattaatac cagattcttc atcattaatt   2826
aatccagttc tttcattaac aactgttgat gtggttttat ttttagatat ttcttgttga   2886
atccaatgaa tcatattatt tgttgataaa cgacatggat gaaacattaa tggataagat   2946
aaagtaacca ttaatacaag agcaaattta ccattttttg aacttaataa tttactttta   3006
tattctaata taacattccc atgaacatta tcaccaaatt gtaaataacc tgcaaatcca   3066
acacttaaga acaataaact tgcaattaaa tttgctaaag tgataacttt tggaacttgt   3126
gattgatcat taatttcatt tataatagaa caaatgtttt gtgcagcagt gaatgcaaat   3186
accacaatgg aaaagttga aaggatttga gatattgaac caatttctaa tattttaaca   3246
tgaccttgac tcttggacca atcatcccat attgaatgag aaataaccaa tattgttaaa   3306
taaccaattg ccaataatcc aattaaagaa ccaattttca aagaatctaa ttttctaaaa   3366
ctgattaaag gtatgatgat aatcaaacta agcaatataa cttgatttct actcaatact   3426
tcattaatta aacttggaac caaatcacca atcaatacta aataacttaa agccacacca   3486
aaacattgaa ttgcaataga aaaatcaaaa atcaaagtca atttaggata agttatacca   3546
caaagagcaa atatgaagt atcaccaggt aatttttttac taacttgact aacaatataa   3606
agaccataag aagatgcaat accagcaatt aaaattaata tagtacctaa tatcaaacca   3666
tcagctttga aagcgaaagg aattgccagg agacctgctc cgatgattgt tttggttaaa   3726
ttgatgactg atgattgaac agaagccatt ttaaacaact tgaacccctt tttgaatcaa   3786
caataataag ttgatctttt tgatggaaag tttggaatgt tcttattgtt ttgatggttt   3846
```

-continued

```
tgttttgatt tggtgaaga agagcgcgaa tattttttgtt tatatacaag agaaaaaaga    3906
tcaaatttac ttgaagattt atttaataaa gacagaaggt gatcatgagt gagtacaagg    3966
tgacgaagaa gaagagtcgg ctggtggcac cggagaacag acagagagca gcgttcagtt    4026
gtgacaggtg caagactaaa aagatcaagt gcaagaggat tggtgacggt ggagatggta    4086
atggtaatgg taatggttca cggtgtatga gttgtgataa gttaggattg gaatgcttga    4146
caagtatacc cagaagaaga agggtttata gctcatatga gaatttagg                4195
```

```
<210> SEQ ID NO 4
<211> LENGTH: 385
<212> TYPE: PRT
<213> ORGANISM: Pichia ciferrii

<400> SEQUENCE: 4

Met Ile Ser Thr Ser Thr Asn Ser Ser Lys Lys Asn Glu Thr Thr
1               5                   10                  15

Ile Ser Gln Val Arg Leu Ser Asp Ser Ser Asp Ser Ser Ser Tyr
            20                  25                  30

Glu Asp Glu Lys Leu Asp Ile Lys Ser Glu Glu Gly Leu Ile Ser Glu
        35                  40                  45

His Gln Glu Gln Ile Lys Gln His Asn Gln Thr Lys Thr Tyr Lys Thr
    50                  55                  60

Asn Lys Ile Asp Lys Tyr Gln Ile Glu Ile Ser Leu Ile Ala Leu Ile
65                  70                  75                  80

Ile Leu Asn Leu Leu Asn Lys Phe Glu Asn Phe Gln Pro Tyr Thr His
                85                  90                  95

Lys Phe Leu Gln Leu Gln Tyr Lys Tyr Pro Glu Thr Asn Tyr Tyr Asp
            100                 105                 110

Ile Gly Lys Asp Asp Ile Tyr Val Val Ile Thr Gly Met Phe Ala Ala
        115                 120                 125

Thr Phe Ile Arg Ala Phe Ser Met His Tyr Ile Leu Lys Pro Leu Ala
    130                 135                 140

Lys Phe Asn Lys Ile Tyr Ser Gln Lys Asp Lys Gln Arg Phe Met Glu
145                 150                 155                 160

Gln Gly Trp Cys Val Met Leu Tyr Ala Ser Ser Phe Ser Val Gly Ser
                165                 170                 175

Trp Leu Tyr Tyr His Ser Ser Tyr Phe Asn Asn Phe Asp Asn Phe Tyr
            180                 185                 190

Ile Asn Trp Pro His Asp Glu Met Ser Gly Leu Phe Lys Leu Tyr Tyr
        195                 200                 205

Leu Met Ser Ile Ala Ser Trp Ser Gln Gln Ile Phe Thr Leu Asn Ile
    210                 215                 220

Glu Ala Lys Arg Lys Asp His Tyr Gln Met Phe Ser His His Ile Ile
225                 230                 235                 240

Thr Val Ala Leu Val Ile Gly Ser Tyr Tyr Tyr Phe Thr Arg Ile
                245                 250                 255

Gly Asn Val Ile Leu Val Ile Met Asp Phe Val Asp Ile Leu Leu Ser
            260                 265                 270

Thr Ala Lys Leu Leu Lys Tyr Cys Gly Tyr Gln Asn Leu Cys Asp Phe
        275                 280                 285

Met Phe Gly Val Phe Val Leu Gly Trp Ile Ala Leu Arg His Gly Val
    290                 295                 300

Tyr Asn Tyr Ile Phe Tyr His Ala Ala Thr Lys Ala Arg Asp Leu Met
305                 310                 315                 320
```

-continued

```
Val Ser Gly Arg Cys Ile Asp Gly Leu Ile Gln Lys Arg Cys Tyr Thr
            325                 330                 335

Asp Arg Ile Val Asp Val Phe Leu Ser Leu Leu Gly Gly Leu Gln Ile
        340                 345                 350

Ile Thr Leu Ile Trp Met Tyr Leu Ile Ala Lys Val Ile Ile Lys Val
355                 360                 365

Leu Thr Gly Asn Gly Ala Asp Asp Val Arg Ser Asp Asp Glu Asp Asp
    370                 375                 380

Asp
385

<210> SEQ ID NO 5
<211> LENGTH: 5106
<212> TYPE: DNA
<213> ORGANISM: Pichia ciferrii
<220> FEATURE:
<221> NAME/KEY: CDS
<222> LOCATION: (2283)..(4076)
<223> OTHER INFORMATION: Product: Pichia ciferrii sphingolipid Delta8
      desaturase

<400> SEQUENCE: 5
gagcatataa atatacccgt gaaggcatga cagttcatac taattttact cattaaatag      60
agctcaattt gattatatgt caaacttgta aagaaaaact atataagcct ccaagaatct     120
ttcatttcat tttattttc tttcttcttc acttcagaat tcataacat taaacattca      180 aaacatcaaa cattcataac atcaaacatt cataatcata taaacactta acatgacaga     240
accattagaa actaaacccc caagttcaac taagattcat aagtgtgtta cactcttact     300
taaagtcatc actgctgaaa cactatacaa cgctttaaaa aaaactggta ttgttacccc     360
tgatgcattc tgtgaaccta cacttgaaag tatctcacat tatcttgagc tttgctatga     420
tgaaaatatt caaccttacg ttacgaattt caattggaaa ctacaaaaag ttggactttg     480
gttaagatat catatttcaa agcctttcaa tttcttaaag attcctttga gctcttttca     540
tgagaaacat acaagttcaa tcatacgttt taaatcattc ttcaaatcaa ttaaagagaa     600
attatcattg acaaaaacat catcagttga agaacttcca tccacaaaact tcaaatcatg     660 ttttcctatt gagatttggc ttttgattgt tgaaattggt gacgttgaac ctgcaaactt     720
gattagagtg aacaaagatt tgttccaagt atttgctcca gtggtttatc gctcaatcca     780
tttagacctt tcattagtt caagtgagat tctcaaattg aatcattctc attgtatgaa     840
atttgcagac tcttgttatt tccaatcctc taatccatat caactttata acgattggaa     900
ggaaagtcaa cattctgatt tgttttttttg gatattagac ataggaatt cccaaatgag     960 aaaacaactg atttagaaat cattcttgaa atggctata caataacttg caagagtaga    1020
gtaatcagaa attttgaaga tgtctataaa tttctcatta gaaccatctt gaatgaaaac    1080
tctatatttt tcaagtatat tgaagagatt gcaactaaca tcaccgttat tgatgttgat    1140
gggtacaaca ctttaatcaa tggagatttt ggtcaaacac tcaaagatct ttcaggtggt    1200
gagtctcaac ttatttctct tgaaagtcgt gcattcaaaa cttttgaatt tgatcatgaa    1260
ctacataaga acccaatttt acaaggtgtt aaaattccag aagaagacta ttttgtcttt    1320
gagatgataa tggaagatga atcatctagg ttagcaactt gttctttccc agacaacct     1380 ttctacagag aattggttat cataggtata ctcttagaca acaatcgaaa tgataagaag    1440
agaatgcaac taaatgcttc aaattttaca acagactcag atgcatttgc aatttggaag    1500
gatgaatgtt tatcactcca cgattatttt tcagaaggca aagctgaaga aaaaggtcct    1560
```

```
atttcaatag aagtaatgaa acataaattc atgaatgata ttcaaactaa tactttcttg    1620
actagattca tcaaatcctt agctttaaaa ggccgtaaag aagacttgaa agaaacaca     1680 gtgatgattt ctggtgttga taaaatcacc agaggaagag acaggacgtt aagaggtaca    1740
tttattgatg aagacaatat cccctatatc aatcatccag tgatcacttt cattgatgac   1800
tgtacaacta agtgattcag caccacgaag tatatagata taaataaaaa tccatacaat   1860
aaacttcagc tgtctggttt gttaaagacc gcatctgatt tcaaccataa tagtgttact   1920
atatcatttg tggccaaatt ttgtcctctt ctggattacc tacgtaatta aagtttatag   1980
gtttgacaca ttctttagta tttggtattt gatttggttt gttaaagtat ttgatatagg   2040
gcccttcctt aactatggtg tgtcccctt acaaatttga tcttttttg tatacgattc      2100 agattcaca gccattctgt ttttaaaaaa acgttccatt ttgcaattaa acgaacttga     2160
cacagttgag atttggatca gatcacgcta ttttggtgaa ccagcagttg gtatataaga   2220
ctagagaagg gtcctgttga aaaaagctag gagctcacaca gactggttag gaaagagttc   2280 aa atg tcc agt tcc aaa gtg ctc tcc aga ggt gaa atc gag cat cgt      2327
   Met Ser Ser Ser Lys Val Leu Ser Arg Gly Glu Ile Glu His Arg
    1               5                  10                  15 atc gct tta ggt gat gcc att gtg atc ttt gaa aac tct gtg ctt cga    2375
Ile Ala Leu Gly Asp Ala Ile Val Ile Phe Glu Asn Ser Val Leu Arg
                20                  25                  30 atg aac aag tgg ttg aag ttc cat cct ggt ggt gat aag gcc gtg ttc    2423
Met Asn Lys Trp Leu Lys Phe His Pro Gly Gly Asp Lys Ala Val Phe
            35                  40                  45 cat ttg gtc ggg aga gat gct act gat gag atg att gcg tac cat tgt    2471
His Leu Val Gly Arg Asp Ala Thr Asp Glu Met Ile Ala Tyr His Cys
        50                  55                  60 gat gag acc caa gcc acg ttc aaa aga tgg aag att ggt gaa atc aat    2519
Asp Glu Thr Gln Ala Thr Phe Lys Arg Trp Lys Ile Gly Glu Ile Asn
65                  70                  75 tat aaa tgg atc aat ttt gtg ccg cct att caa ggt ggg aag ttc aga    2567
Tyr Lys Trp Ile Asn Phe Val Pro Pro Ile Gln Gly Gly Lys Phe Arg
80                  85                  90                  95 act tta gaa gaa caa gag ttg gat gaa att aaa gag gaa caa ctg agt    2615
Thr Leu Glu Glu Gln Glu Leu Asp Glu Ile Lys Glu Glu Gln Leu Ser
                100                 105                 110 aga tca cca gct tca cca gct tca aat tca tct tca agt gaa gat ttg    2663
Arg Ser Pro Ala Ser Pro Ala Ser Asn Ser Ser Ser Ser Glu Asp Leu
            115                 120                 125 aaa ctt tca tct tca act gat cca tca gat gtt gag gat tct att gat    2711
Lys Leu Ser Ser Ser Thr Asp Pro Ser Asp Val Glu Asp Ser Ile Asp
        130                 135                 140 aca aag gcc gag tcc tca tca aat tat gca aaa caa caa caa caa aaa    2759
Thr Lys Ala Glu Ser Ser Ser Asn Tyr Ala Lys Gln Gln Gln Gln Lys
    145                 150                 155 caa caa caa cca aaa tta aac acc aca gcg ggt caa tgc tca gaa gtc    2807
Gln Gln Gln Pro Lys Leu Asn Thr Thr Ala Gly Gln Cys Ser Glu Val
160                 165                 170                 175 acc aaa cca aag ata cca caa gga ctt ata ccg tct tta tca aca aaa    2855
Thr Lys Pro Lys Ile Pro Gln Gly Leu Ile Pro Ser Leu Ser Thr Lys
                180                 185                 190 gaa gca tat gaa agg aaa gtt gtt aaa gat cca agt gat gtt att gat    2903
Glu Ala Tyr Glu Arg Lys Val Val Lys Asp Pro Ser Asp Val Ile Asp
            195                 200                 205 aat tat gat aat ggt caa gtt gaa caa gat tta aaa tca tta cct tca    2951
Asn Tyr Asp Asn Gly Gln Val Glu Gln Asp Leu Lys Ser Leu Pro Ser
        210                 215                 220
```

| | | | | | | | | | | | | | | | |
|---|---|---|---|---|---|---|---|---|---|---|---|---|---|---|---|
| tta | gat | tat | gaa | act | caa | gaa | cat | tta | tca | aaa | gaa | tat | aat | aaa | tta | 2999 |
| Leu | Asp | Tyr | Glu | Thr | Gln | Glu | His | Leu | Ser | Lys | Glu | Tyr | Asn | Lys | Leu | |
| | 225 | | | | 230 | | | | | 235 | | | | | | |

| cat | gat | ata | att | att | gaa | aat | gga | tgg | tat | caa | tgt | cct | tat | tgg | gaa | 3047 |
| His | Asp | Ile | Ile | Ile | Glu | Asn | Gly | Trp | Tyr | Gln | Cys | Pro | Tyr | Trp | Glu | |
| 240 | | | | | 245 | | | | | 250 | | | | | 255 | |

| tat | gca | aaa | gaa | gct | aca | aga | att | gca | act | tta | ttt | agt | att | tca | ttc | 3095 |
| Tyr | Ala | Lys | Glu | Ala | Thr | Arg | Ile | Ala | Thr | Leu | Phe | Ser | Ile | Ser | Phe | |
| | | | | 260 | | | | | 265 | | | | | 270 | | |

| aca | cta | ctt | tat | ttt | aaa | tgg | tat | ttc | ctt | agt | gca | att | ttc | tta | ggt | 3143 |
| Thr | Leu | Leu | Tyr | Phe | Lys | Trp | Tyr | Phe | Leu | Ser | Ala | Ile | Phe | Leu | Gly | |
| | | | 275 | | | | | 280 | | | | | 285 | | | |

| tta | gca | tgg | caa | caa | tta | gtt | ttc | att | gca | cat | gat | gca | ggt | cat | atc | 3191 |
| Leu | Ala | Trp | Gln | Gln | Leu | Val | Phe | Ile | Ala | His | Asp | Ala | Gly | His | Ile | |
| | 290 | | | | | 295 | | | | | 300 | | | | | |

| tca | ata | aca | cat | caa | tat | gaa | act | gat | aat | ata | att | ggt | atg | att | gtt | 3239 |
| Ser | Ile | Thr | His | Gln | Tyr | Glu | Thr | Asp | Asn | Ile | Ile | Gly | Met | Ile | Val | |
| 305 | | | | | 310 | | | | | 315 | | | | | | |

| gca | tca | ttc | att | ggt | gga | tta | tca | tta | ggt | tgg | tgg | aaa | aga | aat | cat | 3287 |
| Ala | Ser | Phe | Ile | Gly | Gly | Leu | Ser | Leu | Gly | Trp | Trp | Lys | Arg | Asn | His | |
| 320 | | | | | 325 | | | | | 330 | | | | | 335 | |

| aat | gtt | cat | cat | ctt | ata | aca | aat | gat | cct | gtt | cat | gat | cct | gat | att | 3335 |
| Asn | Val | His | His | Leu | Ile | Thr | Asn | Asp | Pro | Val | His | Asp | Pro | Asp | Ile | |
| | | | | 340 | | | | | 345 | | | | | 350 | | |

| caa | cat | tta | cca | ttt | ttt | gca | gtt | tca | aca | aga | tta | ttt | gga | aat | gtt | 3383 |
| Gln | His | Leu | Pro | Phe | Phe | Ala | Val | Ser | Thr | Arg | Leu | Phe | Gly | Asn | Val | |
| | | | 355 | | | | | 360 | | | | | 365 | | | |

| tat | tca | act | tat | tat | gaa | aaa | ttt | tta | tgg | ttt | gat | gca | ttt | gct | aaa | 3431 |
| Tyr | Ser | Thr | Tyr | Tyr | Glu | Lys | Phe | Leu | Trp | Phe | Asp | Ala | Phe | Ala | Lys | |
| | 370 | | | | | 375 | | | | | 380 | | | | | |

| aaa | tta | att | cca | att | caa | caa | ttt | atg | tat | tat | cca | att | tta | tca | ttt | 3479 |
| Lys | Leu | Ile | Pro | Ile | Gln | Gln | Phe | Met | Tyr | Tyr | Pro | Ile | Leu | Ser | Phe | |
| 385 | | | | | 390 | | | | | 395 | | | | | | |

| gga | aga | ttt | aat | ctt | tat | aga | tta | tca | tgg | gaa | cat | gtt | tta | ttt | ggc | 3527 |
| Gly | Arg | Phe | Asn | Leu | Tyr | Arg | Leu | Ser | Trp | Glu | His | Val | Leu | Phe | Gly | |
| 400 | | | | | 405 | | | | | 410 | | | | | 415 | |

| cag | ggt | cca | aga | cat | ggt | aaa | gct | gca | tgg | ttt | aga | tat | ttt | gaa | tta | 3575 |
| Gln | Gly | Pro | Arg | His | Gly | Lys | Ala | Ala | Trp | Phe | Arg | Tyr | Phe | Glu | Leu | |
| | | | 420 | | | | | 425 | | | | | 430 | | | |

| gtt | gga | tta | act | ttt | ttc | aat | tgg | tgg | ttt | ttt | tat | tta | att | gtt | tat | 3623 |
| Val | Gly | Leu | Thr | Phe | Phe | Asn | Trp | Trp | Phe | Phe | Tyr | Leu | Ile | Val | Tyr | |
| | 435 | | | | | 440 | | | | | 445 | | | | | |

| aaa | tca | att | gaa | tca | aat | tca | tca | aga | ttt | atg | ttt | gtt | atg | gtt | agt | 3671 |
| Lys | Ser | Ile | Glu | Ser | Asn | Ser | Ser | Arg | Phe | Met | Phe | Val | Met | Val | Ser | |
| | 450 | | | | | 455 | | | | | 460 | | | | | |

| cat | ata | aca | aca | atg | att | gtt | cat | gtt | caa | atc | act | tta | tca | cat | ttt | 3719 |
| His | Ile | Thr | Thr | Met | Ile | Val | His | Val | Gln | Ile | Thr | Leu | Ser | His | Phe | |
| 465 | | | | | 470 | | | | | 475 | | | | | | |

| gca | atg | tca | aca | tca | gat | tta | gga | act | tca | gaa | agt | ttt | gta | agt | aga | 3767 |
| Ala | Met | Ser | Thr | Ser | Asp | Leu | Gly | Thr | Ser | Glu | Ser | Phe | Val | Ser | Arg | |
| 480 | | | | | 485 | | | | | 490 | | | | | 495 | |

| caa | ata | aga | aca | aca | atg | gat | gtt | gat | tgt | cca | gga | tgg | ttt | gat | ttt | 3815 |
| Gln | Ile | Arg | Thr | Thr | Met | Asp | Val | Asp | Cys | Pro | Gly | Trp | Phe | Asp | Phe | |
| | | | | 500 | | | | | 505 | | | | | 510 | | |

| ttc | cat | ggt | gga | tta | caa | ttt | caa | gct | att | cat | cat | tta | ttc | cca | aga | 3863 |
| Phe | His | Gly | Gly | Leu | Gln | Phe | Gln | Ala | Ile | His | His | Leu | Phe | Pro | Arg | |
| | | | 515 | | | | | 520 | | | | | 525 | | | |

| gtt | cca | aga | cat | aat | ttc | aga | aaa | att | caa | cct | tta | gtt | att | gga | ttt | 3911 |
| Val | Pro | Arg | His | Asn | Phe | Arg | Lys | Ile | Gln | Pro | Leu | Val | Ile | Gly | Phe | |
| | 530 | | | | | 535 | | | | | 540 | | | | | |

```
tgt gat aaa gtt gga tta aaa tat tca att tat gga ttt gtt gat ggt    3959
Cys Asp Lys Val Gly Leu Lys Tyr Ser Ile Tyr Gly Phe Val Asp Gly
        545                 550                 555 aat gaa gtt gtt att aat aaa tta tca gat att gct aaa caa gct aaa    4007
Asn Glu Val Val Ile Asn Lys Leu Ser Asp Ile Ala Lys Gln Ala Lys
560                 565                 570                 575 att atg aga gat tgt cat aaa aca atg aaa aaa gaa gct att gaa gaa    4055
Ile Met Arg Asp Cys His Lys Thr Met Lys Lys Glu Ala Ile Glu Glu
                580                 585                 590 gga aaa tac ttt gaa ttc tga aaaagctga aagggaactg aaagactaga         4106
Gly Lys Tyr Phe Glu Phe
            595 agcttcgcta atttatttat attaatacat atttatagat ctggatcaaa atattgtgta   4166 aagaatatgt tctgtatgaa ttgatcattt atattgttta tattgttgtt gtcttgaccg   4226 attctggcta ttttttcttt agacaatata aaaacaaaac gtcattaata agagaatcat   4286 cagatcatca aatttagttc ataaaactca tactttatta gatcaacaat actcaattat   4346 agatcataat accaggttat aattgaagaa aatgcctgaa agtacattca ccaattcact   4406 caaaggtttt ttcaaaaaac aaaaatcgcc atctccatcc ccagaatcaa acacatcatc   4466 aaaatcacca agtataagga ataatgcatt attcatagaa gatccaccat taacaccct    4526 tgaacttcat ggatactcca aaactactaa aaacaagatt ctcacattgg aattgggtga   4586 agaaataagg aatatgttac cttcaagaca tcaagtttca tcaaattggg aattagttta   4646 tagtttagag caacatggag cctctttaaa cactttatat tcaaatatta aaccatcaac   4706 aaaatatgat aagaatggtt atttattagt gattaaagac caacgtggaa caatattggg   4766 gagttataca aatgaacatt ttcatccaac agatatgaag agattttatg ggaatggtga   4826 atgtttcctt tggaaatcaa aattaataga taataaagaa tctggagaga aatttataag   4886 atttcaagca ttcccatata caggattaaa tgatttcata atatattgta caagtaaatt   4946 cttatcttta ggtggtggtg atggtcatta tggactctgg attgatcaag aattattaca   5006 tggtgttagt gatcattctt taactttttgg aaatgaacca ttgagctctc agggaataa   5066 gtttagtata ttaggtgttg aagtatggag aatatcatga                        5106
```

<210> SEQ ID NO 6
<211> LENGTH: 597
<212> TYPE: PRT
<213> ORGANISM: Pichia ciferrii

<400> SEQUENCE: 6

```
Met Ser Ser Ser Lys Val Leu Ser Arg Gly Glu Ile Glu His Arg Ile
1               5                   10                  15

Ala Leu Gly Asp Ala Ile Val Ile Phe Glu Asn Ser Val Leu Arg Met
            20                  25                  30

Asn Lys Trp Leu Lys Phe His Pro Gly Gly Asp Lys Ala Val Phe His
        35                  40                  45

Leu Val Gly Arg Asp Ala Thr Asp Glu Met Ile Ala Tyr His Cys Asp
    50                  55                  60

Glu Thr Gln Ala Thr Phe Lys Arg Trp Lys Ile Gly Glu Ile Asn Tyr
65                  70                  75                  80

Lys Trp Ile Asn Phe Val Pro Pro Ile Gln Gly Lys Phe Arg Thr
                85                  90                  95

Leu Glu Glu Gln Glu Leu Asp Glu Ile Lys Glu Glu Gln Leu Ser Arg
            100                 105                 110
```

```
Ser Pro Ala Ser Pro Ala Ser Asn Ser Ser Ser Glu Asp Leu Lys
        115                 120                 125

Leu Ser Ser Ser Thr Asp Pro Ser Asp Val Glu Asp Ser Ile Asp Thr
130                 135                 140

Lys Ala Glu Ser Ser Asn Tyr Ala Lys Gln Gln Gln Gln Lys Gln
145                 150                 155                 160

Gln Gln Pro Lys Leu Asn Thr Thr Ala Gly Gln Cys Ser Glu Val Thr
            165                 170                 175

Lys Pro Lys Ile Pro Gln Gly Leu Ile Pro Ser Leu Ser Thr Lys Glu
                180                 185                 190

Ala Tyr Glu Arg Lys Val Val Lys Asp Pro Ser Asp Val Ile Asp Asn
        195                 200                 205

Tyr Asp Asn Gly Gln Val Glu Gln Asp Leu Lys Ser Leu Pro Ser Leu
210                 215                 220

Asp Tyr Glu Thr Gln Glu His Leu Ser Lys Glu Tyr Asn Lys Leu His
225                 230                 235                 240

Asp Ile Ile Ile Glu Asn Gly Trp Tyr Gln Cys Pro Tyr Trp Glu Tyr
                245                 250                 255

Ala Lys Glu Ala Thr Arg Ile Ala Thr Leu Phe Ser Ile Ser Phe Thr
            260                 265                 270

Leu Leu Tyr Phe Lys Trp Tyr Phe Leu Ser Ala Ile Phe Leu Gly Leu
        275                 280                 285

Ala Trp Gln Gln Leu Val Phe Ile Ala His Asp Ala Gly His Ile Ser
290                 295                 300

Ile Thr His Gln Tyr Glu Thr Asp Asn Ile Ile Gly Met Ile Val Ala
305                 310                 315                 320

Ser Phe Ile Gly Gly Leu Ser Leu Gly Trp Trp Lys Arg Asn His Asn
                325                 330                 335

Val His His Leu Ile Thr Asn Asp Pro Val His Asp Pro Asp Ile Gln
            340                 345                 350

His Leu Pro Phe Phe Ala Val Ser Thr Arg Leu Phe Gly Asn Val Tyr
        355                 360                 365

Ser Thr Tyr Tyr Glu Lys Phe Leu Trp Phe Asp Ala Phe Ala Lys Lys
370                 375                 380

Leu Ile Pro Ile Gln Gln Phe Met Tyr Tyr Pro Ile Leu Ser Phe Gly
385                 390                 395                 400

Arg Phe Asn Leu Tyr Arg Leu Ser Trp Glu His Val Leu Phe Gly Gln
                405                 410                 415

Gly Pro Arg His Gly Lys Ala Ala Trp Phe Arg Tyr Phe Glu Leu Val
            420                 425                 430

Gly Leu Thr Phe Phe Asn Trp Trp Phe Phe Tyr Leu Ile Val Tyr Lys
        435                 440                 445

Ser Ile Glu Ser Asn Ser Ser Arg Phe Met Phe Val Met Val Ser His
450                 455                 460

Ile Thr Thr Met Ile Val His Val Gln Ile Thr Leu Ser His Phe Ala
465                 470                 475                 480

Met Ser Thr Ser Asp Leu Gly Thr Ser Glu Ser Phe Val Ser Arg Gln
                485                 490                 495

Ile Arg Thr Thr Met Asp Val Asp Cys Pro Gly Trp Phe Asp Phe Phe
            500                 505                 510

His Gly Gly Leu Gln Phe Gln Ala Ile His His Leu Phe Pro Arg Val
        515                 520                 525

Pro Arg His Asn Phe Arg Lys Ile Gln Pro Leu Val Ile Gly Phe Cys
530                 535                 540
```

-continued

```
Asp Lys Val Gly Leu Lys Tyr Ser Ile Tyr Gly Phe Val Asp Gly Asn
545                 550                 555                 560

Glu Val Val Ile Asn Lys Leu Ser Asp Ile Ala Lys Gln Ala Lys Ile
            565                 570                 575

Met Arg Asp Cys His Lys Thr Met Lys Lys Glu Ala Ile Glu Glu Gly
        580                 585                 590

Lys Tyr Phe Glu Phe
        595

<210> SEQ ID NO 7
<211> LENGTH: 3402
<212> TYPE: DNA
<213> ORGANISM: Pichia ciferrii
<220> FEATURE:
<221> NAME/KEY: CDS
<222> LOCATION: (917)..(1771)
<223> OTHER INFORMATION: Product: Pichia ciferrii ceramidase Yxc1p

<400> SEQUENCE: 7
```

| | | |
|---|---|---|
| gattttaatt ttaattgttt tgattttgat agtttataag gggctgctta tgtcagggat | 60 |
| tatgtaacag tgtatgggaa tatactttaa actaaaatat atgtaaatgt ttgtatgtga | 120 |
| tggatgtttt taaaatatat atttataatc agtggatcaa gaggattata attatgtaac | 180 |
| ttattaatgg tttaaaagtg gtttagaaat tgatgatatt gatttcatag attttataca | 240 |
| ctttaataat tttatatttg gttagaaat gaaatattaa taaattaatg gaaaaaatta | 300 |
| aattattaac ttcaaaaatc aacaatttaa actaaacata atgaaattaa ttaaattaaa | 360 |
| aacattataa acattttatt aaatcattat ctatttaata tatatattta taatactaat | 420 |
| attaattctt cttataggta ttacataatc actgacataa gcagcaatca attgtactcg | 480 |
| tatataaaca ataagaata aaactaaaca aaactaaaat aataaaaac caattaaatc | 540 |
| aattatatat ataatcaata taataataat acaatataat tacttattat tttcaaatca | 600 |
| tttagtaatc atagtgttat taaaaagtcg aaattcggaa caaccggtgt gcttagtgca | 660 |
| gtaaattacc tcccttgttt gttttaccgc aaattacaca aattaaatta cctgaaatta | 720 |
| ctacttgtta cacttgttac tattaacaat tcaatacaaa agaaagaaga gaatcaagag | 780 |
| atcaatctca tagatttaaa atctaatcta atatcaattg tttatcaata ggataatcag | 840 |
| tttaccatca aaagatcatt gccccatata tcattaatac ccagacacaa tcggagtata | 900 |

```
caacaacaac aacaaa atg tca tat cat tta cca ttt gct aaa cct tac ccc    952
               Met Ser Tyr His Leu Pro Phe Ala Lys Pro Tyr Pro
                 1               5                  10 aat gaa cca tat cat gct tat tgg aat caa gtc act tca aca ata gat   1000
Asn Glu Pro Tyr His Ala Tyr Trp Asn Gln Val Thr Ser Thr Ile Asp
         15                  20                  25 tgg tgt gaa gaa aat tat att gtg act cca tat att gca gaa gct ata   1048
Trp Cys Glu Glu Asn Tyr Ile Val Thr Pro Tyr Ile Ala Glu Ala Ile
 30                  35                  40 aat act ata tca aat tca att ttt ata tta tta gct gga ttt gcc atg   1096
Asn Thr Ile Ser Asn Ser Ile Phe Ile Leu Leu Ala Gly Phe Ala Met
 45                  50                  55                  60 ttt tct gca ttt aaa aat aat tta gaa ttg aga ttt ata ttg ata agt   1144
Phe Ser Ala Phe Lys Asn Asn Leu Glu Leu Arg Phe Ile Leu Ile Ser
                 65                  70                  75 ttt ggt ttt gct tta gtt ggt gtg gga agt tgg tta ttt cat atg act   1192
Phe Gly Phe Ala Leu Val Gly Val Gly Ser Trp Leu Phe His Met Thr
             80                  85                  90 tta cat tat gag ttc caa tta tta gat gaa tta cca atg att tat gca   1240
```

```
              Leu His Tyr Glu Phe Gln Leu Leu Asp Glu Leu Pro Met Ile Tyr Ala
                       95                  100                 105 act tgt atc cca atg tgg agt gtt ttc agt gaa ggt gtt tcc aag aaa        1288
Thr Cys Ile Pro Met Trp Ser Val Phe Ser Glu Gly Val Ser Lys Lys
        110                 115                 120 aaa tca att aca att ggt att tct ata ata ttg ggt gca aat tta tta        1336
Lys Ser Ile Thr Ile Gly Ile Ser Ile Ile Leu Gly Ala Asn Leu Leu
125                 130                 135                 140 act gca att tat tta tat tta aaa gat cca act gtt cat caa gtt gct        1384
Thr Ala Ile Tyr Leu Tyr Leu Lys Asp Pro Thr Val His Gln Val Ala
                145                 150                 155 tat gcc tta tta aat gtt ttc att gtg ggg aaa tct cat tat tta aca        1432
Tyr Ala Leu Leu Asn Val Phe Ile Val Gly Lys Ser His Tyr Leu Thr
            160                 165                 170 ata aaa aac att cat aat caa aca acc caa aaa caa tta ttt ata aca        1480
Ile Lys Asn Ile His Asn Gln Thr Thr Gln Lys Gln Leu Phe Ile Thr
        175                 180                 185 atg att aaa gga att ggt att ttc ctt tct ggt tat ttc tta tgg aat        1528
Met Ile Lys Gly Ile Gly Ile Phe Leu Ser Gly Tyr Phe Leu Trp Asn
    190                 195                 200 tta gat gtt cat ttt tgt aat tct tgg att tgg tta aga aga agt att        1576
Leu Asp Val His Phe Cys Asn Ser Trp Ile Trp Leu Arg Arg Ser Ile
205                 210                 215                 220 ggt atg cct tat ggt ttc cta tta gaa tta cat gct tgg tgg cat gtt        1624
Gly Met Pro Tyr Gly Phe Leu Leu Glu Leu His Ala Trp Trp His Val
                225                 230                 235 tta act ggt tta ggt gtt tat ttt tat att att tat tta gaa tta tta        1672
Leu Thr Gly Leu Gly Val Tyr Phe Tyr Ile Ile Tyr Leu Glu Leu Leu
            240                 245                 250 aga att aat tta ttg ggg aaa caa gat gat tat gaa ttg att tat aaa        1720
Arg Ile Asn Leu Leu Gly Lys Gln Asp Asp Tyr Glu Leu Ile Tyr Lys
        255                 260                 265 ttt gga ttt tta cct gaa gtt aaa tta tta aaa aag gat aaa aat gaa        1768
Phe Gly Phe Leu Pro Glu Val Lys Leu Leu Lys Lys Asp Lys Asn Glu
    270                 275                 280 taa ttaatcaatc aacatgatca aatagcaatc aattagttca aatggcatga             1821
ttatttgata cacatattat ttatacttta tattgttctt tgttatgtgc cttcttttt       1881 gttatacctt tttatatcat aaatgctcct tttttaacaa aaactttata tatttataca      1941
tgaatagaat attggatgat tttaatgtaa tatttatgaa atattgctgt ttattaatca      2001
aaaatatacg aattgatatt ataattacgt ataatacgtt cctgggagtc aatttacaac      2061
aaaacattat atcaaacaag agtaaaatta aaaagtggta tgataattga ttatatcaat      2121
tgaaacttac atagatctta ttccaacttg aaagggttta gatcttttgt ctctttagat     2181
cttaacgaat aaacgtattt gaatctaact tcttgtttta atccttgttt gtgagatgat      2241
agatctaata atctaatcta taaaacaagg gtttgtaaat attcaaatta agaaggtaca      2301
agacgcttat gcttggtgat tatcctaggc attatcggat caatgtattc atactccgta      2361
ttaatccagg gtacaattag ttcatagtac atacactcca tagcctgtca aatatggaga      2421
gttcacgtag tttaggagtc aaagtaatta ctcgttaata ttacgcaatg gagatcttta     2481
aatgtcaaat cacaaaaact cgaaaatctt tcttaagaat ttaaaaattt taactttta      2541 aattgatttg atttgttgaa tatatattct aacttgtaca cttatcataa ttgtgtaatt    2601
gattatctgt tgatcttatt taaaagtatt ttatacatta gtgtaaagta tgaaggcatt    2661
agtgaagaca tgaggcatga gggatatgag gcattgaaga gttcggttaa actgatgttg   2721
atttaaagaa caaattgaaa agtgtttaat tcaattcaat ccaattcaat tcaattcaat   2781
```

-continued

```
tgttaatgtt aatgatttat actcactgga tcaaagttta tccgatgatt tttatattaa    2841
ttttccgaat atcaacctt  taattttttc ctcaatcgaa gcgcgtttat ataaaagtaa    2901
acaaaccagt tttataatca tcatcaacga aaaatcactg aaactcgcgt cgtgtttttt    2961
cttgaattcc aagtactata tgatgatttt tggagaacaa gagcttcata catgatcgtt    3021
aagccttggg tatgatacga agaagtttga acaagacttg atgaactgat ttttttatca    3081
ttctataagc agtaatcata ttgatctata tgatccatgt tatcatgatt attgaaattt    3141
atataaatat tgatcaaaat cttctgattt aatattcaat attttaaat  gttgatcata    3201 aaccacaaag cttaaacaat gattactaaa atctttcaa  tatttttact tttcagttta    3261
gtaattgctg ctgataaaaa ttataataga cctcaattca tttacacctg aaaaaggttg    3321
gatgaatgat ccaaatggtc tttggtttga tcaaaggat  aaaatatggc atgctattat    3381
caaaaaatcc aaaatcaacg t                                              3402
```

<210> SEQ ID NO 8
<211> LENGTH: 284
<212> TYPE: PRT
<213> ORGANISM: Pichia ciferrii

<400> SEQUENCE: 8

```
Met Ser Tyr His Leu Pro Phe Ala Lys Pro Tyr Pro Asn Glu Pro Tyr
1               5                   10                  15

His Ala Tyr Trp Asn Gln Val Thr Ser Thr Ile Asp Trp Cys Glu Glu
            20                  25                  30

Asn Tyr Ile Val Thr Pro Tyr Ile Ala Glu Ala Ile Asn Thr Ile Ser
        35                  40                  45

Asn Ser Ile Phe Ile Leu Leu Ala Gly Phe Ala Met Phe Ser Ala Phe
    50                  55                  60

Lys Asn Asn Leu Glu Leu Arg Phe Ile Leu Ile Ser Phe Gly Phe Ala
65                  70                  75                  80

Leu Val Gly Val Gly Ser Trp Leu Phe His Met Thr Leu His Tyr Glu
                85                  90                  95

Phe Gln Leu Leu Asp Glu Leu Pro Met Ile Tyr Ala Thr Cys Ile Pro
            100                 105                 110

Met Trp Ser Val Phe Ser Glu Gly Val Ser Lys Lys Ser Ile Thr
            115                 120                 125

Ile Gly Ile Ser Ile Ile Leu Gly Ala Asn Leu Leu Thr Ala Ile Tyr
        130                 135                 140

Leu Tyr Leu Lys Asp Pro Thr Val His Gln Val Ala Tyr Ala Leu Leu
145                 150                 155                 160

Asn Val Phe Ile Val Gly Lys Ser His Tyr Leu Thr Ile Lys Asn Ile
                165                 170                 175

His Asn Gln Thr Thr Gln Lys Gln Leu Phe Ile Thr Met Ile Lys Gly
            180                 185                 190

Ile Gly Ile Phe Leu Ser Gly Tyr Phe Leu Trp Asn Leu Asp Val His
        195                 200                 205

Phe Cys Asn Ser Trp Ile Trp Leu Arg Arg Ser Ile Gly Met Pro Tyr
    210                 215                 220

Gly Phe Leu Leu Glu Leu His Ala Trp Trp His Val Leu Thr Gly Leu
225                 230                 235                 240

Gly Val Tyr Phe Tyr Ile Ile Tyr Leu Glu Leu Leu Arg Ile Asn Leu
                245                 250                 255

Leu Gly Lys Gln Asp Asp Tyr Glu Leu Ile Tyr Lys Phe Gly Phe Leu
```

```
                        260                 265                 270
Pro Glu Val Lys Leu Leu Lys Lys Asp Lys Asn Glu
            275                 280

<210> SEQ ID NO 9
<211> LENGTH: 288
<212> TYPE: PRT
<213> ORGANISM: Emiliana huxleyi

<400> SEQUENCE: 9

Met Tyr Cys Gly Thr Ser Gly Leu Arg Asp Phe Met Tyr Ala Asp Ile
1               5                   10                  15

Met Glu Met Ala Gln Phe Ser Val Ile Met Phe Ser Phe Ala Thr Ile
            20                  25                  30

Leu Arg Thr Phe Val Met Ile Tyr Ile Leu Asp Pro Leu Ser Glu Ile
        35                  40                  45

Met Val Arg Pro Glu Arg Val Leu Lys Phe Gln Gln Ser Ala Trp Arg
    50                  55                  60

Phe Val Leu Tyr Ser Ile Ala Thr Ile Ser Ser Ile Ile Val Phe Met
65                  70                  75                  80

Thr Asp Asp Thr Val Asp Phe Lys Glu Ser Ser Phe Phe Glu Asn Trp
                85                  90                  95

Pro Leu Tyr Asn Pro Gly Ser Gly Ile Lys Phe Met Tyr Ala Leu Tyr
            100                 105                 110

Ala Gly Phe Tyr Ile His Gln Thr Val Tyr Ile Phe Gly Asp Glu Arg
        115                 120                 125

Leu Asp Asp Phe Asn Glu His Val Phe His His Ala Ile Thr Leu Val
    130                 135                 140

Leu Val Tyr Val Ser Trp Val Phe Asn Phe Thr Lys Ile Gly Phe Phe
145                 150                 155                 160

Ile Met Thr Leu His Asp Gly Ser Asp Val Phe Leu Glu Leu Ala Lys
                165                 170                 175

Cys Met Asn Tyr Ala Lys Glu Ile Arg Pro Arg Leu Ser Ile Ile Ser
            180                 185                 190

Asp Val Ser Phe Ile Ile Phe Ala Ser Ser Phe Phe Tyr Leu Arg Leu
        195                 200                 205

Tyr Leu Tyr Pro Val Tyr Ala Ile Gly Ser Ile Val Asn Pro Tyr Asp
    210                 215                 220

Ala Cys Ala His Val Ser Cys Ala Leu Tyr Glu Gly Val Ser Tyr
225                 230                 235                 240

Ser Tyr Cys Ala Ser Lys Pro Ile Tyr Ala Val Ala Ile Ala Ala Leu
                245                 250                 255

Thr Ser Leu Tyr Ile Leu Gln Val Met Trp Ala Gly Arg Ile Ile Asn
            260                 265                 270

Val Ile Ala Lys Val Ile Ala Gly Asn Pro Leu Glu Asp Ser Arg Asp
        275                 280                 285

<210> SEQ ID NO 10
<211> LENGTH: 414
<212> TYPE: PRT
<213> ORGANISM: Mus musculus

<400> SEQUENCE: 10

Met Ala Thr Ala Ala Ala Glu Thr Leu Gly Leu Leu Trp Gly Trp Leu
1               5                   10                  15

Trp Ser Glu Ser Phe Trp Leu Pro Gln Asn Val Ser Trp Ala Asp Leu
            20                  25                  30
```

| Glu | Gly | Pro | Gly | Asp | Gly | Tyr | Gly | Tyr | Pro | Arg | Ala | Gln | His | Val | Leu |
|---|---|---|---|---|---|---|---|---|---|---|---|---|---|---|---|
| | | 35 | | | | 40 | | | | | 45 | | | | |

| Ser | Val | Phe | Pro | Leu | Ala | Val | Cys | Ile | Phe | Ser | Val | Arg | Met | Leu | Phe |
|---|---|---|---|---|---|---|---|---|---|---|---|---|---|---|---|
| 50 | | | | | 55 | | | | | 60 | | | | | |

| Glu | Arg | Phe | Ile | Ala | Lys | Pro | Cys | Ala | Leu | Arg | Val | Gly | Ile | Lys | Asp |
|---|---|---|---|---|---|---|---|---|---|---|---|---|---|---|---|
| 65 | | | | | 70 | | | | | 75 | | | | | 80 |

| Ser | Pro | Val | Asn | Lys | Val | Glu | Pro | Asn | Asp | Thr | Leu | Glu | Lys | Val | Phe |
|---|---|---|---|---|---|---|---|---|---|---|---|---|---|---|---|
| | | | | 85 | | | | | 90 | | | | | 95 | |

| Val | Ser | Val | Thr | Lys | Tyr | Pro | Asp | Glu | Lys | Arg | Leu | Lys | Gly | Leu | Ser |
|---|---|---|---|---|---|---|---|---|---|---|---|---|---|---|---|
| | | | 100 | | | | | 105 | | | | | 110 | | |

| Lys | Gln | Leu | Asp | Trp | Ser | Val | Arg | Lys | Ile | Gln | Cys | Trp | Phe | Arg | His |
|---|---|---|---|---|---|---|---|---|---|---|---|---|---|---|---|
| | | | 115 | | | | | 120 | | | | | 125 | | |

| Arg | Arg | Asn | Gln | Asp | Lys | Pro | Pro | Thr | Leu | Thr | Lys | Phe | Cys | Glu | Ser |
|---|---|---|---|---|---|---|---|---|---|---|---|---|---|---|---|
| | 130 | | | | | 135 | | | | | 140 | | | | |

| Met | Trp | Arg | Phe | Thr | Tyr | Tyr | Leu | Cys | Ile | Phe | Cys | Tyr | Gly | Ile | Arg |
|---|---|---|---|---|---|---|---|---|---|---|---|---|---|---|---|
| 145 | | | | | 150 | | | | | 155 | | | | | 160 |

| Phe | Leu | Trp | Ser | Met | Pro | Trp | Phe | Trp | Asp | Thr | Arg | Gln | Cys | Trp | Tyr |
|---|---|---|---|---|---|---|---|---|---|---|---|---|---|---|---|
| | | | | 165 | | | | | 170 | | | | | 175 | |

| Asn | Tyr | Pro | Tyr | Gln | Pro | Leu | Ser | Arg | Glu | Leu | Tyr | Tyr | Tyr | Ile |
|---|---|---|---|---|---|---|---|---|---|---|---|---|---|---|
| | | | 180 | | | | | 185 | | | | | 190 | |

| Thr | Gln | Leu | Ala | Phe | Tyr | Trp | Ser | Leu | Met | Phe | Ser | Gln | Phe | Ile | Asp |
|---|---|---|---|---|---|---|---|---|---|---|---|---|---|---|---|
| | 195 | | | | | 200 | | | | | 205 | | | | |

| Val | Lys | Arg | Lys | Asp | Phe | Leu | Met | Met | Phe | Ile | His | His | Met | Ile | Gly |
|---|---|---|---|---|---|---|---|---|---|---|---|---|---|---|---|
| | 210 | | | | | 215 | | | | | 220 | | | | |

| Ile | Met | Leu | Thr | Thr | Phe | Ser | Tyr | Val | Asn | Asn | Met | Val | Arg | Val | Gly |
|---|---|---|---|---|---|---|---|---|---|---|---|---|---|---|---|
| 225 | | | | | 230 | | | | | 235 | | | | | 240 |

| Ala | Leu | Ile | Phe | Cys | Leu | His | Asp | Phe | Ala | Asp | Pro | Leu | Leu | Glu | Ala |
|---|---|---|---|---|---|---|---|---|---|---|---|---|---|---|---|
| | | | | 245 | | | | | 250 | | | | | 255 | |

| Ala | Lys | Met | Ala | Asn | Tyr | Ala | Arg | Arg | Glu | Arg | Leu | Cys | Thr | Thr | Leu |
|---|---|---|---|---|---|---|---|---|---|---|---|---|---|---|---|
| | | | 260 | | | | | 265 | | | | | 270 | | |

| Phe | Val | Ile | Phe | Gly | Ala | Ala | Phe | Ile | Val | Ser | Arg | Leu | Ala | Ile | Phe |
|---|---|---|---|---|---|---|---|---|---|---|---|---|---|---|---|
| | | 275 | | | | | 280 | | | | | 285 | | | |

| Pro | Leu | Trp | Ile | Leu | Asn | Thr | Thr | Leu | Phe | Glu | Ser | Trp | Glu | Ile | Ile |
|---|---|---|---|---|---|---|---|---|---|---|---|---|---|---|---|
| 290 | | | | | 295 | | | | | 300 | | | | | |

| Gly | Pro | Tyr | Pro | Ser | Trp | Trp | Leu | Phe | Asn | Ala | Leu | Leu | Leu | Ile | Leu |
|---|---|---|---|---|---|---|---|---|---|---|---|---|---|---|---|
| 305 | | | | | 310 | | | | | 315 | | | | | 320 |

| Gln | Val | Leu | His | Ala | Ile | Trp | Ser | Tyr | Leu | Ile | Val | Gln | Thr | Ala | Ser |
|---|---|---|---|---|---|---|---|---|---|---|---|---|---|---|---|
| | | | | 325 | | | | | 330 | | | | | 335 | |

| Lys | Ala | Leu | Ser | Arg | Gly | Lys | Val | Ser | Lys | Asp | Asp | Arg | Ser | Asp | Val |
|---|---|---|---|---|---|---|---|---|---|---|---|---|---|---|---|
| | | | 340 | | | | | 345 | | | | | 350 | | |

| Glu | Ser | Ser | Ser | Glu | Glu | Glu | Asp | Glu | Thr | Thr | His | Lys | Asn | Asn | Leu |
|---|---|---|---|---|---|---|---|---|---|---|---|---|---|---|---|
| | 355 | | | | | 360 | | | | | 365 | | | | |

| Ser | Gly | Ser | Ser | Ser | Ser | Asn | Gly | Ala | Asn | Cys | Met | Asn | Gly | Tyr | Met |
|---|---|---|---|---|---|---|---|---|---|---|---|---|---|---|---|
| 370 | | | | | 375 | | | | | 380 | | | | | |

| Gly | Gly | Ser | His | Leu | Ala | Glu | Glu | Gln | Gly | Thr | Cys | Lys | Ala | Thr | Gly |
|---|---|---|---|---|---|---|---|---|---|---|---|---|---|---|---|
| 385 | | | | | 390 | | | | | 395 | | | | | 400 |

| Asn | Leu | His | Phe | Arg | Ala | Ser | Pro | His | Leu | His | Ser | Cys | Asp |
|---|---|---|---|---|---|---|---|---|---|---|---|---|---|
| | | | | 405 | | | | | 410 | | | | |

```
<210> SEQ ID NO 11
<211> LENGTH: 1410
<212> TYPE: DNA
<213> ORGANISM: Eremothecium gossypii
<220> FEATURE:
<221> NAME/KEY: CDS
```

<222> LOCATION: (1)..(1242)
<223> OTHER INFORMATION: Product: Ashbya gossypii ceramide synthase
       Lag1p

<400> SEQUENCE: 11

| | | | | | | | | | | | | | | | | |
|---|---|---|---|---|---|---|---|---|---|---|---|---|---|---|---|---|
| atg | gct | gaa | aat | tcg | tta | ttg | aag | cca | cca | tcg | ctc | tcc | cgg | aag | cgg | 48 |
| Met | Ala | Glu | Asn | Ser | Leu | Leu | Lys | Pro | Pro | Ser | Leu | Ser | Arg | Lys | Arg | |
| 1 | | | | 5 | | | | | 10 | | | | | 15 | | |
| agt | tcc | tct | gtg | ggg | aac | att | ggt | ctt | ggt | gat | aca | aaa | gtg | cct | ggg | 96 |
| Ser | Ser | Ser | Val | Gly | Asn | Ile | Gly | Leu | Gly | Asp | Thr | Lys | Val | Pro | Gly | |
| | | | 20 | | | | | 25 | | | | | 30 | | | |
| cta | tcc | acg | atg | tct | gaa | tcg | aaa | gaa | tcc | aag | att | gcc | gcg | agg | gcg | 144 |
| Leu | Ser | Thr | Met | Ser | Glu | Ser | Lys | Glu | Ser | Lys | Ile | Ala | Ala | Arg | Ala | |
| | | 35 | | | | | 40 | | | | | 45 | | | | |
| cgg | ttg | cgg | gca | ctt | tct | gga | gca | tcg | aag | acg | gat | atc | gac | atc | tac | 192 |
| Arg | Leu | Arg | Ala | Leu | Ser | Gly | Ala | Ser | Lys | Thr | Asp | Ile | Asp | Ile | Tyr | |
| 50 | | | | | 55 | | | | | 60 | | | | | | |
| tac | aag | ctg | tgg | cta | tcg | tat | aga | gag | ctg | aat | tat | cgt | cac | gcg | tgg | 240 |
| Tyr | Lys | Leu | Trp | Leu | Ser | Tyr | Arg | Glu | Leu | Asn | Tyr | Arg | His | Ala | Trp | |
| 65 | | | | 70 | | | | | 75 | | | | | 80 | | |
| ctg | act | cct | ctg | att | atc | ctg | ttt | ctg | att | tat | agc | tgt | tat | ttt | gct | 288 |
| Leu | Thr | Pro | Leu | Ile | Ile | Leu | Phe | Leu | Ile | Tyr | Ser | Cys | Tyr | Phe | Ala | |
| | | | | 85 | | | | | 90 | | | | | 95 | | |
| tcc | ggc | aac | agg | aca | gag | agt | aac | cca | ctt | cat | atg | ttc | gtt | gcg | ata | 336 |
| Ser | Gly | Asn | Arg | Thr | Glu | Ser | Asn | Pro | Leu | His | Met | Phe | Val | Ala | Ile | |
| | | | 100 | | | | | 105 | | | | | 110 | | | |
| tct | tat | aga | gtt | ggc | aac | acg | aac | atg | tac | ggg | aaa | ggt | gtc | aaa | gac | 384 |
| Ser | Tyr | Arg | Val | Gly | Asn | Thr | Asn | Met | Tyr | Gly | Lys | Gly | Val | Lys | Asp | |
| | | 115 | | | | | 120 | | | | | 125 | | | | |
| atg | tgc | ttt | gtg | ttc | tac | tac | atg | gta | ttc | ttc | acc | ttt | ctg | cgc | gaa | 432 |
| Met | Cys | Phe | Val | Phe | Tyr | Tyr | Met | Val | Phe | Phe | Thr | Phe | Leu | Arg | Glu | |
| 130 | | | | | 135 | | | | | 140 | | | | | | |
| ttt | atg | atg | gag | atg | gtg | ttg | cgc | cca | ttg | acg | ttc | cgg | ctc | ggt | gtc | 480 |
| Phe | Met | Met | Glu | Met | Val | Leu | Arg | Pro | Leu | Thr | Phe | Arg | Leu | Gly | Val | |
| 145 | | | | 150 | | | | | 155 | | | | | 160 | | |
| acc | aag | cca | cac | aag | gtc | aag | cgt | atg | atg | gag | caa | gct | tat | tcc | acg | 528 |
| Thr | Lys | Pro | His | Lys | Val | Lys | Arg | Met | Met | Glu | Gln | Ala | Tyr | Ser | Thr | |
| | | | | 165 | | | | | 170 | | | | | 175 | | |
| ttc | tac | tat | ggt | ctt | tct | ggt | ccc | ttt | ggg | ttg | ttt | gtg | atg | tac | cgt | 576 |
| Phe | Tyr | Tyr | Gly | Leu | Ser | Gly | Pro | Phe | Gly | Leu | Phe | Val | Met | Tyr | Arg | |
| | | | 180 | | | | | 185 | | | | | 190 | | | |
| acc | gat | ctg | tgg | tta | ttc | aag | aca | gca | gaa | atg | tac | aag | act | tat | cca | 624 |
| Thr | Asp | Leu | Trp | Leu | Phe | Lys | Thr | Ala | Glu | Met | Tyr | Lys | Thr | Tyr | Pro | |
| | | 195 | | | | | 200 | | | | | 205 | | | | |
| gac | ctc | acc | aac | gag | tac | tat | tat | aaa | atc | ttc | tac | ctc | ggc | caa | gca | 672 |
| Asp | Leu | Thr | Asn | Glu | Tyr | Tyr | Tyr | Lys | Ile | Phe | Tyr | Leu | Gly | Gln | Ala | |
| 210 | | | | | 215 | | | | | 220 | | | | | | |
| gct | ttc | tgg | gcg | caa | cag | gcg | tgt | atc | ctg | gtt | ttg | caa | cta | gag | aag | 720 |
| Ala | Phe | Trp | Ala | Gln | Gln | Ala | Cys | Ile | Leu | Val | Leu | Gln | Leu | Glu | Lys | |
| 225 | | | | | 230 | | | | | 235 | | | | | 240 | |
| cca | aga | aag | gac | ttc | agg | gaa | ctt | gtc | ttt | cac | cat | att | gtc | acc | ttg | 768 |
| Pro | Arg | Lys | Asp | Phe | Arg | Glu | Leu | Val | Phe | His | His | Ile | Val | Thr | Leu | |
| | | | | 245 | | | | | 250 | | | | | 255 | | |
| gcg | cta | att | tca | tta | tca | tac | gtt | ttc | cac | ttc | aca | aag | atg | ggc | ctg | 816 |
| Ala | Leu | Ile | Ser | Leu | Ser | Tyr | Val | Phe | His | Phe | Thr | Lys | Met | Gly | Leu | |
| | | | 260 | | | | | 265 | | | | | 270 | | | |
| gca | gtg | tac | atc | acc | atg | gat | gta | tcg | gat | ttt | ttc | cta | gcc | ctt | tca | 864 |
| Ala | Val | Tyr | Ile | Thr | Met | Asp | Val | Ser | Asp | Phe | Phe | Leu | Ala | Leu | Ser | |
| | | 275 | | | | | 280 | | | | | 285 | | | | |
| aag | att | ttc | aat | tac | atg | gag | tct | tcg | ttc | aca | gct | ccg | tta | ttt | ctt | 912 |
| Lys | Ile | Phe | Asn | Tyr | Met | Glu | Ser | Ser | Phe | Thr | Ala | Pro | Leu | Phe | Leu | |

```
                290                 295                 300
cta ttt gtg tcg tcc tgg gtc tat ctg aga cac tac gtt aat att aag      960
Leu Phe Val Ser Ser Trp Val Tyr Leu Arg His Tyr Val Asn Ile Lys
305                 310                 315                 320 atc ctc tgg tct gtg ttg aca gag ttc cgt acc gtg ggt gac tac aca     1008
Ile Leu Trp Ser Val Leu Thr Glu Phe Arg Thr Val Gly Asp Tyr Thr
                325                 330                 335 ttg aac ttc gct acc gag caa tac aaa agt tgg atc gct ttg ccg att     1056
Leu Asn Phe Ala Thr Glu Gln Tyr Lys Ser Trp Ile Ala Leu Pro Ile
                340                 345                 350 gtt ttt ggt tta ata ttt gcg ttg cat ctt gtt aat ctc tat tgg ctt     1104
Val Phe Gly Leu Ile Phe Ala Leu His Leu Val Asn Leu Tyr Trp Leu
                355                 360                 365 gcc cta ata ttc cgt att tta tac cgc atg ctc ttc caa ggt gtc caa     1152
Ala Leu Ile Phe Arg Ile Leu Tyr Arg Met Leu Phe Gln Gly Val Gln
370                 375                 380 aag gat gag aga agc gac agt gag tcc gaa gat aat gaa gag gag ctg     1200
Lys Asp Glu Arg Ser Asp Ser Glu Ser Glu Asp Asn Glu Glu Glu Leu
385                 390                 395                 400 gat gac tca tcg gat gag act gat aag aaa aag aac caa taa              1242
Asp Asp Ser Ser Asp Glu Thr Asp Lys Lys Lys Asn Gln
                405                 410 attggcattg tcattggcac ttcgtgttta tgtattgaat gtatagcata tcgattacgg    1302
cttgccatgg gatttcgtaa tgcaggagta aaagcacaaa aatgatagtt ctaacatctt    1362
ccgactgcgt gttccaccgc cattacacta ctagaatata tacaggtc                 1410
```

<210> SEQ ID NO 12
<211> LENGTH: 413
<212> TYPE: PRT
<213> ORGANISM: Eremothecium gossypii

<400> SEQUENCE: 12

Met Ala Glu Asn Ser Leu Leu Lys Pro Pro Ser Leu Ser Arg Lys Arg
1               5                   10                  15

Ser Ser Ser Val Gly Asn Ile Gly Leu Gly Asp Thr Lys Val Pro Gly
                20                  25                  30

Leu Ser Thr Met Ser Glu Ser Lys Glu Ser Lys Ile Ala Ala Arg Ala
            35                  40                  45

Arg Leu Arg Ala Leu Ser Gly Ala Ser Lys Thr Asp Ile Asp Ile Tyr
    50                  55                  60

Tyr Lys Leu Trp Leu Ser Tyr Arg Glu Leu Asn Tyr Arg His Ala Trp
65                  70                  75                  80

Leu Thr Pro Leu Ile Ile Leu Phe Leu Ile Tyr Ser Cys Tyr Phe Ala
                85                  90                  95

Ser Gly Asn Arg Thr Glu Ser Asn Pro Leu His Met Phe Val Ala Ile
                100                 105                 110

Ser Tyr Arg Val Gly Asn Thr Asn Met Tyr Gly Lys Gly Val Lys Asp
            115                 120                 125

Met Cys Phe Val Phe Tyr Tyr Met Val Phe Thr Phe Leu Arg Glu
130                 135                 140

Phe Met Met Glu Met Val Leu Arg Pro Leu Thr Phe Arg Leu Gly Val
145                 150                 155                 160

Thr Lys Pro His Lys Val Lys Arg Met Met Glu Gln Ala Tyr Ser Thr
                165                 170                 175

Phe Tyr Tyr Gly Leu Ser Gly Pro Phe Gly Leu Phe Val Met Tyr Arg
            180                 185                 190

```
          Thr Asp Leu Trp Leu Phe Lys Thr Ala Glu Met Tyr Lys Thr Tyr Pro
                  195                 200                 205

Asp Leu Thr Asn Glu Tyr Tyr Lys Ile Phe Tyr Leu Gly Gln Ala
              210                 215                 220

Ala Phe Trp Ala Gln Gln Ala Cys Ile Leu Val Leu Gln Leu Glu Lys
          225                 230                 235                 240

Pro Arg Lys Asp Phe Arg Glu Leu Val Phe His His Ile Val Thr Leu
                          245                 250                 255

Ala Leu Ile Ser Leu Ser Tyr Val Phe His Phe Thr Lys Met Gly Leu
                      260                 265                 270

Ala Val Tyr Ile Thr Met Asp Val Ser Asp Phe Leu Ala Leu Ser
                  275                 280                 285

Lys Ile Phe Asn Tyr Met Glu Ser Ser Phe Thr Ala Pro Leu Phe Leu
              290                 295                 300

Leu Phe Val Ser Ser Trp Val Tyr Leu Arg His Tyr Val Asn Ile Lys
          305                 310                 315                 320

Ile Leu Trp Ser Val Leu Thr Glu Phe Arg Thr Val Gly Asp Tyr Thr
                          325                 330                 335

Leu Asn Phe Ala Thr Glu Gln Tyr Lys Ser Trp Ile Ala Leu Pro Ile
                      340                 345                 350

Val Phe Gly Leu Ile Phe Ala Leu His Leu Val Asn Leu Tyr Trp Leu
                  355                 360                 365

Ala Leu Ile Phe Arg Ile Leu Tyr Arg Met Leu Phe Gln Gly Val Gln
              370                 375                 380

Lys Asp Glu Arg Ser Asp Ser Glu Ser Glu Asp Asn Glu Glu Glu Leu
          385                 390                 395                 400

Asp Asp Ser Ser Asp Glu Thr Asp Lys Lys Lys Asn Gln
                          405                 410

<210> SEQ ID NO 13
<211> LENGTH: 1309
<212> TYPE: DNA
<213> ORGANISM: Eremothecium gossypii
<220> FEATURE:
<221> NAME/KEY: CDS
<222> LOCATION: (1)..(1119)
<223> OTHER INFORMATION: Product: Ashbya gossypii ceramide synthase
      Laf1p

<400> SEQUENCE: 13 atg tcg ggc caa gtc agg cag agg ttc gct aag gac cag cac gcg gga         48
Met Ser Gly Gln Val Arg Gln Arg Phe Ala Lys Asp Gln His Ala Gly
1               5                   10                  15 tcg cag atc gag gtc gag tac ggg agc aag gat gca gca ttc gag gcg         96
Ser Gln Ile Glu Val Glu Tyr Gly Ser Lys Asp Ala Ala Phe Glu Ala
                20                  25                  30 gac aag tct gtc gag ctc gaa gag cgg gaa gaa ctc ctg ccc atc aga        144
Asp Lys Ser Val Glu Leu Glu Glu Arg Glu Glu Leu Leu Pro Ile Arg
            35                  40                  45 ggg cag ctg gcc gtg agc aag gtc gac ttg tac acg gtc tac gcg tcg        192
Gly Gln Leu Ala Val Ser Lys Val Asp Leu Tyr Thr Val Tyr Ala Ser
        50                  55                  60 ggc gcg ctg ctg gtg gca ctg gct gtt ggt ttt ctg cgg cag gct gca        240
Gly Ala Leu Leu Val Ala Leu Ala Val Gly Phe Leu Arg Gln Ala Ala
65                  70                  75                  80 tgg tgc gac aag ttt ctg agg ctc cag tac gcg agc gtg gag tcg ccg        288
Trp Cys Asp Lys Phe Leu Arg Leu Gln Tyr Ala Ser Val Glu Ser Pro
                85                  90                  95 ggg aag tac gac ata ggg ata gac gat gcc tac atc gtc ggc acg ttc        336
```

```
                Gly Lys Tyr Asp Ile Gly Ile Asp Asp Ala Tyr Ile Val Gly Thr Phe
                                100                 105                 110 gtg gtc gtg ctg tgc ctg gtc cgc tcg agc ctg ctg gag ttt gtc ctc        384
Val Val Val Leu Cys Leu Val Arg Ser Ser Leu Leu Glu Phe Val Leu
                115                 120                 125 aag ccg ctc gcg cac tac aag ttc cgg atc tcg tcg ggt aag ata caa        432
Lys Pro Leu Ala His Tyr Lys Phe Arg Ile Ser Ser Gly Lys Ile Gln
        130                 135                 140 cag cga tac ggc gag cag agt tgg tcg atg ctg tac tac acc gcg tcg        480
Gln Arg Tyr Gly Glu Gln Ser Trp Ser Met Leu Tyr Tyr Thr Ala Ser
145                 150                 155                 160 tgg gtg acg ggc ttc tac ctg tac tac cac tcg ccc tac ttc ctg aac        528
Trp Val Thr Gly Phe Tyr Leu Tyr Tyr His Ser Pro Tyr Phe Leu Asn
                165                 170                 175 tgc gac cac atc tat ctg aac tgg ccg cac gac aag atg gcc ggc gtc        576
Cys Asp His Ile Tyr Leu Asn Trp Pro His Asp Lys Met Ala Gly Val
                180                 185                 190 ttc aag gtg tac tac ctg gtg cag atc gca tcg tgg ctg cag cag atc        624
Phe Lys Val Tyr Tyr Leu Val Gln Ile Ala Ser Trp Leu Gln Gln Ile
        195                 200                 205 atc gtg ctc aac gtg gag gag aag cgc aag gac tac tgg cag atg ttt        672
Ile Val Leu Asn Val Glu Glu Lys Arg Lys Asp Tyr Trp Gln Met Phe
210                 215                 220 gcg cac cac ata atc acg gtc gcg ctg acc acg ggg tcg tac tac tat        720
Ala His His Ile Ile Thr Val Ala Leu Thr Thr Gly Ser Tyr Tyr Tyr
225                 230                 235                 240 tac ttc aac cgc att ggc cat gtg att ctg att atc atg gac gtg gtc        768
Tyr Phe Asn Arg Ile Gly His Val Ile Leu Ile Ile Met Asp Val Val
                245                 250                 255 gat atc ttg ctc tcc agc gcc aag atc ctg aag tac tgt ggc ttc tct        816
Asp Ile Leu Leu Ser Ser Ala Lys Ile Leu Lys Tyr Cys Gly Phe Ser
                260                 265                 270 gtt gcc tgt gac tac atg ttt gtc gtt ttc ctg ggc ttc tgg gtc gtg        864
Val Ala Cys Asp Tyr Met Phe Val Val Phe Leu Gly Phe Trp Val Val
        275                 280                 285 ttg agg cac ggg gtg tac aat tac att cta cac cac gcg tgg gcc aag        912
Leu Arg His Gly Val Tyr Asn Tyr Ile Leu His His Ala Trp Ala Lys
        290                 295                 300 tcg cga ggg ctc atg cag aac cag cgg tgc ggg gta cac gcc cct ggc        960
Ser Arg Gly Leu Met Gln Asn Gln Arg Cys Gly Val His Ala Pro Gly
305                 310                 315                 320 acg cgc tgc tgg act ccg ctg gtg atc gat atc ttt gtg ctc cta ctg       1008
Thr Arg Cys Trp Thr Pro Leu Val Ile Asp Ile Phe Val Leu Leu Leu
                325                 330                 335 gca ggg ttg caa ctg atc aca gtg atc tgg tct ttc ctc att gtc aaa       1056
Ala Gly Leu Gln Leu Ile Thr Val Ile Trp Ser Phe Leu Ile Val Lys
        340                 345                 350 gta ttt atg aaa gtt atc agg gga agc ggt gca gag gat gtg cgc agt       1104
Val Phe Met Lys Val Ile Arg Gly Ser Gly Ala Glu Asp Val Arg Ser
        355                 360                 365 gat gac gag gaa tag ggcctacgga tctcgttcgt gctgccacat acccgacggc       1159
Asp Asp Glu Glu
        370 atgcctcgct tgtattgtaa aagcactatg ttaatgtaaa gtagtttccg tcctacctgg     1219 tgatcggtaa tgcatagttt tgtgtatatt aaatgtcaca cagatcggac gagcagtcag     1279 cagcccagca gcgccagaca gcgcatgcag                                      1309

<210> SEQ ID NO 14
<211> LENGTH: 372
```

```
<212> TYPE: PRT
<213> ORGANISM: Eremothecium gossypiii

<400> SEQUENCE: 14

Met Ser Gly Gln Val Arg Gln Arg Phe Ala Lys Asp Gln His Ala Gly
1               5                   10                  15

Ser Gln Ile Glu Val Glu Tyr Gly Ser Lys Asp Ala Ala Phe Glu Ala
            20                  25                  30

Asp Lys Ser Val Glu Leu Glu Arg Glu Leu Leu Pro Ile Arg
        35                  40                  45

Gly Gln Leu Ala Val Ser Lys Val Asp Leu Tyr Thr Val Tyr Ala Ser
65              55                  60

Gly Ala Leu Leu Val Ala Leu Ala Val Gly Phe Leu Arg Gln Ala Ala
65                  70                  75                  80

Trp Cys Asp Lys Phe Leu Arg Leu Gln Tyr Ala Ser Val Glu Ser Pro
                85                  90                  95

Gly Lys Tyr Asp Ile Gly Ile Asp Asp Ala Tyr Ile Val Gly Thr Phe
            100                 105                 110

Val Val Val Leu Cys Leu Val Arg Ser Ser Leu Leu Glu Phe Val Leu
        115                 120                 125

Lys Pro Leu Ala His Tyr Lys Phe Arg Ile Ser Ser Gly Lys Ile Gln
130                 135                 140

Gln Arg Tyr Gly Glu Gln Ser Trp Ser Met Leu Tyr Tyr Thr Ala Ser
145                 150                 155                 160

Trp Val Thr Gly Phe Tyr Leu Tyr Tyr His Ser Pro Tyr Phe Leu Asn
                165                 170                 175

Cys Asp His Ile Tyr Leu Asn Trp Pro His Asp Lys Met Ala Gly Val
            180                 185                 190

Phe Lys Val Tyr Tyr Leu Val Gln Ile Ala Ser Trp Leu Gln Gln Ile
        195                 200                 205

Ile Val Leu Asn Val Glu Glu Lys Arg Lys Asp Tyr Trp Gln Met Phe
210                 215                 220

Ala His His Ile Ile Thr Val Ala Leu Thr Thr Gly Ser Tyr Tyr Tyr
225                 230                 235                 240

Tyr Phe Asn Arg Ile Gly His Val Ile Leu Ile Met Asp Val Val
                245                 250                 255

Asp Ile Leu Leu Ser Ser Ala Lys Ile Leu Lys Tyr Cys Gly Phe Ser
            260                 265                 270

Val Ala Cys Asp Tyr Met Phe Val Phe Leu Gly Phe Trp Val Val
        275                 280                 285

Leu Arg His Gly Val Tyr Asn Tyr Ile Leu His His Ala Trp Ala Lys
290                 295                 300

Ser Arg Gly Leu Met Gln Asn Gln Arg Cys Gly Val His Ala Pro Gly
305                 310                 315                 320

Thr Arg Cys Trp Thr Pro Leu Val Ile Asp Ile Phe Val Leu Leu Leu
                325                 330                 335

Ala Gly Leu Gln Leu Ile Thr Val Ile Trp Ser Phe Leu Ile Val Lys
            340                 345                 350

Val Phe Met Lys Val Ile Arg Gly Ser Gly Ala Glu Asp Val Arg Ser
        355                 360                 365

Asp Asp Glu Glu
        370

<210> SEQ ID NO 15
<211> LENGTH: 273
```

```
<212> TYPE: PRT
<213> ORGANISM: Mus musculus

<400> SEQUENCE: 15

Met His Val Pro Gly Thr Arg Ala Lys Met Ser Ser Ile Phe Ala Tyr
1               5                   10                  15

Gln Ser Ser Glu Val Asp Trp Cys Glu Ser Asn Phe Gln His Ser Glu
            20                  25                  30

Leu Val Ala Glu Phe Tyr Asn Thr Phe Ser Asn Val Phe Leu Ile
        35                  40                  45

Phe Gly Pro Leu Met Met Phe Leu Met His Pro Tyr Ala Gln Lys Arg
50                  55                  60

Thr Arg Cys Phe Tyr Gly Val Ser Val Leu Phe Met Leu Ile Gly Leu
65              70                  75                  80

Phe Ser Met Tyr Phe His Met Thr Leu Ser Phe Leu Gly Gln Leu Leu
            85                  90                  95

Asp Glu Ile Ser Ile Leu Trp Leu Leu Ala Ser Gly Tyr Ser Val Trp
            100                 105                 110

Leu Pro Arg Cys Tyr Phe Pro Lys Phe Val Lys Gly Asn Arg Phe Tyr
        115                 120                 125

Phe Ser Cys Leu Val Thr Ile Thr Thr Ile Ile Ser Thr Phe Leu Thr
130                 135                 140

Phe Val Lys Pro Thr Val Asn Ala Tyr Ala Leu Asn Ser Ile Ala Ile
145                 150                 155                 160

His Ile Leu Tyr Ile Val Arg Thr Glu Tyr Lys Lys Ile Arg Asp Asp
            165                 170                 175

Asp Leu Arg His Leu Ile Ala Val Ser Val Val Leu Trp Ala Ala Ala
        180                 185                 190

Leu Thr Ser Trp Ile Ser Asp Arg Val Leu Cys Ser Phe Trp Gln Arg
    195                 200                 205

Ile His Phe Tyr Tyr Leu His Ser Ile Trp His Val Leu Ile Ser Ile
210                 215                 220

Thr Phe Pro Tyr Gly Ile Val Thr Met Ala Leu Val Asp Ala Lys Tyr
225                 230                 235                 240

Glu Met Pro Asp Lys Thr Leu Lys Val His Tyr Trp Pro Arg Asp Ser
            245                 250                 255

Trp Val Ile Gly Leu Pro Tyr Val Glu Ile Gln Glu Asn Asp Lys Asn
        260                 265                 270

Cys

<210> SEQ ID NO 16
<211> LENGTH: 379
<212> TYPE: PRT
<213> ORGANISM: Eremothecium gossypii

<400> SEQUENCE: 16

Met Asn Gln Arg Gly Ile Ala Thr Ala Val Thr Ala Glu Pro Pro Ser
1               5                   10                  15

Ala Asp Ala Asp Val Glu Val Leu His Asn Phe Tyr Trp Thr Ser Leu
            20                  25                  30

Lys Glu Pro His Ala His Arg Arg Lys Glu Ile Leu Arg Ala His Pro
        35                  40                  45

Glu Val Lys Lys Leu Met Gly His Glu Pro Arg Thr Lys Tyr Leu Val
50                  55                  60

Ala Leu Val Val Gly Leu Gln Leu Leu Ser Ala Tyr Met Leu Arg Asp
65                  70                  75                  80
```

```
Thr Asp Pro Leu Ser Leu Lys Phe Leu Ala Trp Ala Tyr Val Val Gly
                85                  90                  95

Ala Thr Ala Thr Gln Asn Leu Tyr Leu Ala Ile His Glu Leu Ser His
            100                 105                 110

Asn Leu Ala Phe Lys Lys Pro Lys His Asn Arg Leu Phe Ser Ile Phe
            115                 120                 125

Cys Lys Pro Ala Glu Ser Gly Ile Pro Phe Ala Ala Ser Phe Gly Pro
            130                 135                 140

Tyr His Gln Leu His His Lys Phe Leu Gly Asp Glu Val Tyr Asp Thr
145                 150                 155                 160

Asp Val Pro Thr Val Leu Glu Ala Val Leu Leu Ser Asn Val Leu Gly
                165                 170                 175

Lys Thr Phe Phe Ala Thr Phe Gln Ile Phe Phe Tyr Ala Leu Arg Pro
                180                 185                 190

Met Met Val Val Arg Ile Pro Ile Thr Gly Phe His Val Leu Asn Val
                195                 200                 205

Val Cys Gln Phe Val Phe Asp Val Ile Trp Ile Arg Gln Phe Gly Leu
                210                 215                 220

Asn Gly Phe Phe Tyr Phe Leu Leu Ser Ser Phe Leu Ala Gly Ser Leu
225                 230                 235                 240

His Pro Cys Ser Gly His Phe Ile Ala Glu His Tyr Leu Phe Ser Ile
                245                 250                 255

Glu Glu Ala Ile Val Gly Gly Lys Val Ala Met Lys Ser Ala Ala Gly
                260                 265                 270

Glu Ala Glu Pro Val Tyr Val Thr Asp Glu Ser Ala Val Lys Arg Pro
                275                 280                 285

Asp Val Glu Phe Arg Lys Asp Tyr Ala Leu Glu Thr Tyr Ser Tyr Tyr
290                 295                 300

Gly Ile Leu Asn Ala Val Thr Trp Asn Val Gly Leu His Asn Glu His
305                 310                 315                 320

His Asp Phe Pro Phe Ile Ala Trp Ser Lys Leu Trp Glu Leu Asn Arg
                325                 330                 335

Met Cys Pro Glu Phe Tyr Glu Thr Leu Pro Lys His Asp Ser Trp Val
                340                 345                 350

Arg Val Leu Trp Asp Phe Ile Phe Lys Tyr Asp Val Thr Leu Tyr Asn
                355                 360                 365

Arg Val Arg Arg Val Asn Lys His Leu Glu Ser
            370                 375

<210> SEQ ID NO 17
<211> LENGTH: 351
<212> TYPE: PRT
<213> ORGANISM: Pichia ciferrii

<400> SEQUENCE: 17

Met Ala Thr Ile Thr His Arg Lys Asn Pro Ser Gln Pro Ile Thr Phe
1               5                   10                  15

Gln Thr Pro Pro Ala Asp Ala Pro Ile Glu Lys Leu Asn Asp Phe Tyr
                20                  25                  30

Trp Thr Asn Glu Thr Glu Pro His Thr Ile Arg Arg Lys Leu Ile Leu
            35                  40                  45

Lys Lys Tyr Pro Lys Ile Thr Glu Leu Cys Gly Pro Glu Pro Leu Thr
50                  55                  60

Lys Tyr Ile Ile Phe Gly Val Val Ser Leu Gln Leu Ser Ile Ala Tyr
65                  70                  75                  80
```

```
Tyr Leu Arg Asn Thr Pro Phe Leu Ser Trp Lys Phe Leu Leu Ser
                85                  90                  95

Tyr Ile Ile Gly Ala Thr Ala Asn Gln Asn Val Phe Leu Ala Ile His
            100                 105                 110

Glu Leu Thr His Asn Leu Ala Phe Lys Lys Pro Leu His Asn Lys Leu
            115                 120                 125

Tyr Ala Ile Phe Thr Asn Ile Pro Ile Gly Ile Pro Tyr Ser Ala Ser
130                 135                 140

Phe Gln Pro Tyr His Gln Leu His His Lys Tyr Leu Gly Asp Glu Val
145                 150                 155                 160

Leu Asp Thr Asp Val Pro Thr Lys Tyr Glu Ala Ile Val Leu Ser Asn
                165                 170                 175

Val Leu Gly Lys Ser Phe Phe Ala Thr Phe Gln Ile Leu Phe Tyr Ala
            180                 185                 190

Leu Arg Pro Met Phe Ile Thr Gln Ile Lys Phe Thr Tyr Ile His Leu
            195                 200                 205

Leu Asn Val Leu Val Gln Leu Phe Val Asp Phe Leu Ile Val Lys Tyr
210                 215                 220

Trp Gly Trp Lys Ser Leu Ser Tyr Phe Ile Phe Ser Ser Phe Leu Ala
225                 230                 235                 240

Gly Ser Leu His Pro Cys Ser Gly His Phe Ile Ala Glu His Tyr Ile
                245                 250                 255

Met Asp Pro Pro Lys Thr Tyr Asn Arg Tyr Lys Asp His Pro Pro Leu
            260                 265                 270

Glu Thr Tyr Ser Tyr Tyr Gly Ala Leu Asn Leu Val Thr Trp Asn Val
            275                 280                 285

Gly Leu His Asn Glu His His Asp Phe Pro Tyr Val Ala Trp Ser Lys
290                 295                 300

Leu His Lys Leu Asn Glu Val Ala Asn Glu Phe Tyr Cys Asp Leu Pro
305                 310                 315                 320

Lys His Asp Ser Trp Thr Met Val Ile Val Asn Phe Ile Leu Asp Lys
                325                 330                 335

Asn Val Leu Leu Tyr Asn Arg Val Lys Arg Glu Thr Ala Lys Lys
            340                 345                 350

<210> SEQ ID NO 18
<211> LENGTH: 320
<212> TYPE: PRT
<213> ORGANISM: Emiliana huxleyi

<400> SEQUENCE: 18

Met Ser Arg Ser Asp Tyr Ile Trp Val Asn Glu Asp Lys Val Ala Asp
1               5                   10                  15

Trp His Ala Glu Arg Lys Gln Lys Ile Leu Lys Asp His Pro Glu Val
            20                  25                  30

Lys Thr Leu Met Gly Ile Glu Pro Ile Thr Lys Tyr Leu Ala Val Leu
            35                  40                  45

Met Thr Ala Ser Gln Leu Val Thr Ala Ile Tyr Ser Val Asn Leu Ser
50                  55                  60

Trp Phe Met Tyr Leu Leu Ser Ala Tyr Phe Val Gly Ala Thr Leu Met
65                  70                  75                  80

Gln Thr Ser Phe Leu Phe Thr His Glu Ile Thr His Asn Thr Val Phe
                85                  90                  95

Lys Lys Val Arg Tyr Asn Arg Ile Phe Ala Tyr Val Ile Gln Thr Pro
            100                 105                 110
```

```
Ala Ile Val Ala Tyr His Glu Ser Phe Arg Phe Tyr His Thr Ser His
            115                 120                 125

His Leu Glu Leu Thr Arg Gly Gly Asp Pro Asp Ile Ser Ser Val
130                 135                 140

Met Glu Ala Asn Phe Thr Arg Gln Gly Val Leu Ala Lys Met Met Trp
145                 150                 155                 160

Leu Gln Thr Asn Leu Ile Thr Tyr Leu Leu Arg Pro Met Phe Val Lys
                165                 170                 175

Asn Met Pro Phe Ser Trp Tyr Leu Leu Ala Asn Trp Thr Val Gln Met
            180                 185                 190

Thr Phe Asn Ile Gly Phe Phe Met Met Tyr Gly Ile Ala Pro Phe Leu
        195                 200                 205

Tyr Leu Met Leu Ser Ala Phe Leu Ala Gly Gly Ile His Pro Leu Ala
    210                 215                 220

Ala His Phe Ile Thr Glu His Tyr Asn Phe Pro Gly Met Pro Glu Asp
225                 230                 235                 240

Gln Glu Thr Ser Ser Tyr Tyr Gly Pro Phe Asn Met Phe Ile Trp Asn
                245                 250                 255

Ala Gly Tyr His Val Glu His His Asp Phe Lys Ser Ile Pro Trp Thr
            260                 265                 270

Arg Leu Pro Asp Leu Arg Lys Met Ala Pro Glu Tyr Tyr Asp Ser Leu
        275                 280                 285

Tyr Gln Phe Asp Ser Tyr Phe Ser Thr Ile Tyr Ser Phe Ile Thr Asp
    290                 295                 300

Ala Arg Ile Asn Gly Phe Cys Arg Val Arg Val Ala Lys Val Glu
305                 310                 315                 320

<210> SEQ ID NO 19
<211> LENGTH: 323
<212> TYPE: PRT
<213> ORGANISM: Homo sapiens

<400> SEQUENCE: 19

Met Gly Ser Arg Val Ser Arg Glu Asp Phe Glu Trp Val Tyr Thr Asp
1               5                   10                  15

Gln Pro His Ala Asp Arg Arg Glu Ile Leu Ala Lys Tyr Pro Glu
            20                  25                  30

Ile Lys Ser Leu Met Lys Pro Asp Pro Asn Leu Ile Trp Ile Ile Ile
        35                  40                  45

Met Met Val Leu Thr Gln Leu Gly Ala Phe Tyr Ile Val Lys Asp Leu
50                  55                  60

Asp Trp Lys Trp Val Ile Phe Gly Ala Tyr Ala Phe Gly Ser Cys Ile
65                  70                  75                  80

Asn His Ser Met Thr Leu Ala Ile His Glu Ile Ala His Asn Ala Ala
                85                  90                  95

Phe Gly Asn Cys Lys Ala Met Trp Asn Arg Trp Phe Gly Met Phe Ala
            100                 105                 110

Asn Leu Pro Ile Gly Ile Pro Tyr Ser Ile Ser Phe Lys Arg Tyr His
        115                 120                 125

Met Asp His His Arg Tyr Leu Gly Ala Asp Gly Val Asp Val Asp Ile
    130                 135                 140

Pro Thr Asp Phe Glu Gly Trp Phe Phe Cys Thr Ala Phe Arg Lys Phe
145                 150                 155                 160

Ile Trp Val Ile Leu Gln Pro Leu Phe Tyr Ala Phe Arg Pro Leu Phe
                165                 170                 175
```

```
Ile Asn Pro Lys Pro Ile Thr Tyr Leu Glu Val Ile Asn Thr Val Ala
            180                 185                 190
Gln Val Thr Phe Asp Ile Leu Ile Tyr Tyr Phe Leu Gly Ile Lys Ser
        195                 200                 205
Leu Val Tyr Met Leu Ala Ala Ser Leu Leu Gly Leu Gly Leu His Pro
    210                 215                 220
Ile Ser Gly His Phe Ile Ala Glu His Tyr Met Phe Leu Lys Gly His
225                 230                 235                 240
Glu Thr Tyr Ser Tyr Tyr Gly Pro Leu Asn Leu Leu Thr Phe Asn Val
            245                 250                 255
Gly Tyr His Asn Glu His His Asp Phe Pro Asn Ile Pro Gly Lys Ser
        260                 265                 270
Leu Pro Leu Val Arg Lys Ile Ala Ala Glu Tyr Tyr Asp Asn Leu Pro
    275                 280                 285
His Tyr Asn Ser Trp Ile Lys Val Leu Tyr Asp Phe Val Met Asp Asp
290                 295                 300
Thr Ile Ser Pro Tyr Ser Arg Met Lys Arg His Gln Lys Gly Glu Met
305                 310                 315                 320
Val Leu Glu

<210> SEQ ID NO 20
<211> LENGTH: 1627
<212> TYPE: DNA
<213> ORGANISM: Eremothecium gossypii
<220> FEATURE:
<221> NAME/KEY: CDS
<222> LOCATION: (1)..(1617)
<223> OTHER INFORMATION: Product: Sphingolipid Delta8 desaturase

<400> SEQUENCE: 20
```

| | | | | | | | | | | | | | | | | |
|---|---|---|---|---|---|---|---|---|---|---|---|---|---|---|---|---|
| atg | gcg | gtg | ctt | tcg | aaa | agc | gag | gtg | gaa | gag | cgt | att | gct | aat | ggc | 48 |
| Met | Ala | Val | Leu | Ser | Lys | Ser | Glu | Val | Glu | Glu | Arg | Ile | Ala | Asn | Gly | |
| 1 | | | | 5 | | | | | 10 | | | | | 15 | | |
| gag | gtc | ata | gtg | atc | tat | aag | agt | gcg | gtg | ttg | aag | ctg | gac | aag | tgg | 96 |
| Glu | Val | Ile | Val | Ile | Tyr | Lys | Ser | Ala | Val | Leu | Lys | Leu | Asp | Lys | Trp | |
| | | | 20 | | | | | 25 | | | | | 30 | | | |
| atc | aag | tac | cac | ccg | ggc | gga | gat | aag | gct | ata | tat | cat | atg | gtt | ggg | 144 |
| Ile | Lys | Tyr | His | Pro | Gly | Gly | Asp | Lys | Ala | Ile | Tyr | His | Met | Val | Gly | |
| | | | 35 | | | | | 40 | | | | | 45 | | | |
| cgc | gat | gcg | aca | gac | gag | atg | aac | gcg | tac | cat | agc | gat | gaa | agc | gtg | 192 |
| Arg | Asp | Ala | Thr | Asp | Glu | Met | Asn | Ala | Tyr | His | Ser | Asp | Glu | Ser | Val | |
| | | 50 | | | | | 55 | | | | | 60 | | | | |
| cag | cag | ttc | atg | cgc | tgg | aag | att | ggg | cat | gtg | gag | ggg | gaa | tgg | aag | 240 |
| Gln | Gln | Phe | Met | Arg | Trp | Lys | Ile | Gly | His | Val | Glu | Gly | Glu | Trp | Lys | |
| 65 | | | | | 70 | | | | | 75 | | | | | 80 | |
| aac | ctg | gtg | cct | cca | ata | cag | cgc | aat | gcc | tgc | gag | acg | agc | atg | cag | 288 |
| Asn | Leu | Val | Pro | Pro | Ile | Gln | Arg | Asn | Ala | Cys | Glu | Thr | Ser | Met | Gln | |
| | | | | 85 | | | | | 90 | | | | | 95 | | |
| ccg | ggc | act | ccg | ggc | gat | gag | gac | acc | tgc | tac | gag | gac | gac | gcg | tgc | 336 |
| Pro | Gly | Thr | Pro | Gly | Asp | Glu | Asp | Thr | Cys | Tyr | Glu | Asp | Asp | Ala | Cys | |
| | | | 100 | | | | | 105 | | | | | 110 | | | |
| gac | gcc | aag | gtg | gag | acg | atg | ggg | cag | gcg | tac | aag | aac | cac | gta | gta | 384 |
| Asp | Ala | Lys | Val | Glu | Thr | Met | Gly | Gln | Ala | Tyr | Lys | Asn | His | Val | Val | |
| | | | 115 | | | | | 120 | | | | | 125 | | | |
| gtc | gat | ccg | atg | cag | ctc | agc | gag | ctg | ttc | gac | gag | gag | aga | gcg | gcg | 432 |
| Val | Asp | Pro | Met | Gln | Leu | Ser | Glu | Leu | Phe | Asp | Glu | Glu | Arg | Ala | Ala | |
| | | 130 | | | | | 135 | | | | | 140 | | | | |
| ctc | gac | cgc | aag | ctg | ttt | ccc | agc | gcc | gat | agt | gaa | act | cag | cag | agg | 480 |
| Leu | Asp | Arg | Lys | Leu | Phe | Pro | Ser | Ala | Asp | Ser | Glu | Thr | Gln | Gln | Arg | |

```
                           145                 150                 155                 160
att tcg gcg gag tac aac aag ctg cat cag gag ctc ata gac gcg ggc       528
Ile Ser Ala Glu Tyr Asn Lys Leu His Gln Glu Leu Ile Asp Ala Gly
                165                 170                 175 ttc tac gcc tgt ccg tat tgg aag tac ggc gtc gag ctg cta cgg ata       576
Phe Tyr Ala Cys Pro Tyr Trp Lys Tyr Gly Val Glu Leu Leu Arg Ile
                180                 185                 190 tcc acg ctg ctg ggc gcg tcg tat ttc aca ttg atc agg ctc aat tgg       624
Ser Thr Leu Leu Gly Ala Ser Tyr Phe Thr Leu Ile Arg Leu Asn Trp
            195                 200                 205 cag atc gtg tcc gcg ctg ctg ctg ggc gtt gcg tgg cag cag gca gtc       672
Gln Ile Val Ser Ala Leu Leu Leu Gly Val Ala Trp Gln Gln Ala Val
        210                 215                 220 ttc att gcc cac gac gcc ggc cac atc tcg atc aca cac aac tac cag       720
Phe Ile Ala His Asp Ala Gly His Ile Ser Ile Thr His Asn Tyr Gln
225                 230                 235                 240 gtg gac agc gtt ttt gga atg ctg gtg tcc gcg tgg ttc ggg ggc ctg       768
Val Asp Ser Val Phe Gly Met Leu Val Ser Ala Trp Phe Gly Gly Leu
                245                 250                 255 tcg ctg gga tgg tgg aag cgc aac cac aac gtg cac cac ctg gtg acg       816
Ser Leu Gly Trp Trp Lys Arg Asn His Asn Val His His Leu Val Thr
                260                 265                 270 aac gac ccg gag cac gat ccc gac atc cag cat ctg ccg ttc ttt gcg       864
Asn Asp Pro Glu His Asp Pro Asp Ile Gln His Leu Pro Phe Phe Ala
            275                 280                 285 gtc acc tcg cgc ctg ttc acg ggc ctc aag tcc acg tac tac gag cgt       912
Val Thr Ser Arg Leu Phe Thr Gly Leu Lys Ser Thr Tyr Tyr Glu Arg
        290                 295                 300 gac ctg gcc ttc gac ctg ccc gcg cgc atc ttt atc ccc ctg cag cac       960
Asp Leu Ala Phe Asp Leu Pro Ala Arg Ile Phe Ile Pro Leu Gln His
305                 310                 315                 320 ata ctg tac tac ccg att ctt gcg ttc ggt agg ttc aat ctc tac gtg      1008
Ile Leu Tyr Tyr Pro Ile Leu Ala Phe Gly Arg Phe Asn Leu Tyr Val
                325                 330                 335 tta agc tgg act cac ttg ctg ggc ggc aaa ggg cca cgc cac ggc caa      1056
Leu Ser Trp Thr His Leu Leu Gly Gly Lys Gly Pro Arg His Gly Gln
                340                 345                 350 gcc gcg tgg ttc cgt tac ttc gag ctc tgt ggc ctt gtc ttc ttc tgc      1104
Ala Ala Trp Phe Arg Tyr Phe Glu Leu Cys Gly Leu Val Phe Phe Cys
            355                 360                 365 tac tgg ttc tgc tac cgc ctg ctc gcc tgc tcg ctc tcc acc gcg acc      1152
Tyr Trp Phe Cys Tyr Arg Leu Leu Ala Cys Ser Leu Ser Thr Ala Thr
        370                 375                 380 gac cgc gtg ctg tac gtg ctc gtg tcc cac ctc acc acc atg atc gtc      1200
Asp Arg Val Leu Tyr Val Leu Val Ser His Leu Thr Thr Met Ile Val
385                 390                 395                 400 cat gtg cag atc acg ctc tcg cac ttc gcc atg tcc aca gcc gac ctt      1248
His Val Gln Ile Thr Leu Ser His Phe Ala Met Ser Thr Ala Asp Leu
                405                 410                 415 ggc gtg tcg gaa tcc ttc ccg cag cgg cag ctg cgg acc tca atg gac      1296
Gly Val Ser Glu Ser Phe Pro Gln Arg Gln Leu Arg Thr Ser Met Asp
                420                 425                 430 gtc gcc tgc ccg cgc tgg ctg gac ttc ttc cac ggc ggc ctg cag ttc      1344
Val Ala Cys Pro Arg Trp Leu Asp Phe Phe His Gly Gly Leu Gln Phe
            435                 440                 445 cag gtc ata cac cac ctc ttc cct cgg ctc cct cgc cac aac ctg cgc      1392
Gln Val Ile His His Leu Phe Pro Arg Leu Pro Arg His Asn Leu Arg
        450                 455                 460 gat gct cag ccg tac ctc ttg cgc ttc tgc gag cgt gtg ggc att aag      1440
Asp Ala Gln Pro Tyr Leu Leu Arg Phe Cys Glu Arg Val Gly Ile Lys
```

```
                465                 470                 475                 480
tac tcc atc tac ggg ttt tcg cac tgc aat tcc atg gtg ctg tcc cac     1488
Tyr Ser Ile Tyr Gly Phe Ser His Cys Asn Ser Met Val Leu Ser His
                    485                 490                 495 ctc gag cag att gcc cag cag gcc cgc acc gtt ctt gca tgt gcc cac     1536
Leu Glu Gln Ile Ala Gln Gln Ala Arg Thr Val Leu Ala Cys Ala His
                500                 505                 510 acg atg gga cct cac aaa gac gtg gca atg ccg gcc cca ggc gga gac     1584
Thr Met Gly Pro His Lys Asp Val Ala Met Pro Ala Pro Gly Gly Asp
            515                 520                 525 agc cgc cag tat agt aac cct aag cat gca tag agctgcgcgc              1627
Ser Arg Gln Tyr Ser Asn Pro Lys His Ala
530                 535

<210> SEQ ID NO 21
<211> LENGTH: 538
<212> TYPE: PRT
<213> ORGANISM: Eremothecium gossypii

<400> SEQUENCE: 21

Met Ala Val Leu Ser Lys Ser Glu Val Glu Arg Ile Ala Asn Gly
1               5                   10                  15

Glu Val Ile Val Ile Tyr Lys Ser Ala Val Leu Lys Leu Asp Lys Trp
                20                  25                  30

Ile Lys Tyr His Pro Gly Gly Asp Lys Ala Ile Tyr Met Val Gly
            35                  40                  45

Arg Asp Ala Thr Asp Glu Met Asn Ala Tyr His Ser Asp Glu Ser Val
        50                  55                  60

Gln Gln Phe Met Arg Trp Lys Ile Gly His Val Glu Gly Glu Trp Lys
65                  70                  75                  80

Asn Leu Val Pro Pro Ile Gln Arg Asn Ala Cys Glu Thr Ser Met Gln
                85                  90                  95

Pro Gly Thr Pro Gly Asp Glu Thr Cys Tyr Glu Asp Ala Cys
            100                 105                 110

Asp Ala Lys Val Glu Thr Met Gly Gln Ala Tyr Lys Asn His Val Val
        115                 120                 125

Val Asp Pro Met Gln Leu Ser Glu Leu Phe Asp Glu Arg Ala Ala
130                 135                 140

Leu Asp Arg Lys Leu Phe Pro Ser Ala Asp Ser Glu Thr Gln Gln Arg
145                 150                 155                 160

Ile Ser Ala Glu Tyr Asn Lys Leu His Gln Glu Leu Ile Asp Ala Gly
                165                 170                 175

Phe Tyr Ala Cys Pro Tyr Trp Lys Tyr Gly Val Glu Leu Leu Arg Ile
            180                 185                 190

Ser Thr Leu Leu Gly Ala Ser Tyr Phe Thr Leu Ile Arg Leu Asn Trp
        195                 200                 205

Gln Ile Val Ser Ala Leu Leu Leu Gly Val Ala Trp Gln Gln Ala Val
210                 215                 220

Phe Ile Ala His Asp Ala Gly His Ile Ser Ile Thr His Asn Tyr Gln
225                 230                 235                 240

Val Asp Ser Val Phe Gly Met Leu Val Ser Ala Trp Phe Gly Gly Leu
                245                 250                 255

Ser Leu Gly Trp Trp Lys Arg Asn His Asn Val His His Leu Val Thr
            260                 265                 270

Asn Asp Pro Glu His Asp Pro Asp Ile Gln His Leu Pro Phe Phe Ala
        275                 280                 285
```

```
Val Thr Ser Arg Leu Phe Thr Gly Leu Lys Ser Thr Tyr Tyr Glu Arg
        290                 295                 300

Asp Leu Ala Phe Asp Leu Pro Ala Arg Ile Phe Ile Pro Leu Gln His
305                 310                 315                 320

Ile Leu Tyr Tyr Pro Ile Leu Ala Phe Gly Arg Phe Asn Leu Tyr Val
                325                 330                 335

Leu Ser Trp Thr His Leu Leu Gly Gly Lys Gly Pro Arg His Gly Gln
            340                 345                 350

Ala Ala Trp Phe Arg Tyr Phe Glu Leu Cys Gly Leu Val Phe Phe Cys
                355                 360                 365

Tyr Trp Phe Cys Tyr Arg Leu Leu Ala Cys Ser Leu Ser Thr Ala Thr
        370                 375                 380

Asp Arg Val Leu Tyr Val Leu Val Ser His Leu Thr Thr Met Ile Val
385                 390                 395                 400

His Val Gln Ile Thr Leu Ser His Phe Ala Met Ser Thr Ala Asp Leu
                405                 410                 415

Gly Val Ser Glu Ser Phe Pro Gln Arg Gln Leu Arg Thr Ser Met Asp
            420                 425                 430

Val Ala Cys Pro Arg Trp Leu Asp Phe Phe His Gly Gly Leu Gln Phe
                435                 440                 445

Gln Val Ile His His Leu Phe Pro Arg Leu Pro Arg His Asn Leu Arg
450                 455                 460

Asp Ala Gln Pro Tyr Leu Leu Arg Phe Cys Glu Arg Val Gly Ile Lys
465                 470                 475                 480

Tyr Ser Ile Tyr Gly Phe Ser His Cys Asn Ser Met Val Leu Ser His
                485                 490                 495

Leu Glu Gln Ile Ala Gln Gln Ala Arg Thr Val Leu Ala Cys Ala His
            500                 505                 510

Thr Met Gly Pro His Lys Asp Val Ala Met Pro Ala Pro Gly Gly Asp
                515                 520                 525

Ser Arg Gln Tyr Ser Asn Pro Lys His Ala
            530                 535

<210> SEQ ID NO 22
<211> LENGTH: 2267
<212> TYPE: DNA
<213> ORGANISM: Eremothecium gossypii

<400> SEQUENCE: 22
tccatcagcg cgacaacagg cttcgggtac gtcgccagca tccagttcat ggtgtactcg     60
ccctggaaga agtcgtccac cttctccagc atgtcccgcc gcatggcctt cgccatcagc    120
acgatgtcgc caccggcgca gaacgcccgt ggcgcgcacg cagagtcgaa cacaatcacg    180
ttggccacat cgcttttggc gtactcctgc atcaccggca gaatcgagtg cagatctca    240 tggttgatgg cgttcagctt ctcgggccga ttgagcgtga ccacacgggc cgtgttattc    300
gttttgaact tgactaaaga cgacatctgc cttctctgga ccatgcctct aacggtgctt    360
cttatcatta tcactcggtg ccgctttat attgttgtga aggacaaact gcatgcgcaa    420
ccctgctttt agcaaggacg tgatttctga cgatagccta gatccgaatg agatgaccag    480
gccgctcggc tctcgttagt tctccggtct ccacgttcag tgctactgat acgacggtca    540
cgtttccaca tcgtggacgg tctcacatca tgtgaaacga caattacccg gacataccct    600
tcgtgatgta cagattgtag aaacataacg gagcatgagg tgatcttgct ccaatggtgg    660
ttcaaagcag acattgcact ctccaggtgg gaccacagac cgaatcgcac caccgatctg    720
```

```
catctatggt gccggtttcg acgtagagcg cacataagcg acgtccgtag atccgaatta    780
ttgagatgtg gcctataaaa acgatgctgt atattggcct cgtgttctac tacacacgcc    840
tcgattcgga tgactgcaag cagcctagtc ctccatagtg cgaacagaca gcgacgagac    900
tgacatgaac caacggggta tagcgacagc agtgacggcg gagccgccga gcgcggacgc    960
cgacgtcgag gtgcttcaca acttctactg gacctcgctg aaggaaccgc acgcgcatcg   1020
gcggaaagag atcctccgcg cgcacccgga ggtgaagaag ctgatggggc acgagccgcg   1080
cacaaagtac ctcgtggcgc tggtggtggg gctgcagctg ttgtctgcgt acatgctgcg   1140
ggacaccgac ccgctgagcc tgaagttcct tgcgtgggcg tacgtggtcg gcgcgacggc   1200
cacgcagaac ctgtacctgg cgatccacga gctatcgcac aacctggcct tcaagaagcc   1260
aaagcacaac cgtctgttct ccatctttgc aaacctgccg atcgggatcc cgttcgcggc   1320
ctcttttggc ccgtaccacc agctgcacca caagtttctc ggggacgagg tgtacgacac   1380
ggacgtgccg acggtgctcg aggcggtcct tttgtccaat gtgctcggga agacattctt   1440
tgcgacgttc cagatcttct tctatgccct gcgccccatg atggtcgtgc gcatcccgat   1500
caccggtttc cacgtactga acgttgtttg ccagtttgta ttcgatgtga ctggatccg   1560 tcagtttggc ctgaatgggt tcttctactt tctgctctcg tcgttcttgg ccggctcgct   1620
gcacccttgc tctgggcact tcatcgcgga gcactacctc ttcagcattg aagaggccat   1680
cgttggcggc aaggttgcga tgaagagcgc cgctggcgag gccgagcccg tctacgtgac   1740
tgatgagagc gccgtcaagc ggcccgatgt cgagttccgc aaggattatg ctttggagac   1800
gtattcgtac tatggaatcc tgaacgctgt tacttggaac gttggactgc acaatgagca   1860
ccacgacttt ccgttcatcg cctggtcgaa gctctgggag ctgaatcgca tgtgcccgga   1920
gttttatgag acacttccaa aacacgattc gtgggtccgc gttctctggg atttcatatt   1980
caagtacgac gttactctct acaaccgtgt caggcgtgta aataagcatt tggagtcata   2040
attgcgcccc tccactcgcc aaactcttat agatgattcg tttatgctat atgttaagta   2100
ttattaattc atgatgccgc gtcgtttaca atcactgccc cgttgcagcg taggccatgt   2160
atccaactgt tgcccagtac aagctgagga cccacttcag tagtccgaag agcgacagcg   2220
tgaacaccac aaggaagaac acatggagac agaaggagtc aaaactc                2267
```

<210> SEQ ID NO 23
<211> LENGTH: 2521
<212> TYPE: DNA
<213> ORGANISM: Eremothecium gossypii

<400> SEQUENCE: 23

```
cgtctgtacc agaacctgtg ccgcctgcgc tacctgcgcg aggtgccgca gcgcaaggcc     60
gcggagcagc tgcgcaagcg caacgagttc ggccacatct ggtactccgc gcagtaccgc    120
cccacctaca cgcaggaggc tgtcgcggac ctgcgcgagt gcctgctgcg cgcgcgcggc    180
ggcgccaccg tccactggga ggaccctgg cgcatgggcg accgcgccaa gcactgggcc    240
gcgctgcccg ccgtccagca ccagttcctg ccgcgcatgg ccaacgtggc tcgcgaggag    300
agcgccatcc tcaagcagct cggcgagcgc gcgaagcgcg ccttcgccgc gcccgccccg    360
cctgcgcccg ccccgcaaag cctctgatga ggggtgctgc agcctgcgcc gcatttgctg    420
gcgtgcgccg cccccaccctg taaatagcgc aaaatccgg ctcgcctcga cctgctacgc    480
ccgcgcgccg ccgggactgc ttgccgaaga ttaccaatcc gccagcaccc tgcatgcttc    540
gggacggtgg tctcgcttcg agacatgcgt gatgctgtac gagaatttct ttttctccta    600
```

-continued

```
tgagttgaaa tattatataa gtacatcgtt acatcgtttc tcaggaccgt tcgggacatc    660
accttagcgc agaatcatta gtaccggagg ttcgtagatt agagcaaacc gtggtcagac    720
acttggaggt tgctttgaga tgttaaacca cacttatagc gatattggcg ttaggctggc    780
gccccggttc ctcccggacg tgtcgttcat ggatgacgta gtcgcgccgt tgacggcagt    840
caagccgcga cccacgctgg tgccagggat atcgacgggc acctgtcgt tgctggcgcc     900 agtgctggcg tactgggtgt ctcggggct gttccacgtg atggatacgc tgcggctggc     960
ggaaaagtac cggatccacc cgagcgagga agtagcgtcg cggaacaggg ccggcaggct   1020
ggacgttctg gcgcaggtgg tgctgcagca catcatccag acgctgacgg ggctggtgct   1080
ggtatactat gacggggagc cgcagacggg gatggagcag ctggcgatgt ggcggtggcg   1140
gcaggcggcg ccaggtgggg tgtcgaacga ggcgatatac gtggcgtacc actacggctt   1200
gtcggtggcg aagctgctgg tggggttctt cctgatcgat acatggcagt tctggctcca   1260
ctacctgatg cacatgaaca agacgctgta ccggaagttc cacgcgcacc accaccgcct   1320
gtacgtcccg tacgcgtacg gcgcgctgta caacaacccc gtggaggcct ttgtgctcga   1380
ttcctgcggc accgcactgg ctgctcttgt cactcgtatg acgcacaggg aggagatgct   1440
gctctacaca tttgcaacca tgaagacggt ggacgaccac tgtggctacg cgctgccgtg   1500
ggatccgttc cagtggctct ccccgaacaa cgcggtgtac cacgacatcc accaccagaa   1560
cttcggtatc aagagcaact cgcgcagcc gttctttacc atatgggact cgttttgccg    1620
caccaagttc ccgcagttcg aggagtacga gaagaagcaa agacgagtga cggtggaccg   1680
gtacaagcag tttttggcag agcgccagat ggaacgggag gcaaagctga cgctgctctc   1740
caaaaaacta agctgagcgc taattaatac ttatctcaaa cacttaatac catctattgg   1800
gctgcaacca agtgcagtcg gttctgttct ataacgccac actagggcta cgacgttgtt   1860
taagcatacg actcttttaa tgtaatatct ggccccgcct ggggcggtca tgtgtacgca   1920
tatccatggg cagtggcgca tgcgtgcggc gagcccgcag cgcatgccgg ttctaacggg   1980
cctatttcct ttaagagaat atatgtagga ttacactaga tcgtttggcg ccggagcgcg   2040
tagggcctcc gagtgcgcag gcgtcgcaac ggggaccgct gctcccagcc ccggaccttc   2100
caagctggtg ttccgtgatg atatcgtggg taaacatggg gtcataagtc tggatggagc   2160
tcccatcacg agcttaaatg gactccttta gcacctggtt cagcttgctg attctggaag   2220
cgatgctcaa gtccacggtt ctgtcggcga cctccacaat caacccgccc tgaatctctg   2280
gcttcacgac gttctccagc ttcaaggtct tgccggcgcc gatgaagctc gactgtgcca   2340
gcgccttctc gactcttctg aacagcttgc cctccagagg ctgcgcggtg gtcacagtcg   2400
cctggaccag gccgttgtgc gcgtctgtca acttggtgaa ttcgccagcc acaccctgca   2460
gcaggttcag tctgttgttc tctgctagca cctgcatcag gttctgcact gcagcgtcca   2520
t                                                                   2521
```

<210> SEQ ID NO 24
<211> LENGTH: 518
<212> TYPE: DNA
<213> ORGANISM: Eremothecium gossypii

<400> SEQUENCE: 24

```
cggctctcct cgctctgctc aagggcccac gcacacccctt atatacgtct cccgcgctgc     60
ccgtccgctg cttgagctca cccgatgcca gtcagcctcc ccggaatcac cagtcgcaca    120
cctcgccacg gggtgggccg ccggtgtctg ggtgcacgac acctgacctc cgccccgcgg    180
```

```
gcttcctgtt ttcgccgggc gcggcacatg gtgcggcttc ctccgacagg aagccgggcc    240
gccggacgcg cacgtcagag gcgtcaccag ggcaaatggg tggaagcgaa gggaactacg    300
acgaacggtc agcacccctg ggcccccac gctcgcacca cagccgctgc gcgtgggcgt     360
gaaaaatttt acctgcgggc tctccttacg atctcctatt ttatttcctg gggggcagtc    420
gaaatctata taagagggcc ccgggacgca caacgggagg actctggtgg agagaccagg    480
agtttgaatt aattcagtcc acacatacac accgcaca                            518

<210> SEQ ID NO 25
<211> LENGTH: 467
<212> TYPE: DNA
<213> ORGANISM: Eremothecium gossypii

<400> SEQUENCE: 25
ctgttcacag ccttctgaga caatcagacg ataaaaagga agctgagaag ttacgttttt    60
ttgatagctt cctctaactg gacacggctt cttgttgtcc ctgtgtctcg tgctaggcgt    120
aggaacgctc cctacatcac gttcatagct agcatccttt ggggccccctt tcggccaagt   180 aaagcccata tgcgcgacgc aaacggcacg cccaattacg aacgtgcacg aacagcggaa    240
tcctcgcgtg gtgattaagc agctcctagt gtgatgccgc agttgaatgc ctaaaaaaat    300
tcgtggggcg gaccgacatc agaggcgata catgtgaaaa cttagagaaa agtgctaaac    360
ggtataaata ggagagaaat aagagtgcat tagccgttgc tcttgcagga ttttttctgg    420
gctcagagca gtagagatta acacctccga aactcaaata attcaaa                 467

<210> SEQ ID NO 26
<211> LENGTH: 2534
<212> TYPE: DNA
<213> ORGANISM: Pichia ciferrii

<400> SEQUENCE: 26
catatggtat tattctaatt atacatagac aagtgttacc acaagtttct catgataaat    60
ggaaagtatt tggattatgg actttagtta acgcatttgc tgttggttat catccgattc    120
aaaatacttg gttacaacta aactgtgatt ctccacagga agaagtatt tcaattgcac     180 tttgggtaat gtttgccatg attggactaa tgagtggatc tcagttgttt agacaagatg    240
ataaaccttt atatcaaaag ggaactttag ccatgatttg tatggttttt ggaggattcc    300
tcatatcctt gggacagtat ctcttatact atcatctaaa caggaaaaag caatcaaatg    360
agcgtaaatg gctattataa aatgatattt gactcattaa tttgtgaata ttttgtagtt    420
tatactgatt acataaccat gacataagca atcaggaac gttttttttt ttattttat     480 ttttattttt acttttgcga atcgcctcgt ttaaacgtt taaaaaacca aaaatttaat    540
tgttttctat taacatcagc tcattttaat tgtatttaaa gaacagctca acttttcctt    600
tgaaaggaag atcagactac aaatttgtca aactccaaaa ctcctattta tacacagaga    660 aattctttt tctctttttc cattcattta taccctaat atcattggat ctcaaaaaag     720
ttgttattcg agatctgaat ctggatctat attatattaa taaaaagatt ccaaaagctc    780
atcatggcta caattacaca tagaaaaaac ccttcacaac caataacttt ccaaacacct    840
ccagcagatg ctccaattga aaattaaat gatttttatt ggacaaatga aactgaacct    900
catacaatta gaagaaaatt aatattgaaa aaatatccaa aaattacaga actttgtgga    960
cctgaacctt taactaaata tattattttc ggagttgttt cattcaatt atcaattgct    1020 tattatttaa gaaatactcc attttaaagt tggaaattct ttttgttaag ttatataatt   1080
```

-continued

```
ggtgctactg caaatcaaaa tgtctttta gctattcatg aattaactca taatttagca      1140
tttaaaaaac cattacataa caaattatat gcaattttca caaatattcc aattggtata     1200
ccttattcag cttctttcca accttatcat caattacatc ataaatattt aggtgatgaa     1260
gttttagata ctgatgtccc aacaaaatat gaagctatag ttttatcaaa tgtcttgggg    1320
aaatcatttt ttgcaacttt ccaaatctta ttttatgctt taagaccaat gtttattaca    1380
caaattaaat ttacttatat tcatttactt aacgtcttgg ttcaactatt tgttgatttc    1440
ttaattgtga atactgggg ttggaaatca ttaagttatt tcatctttag ttcatttta      1500
gctggttctt tacatccatg ttcaggtcat tcattgctg aacattatat catggatcca     1560
ccaaagactt ataacagata taaagatcat ccacctttag aaacttattc atattatggt    1620
gccttaaatt tagttacatg gaatgttggt ctacataatg aacatcatga tttcccatat    1680
gttgcttggt caaaacttca taaattgaat gaagttgcta atgagtttta ttgtgattta    1740
ccaaaacatg attcatggac tatggttatt gttaacttca ttcttgataa aaatgtctta    1800
ttatacaata gagttaaaag agaaactgca agaaataaa atccataaaa ttatcattat     1860
ttataaacta tatatgtacg aattgggctg gagaatagag gtaacaaa atatacaaaa      1920
catatcatta tttatacgaa aattgtagtc accagatagt catctaaaat gctgacatgt    1980
aactgtcgtc gtattcgttc aatttgatgt gaagtatcca tgctcaatgc tgagatcctc    2040
atacaaaaaa taattagcga aaagcaaaaa ataaaaaaaa aaaaaacct ttaatctcct     2100
gataatttaa ctaacaaatt ttgtcaaacg gtagaaacga ttcgaacttt atcaattcta    2160
gttttgaaca agatcagttg tcacaaaaga acgaagtgtt aaacgataaa tcattgattg    2220
tcaattgtat ataaacacag acaggaaacc gttgaattcg ttgtatcttt atcaaaactt    2280
aatcattaat actcaagtac aatagaattg acaatatgcc tttcactgat caaacatcac    2340
caaatgcccc aattagggaa aagatggaag ctttaatccg tcaaaacaa caagaaatca    2400
ctaaaggtct tgaagcttta gaaccaactg ctagattctt tgctgattct tggtctcgtg    2460
gtgaaagtgc tggaggtggt acttcatgtg ttattcaaga tggtgaagtt tttgaaaaag    2520
gtggtgtgaa tatt                                                     2534
```

<210> SEQ ID NO 27
<211> LENGTH: 655
<212> TYPE: DNA
<213> ORGANISM: Pichia ciferrii

<400> SEQUENCE: 27

```
gacgcaccgg ccatttcaa acacctgatg cgaaaaaacg aaaagtaaat ttatcgattt      60
tgaattcaaa attcaataat acattcaatt gataatttgt ttggtttgaa aatagtagaa    120
gtattcaact tttattagag gtttgcaatt ctcccccatt ttcaactaaa tattcaacac    180
aactaaactt tcccggagga gttcagacta ctatacaaag atgatgttga agaatattgt    240
tcgtcctctt tcaaacacaa cttctttgag atcaactcaa agagttgcca gaactatggc    300
cactgaagcc aaccaagatg atgaagtaag tagattgtta ttatatttt ggatcgatga     360
tgaattgtgg ataatggaga tgaattgatt ggattttaat tggttctttg attgtttgt    420
gattgttttt ttgatatcta ggaaagatag gggacaatca agatttagat ctatacaacc    480
acaaatcacc aaatttcaa tccaaatcag tgggaaacac tagacaatgt ttaattacta    540
acccgttttc acacagattg tcactattaa cttaccagct tcatcatttg aaggttatga    600
attagaagtt ccagaaacta ctttccaaac ttcaaaatca actttattat caatg         655
```

<210> SEQ ID NO 28
<211> LENGTH: 332
<212> TYPE: DNA
<213> ORGANISM: Pichia ciferrii

<400> SEQUENCE: 28

```
atttagcttc ggtgctttcc tatataacgc ttttataagt ttatgaataa tttacgtttt      60
tactgaaatt acctattgta gatacttcat ttgcaacatt ttctcataat aagtaggtgt     120
ttgatgacat ggctatattt tgtgattcat caactgattg ttttattttg aaaattgtcg     180
tcttacatat aattcttcca tcataaagct cataaattat atataaaagt tatgtttaat     240
gacatgccaa agtttcatta atttcaccac cataaagata attacctaaa attgcaccag     300
caacaacact caacattgcc caaccgttat aa                                   332
```

<210> SEQ ID NO 29
<211> LENGTH: 576
<212> TYPE: DNA
<213> ORGANISM: Artificial Sequence
<220> FEATURE:
<223> OTHER INFORMATION: Synthetic DNA encoding nourseothricin
      acetyltransferase Nat1 from Streptomyces noursei

<400> SEQUENCE: 29

```
atgggtacta ctttagatga tactgcttat agatatagaa cttcagttcc aggtgatgct      60
gaagctattg aagctttaga tggttcattt actactgata ctgtttttag agttactgct     120
actggtgatg gttttacttt aagagaagtt ccagttgatc caccattaac taaagttttt     180
ccagatgatg aatcagatga cgagtctgat gacggtgaag atggtgatcc agattcaaga     240
acttttgttg cttatggtga tgacggagac ttagctggtt tgttgttgt ttcatattca     300
ggttggaata aagattaac tgttgaagat attgaagttg ctccagaaca tagaggtcat     360
ggtgttggta gagctttaat gggtttagct actgaatttg ctagagaacg tggtgctggt     420
catttatggt tagaagttac taatgttaat gctccagcta ttcatgctta tagaagaatg     480
ggtttcacat tatgtggttt agatactgct ttatatgatg gtactgcttc agatggtgaa     540
caagctttat atatgtcaat gccatgtcca taataa                              576
```

<210> SEQ ID NO 30
<211> LENGTH: 847
<212> TYPE: DNA
<213> ORGANISM: Artificial Sequence
<220> FEATURE:
<223> OTHER INFORMATION: Synthetic DNA encoding alkaline ceramidase mCER
      from mouse

<400> SEQUENCE: 30

```
ggtaccttaa ttaacaatgc atgttccagg tactagagct aaaatgtcat caattttgc       60
ttatcaatca tctgaagttg attggtgtga atcaaatttt caacattcag aattagttgc     120
tgaattctat aatactttt caaatgtttt tttcttaatt tttggtccat taatgatgtt      180
tttaatgcat ccatatgctc aaaaaagaac tagatgtttt tatggtgttt cagttttatt     240
catgttaatt ggtttatttt caatgtattt tcatatgact ttatcatttt taggtcaatt     300
attagatgaa atttcaattt tatggttatt agcttcaggt tattcagttt ggttaccaag     360
atgttatttt ccaaaatttg ttaaaggtaa tagatttat ttctcatgtt tagttactat      420
tactactatt atttcaactt ttttaacttt tgttaaaccaa actgttaatg cttatgcttt     480
aaattcaatt gctattcata tcttatacat tgttagaact gaatacaaaa aaattagaga     540
```

```
tgatgattta agacatttaa ttgctgtttc agttgtttta tgggctgctg ctttaacttc    600
atggatttca gatagagttt tgtgttcatt ttggcaaaga attcatttct attatttgca    660
ttcaatttgg catgttttaa tttcaattac ttttccatat ggtattgtta ctatggcttt    720
agttgatgca aaatatgaaa tgccagataa aacttaaaaa gttcattatt ggccaagaga    780
ttcttgggtt attggtttac catatgtcga aattcaagaa aatgataaaa attgttaata    840
agagctc                                                              847
```

<210> SEQ ID NO 31
<211> LENGTH: 913
<212> TYPE: DNA
<213> ORGANISM: Artificial Sequence
<220> FEATURE:
<223> OTHER INFORMATION: Synthetic DNA encoding dihydroceramide synthase
      Lag1p from Coccolithovirus EhV-86

<400> SEQUENCE: 31

```
ggtaccgtta acgtacctaa taatatgtat tgtggtactt caggtttaag agatttcatg     60
tatgcagata ttatggaaat ggctcaattc tcagttatta tgttttcatt tgctacaatt    120
ttaagaactt ttgttatgat ttatatttta gatccattat cagaaattat ggttagacca    180
gaaagagttt taaaatttca acaatcagct tggagatttg ttttatattc aattgctact    240
atttcatcaa ttattgtttt tatgactgat gatactgttg atttttaaaga atcttcattt    300 ttcgaaaatt ggccattata taatccaggt tcaggtatta aattcatgta tgcattatat    360
gctggtttct atattcatca aactgtttat attttcggtg atgaaagatt agatgatttt    420
aatgaacatg ttttcatca tgctattact ttagttttag tttatgtttc atgggttttc    480
aatttcacta aaattggttt tttcattatg actttacatg atggttcaga tgttttttta    540
gaattagcta atgtatgaa ttatgctaaa gaaattagac caagattatc aattatttca    600
gatgtttcat tcattatttt tgcttcatca ttttttctatt taagattata tttatatcca    660
gtttatgcta ttggttcaat tgttaatcca tatgatgctt gtgctcatgt ttcatgtgct    720
ttatatgaag gtggtgtttc atattcatat tgtgcttcaa aaccaattta tgctgttgct    780
attgctgctt taacttcatt atatattta caagttatgt gggctggtag aattattaat    840
gttattgcta aagttattgc tggtaatcca ttagaagatt caagagatta aatttatagt    900
atcccgggag ctc                                                      913
```

<210> SEQ ID NO 32
<211> LENGTH: 1293
<212> TYPE: DNA
<213> ORGANISM: Artificial Sequence
<220> FEATURE:
<223> OTHER INFORMATION: Synthetic DNA encoding dihydroceramide synthase
      LASS5 from mouse

<400> SEQUENCE: 32

```
ggtaccgtta accgggcgcg cgtaagatgg ctactgctgc tgctgaaact ttaggtttat     60 tatgggggttg gttatggtca gaatcatttt ggttaccaca aaatgtttca tgggctgatt    120
tagaaggtcc aggtgatggt tatggttatc caagagcaca acatgtttta tcagttttttc    180 cattagctgt ttgtattttt tcagttagaa tgttatttga agattttatt gctaaaccat    240
gtgctttaag agttggtatt aaagattcac cagttaataa agttgaacca aatgatactt    300
tagaaaaagt ttttgtttca gttactaaat atccagatga aaaagattaa aaggtttat    360 caaaacaatt agattggtca gttagaaaaa ttcaatgttg gtttagacat agaagaaatc    420
```

```
aagataaacc accaacttta actaaatttt gtgaatcaat gtggagattt acttattatt    480
tatgtatttt ttgttatggt attagatttt tatggtcaat gccatggttt tgggatacta    540
gacaatgttg gtataattat ccatatcaac cattatcaag agaattatat tattattata    600
ttactcaatt agctttttat tggtcattaa tgttttcaca atttattgat gttaaaagaa    660
aagatttctt aatgatgttt attcatcata tgattggtat tatgttgact acttttcat    720 atgttaataa tatggttaga gttggtgctt taattttctg tttacatgat tttgctgatc    780
cattattaga agctgctaaa atggctaatt atgctagaag agaaagatta tgtactactt    840
tattcgttat ttttggtgct gcttttattg tttcaagatt agctatttt ccattatgga    900 ttttaaatac tactttattt gaatcatggg aaattattgg tccatatcca tcatggtggt    960
tatttaatgc tttattatta attttacaag ttttacatgc tatttggtct tatttaattg    1020
ttcaaactgc ttcaaaagct ttatcaagag gtaaagtttc aaaagatgat agatcagatg    1080
ttgaatcatc atcagaagaa gaagatgaaa ctactcataa aaataattta tcaggttcat    1140
catcatcaaa tggtgctaat tgtatgaatg gttatatggg tggttcacat ttagctgaag    1200
aacaaggtac ttgtaaagct actggtaatt tacatttag agcttcacca catttacatt    1260
catgtgatta aagggactgc aacccgggag ctc                                1293
```